(12) United States Patent
Koide et al.

(10) Patent No.: US 12,391,770 B2
(45) Date of Patent: *Aug. 19, 2025

(54) COMPOSITIONS AND METHODS COMPRISING ANTIBODIES THAT BIND TO COVALENT PEPTIDE CONJUGATES

(71) Applicant: New York University, New York, NY (US)

(72) Inventors: Shohei Koide, New York, NY (US); Benjamin Neel, New York, NY (US); Carmine Fedele, New York, NY (US); Kai Wen Teng, Flushing, NY (US); Akiko Koide, New York, NY (US); Takamitsu Hattori, West New York, NJ (US); Lorenzo Maso, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/585,676

(22) Filed: Feb. 23, 2024

(65) Prior Publication Data

US 2024/0327542 A1    Oct. 3, 2024

Related U.S. Application Data

(63) Continuation of application No. 18/547,623, filed as application No. PCT/US2022/018171 on Feb. 28, 2022.

(60) Provisional application No. 63/253,499, filed on Oct. 7, 2021, provisional application No. 63/154,627, filed on Feb. 26, 2021.

(51) Int. Cl.
*C07K 16/44* (2006.01)
*A61K 47/68* (2017.01)
*C07K 16/28* (2006.01)

(52) U.S. Cl.
CPC .......... *C07K 16/44* (2013.01); *A61K 47/6849* (2017.08); *C07K 16/2833* (2013.01); *C07K 2317/56* (2013.01); *C07K 2317/626* (2013.01)

(58) Field of Classification Search
None
See application file for complete search history.

(56) References Cited

U.S. PATENT DOCUMENTS

| | | | |
|---|---|---|---|
| 8,945,571 B2 | 2/2015 | Mössner et al. | |
| 9,447,159 B2 | 9/2016 | Ast et al. | |
| 10,344,091 B2* | 7/2019 | Koide | A61P 37/06 |
| 11,242,405 B2 | 2/2022 | Scheinberg et al. | |
| 2005/0059113 A1 | 3/2005 | Bedian et al. | |
| 2019/0256604 A1 | 8/2019 | Koide et al. | |
| 2020/0129555 A1 | 4/2020 | Hanada et al. | |
| 2020/0399377 A1 | 12/2020 | Weidanz | |
| 2022/0227883 A1 | 7/2022 | Holt et al. | |
| 2022/0289866 A1 | 9/2022 | Craik et al. | |
| 2022/0324998 A1 | 10/2022 | O'Bryan et al. | |

FOREIGN PATENT DOCUMENTS

| | | |
|---|---|---|
| EP | 3286222 A1 | 2/2018 |
| EP | 2723380 B1 | 8/2019 |
| EP | 4178976 A1 | 5/2023 |
| EP | 4182029 A1 | 5/2023 |
| WO | 01/98324 A1 | 12/2001 |
| WO | 2015160928 A2 | 10/2015 |
| WO | 2020154617 A1 | 7/2020 |
| WO | 2022072760 A1 | 4/2022 |
| WO | 2022241017 A2 | 11/2022 |

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Khan and Salunke., J. Immunol 192: 5398-5405 (Year: 2014).*
Poosarla et al., Biotechn. Bioeng. 114(6): 1331-1342 (Year: 2017).*
Rudikoff et al, Proc Natl Acad Sci USA 79: 1979-1983 (Year: 1982).*
Piatesi et al., ChemBio Chem 5: 460-466 (Year: 2004).*
Wu et al., J. Mol. Biol. 294: 151-162 (Year: 1999).*
Lambert, J.M., et al., Antibody-Drug Conjugates (ADCs) for Personalized Treatment of Solid Tumors: A Review, Advances in Therapy, Mar. 30, 2017, vol. 34, pp. 1015-1035.
Teng, K.W., et al., Selective and noncovalent targeting of RAS mutants for inhibition and degradation, Nature Communications, May 11, 2021, vol. 12, No. 2656, 13 pages.

(Continued)

*Primary Examiner* — Phuong Huynh
(74) *Attorney, Agent, or Firm* — Hodgson Russ LLP

(57) ABSTRACT

Provided are compositions and methods that include binding partners that bind with specificity to target sites on proteins or peptides that comprise a covalently attached molecule. The binding partners are provided as antibodies and antibody derivatives that specifically bind to proteins and peptides that have been covalently modified by attachment of a molecule, such as a drug. The binding partners can bind with specificity to covalently modified peptides when presented in the context of a major histocompatibility complex (MHC). Uses of the compositions and methods for prophylaxis or therapy of disorders are also provided.

8 Claims, 30 Drawing Sheets

Specification includes a Sequence Listing.

(56) References Cited

OTHER PUBLICATIONS

Visscher, M., et al., Covalent targeting of acquired cysteines in cancer, Current Opinion in Chemical Biology, Nov. 28, 2015, vol. 30, pp. 61-67.
Maserati et al., "Abstract PR04: Anti peptide-HLA (TCR-like) antibodies specific for the KRAS G12V neoantigen," Molecular Cancer Research: American Association for Cancer Research, May 1, 2020.

\* cited by examiner

A

B

A

B

COMPOSITIONS AND METHODS COMPRISING ANTIBODIES THAT BIND TO COVALENT PEPTIDE CONJUGATES

CROSS REFERENCE TO RELATED APPLICATIONS

This application is a continuation of U.S. patent application Ser. No. 18/547,623, filed Aug. 23, 2023, which is a National Stage entry of International Patent Application No. PCT/US2022/018171, filed Feb. 28, 2022, which claims the benefit of U.S. Provisional Patent Application No. 63/253, 499, filed Oct. 7, 2021, and U.S. Provisional Patent Application No. 63/154,627, filed Feb. 26, 2021, the entire disclosures of each of which are incorporated herein by reference.

STATEMENT REGARDING FEDERALLY SPONSORED RESEARCH

This invention was made with government support under grand nos. CA194864, CA267362 and CA049152 awarded by the National Institutes of Health. The government has certain rights in the invention.

SEQUENCE LISTING

The instant application contains a Sequence Listing, which has been submitted electronically in XML format and is hereby incorporated by reference in its entirety. Said XML copy, created on Jan. 2, 2025, is named 64443-701_301_SL.xml, and is 449,032 bytes in size.

BACKGROUND

There is an ongoing and unmet need for agents that can bind to targets that include drugs that are covalently bound to proteins or peptides. In particular, there is a need to improve the efficacy of targeted therapy and also to increase tumor immunogenicity and the efficacy of immune therapy against cancer driven by intracellular oncogenes. The disclosure is pertinent to these needs.

BRIEF SUMMARY

The present disclosure provides compositions and methods that include binding partners that bind with specificity to target sites on proteins or peptides that comprise a covalently attached molecule. It is believed that this is the first disclosure of binding partners with this binding function. The disclosure illustrates this approach using binding partners in the form of numerous antibodies and antibody derivatives that specifically bind to proteins and peptides that have been covalently modified by attachment of a molecule, wherein the molecules are illustrated by a variety of drugs. Further, the disclosure demonstrates binding partners that bind with specificity to peptides that have been covalently modified by attachment of a small molecule drug are specific for the described covalently modified peptides when presented in the context of a human leukocyte antigen (HLA), wherein HLA is a representative example of a major histocompatibility complex (MHC). Thus, binding partners that are specific for peptide-drug conjugates in an HLA complex are demonstrated. The disclosure includes polynucleotides encoding the described binding partners and cells that are modified to express the binding partners. The disclosure includes diagnostic, prophylactic and therapeutic approaches using the binding partners.

BRIEF DESCRIPTION OF THE FIGURES

FIG. 23 discloses "GGWYPA" as SEQ ID NO: 155 and "ISYVKKLI" as SEQ ID NO: 153.

FIG. 24 discloses "EYVTMAL" SEQ ID NO: 159 and "YSYWPI" as SEQ ID NO: 157.

DETAILED DESCRIPTION

Figure 1:
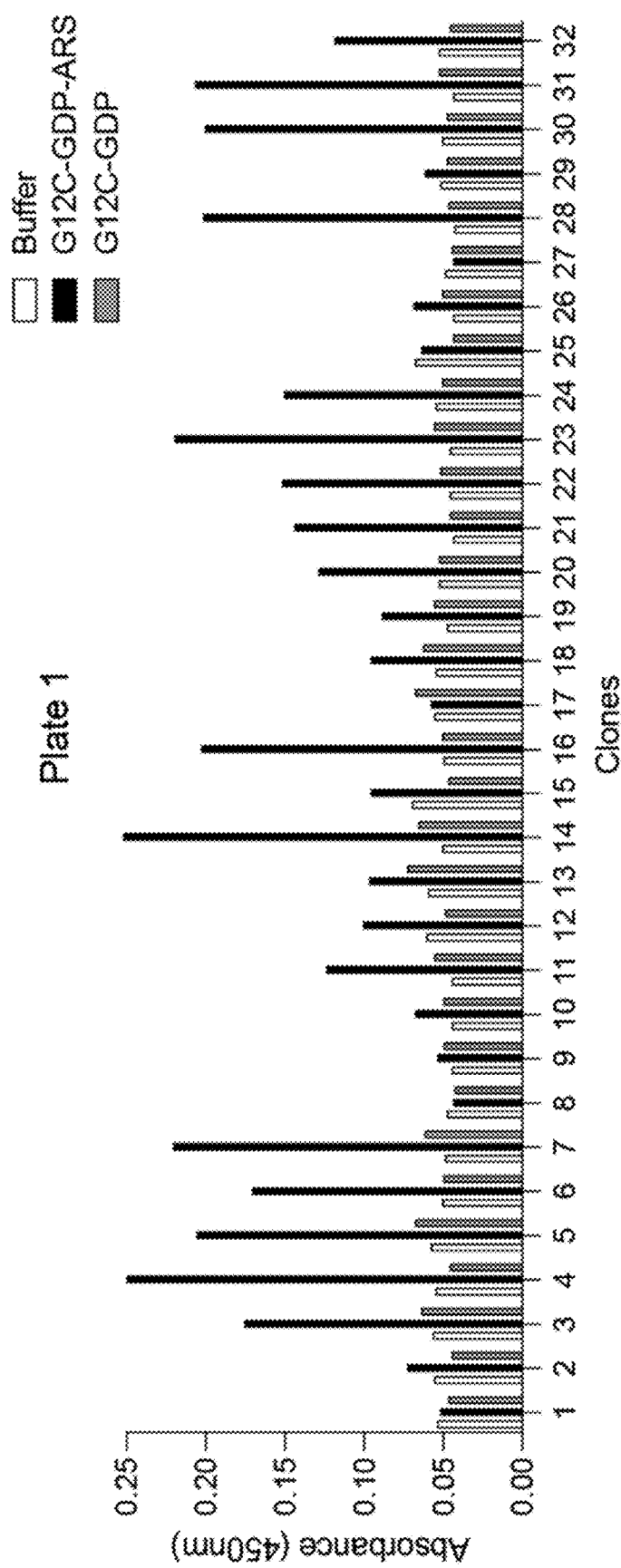
FIG. 1. Graphs depicting results of phage enzyme-linked immunosorbent assay (ELISA) of phage-displayed antibody clones. Binding to $KRAS^{G12C}$-GDP and $KRAS^{G12C}$-GDP-ARS-1620 conjugate was determined. For each clone, the bars in the graph are, from left to right, Buffer, G12C-GDP-ARS, and G12C-GDP.
Figure 1:
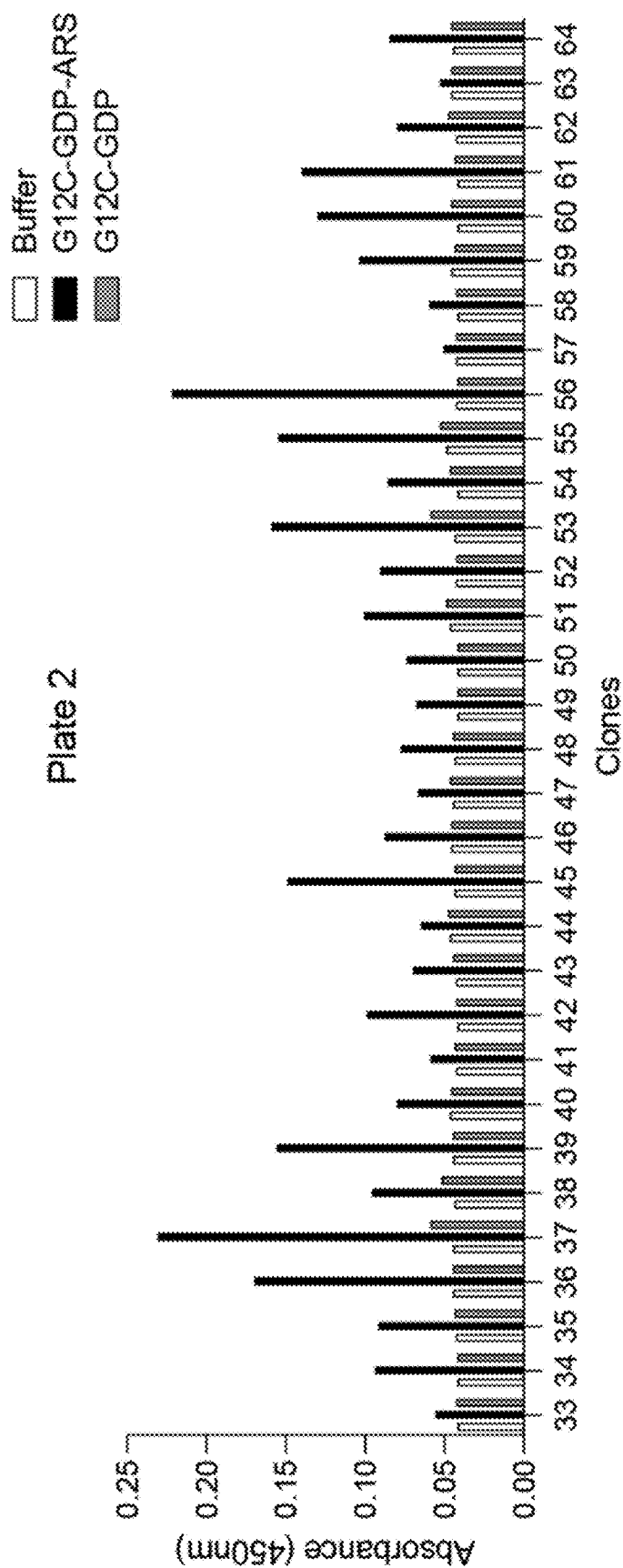
Figure 1:
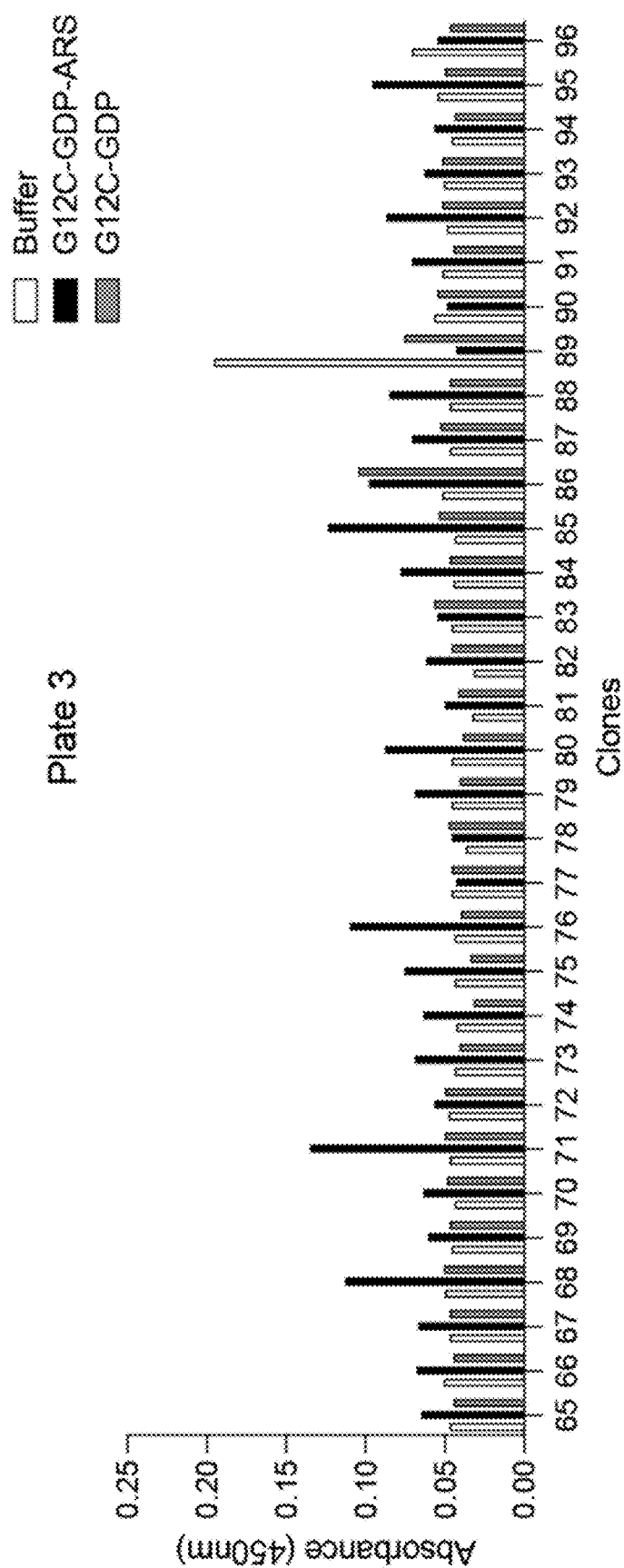

Unless defined otherwise, all technical and scientific terms used herein have the same meaning as commonly understood by one of ordinary skill in the art to which this invention belongs.

Every numerical range given throughout this specification includes its upper and lower values, as well as every narrower numerical range that falls within it, as if such narrower numerical ranges were all expressly written herein.

As used in the specification and the appended claims, the singular forms "a" "and" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about" it will be understood that the particular value forms another embodiment. The term "about" in relation to a numerical value is optional and means for example +/−10%.

This disclosure includes every amino acid sequence described herein and all nucleotide sequences encoding the amino acid sequences. Every antibody sequence and antigen binding fragments of them are included. Polynucleotide and amino acid sequences having from 80-99% similarity, inclusive, and including and all numbers and ranges of numbers there between, with the sequences provided here are included in the invention. All of the amino acid sequences described herein can include amino acid substitutions, such as conservative substitutions, that do not adversely affect the function of the protein that comprises the amino acid sequences. In this regard, the disclosure provides alternative residues for certain positions in described binding partner as described below. In certain examples, the alternative residues were identified by deep mutational scanning, which demonstrates binding functionality for each binding partner that contains the described amino acid change(s). The disclosure includes each binding partner with each alternative residue substituted for the original residue alone and in any combination with the described alternative residues. Thus, any binding partner described herein may have any single described residue change or a combination of described changes. Representative changes for particular antibodies are described in Table A, Table B, Table C, and Table D. The changes may be in CDR1, CDR2, CDR3, and combinations thereof. The changes can also include amino acid insertions. The disclosure includes each amino acid sequence that is encompassed by the description of alternative amino acids by reference to a specific sequence identifier and those described in the aforementioned Tables.

As described above, the present disclosure provides antibodies and antigen binding fragments thereof (collectively "binding partners" and each individually a "binding partner"). The term "antibody" includes each binding partner format herein. The binding partners bind with specificity to a protein or fragment thereof, or a peptide provided in peptide form, that comprises a covalently attached molecule. The covalently attached molecule forms a peptide conjugate. A "peptide conjugate" as used herein means any protein or peptide that has been modified so that it is covalently conjugated to another molecule. The peptide conjugate is considered to be a novel antigen, i.e., a neoantigen. The other molecule that is covalently conjugated to the protein or peptide to form the peptide conjugate is not particularly limited, with the proviso that the other molecule is not an additional amino acid that is added to the described peptide conjugates. In embodiments, the molecule that is covalently conjugated to the protein or peptide has or had biological activity before conjugation, or it may be biologically inert before conjugation. In embodiments, the molecule is a drug, including but not necessarily limited to small molecule drugs. Representative and non-limiting examples of drugs that covalently attach to a peptide or protein to form a peptide conjugate are described below. Peptide conjugates include but are not limited to covalently modified full length proteins and fragments thereof. Peptide conjugates include fragments of full length proteins that include a covalent modification and are produced, for example, by intracellular processing. In certain embodiments, a full length protein may be covalently modified within a cell and subsequently processed such that a peptide conjugate that is a fragment of the full length protein is produced. As described further below, the produced peptide conjugate may be displayed on a cell surface. The cell surface display of the peptide conjugate may be any form of cell surface display, including but not limited to by way of any receptor having an extracellular segment, or it may be displayed by way of any type of major histocompatibility complex (MHC) or human leukocyte antigen (HLA). Non-limiting examples of HLA types that display peptide conjugates, and to which the described binding partners bind with specificity, are described further below.

In embodiments, the binding partners preferentially bind to the protein or peptide or a complex comprising the protein or peptide when covalently bound to the peptide conjugate, relative to the same protein or peptide that is not bound to the drug. Accordingly, binding partners described herein either do not detectably bind, or bind with a lower affinity, to the same protein or fragment thereof in the absence of the covalently attached molecule. In embodiments, the binding partners bind to the protein or peptide comprising the covalently attached drug with an affinity that is 10-10,000 fold, including all numbers and ranges of numbers from 10-10,000, greater than the affinity for the protein or peptide that does not comprise the covalently bound molecule. In this regard, and without intending to be bound by any particular theory, it is considered that the presence of the covalently bound molecule contributes to the presence of an epitope to which the binding partners bind with specificity.

In embodiments, the molecule that is covalently bound to form the peptide conjugate is a drug and may be any targeted covalent inhibitor (TCI), but an inhibition property is not necessarily required. In embodiments, the molecule reacts with a specific residue within the target protein. In embodiments, the molecule reacts at least in part with a segment of the protein or peptide that comprises a nucleophilic, or an electrophilic, residue. In embodiments, the segment of the protein or peptide to which the molecule reacts comprises any of Cys, Lys, Tyr, and His. In embodiments, the molecule reacts at least in part with a segment of the protein or peptide that comprises a wild type Cys, or a mutation of a residue to a Cys, and thus may be covalently attached by a so-called sulfur tether. In embodiments, the drug is any drug described in Ghosh A K, Samanta I, Mondal A, Liu W R. Covalent Inhibition in Drug Discovery. ChemMedChem. 2019; 14(9): 889-906. doi:10.1002/cmdc.201900107, or in De Cesco, et al., European Journal of Medicinal Chemistry 138 (2017) 96e114, or in Bauer, RA, Drug Discovery Today, Volume 20, Number 9, September 2015, from which the disclosures of compounds that covalently modify protein targets is incorporated herein by reference.

In non-limiting embodiments, any of said Cys, Lys, Tyr, and His amino acids are present in the protein or peptide to which the molecule binds because the wild type protein has been mutated to include one or a combination of the described residues. In non-limiting embodiments, the molecule binds to a protein or peptide that is correlated with a condition, such as a cancer. In embodiments, the target (e.g., the protein or peptide to which the molecule covalently binds) is a receptor, including but not necessarily limited to any receptor having a catalytically active segment. In embodiments, the drug binds to an enzyme that is not necessarily a receptor, including but not limited to any kinase. In embodiments, a protein target comprises a receptor with one or more activating mutations, which promote ligand-independent enzyme activity.

In embodiments, the molecule targets and thus covalently binds to an amino acid sequence present within any of the following proteins and/or variants thereof, which may or may not comprise a mutation, such as a mutation that is related to a particular condition, including but not limited to any type of cancer. In embodiments, the protein is any protein described in Visscher M, et al., Covalent targeting of acquired cysteines in cancer. Curr Opin Chem Biol. 2016; 30:61-67. doi: 10.1016/j.cbpa.2015.11.004, from which the description is incorporated herein by reference. Visscher et al. also teaches methods for identifying disease-associated mutated genes that introduces a Cys residue suitable for covalent modification. In embodiments, the protein is KRAS, Bruton's tyrosine kinase (BTK), any member of the epidermal growth factor receptor (EGFR) family, also referred to as the ERBB family, including but not limited to EGFR (ERBB1), HER2/NEU (ERBB2), HER3 (ERBB3), and HER4 (ERBB4); a fibroblast growth factor receptor (FGFR); the receptor kinase known in the art as MET, BRAF, a cyclin-dependent kinase (CDK); Acetyl Choline Esterase (ACHE); TP53, IDH1, GNAS, FBXW7, CTNNB1, DNMT3A, any cathepsin, including cathepsin B, C, F, H, K, L, O, S, V, W and X; any caspase; any protein involved in obesity, such as Pancreatic lipase and METAP2, or any Cancer Testis Antigen. In embodiments, the drug targets and therefore covalently binds to any viral protein, including but not limited to a polymerase, including any viral DNA polymerase, RNA polymerase, reverse transcriptase, or RNA-dependent RNA polymerase, or a viral protein that is required, for example, viral cell entry, or a protein encoded by any a transposable element. In embodiments, the drug targets EGFR and may be selected from PD168393, PF00299804 (dacomitinib), EKB569 (pelitinib), afatinib, WZ4002, osimertinib (formerly known as AZD9291), PF-06459988, nazartinib, naquotinib, olmutinib, avitinib, and rociletinib, neratinib, pyrotinib, poziotinib, and derivatives thereof. In embodiments, the drug targets Bruton's tyrosine kinase (BTK), and may be selected from ibrutinib, acalabrutinib, zanubrutinib, CHMFL-BTK-11, ONO/GS-405, PRN1008, and CC-292. In embodiments, the drug targets any p90 ribosomal S6 kinase (RSK), and may be selected from fluoromethylketone (FMK) and dimethyl fumarate. In embodiments, the drug targets any FGFR, and may be selected from FIIN-1, FIIN-2, FIIN-3, BGJ398, AZD4547, PRN1371, FGF401.

In a non-limiting embodiment, the binding partner binds with specificity to a site comprised by a neoantigen that includes a covalently linked small molecule drug or other covalently linked molecule as a component of an antigen in a specific MHC context.

In embodiments, the molecule that becomes covalently bound to form the peptide conjugate targets any RAS oncogene protein product, including but not necessarily limited to HRAS, NRAS, KRAS4A, and KRAS4B. The amino acid sequences of RAS proteins are known in the art, and residue numbering is identical for the relevant part of all RAS isotypes that are discussed in this disclosure for which the amino acid sequence is available from, for example, UniProt P01116, from which the amino acid sequence is incorporated herein as of the effective filing date of this application or patent. The G12 position is numbered according to the known amino acid sequence, regardless of whether or not the G12 is the twelfth amino acid in an express RAS peptide sequence of this disclosure.

In one embodiment, the molecule covalently binds to a KRAS protein or peptide that comprises a mutation. In embodiments, the mutation is at least one of KRAS residues 12, 13, or 61. Reference to any drug herein includes its name in capitalized and un-capitalized form.

In embodiments, the drug targets a KRAS protein comprising a KRAS G12C mutation. In non-limiting embodiments, the drug that targets a KRAS protein is selected from 2E07, 6H05, SML-8-73-1, MRTX849, JNJ74699157, LY3499446, ARS-853, ARS-1620, MRTX1275, AMG510, or derivatives thereof. In an embodiment the drug comprises a proteolysis targeting chimera (PROTAC) derivative of a covalent drug, a non-limiting description of which is available in doi: 10.1021/acscentsci.Oc00411, from which the description of PROTACs is incorporated herein by reference. In embodiments, the PROTAC is LC-1 or LC-2. In embodiments, the disclosure relates to an autophagy-mediated degrader, referred to as an AUTAC, as described in doi.org/10.1080/15548627.2020.1718362, from which the description of AUTACs is incorporated herein by reference.

A non-limiting example of a binding partner that binds to KRAS(G12C)-AMG510 is referred to herein as AMRA3-7D. The disclosure includes all derivatives of AMRA3-7D that are described herein, including the alternative residues described below by way of deep mutational analysis, and in the forms of an scDb and a CrossMab, for which representative amino acid sequences are provided. The amino acid sequence of the light chain ($V_L$) and heavy chain ($V_H$) of AMRA3-7D are:

$V_L$:

(SEQ ID NO: 3)
DIQMTQSPSSLSASVGDRVTITCRASQSVSSAVAWYQQKPGKAPKLLIY

SASSLYSGVPSRFSGSRSGTDFTLTISSLQPEDFATYYCQQISYVKKLI

TFGQGTKVEIKRTV
(Bolded CDR sequences are disclose as SEQ ID NOS
166, 167, and 168, respectively, in order of
appearance)

$V_H$:

(SEQ ID NO: 4)
EVQLVESGGGLVQPGGSLRLSCAASGFTFSDYSIHWVRQAPGKGLEWVA

SISSSSGSTSYADSVKGRFTISADTSKNTAYLQMNSLRAEDTAVYYCAR

GGWYPAMDYWGQGTLVTVSS
(Bolded CDR sequences are disclosed as SEQ ID NOS
169, 170, and 171, respectively, in order of
appearance)

A non-limiting example of a binding partner that binds to an Epidermal Growth Factor receptor (EGFR)-osimertinib conjugate is referred to herein as OEA2-5. The disclosure includes all derivatives of OEA2-5 that are described herein, including the alternative residues described below by way of deep mutational analysis, and in the form of an scDb, for which representative amino acid sequences are provided.

The amino acid sequences of the light chain (V$_L$) and heavy chain (V$_H$) of OEA2-5 are:

V$_L$:
(SEQ ID NO: 5)
DIQMTQSPSSLSASVGDRVTITCRASQSVSSAVAWYQQKPGKAPKLLIY

SASSLYSGVPSRFSGSRSGTDFTLTISSLQPEDFATYYCQQYSYWPITF

GQGTKVEIKRTV
(Bolded CDR sequences are disclosed as SEQ ID NOS 166, 167, and 172, respectively, in order of appearance)

V$_H$:
(SEQ ID NO: 6)
EVQLVESGGGLVQPGGSLRLSCAASGFTISSSYIHWVRQAPGKGLEWVA

YISPSYGSTSYADSVKGRFTISADTSKNTAYLQMNSLRAEDTAVYYCAR

EYVTMALDYWGQGTLVTVSS
(Bolded CDR sequences are disclosed as SEQ ID NOS 173, 174, and 175, respectively, in order of appearance)

In embodiments, the binding partner binds to a protein in its native form, with the exception that the drug or other molecule is covalently attached to it. "Native form" means the intact protein that retains its biological function before covalent attachment of the drug or other molecule. In embodiments, the native form or the protein is its form before being fragmented such as by intracellular processing. In embodiments, the binding proteins therefore bind to full length polypeptides that are covalently attached to the drug or other molecule and wherein the covalently bound drug or other molecule at least in part permits the preferential binding of the binding partners. In general, a polypeptide, which is used interchangeably herein with the term "protein," comprises more than 50 contiguous amino acids. In embodiments, a binding partner binds with specificity to an intact protein that is covalently attached to a drug or other molecule. In other embodiments, the binding partners bind with specificity to a peptide comprising the covalently bound molecule. In embodiments, the binding partner binds with specificity to a peptide having a specific amino acid sequence and is covalently conjugated to another molecule, such as a drug. In embodiments, the binding partner binds preferentially to a peptide covalently bound to a molecule such as a drug, where the sequence of the peptide is not relevant. This preferential binding is relative to binding to the same peptide that is not conjugated to the drug. In embodiments, the binding partner binds preferentially to a peptide comprising a KRAS(G12) mutation, or to a variant thereof, wherein the variant is at least 50% similar to the KRAS(G12)-containing peptide. This preferential binding is relative to binding to a KRAS(G12)-containing peptide, or the variant thereof, respectively, that is not covalently conjugated to the drug or other molecule.

In embodiments, the described binding partners bind with specificity to peptide conjugates that are of suitable length to be presented in a major histocompatibility complex (MHC), referred to as human leukocyte antigen (HLA) in humans, or to MHC or its equivalent complex in non-human animals, including but not limited to non-human mammals.

In general, the peptide conjugate comprises fewer than 50 contiguous amino acids. In embodiments, peptide conjugates which comprise the described epitope may therefore be from 2-49 amino acids in length. In embodiments, the peptide to which the drug or other molecule is covalently attached, and which attached drug may be comprised by the epitope, comprises from 4-12 contiguous amino acids, which may or may not be derived from a longer protein during the processing of a protein, such as an antigen processed for presentation by an MHC molecule. In embodiments, the drug is conjugated to a peptide that comprises, or consists of 7-30 amino acids. In embodiments, the drug or other molecule is conjugated to a peptide that comprises, or consists of, 7, 8, 9, 10, 11, 12, 13, 14, or 15 amino acids, and which may be presented in an MHC Class I context. In embodiments, the drug or other molecule is conjugated to a peptide that is 9-30 amino acids, inclusive, and including all numbers and ranges of numbers there between, and which may be presented in an MHC Class II context. In embodiments, the drug or other molecule is conjugated to a peptide comprises at least 7 amino acids.

In embodiments, a binding partner binds with specificity to a peptide conjugate that is covalently conjugated to a drug or other molecule independent of MHC presentation. In embodiments, non-limiting examples of which are described below in Example 3, the binding partner binds with specificity to the peptide conjugate only when the peptide conjugate is presented by an MHC molecule. In embodiments, the binding partner can bind with specificity to a peptide conjugate in both an MHC-independent and an MHC-presentation context. In embodiments, the MHC-peptide conjugate complex comprises an antigen to which a described binding partner binds with specificity.

In embodiments, the binding partners accordingly can bind to cells via any MHC that can present peptide conjugates. In embodiments, the HLA is expressed by cells that are restricted to Class I, Class II, or Class III MHC presentation. In embodiments, the binding partners can bind to cells that express Class I MHC that presents the peptide conjugate. Those skilled in the art will recognize that Class I MHC includes, among other components, a polymorphic α chain and β2 microglobulin, wherein the peptide conjugate binds to the polymorphic chain.

In embodiments, the cells are antigen presenting cells (APCs). In embodiments, the cells are so-called professional antigen presenting cells, and thus may include but are not limited to macrophages and dendritic cells, which display Class II MHC. Those skilled in the art will recognize that Class II MHC includes, among other components, MHC polymorphic α and β chains, and the displayed peptide conjugate binds to both chains. In other embodiments, Class II MHC may be displayed with the peptide conjugate by other cell types, such as cancer/tumor cells, and thus the disclosure provides for direct recognition of such cells using the described binding partners, without requirement for a professional APC.

In embodiments, the peptide conjugate is displayed by a non-classical MHC complex, which may include CD1d, MR1, MHC-E, -F, -G and/or other emerging family members that will be recognized by those skilled in the art.

The disclosure includes binding partners that bind with specificity to a peptide conjugate displayed only by a specific MHC type, and thus provides binding partners that discriminate between MHC types. Representative examples of such binding partners are described herein at least by way of FIG. 17.

In embodiments, a binding partner of this disclosure can bind with specificity to a peptide conjugate comprising a covalently conjugated drug or other molecule that is displayed by more than one specific MHC type. In embodiments, a binding partner of this disclosure can bind with specificity to a peptide conjugate comprising a covalently conjugated drug only in a specific MHC context. In embodiments, the peptide conjugate is displayed by an MHC class I type selected from HLA-A, -B, -C, and combinations thereof. In certain aspects, the peptide conjugate is displayed in the context of any MHC class I that is A*02/B*35/C*04. In embodiments, the peptide conjugate is displayed by any of MHC of class II that is DR*01/DR*04/DR*07/DP*04. In embodiments, the HLA comprises A*01:01, A*02:01, A*03:01, A*11:01, A*24:02, A*26:01, B*07:02, B*08:01, B*27:05, B*39:01, B*40:01, B*58:01, or B*15:01. Specific examples of antibodies include antibodies that bind to KRAS(G12C)-AMG510 conjugate presented on HLA-A*03:01 and HLA-A*11:01, BTK-Ibrutinib conjugate presented on HLA-A*01:01, and EGFR-Osimertinib conjugate presented on HLA-A*02:01. In non-limiting embodiments, the disclosure provides scDbs that are specific for a particular drug that is covalently bound to a described peptide that is present on a specific HLA, or the same drug that is covalently bound to a described peptide that is present on two different HLAs. Representative scDbs are described in Example 4. Data obtained using the scDbs are presented via FIGS. 18 and 19. Data obtained using CrossMab formats are provided in Example 5 and its accompanying figures.

In embodiments, the peptide conjugate is displayed by cells that participate in, or can be the targets of, cell-mediated immune responses. In embodiments the peptide conjugate that is displayed in any suitable MHC context is comprised by a cell that is recognized by a leukocyte, including but not necessarily limited to a T cell or a natural killer (NK) cell. In embodiments, the T cell is a CD4+ T cell, a CD8+ T cell, a double positive CD4+/CD8+ T cell, a CD4+/CD8+ double negative T cell, or a γδ T cell. Thus, and as described further below, the disclosure provides binding partners that are configured to interact with both the presented peptide conjugate and cells that participate in cell-mediated immune responses. In embodiments, certain described binding partners are capable of binding to a complex of 1) a specific MHC and 2) a specific peptide conjugate. In embodiments, certain described binding partners are capable of being bound to a specific peptide conjugate presented by at least two different MHCs.

In embodiments, any binding partner of this disclosure comprises at least one chain that comprises a complementary determining region (CDR) that is CDR1, CDR2, or CDR3 from any heavy or light chain amino acid sequence described herein. In certain examples in the present specification, the CDRs are shown in bold font. The amino acid sequences of the CDR sequences are separately encompassed by this disclosure by way of their positions in the described heavy and light chain amino acid sequences. The disclosure includes binding partners that comprise a described heavy chain CDR1, CDR2, and CDR3. The disclosure also includes binding partners that comprise a described light chain CDR1, CDR2, and CDR3. The disclosure also includes binding partners that comprise a described heavy chain CDR1, CDR2, and CDR3 and a described light chain CDR1, CDR2, and CDR3. For amino acid sequences of this disclosure that include amino acids that comprise purification or protein production tags, such as HIS tags and/or AVI-tags, the disclosure includes the proviso that the sequences of the described tags may be excluded from the amino acid sequences. Amino acids between the described tags may also be excluded.

Binding partners of this disclosure can be provided as intact immunoglobulins or as fragments of immunoglobulins, including but not necessarily limited to antigen-binding (Fab) fragments, Fab' fragments, (Fab')$_2$ fragments, Fd (N-terminal part of the heavy chain) fragments, Fv fragments (two variable domains), diabodies (Dbs), dAb fragments, single domain fragments or single monomeric variable antibody domains, single-chain Diabodies (scDbs), isolated complementary determining regions (CDRs), single-chain variable fragment (scFv), and other antibody fragments that retain antigen binding function. In embodiments, one or more binding partners are provided as a component of a Bi-specific T-cell engager (BiTE), bispecific killer cell engager (BiKE), CrossMab (e.g., a binding partner containing four different chains; immunoglobulin crossover (also known as Fab domain exchange or CrossMab format) technology (see eg., WO2009/080253; Schaefer et al., Proc. Natl. Acad. Sci. USA, 108:11187-11192 (2011).), or a chimeric antigen receptor (CAR), such as for producing chimeric antigen receptor T cells (e.g., CAR T cells) and CAR natural killer (NK) cells, and killer macrophages. The disclosure includes binding partners that include the described heavy and light chain variable regions.

In embodiments, the binding partners are multivalent. In embodiments, a tri-specific binding partner is provided. In embodiments, cells express at least a segment of one or more binding partners in the form of a CAR. In an embodiment, a binding partner of this disclosure may be provided as a complex with a polynucleotide, such as an RNA polynucleotide, to form an aptamer. In embodiments, a multi-valent binding partner includes one binding component, such as a paratope, that confers specificity to a particular target on a desired cell type, such as any cancer cell marker. In embodiments, a tri-specific leukocyte engager is provided. In embodiments, the binding partners may be part of a molecule that is activated only in the presence of a protease or other enzyme present in a tumor microenvironment, such embodiments being pertinent to, for instance, a probody, examples of which are known in the art, for example in doi: 10.1126/scitranslmed.3006682, doi: 10.1038/s41467-020-16838-w, and doi: 10.1038/s41587-019-0135-x, from which the descriptions of probodies, and protease activation, are incorporated herein by reference. In an embodiment, the disclosure provides a universal hapten that can be grafted onto inhibitors.

In embodiments, a CAR of this disclosure comprises scFv that comprises heavy and light chains as described herein. As is known in the art for previously described CARs, the scFv is present in a contiguous polypeptide that further comprises a CD3zeta chain and a costimulatory domain. In embodiments, the costimulatory domain comprises a 4-1BB costimulatory domain or a CD28 costimulatory domain. A CAR may also contain a co-receptor hinge sequence, such as a CD8 a co-receptor hinge sequence.

In embodiments, binding partners of this disclosure may comprise a constant region, e.g., an Fc region. Any isotype of constant region can be included. Binding partners that comprise a constant region may be particularly adapted for antibody-dependent cell mediated cytotoxicity (ADCC) and thus may function to kill targeted cells by cell-mediated responses by any of a variety of effector cells. Similarly, a constant region may be particularly adapted for enhancing complement-mediated responses.

In embodiments, a binding partner of this disclosure may be modified such that it is present in a fusion protein. In embodiments, an antigen binding segment of a binding partner may be present in a fusion protein, and/or the constant region may be a component of a fusion protein. In embodiments, a fusion protein comprises amino acids from at least two different proteins. Fusion proteins can be produced using any of a wide variety of standard molecular biology approaches, including but not necessarily limited to expression from any suitable expression vector. In embodiments, a binding partner described herein may be present in a fusion protein with a detectable protein, such as green fluorescent protein (GFP), enhanced GFP (eGFP), mCherry, and the like. In embodiments, as an alternative to an expression vector, an mRNA or chemically modified mRNA encoding any binding partner described herein can be delivered to cells such that the binding partner is translated by the cells.

In embodiments, binding partners described herein are used to carry drugs or toxins, and thus the binding partners may be provided as immunotoxins, or in the form of antibody-drug conjugates (ADCs).

In embodiments, agents useful in the generation of immunotoxins include enzymatically active toxins and enzymatically active fragments thereof. Suitable enzymatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. These can be provided as components of fusion proteins or can be covalently attached to the binding partner by any suitable conjugation approach.

The binding partner may be connected to a chemotherapeutic agent by using any suitable linker to form an antibody drug conjugate (ADC). In embodiments, the linker comprises a disulfide, a hydrazine, or a thioether. The chemotherapeutic agent may be reversibly or irreversibly attached to the binding partner.

Cleavable linkers may be particularly useful for killing bystander cells. In embodiments, a protease recognition site may be included to liberate the chemotherapeutic agent from the binding partner by operation of a protease that recognizes and cleaves at the protease recognition site. The ADC may therefore be considered to contain a prodrug.

In embodiments, binding partners of this disclosure may comprise linking sequences. As a non-limiting example, an ScFv may comprise a linker that links segments comprising paratopes to one another. Suitable amino acid linkers may be mainly composed of relatively small, neutral amino acids, such as glycine, serine, and alanine, and can include multiple copies of a sequence enriched in glycine and serine. In specific and non-limiting embodiments, the linker comprises 3, 4, 5, 6, 7, 8, 9, 10, 11, 12, 13, 14, 15, 16, 17, 18, 19, and 20 amino acids. In an example, the linker may be the glycine-serine-alanine linker $G_4SA_3$ (SEQ ID NO: 11) or a glycine-serine linker $(G_4S)_4$ linker (SEQ ID NO: 12). In embodiments, a binding partner may include a cellular localization signal, or a secretion signal. In embodiments, binding partner may comprise a transmembrane domain, and thus may be trafficked to, and anchored in a cell membrane. For secretion, any suitable secretion signal can be used, and many are known in the art.

In embodiments, the binding partners can be part of an ADC and therefore the binding partners comprise a drug. The drug can include, but is not necessarily limited to, any suitable chemotherapeutic agent. In embodiments, the ADC comprises a binding partner and a chemotherapeutic agent that is an anti-microtubule agent, an alkylating agent, or a DNA minor groove binding agent. In embodiments, the chemotherapeutic agent comprises a maytansinoid, a dolastatin, an auristatin drug analog, or a cryptophycin. In embodiments, the chemotherapeutic agent is a duocarmycin derivative, or an antibiotic, such as an enediyne antibiotic, or pyrolobenodiazepine (PBD), including dimers thereof. In embodiments, the chemotherapeutic agent is an enzyme inhibitor, such as a topoisomerase or polymerase inhibitor. In embodiments, the chemotherapeutic agent comprises doxorubicin, or a metal-containing compound, such as a platinum-containing compound, non-limiting examples of which include cisplatin, carboplatin or oxaliplatin. In embodiments, the ADC comprises a binding partner described herein, and any drug that is described in Barf and Kaptein, dx.doi.org/10.1021/jm3003203, J. Med. Chem. 2012, 55, 6243-6262, or in Wilson et al., dx.doi.org/10.1021/jm400224q, J. Med. Chem. 2013, 56, 7463-7476, or Lambert and Morris, Adv Ther (2017) 34:1015-1035, from which the descriptions of drugs for use as components as ADCs is incorporated herein by reference. In embodiments, the binding partner is conjugated to or otherwise includes a cytokine, including but not necessarily limited to an interleukin, including but not limited to IL-2 and IL-12, or an interferon (IFN), to thereby provide a cytokine conjugate.

For production of binding partners, any suitable expression system may be used. In general, polynucleotides encoding binding partners are used to express the binding partners in any suitable cell system, non-limiting embodiments of which include NS0 murine myeloma cells, human cell lines, and Chinese hamster ovary (CHO) cells. In embodiments, the disclosure provides a polynucleotide that can selectively hybridize to a polynucleotide encoding any CDR or combination of CDRs described herein. In embodiments, the polynucleotide selectively hybridizes to a polynucleotide encoding a heavy chain CDR1, CDR2, and CDR3 of any described binding partner. In embodiments, the polynucleotide selectively hybridizes to a polynucleotide encoding a light chain CDR1, CDR2, and CDR3 of any described binding partner. In embodiments, the polynucleotide selectively hybridizes to a polynucleotide encoding CDR1, CDR2, and CDR3 of a heavy and light chain of any described binding partner.

In embodiments, a binding partner described herein may be a component of a fusion protein. In embodiments, such as for a binding partner that is produced as a fusion protein, a peptide linker may be used. In embodiments, the peptide linker comprises any self-cleaving signal. In embodiments, the self-cleaving signal may be present in the same open reading frame (ORF) as the ORF that encodes the binding partner. A self-cleaving amino acid sequence is typically about 18-22 amino acids long. Any suitable sequence can be used, non-limiting examples of which include: T2A (EGRGSLLTCGDVEENPGP (SEQ ID NO: 7)); P2A (ATNFSLKQAGDVENPGP (SEQ ID NO: 8)); E2A (QCTNYALKLAGDVESNPGP (SEQ ID NO: 9)) and F2A (VKQTLNFDLKLAGDVESNPGP (SEQ ID NO: 10)).

To the extent any segment of a protein comprising a binding partner described herein was a component of a library, including but not necessarily limited to a phage display library or a yeast surface display library, the disclosure includes the proviso that the binding partner may be free of any segment of the library that comprises a bacteriophage or yeast amino acid sequence, including but not limited to phage coat protein or a yeast host protein, including but not limited to Aga2. Thus, in certain embodiments, the binding partner may be present in a fusion protein, but the fusion protein does not comprise bacteriophage coat protein. In embodiments, any binding partner described herein may be free of any of pIII phage coat protein, or any part of M1, fd filamentous phage, T4, T7, or λ phage protein.

In embodiments, a binding partner of this disclosure comprises a detectable label, which may be used for diagnostic or therapeutic purposes. For example, a detectable label can be used for localization of the binding partner for pathology and/or in vivo imaging approaches. In embodiments, a binding partner is conjugated to any of a variety of radioactive agents, including but not limited to a highly radioactive atom, such as In111, At211, I131, I125, Y90, Re186, Re188, Sm153, Bi212, P32, Pb212, and radioactive isotopes of Lu. In particular embodiments, such as for imaging, the binding partner may be conjugated to a radioactive atom for scintigraphic approaches, for example Tc99m (metastable technetium-99), 1123, or a spin label for nuclear magnetic resonance (NMR) imaging (also known as magnetic resonance imaging, or "MRI"), such as 1123, 1131, 1124, F19, C13, N15, O17 or Gadlinium (III) or Manganese (II). In embodiments, the radioactive agent is suitable for use in CAT scan or PET imaging. In embodiments, Indium 111, Technetium99 or Iodine131 can be used for planar scans or single photon emission computed tomography (SPECT). Positron emitting labels such as Fluorine19 Iodine 123 and Iodine 124 can be used in positron emission tomography. Paramagnetic ions such as Gadlinium (III) or Manganese (II) can used in magnetic resonance imaging MRI. In embodiments, the described radioactive isotopes that are attached to a described binding partner can also be used in therapeutic approaches. In embodiments, radioactive agents or isotopes include alpha-emitting radionuclides. In embodiments, radioactive agents or isotopes include beta-emitting radionuclides. In some embodiments, the present disclosure provides an antibody of the present technology conjugated to a diagnostic or therapeutic agent. The diagnostic agent may comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope. A diagnostic agent is a molecule which is administered conjugated to an antibody moiety, i.e., antibody or antibody fragment, or subfragment, and is useful in diagnosing or detecting a disease by locating the cells containing the antigen.

Any binding partner described herein may be fully or partially humanized. Techniques for humanization of antibodies are known in the art and can be adapted for use in the present disclosure. In embodiments, humanization may be performed, for example, by CDR-grafting. In embodiments, for humanization or to otherwise improve a characteristic of the binding partners, one or more amino acids in a variable region can be changed. In embodiments, one or more amino acids in a framework region can be changed.

The disclosure includes binding partners for use in diagnostic and therapeutic approaches. For therapeutic approaches, in certain embodiments, binding partners may be delivered as mRNA or DNA polynucleotides that encode the binding partners. It is considered that administering a DNA or RNA encoding any binding partner described herein is also a method of delivering such binding partners to an individual or one or more cells. Methods of delivering DNA and RNAs encoding proteins are known in the art and can be adapted to deliver the binding partners, given the benefit of the present disclosure. In embodiments, one or more expression vectors are used and comprise viral vectors. Thus, in embodiments, a viral expression vector is used. Viral expression vectors may be used as naked polynucleotides, or may comprise any of viral particles, including but not limited to defective interfering particles or other replication defective viral constructs, and virus-like particles. In embodiments, the expression vector comprises a modified viral polynucleotide, such as from an adenovirus, a herpesvirus, or a retrovirus. In embodiments, a retroviral vector adapted from a murine Moloney leukemia virus (MLV) or a lentiviral vector may be used, such as a lentiviral vector adapted from human immunodeficiency virus type 1 (HIV-1).

In an embodiment, an oncolytic viral vector is used. Oncolytic viruses (OVs), including vaccinia (OVV), mediate anticancer effects by both direct oncolysis and stimulation of innate immune responses through production of damage-associated molecular patterns (DAMPs) and the presence of virus-derived pathogen-associated molecular patterns (PAMPs), leading to increased type I interferon production. Additionally, OVV-mediated oncolysis may facilitate the direct acquisition of tumor-derived antigens by host antigen-presenting cells within the tumor microenvironment, thereby leading to improved T cell priming as well as coordination of the effector phase of antitumor immune responses. In alternative embodiments, a recombinant adeno-associated virus (AAV) vector may be used. In certain embodiments, the expression vector is a self-complementary adeno-associated virus (scAAV).

Pharmaceutical formulations containing binding partners are included in the disclosure and can be prepared by mixing them with one or more pharmaceutically acceptable carriers. Pharmaceutically acceptable carriers include solvents, dispersion media, isotonic agents, and the like. The carrier can be liquid, semi-solid, e.g. pastes, or solid carriers. Examples of carriers include water, saline solutions or other buffers (such as phosphate, citrate buffers), oil, alcohol, proteins (such as serum albumin, gelatin), carbohydrates (such as monosaccharides, disaccharides, and other carbohydrates including glucose, sucrose, trehalose, mannose, mannitol, sorbitol or dextrins), gel, lipids, liposomes, resins, porous matrices, binders, fillers, coatings, stabilizers, preservatives, liposomes, antioxidants, chelating agents such as EDTA, salt forming counter-ions such as sodium; non-ionic surfactants such as TWEEN, PLURONICS or polyethylene glycol (PEG), or combinations thereof. In embodiments, a liposomal formulation comprising one or more binding partners is provided. Liposomal formulations include but are not limited to liposomal nanoparticles.

In embodiments, an effective amount of one or more binding partners is administered to an individual in need thereof. In embodiments, an effective amount is an amount that reduces one or more signs or symptoms of a disease and/or reduces the severity of the disease. An effective amount may also inhibit or prevent the onset of a disease or a disease relapse. A precise dosage can be selected by the individual physician in view of the patient to be treated. Dosage and administration can be adjusted to provide sufficient levels of binding partner to maintain the desired effect. Additional factors that may be taken into account include the severity and type of the disease state, age, weight, and gender of the patient, desired duration of treatment, method of administration, time and frequency of administration, drug combination(s), reaction sensitivities, and/or tolerance/response to therapy.

Binding partners and pharmaceutical compositions comprising the binding partners can be administered to an individual in need thereof using any suitable route, examples of which include intravenous, intramuscular, intraperitoneal, intracerobrospinal, subcutaneous, intra-articular, intrasynovial, oral, topical, or inhalation routes, depending on the particular condition being treated. The compositions may be administered parenterally or enterically. The compositions may be introduced as a single administration or as multiple administrations or may be introduced in a continuous manner over a period of time. For example, the administration(s) can be a pre-specified number of administrations or daily, weekly, or monthly administrations, which may be continuous or intermittent, as may be therapeutically indicated.

In embodiments, the individual in need of a composition of this disclosure has been diagnosed with or is suspected of having cancer. In embodiments, the cancer is a solid tumor or a hematologic malignancy. In embodiments, the cancer is renal cell carcinoma, breast cancer, prostate cancer, pancreatic cancer, lung cancer, liver cancer, ovarian cancer, cervical cancer, colon cancer, esophageal cancer, glioma, glioblastoma or another brain cancer, stomach cancer, bladder cancer, testicular cancer, head and neck cancer, melanoma or another skin cancer, any sarcoma, including but not limited to fibrosarcoma, angiosarcoma, osteosarcoma, and rhabdomyosarcoma, and any blood cancer, including all types of leukemia, lymphoma, and myeloma. In embodiments, the individual is in need of treatment for any pre-neoplastic disorder, including myelodysplastic syndromes or myeloproliferative neoplasms. In embodiments, a described binding partner is used prophylactically for any of the described types of cancer.

In embodiments, administering one or more binding partners, including but not necessarily in a pharmaceutical formulation, to an individual in need thereof, exhibits an improved activity relative to a control. In an embodiment, the control comprises different antibodies, a different form of the same antibodies/binding partner, or antibodies/binding partners that are delivered without adding additional agents. In embodiments, a binding partner described herein provides for improved antibody dependent cell cytotoxicity (ADCC), or for internalization (such as for an ADC), relative to a control. In embodiments, a control protein or peptide does not comprise the covalently linked molecule. The control peptide may comprise the same sequence as the experimental peptide, or if the experimental peptide comprises a mutation the control peptide may comprise the wild type sequence.

A composition of this disclosure, such as a pharmaceutical formulation, can contain only one, or more than one binding partner, and thus combinations of different binding partners are included. Likewise, one or more binding partners can be combined with any other therapeutic agent, non-limiting examples of which include conventional chemotherapeutic agents, and modulators of T-cell costimulatory molecules, often referred to as immune checkpoint inhibitors. T-cell costimulatory molecules are known in the art (PMID 30115704), including, but not limited to, CTLA4, PD-1, PD-L1, LAG3, TIM3, TIGIT, VISTA, B7-1, B7-2, PD-L2, LSECtin, Galectin-9, CEACAM-1, CD155, CD112, CD28, ICOS, ICOSL, OX40, OX40L, GITR, GITRL, 4-1BB, 4-1BBL, CD40, CD40L, CD27, and CD70. Thus, the disclosure includes combination therapy using one or more described binding partners and any of modulators of T-cell costimulatory molecules, including but not limited to CTLA-4 inhibitors, PD-1 inhibitors and PD-L1 inhibitors. As non-limiting examples, anti-PD-1 agents include Pembrolizumab and Nivolumab. Anti-PD-L1 examples include Avelumab and Atezolizumab. An anti-CTLA-4 example is Ipilimumab. The binding partners may also be combined with any form of adoptive immunotherapy.

In embodiments, the disclosure comprises administering to an individual in need thereof one or more binding partners and at least one additional agent to provide an additive effect, or a greater than additive effect such as a synergistic result. In embodiments, the described effect comprises inhibition of cancer growth, inhibition of metastasis, or other beneficial effect. An additive effect or synergistic effect may also be achieved by using a combination of at least two described binding partners.

Various techniques have been developed for the production of binding partners and are included in the scope of this disclosure. In embodiments, the binding partners are produced by host cells by way of recombinant expression vectors. The present disclosure includes all polynucleotide sequences encoding the amino acid sequences described herein, expression vectors comprising such polynucleotide sequences, and in vitro cell cultures comprising such expression vectors. In embodiments, the cell cultures include prokaryotic cells or eukaryotic cells. In embodiments, the cell cultures are mammalian cells. In embodiments, the cells are CHO cells. In embodiments, the cells are HEK293 cells and their derivatives. Kits comprising the binding partners, and/or cell cultures expressing the binding partners, are provided by this disclosure. In general, the kits comprise one or more sealed containers that contain the binding partners, or cells expressing them. Instructions for using the binding partners for therapeutic and/or diagnostic purposes can be included in the kits.

Cells that are modified to express any described binding partner include but are not necessarily limited CD4+ T cells, CD8+ T cells, Natural Killer T cells, γδ T cells, and cells that are progenitors of T cells, such as hematopoietic stem cells or other lymphoid progenitor cells, such as immature thymocytes (double-negative CD4–CD8–) cells, or double-positive thymocytes (CD4+CD8+). In embodiments, the progenitor cells comprise markers, such as CD34, CD117 (c-kit) and CD90 (Thy-1). In embodiments, the modified cells comprise macrophages. The described modified cells may be used therapeutically or prophylactically.

In embodiments, the disclosure provides for generation of a binding partner. This approach comprises providing a plurality of distinct binding partners, exposing the plurality of distinct (e.g., different) binding partners to one or a diversity of peptide conjugates, and selecting binding partners that bind with specificity to the peptide conjugates that contain the covalently conjugated drug or other molecule, but do not bind to the protein or peptide that does not comprise the covalently conjugated drug or other molecule. As described above, this approach can be performed on a manner that either does, or does not, require the amino acid sequence of the protein or peptide to be part of the antigenic determinant. The described approach can be used to select binding partners that are specific for presentation of a peptide conjugate as a component of any MHC complex.

In embodiments, binding partners described herein and as otherwise will be apparent by those skilled in the art, can be used to determine whether or not a particular drug or other molecule forms a covalent interaction with a protein or peptide. Thus, the disclosure provides for exposing protein or peptide substrates to drug candidates and using the binding partners described herein or as identified as described herein to determine whether or not the drug forms a covalent interaction with the pertinent substrate. This determination can be made based on whether or not the binding partner binds to the protein or peptide that has been covalently attached to the drug. This approach can be used in lieu of currently available techniques, such as mass spectroscopy and the like.

In embodiments, binding partners of this disclosure may be used in any immunological diagnostic test, including but not limited to the imaging approaches described above. In embodiments, one or more binding partners described herein can be used as a component in any form of, for example, enzyme-linked immunosorbent assay (ELISA) assay, including but not limited to a direct ELISA, a sandwich ELISA, a competitive ELISA, and a reverse ELISA. In embodiments, one or more binding partners described herein can also be incorporated into an immunodiagnostic device, such as a microfluidic device, a lateral flow device, and the like. The binding partners may also be used in, for example, Western blots and immunoprecipitation assays.

The following Examples are intended to illustrate but not limit the disclosure. In embodiments, antibodies described in Example 3 have different properties relative to those described in Example 1. Other differences between binding partners will be apparent from the Examples and their accompanying figures. The different properties include, but are not necessarily limited to, specificity for a drug conjugate displayed in the context of a specific MHC type. Thus, binding partners may exhibit different binding partners when a peptide conjugates is in a particular MHC complex.

Example 1

This Example provides a description of the identification and characterization of binding partners that bind with specificity to ARS-1620, which forms a covalent interaction with $KRAS^{G12C}$.

In particular, FIG. 1 demonstrates phage ELISA of phage-displayed antibody clones.

Figure 2:
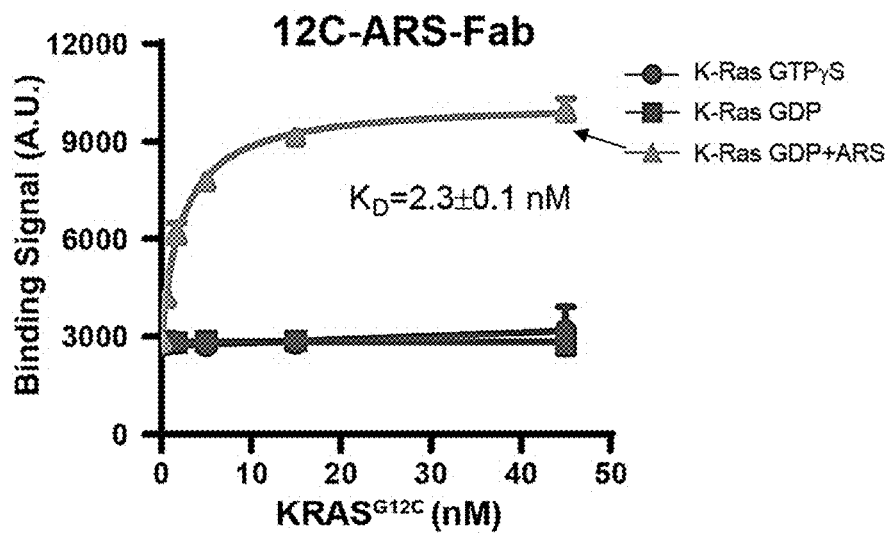
FIG. 2. Graph showing 12C-ARS Fab59 binding to $KRAS^{G12C}$ in GTPγS- or GDP-bound nucleotide state with or without ARS-1620 was characterized using the bead binding assay.
Figure 3:
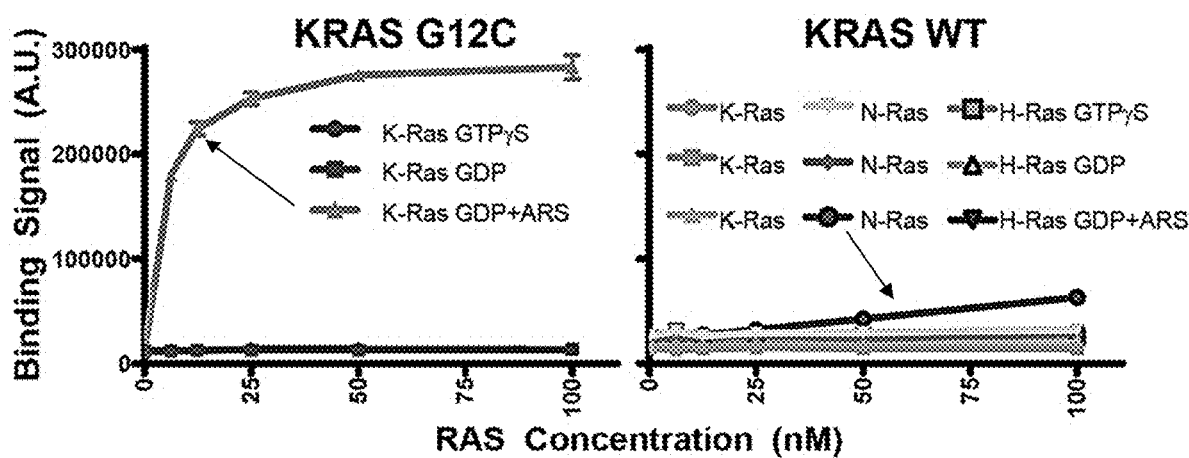
FIG. 3. Graphs showing that 12C-ARS-Fab59 specifically binds $KRAS^{G12C}$-GDP conjugated to ARS-1620.

Binding to $KRAS^{G12C}$-GDP and $KRAS^{G12C}$-GDP-ARS-1620 conjugate was determined. Buffer denotes binding signal to the wells that did not contain $KRAS^{G12C}$. From these candidates, four different antibodies were identified. Among these, 12C-ARS-Fab59 showed high affinity binding to KRASG12C-GDP covalently bound to ARS-1620. The results are presented in FIG. 2, which shows 12C-ARS Fab59 binding to $KRAS^{G12C}$ in the GTPγS- or GDP-bound nucleotide state with or without ARS-1620, as characterized by the bead binding assay (PMID: 33358997). FIG. 3 also demonstrates that 12C-ARS-Fab59 specifically binds $KRAS^{G12C}$-GDP conjugated to ARS-1620. In particular, 12C-ARS-Fab binding to $KRAS^{G12C}$ (left) or WT RAS isoforms (right) in the GTPγS- or GDP-bound nucleotide state with or without ARS-1620 conjugation, is shown as indicated.

Figure 4:
FIG. 4. Shown in (A) is data obtained using 12C-ARS-Fab59 to measure ARS-1620/$KRAS^{G12C}$ adducts by pull-down assays from lysates prepared from cell lines. Shown in (B) are immunoblots of whole cell lysates and 12C-ARS Fab-pull-downs (PD) from RAS-less MEFs reconstituted with the indicated KRAS mutants (4A) and KCP ($Kras^{G12C}$; $Tp53^{R172H}$; Pdx-Cre) mouse pancreas cancer cells (4B), treated in the presence or absence of ARS-1620. Shown in (C) are whole cell lysates and 12C-ARS Fab pull-downs (PD) from H358 and MIAPaCa-2 cells, treated as indicated. Shown in (D) is ARS-adduct formation in samples from C, quantified by LC/MS-MS assay. ARS-1620 and SHP099 concentrations were 10 μM in all panels.
Figure 4:
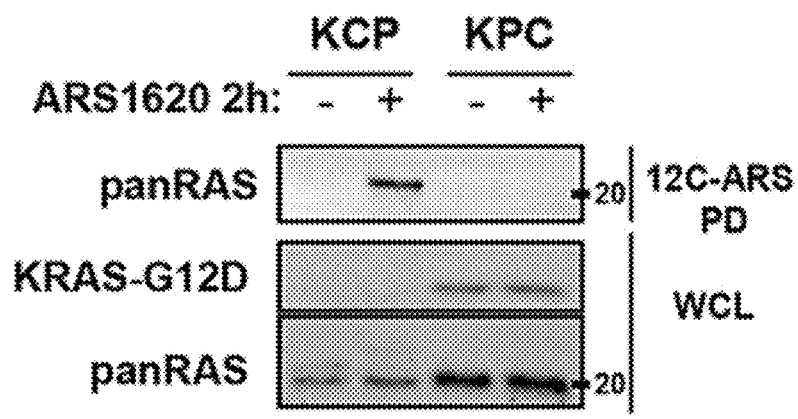
Figure 4:
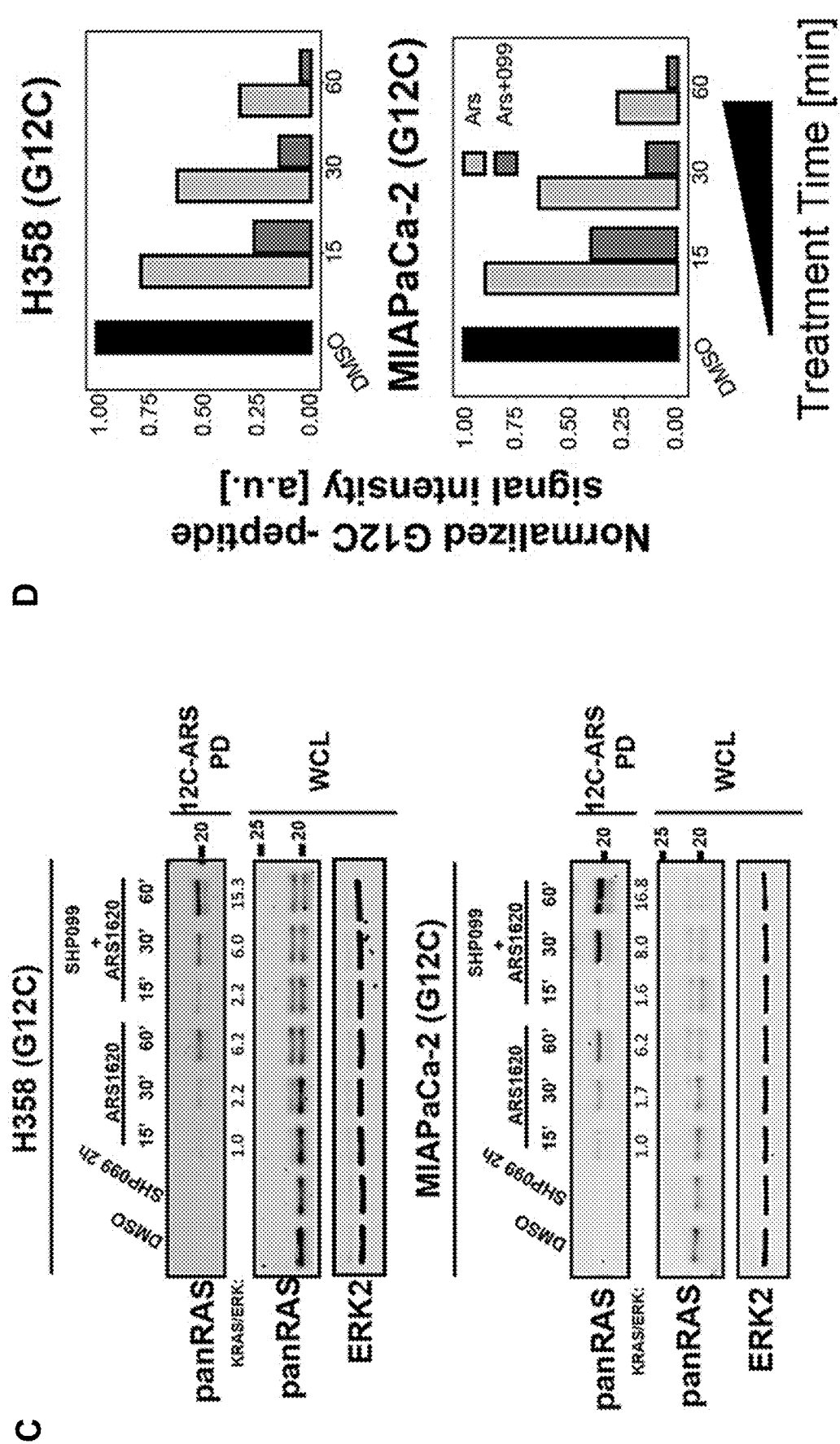

FIG. 4 demonstrates the use of 12C-ARS-Fab59 to measure ARS-1620/$KRAS^{G12C}$ adducts by pull-down assays from lysates prepared from cell lines. To produce the data shown in FIG. 4, immunoblots were performed on whole cell lysates and 12C-ARS Fab-pull-downs (PD) from RAS-less MEFs reconstituted with the indicated KRAS mutants (4A) and from KCP ($Kras^{G12C}$; $Tp53^{R172H}$; Pdx-Cre) mouse pancreas cancer cells (4B), treated in the presence or absence of ARS-1620. FIG. 4C shows whole cell lysates and 12C-ARS Fab pull-downs (PD) from H358 and MIAPaCa-2 cells, treated as indicated, which were subjected to SDS-PAGE and immunoblotting with anti-pan RAS and anti-ERK2 antibodies, the latter as a loading control. FIG. 4D shows ARS-adduct formation in samples from 4C, quantified by LC/MS-MS assay. ARS-1620 and SHP099 concentrations were 10 μM in all panels.

Figure 5:
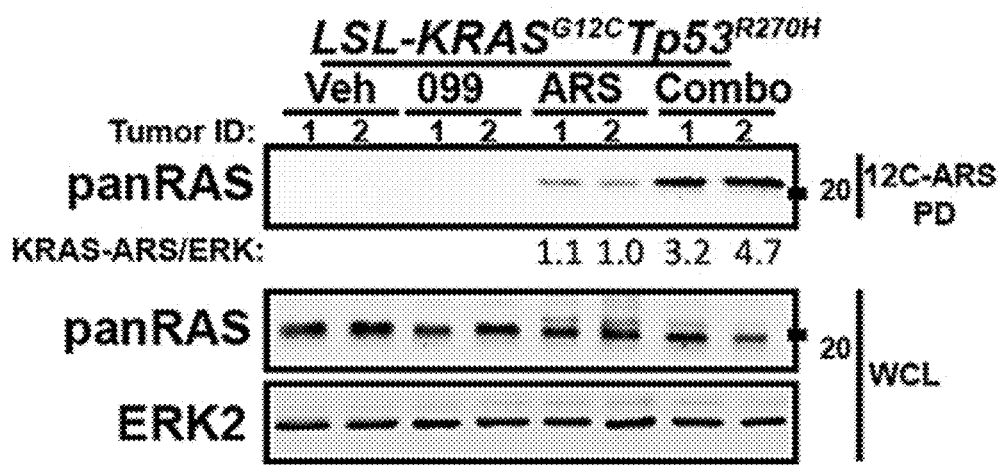
FIG. 5. Data showing that 12C-ARS-Fab59 can be used to measure the engagement of ARS-1620 to mutant KRAS by pull-down assay with lysates prepared from animal tissues. A, B, anti-pan RAS and anti-ERK2 (loading control) immunoblots of lysates and 12C-ARS Fab pull-downs (PD) from LSL-$KRAS^{G12C}$-$Tp53^{R270H}$ (A) and LSL-$KRAS^{G12C}$ (B) tumors after 3 days of oral gavage with ARS-1620 (200 mg/kg/d) alone or with the SHP2 inhibitor SHP099 (75 mg/kg/d) are shown.
Figure 5:
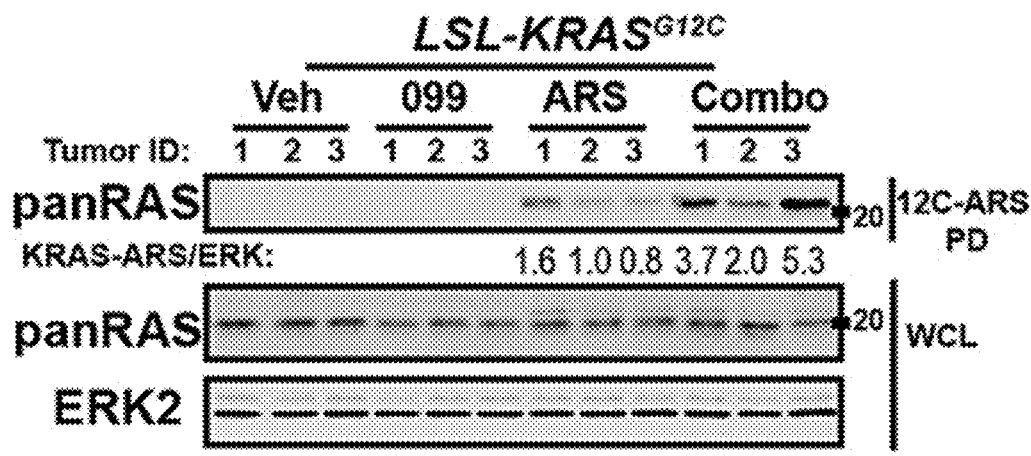

FIG. 5 shows that 12C-ARS-Fab59 can be used to measure the engagement of ARS-1620 to mutant KRAS by pull-down assay with lysates prepared from animal tissues. In particular, in FIGS. 5A-B, anti-pan RAS and anti-ERK2 (loading control) immunoblots of lysates and 12C-ARS Fab pull-downs (PD) from LSL-$KRAS^{G12C}$-$Tp53^{R270H}$ (A) and LSL-$KRAS^{G12C}$ (B) tumors after 3 days of oral gavage with ARS-1620 (200 mg/kg/d) alone or with the SHP2 inhibitor SHP099 (75 mg/kg/d) are shown.

To produce the foregoing results, the following materials and methods were used.

RAS Nucleotide Exchange and Generation of ARS-1620-Conjugated RAS

Purified RAS (1-174) proteins containing a 6×HIS-tag (SEQ ID NO: 13) and an AVI-tag (1), used in the binding experiments and phage display selections, were prepared by diluting stock protein (typically containing 20-100 μM RAS) 25-fold with 20 mM Tris-Cl buffer pH 7.5 containing 5 mM EDTA, 0.1 mM DTT, and 1 mM (final concentration) of nucleotide (GDP or GTPγS). For generating ARS-bound RAS, ARS-1620 (final concentration: 100 μM) was added during the nucleotide exchange reaction of RAS along with GDP. Samples were incubated at 30° C. for 30 minutes. $MgCl_2$ was then added to a final concentration of 20 mM to quench the nucleotide exchange reaction, and the solution was incubated on ice for at least 5 minutes prior to use.

Selection of Phage-Displayed Antibody Fragments Against ARS-Bound $KRAS^{G12C}$

General procedures for the development of Fabs against purified protein targets have been described (2). Four rounds of phage display library selection were performed, with biotinylated KRAS(G12C)-GDP+ARS-1620 at 100 nM, 100 nM, 50 nM, and 20 nM in the first, second, third and fourth rounds, respectively. The first round recovered clones that bound to $KRAS^{G12C}$-GDP+ARS-1620; the second round recovered clones that bound to $KRAS^{G12C}$-GDP+ARS-1620, previously pre-cleared with $KRAS^{G12C}$-GDP; the third round recovered clones that bound to $KRAS^{G12C}$-GDP+ARS-1620, previously pre-cleared with $KRAS^{G12C}$-GTP. The final round recovered clones that bound to $KRAS^{G12C}$-GDP+ARS-1620, previously precleared with $KRAS^{G12C}$-GDP. Phage captured on beads were eluted in 100 μl of 0.1 M Gly-HCl (pH 2.1) and immediately neutralized with 35 μl of 1M Tris-Cl (pH 8). Recovered clones were analyzed by phage ELISA and DNA sequencing, as described (2).

Bead Binding Assays

General methods have been previously described (3). Fifty microliters (50 μl) of M280 streptavidin beads (Thermo Fisher) were incubated with 100 μl of biotinylated 12C-ARS Fab, at 30 nM or 4 nM. Ligand-free streptavidin on the beads was then blocked by adding excess biotin. Beads were washed with supplemented TBST (50 mM Tris pH7.5, 150 mM NaCl, 20 mM $MgCl_2$, 0.1 mM DTT, 0.05% Tween-20) and dispensed into wells of a 96-well U bottom plate (Greiner). Beads were then incubated at 1:1 ratio with purified RAS proteins diluted in supplemented TBS (50 mM Tris pH7.5, 150 mM NaCl, 20 mM $MgCl_2$, 0.1 mM DTT) at 2× the concentration stated for the titration curve for 30 minutes at room temperature. Beads containing bound Fab and RAS were transferred to the wells of a 96-well filter plate (Millipore, MSHVN4550) and washed twice with supplemented TBST before incubating with Neutravidin-Dylight 650 (Thermo Fisher Scientific) for 30 minutes at 4° C. The beads were washed twice with supplemented TBST before resuspension in supplemented TBS for flow cytometry using an iQue screener (Sartorius). The median signal intensity in the Dylight650 channel for the 75-95th percentile population was taken as binding signal to the target. $K_D$ was calculated by fitting the binding signals to a 1:1 binding model.

Expression, Purification, and Characterization of Recombinant Fabs

Phage display vectors were converted into Fab expression vectors that contain a substrate tag for the biotin ligase BirA at the carboxyl terminus of the heavy chain. Fabs were expressed in *E. coli* strain 55244 (ATCC), and were purified by protein G affinity chromatography, followed by cation exchange chromatography, as described (2). Purified Fabs were biotinylated in vitro using purified BirA. Approximately 2-5 mg of purified Fabs were obtained routinely from a 1 L bacterial culture. SDS-PAGE showed that Fabs were >90% pure.

$KRAS^{G12C}$-Adduct Assays

Cells cultured in 6-well plates were treated with ARS-1620 and/or SHP099 as described in the Figures. Cells were lysed by incubation in GTPase lysis buffer (25 mM Tris-Cl pH7.2, 150 mM NaCl, 5 mM $MgCl_2$, 1% NP-40 and 5% glycerol), supplemented with protease inhibitors and phosphatase inhibitors on ice for 15 minutes immediately before analysis. After centrifugation for 15 minutes at 15,000 g, supernatants were collected and incubated with streptavidin (SA) agarose resin (Thermo Fisher Scientific) for 1 hour at 4° C., followed by a brief centrifugation, to decrease non-specific binding to the resin. Pre-cleared lysates were incubated with biotinylated 12C-ARS-Fab bound to SA agarose for 1.5 hours at 4° C. while rotating. Agarose beads were then washed twice with GTPase lysis buffer, boiled in 1×SDS-PAGE sample buffer, and subjected to immunoblotting with a pan-RAS antibody (Millipore).

Immunoblotting

Whole cell lysates were generated in modified radioimmunoprecipitation (RIPA) buffer (50 mM Tris-HCl pH 8.0, 150 mM NaCl, 2 mM EDTA, 1% NP-40, and 0.1% SDS, without sodium deoxycholate), supplemented with protease (40 µg/ml PMSF, 2 µg/ml antipain, 2 µg/ml pepstatin A, 20 µg/ml leupeptin, and 20 µg/ml aprotinin) and phosphatase (10 mM NaF, 1 mM $Na_3VO_4$, 10 mM β-glycerophosphate, and 10 mM sodium pyrophosphate) inhibitors. After clarification of debris by centrifugation in a microfuge, samples were quantified with the DC Protein Assay Kit (Bio-Rad). Total lysate protein was resolved by standard SDS-PAGE and transferred in 1× transfer buffer and 15% methanol. Membranes were incubated with their respective primary and secondary antibodies labeled with IRDye (680 nm and 800 nm) and then visualized by using a LICOR device. Monoclonal pan-RAS antibody (clone Ab-3; OP40-100UG; 1:1000) was obtained from Millipore, and mouse monoclonal ERK-2 (D2: sc-1647; 1:1000) was purchased from Santa Cruz Biotechnology.

LC/MS-MS Assay for ARS Binding to $KRAS^{G12C}$

Cells ($5\times10^5$) were treated with the indicated compounds for the times listed and subsequently washed twice with PBS and prepared for protein extraction and LC/MS-MS analysis, as described (4). LC/MS-MS was performed at the PCC Proteomics Shared Resource at NYU School of Medicine.

Similar methods were used to obtain the results described in Example 2.

The antibodies described in this Example are as follows:

Exemplary Antibody Clones Binding to the KRAS(G12C)-ARS-1620 Conjugate

CDR residues (Kabat numbering) in bold.

```
12C-ARS-Fab59
V_L:
                                      (SEQ ID NO: 14)
DIQMTQSPSSLSASVGDRVTITCRASQSVSSAVAWYQQKPGKAPKLLIY
SASSLYSGVPSRFSGSRSGTDFTLTISSLQPEDFATYYCQQDWYFPITF
GQGTKVEIK
(Bolded CDR sequences are disclose as SEQ ID NOS
166, 167, and 176, respectively, in order of
appearance)

V_H:
                                      (SEQ ID NO: 15)
EVQLVESGGGLVQPGGSLRLSCAASGFTFSSYYIHWVRQAPGKGLEWVA
SISPSSGSTYYADSVKGRFTISADTSKNTAYLQMNSLRAEDTAVYYCAR
YGGRSYWQKQDSYFYQHGLDYWGQGTLVSS
(Bolded CDR sequences are disclose as SEQ ID NOS
177, 178, and 179, respectively, in order of
appearance)

12C-ARS-Fab56
V_L:
                                      (SEQ ID NO: 16)
DIQMTQSPSSLSASVGDRVTITCRASQSVSSAVAWYQQKPGKAPKLLIY
SASSLYSGVPSRFSGSRSGTDFTLTISSLQPEDFATYYCQQSSSSLITF
GQGTKVEIK
(Bolded CDR sequences are disclose as SEQ ID NOS
166, 167, and 180, respectively, in order of
appearance)

V_H:
                                      (SEQ ID NO: 17)
EVQLVESGGGLVQPGGSLRLSCAASGFTFSSSSIHWVRQAPGKGLEWVA
SISSYSGYTSYADSVKGRFTISADTSKNTAYLQMNSLRAEDTAVYYCAR
SYSYSEFRYYYSGQGMDYWGQGTLVSS
(Bolded CDR sequences are disclose as SEQ ID NOS
181, 182, and 183, respectively, in order of
appearance)

12C-ARS-Fab30
V_L:
                                      (SEQ ID NO: 18)
DIQMTQSPSSLSASVGDRVTITCRASQSVSSAVAWYQQKPGKAPKLLIY
SASSLYSGVPSRFSGSRSGTDFTLTISSLQPEDFATYYCQQSSSSLITF
GQGTKVEIK
(Bolded CDR sequences are disclose as SEQ ID NOS
166, 167, and 180, respectively, in order of
appearance)

V_H:
                                      (SEQ ID NO: 19)
EVQLVESGGGLVQPGGSLRLSCAASGFTFSSSSIHWVRQAPGKGLEWVA
SISSSSGSTSYADSVKGRFTISADTSKNTAYLQMNSLRAEDTAVYYCAR
SNYGWRWHLVGMDYWGQGTLVTVSS
(Bolded CDR sequences are disclose as SEQ ID NOS
181, 170, and 184, respectively, in order of
appearance)

12C-ARS-Fab85
V_L:
                                      (SEQ ID NO: 20)
DIQMTQSPSSLSASVGDRVTITCRASQSVSSAVAWYQQKPGKAPKLLIY
SASSLYSGVPSRFSGSRSGTDFTLTISSLQPEDFATYYCQQSSSSLITF
GQGTKVEIK
(Bolded CDR sequences are disclose as SEQ ID NOS
166, 167, and 180, respectively, in order of
appearance)
```

-continued

V_H:

(SEQ ID NO: 21)
EVQLVESGGGLVQPGGSLRLSCAASGFTFSSSSIHWVRQAPGKGLEWVA
SISSSSGSTSYADSVKGRFTISADTSKNTAYLQMNSLRAEDTAVYYCAR
SPYVYYWYMVGFDYWGQGTLVTVSS
(Bolded CDR sequences are disclose as SEQ ID NOS
185, 170, and 186, respectively, in order of
appearance)

This reference listing pertains to Example 1.
1. Spencer-Smith R, Koide A, Zhou Y, Eguchi R R, Sha F, Gajwani P, Santana D, Gupta A, Jacobs M, Herrero-Garcia E, Cobbert J, Lavoie H, Smith M, Rajakulendran T, Dowdell E, Okur M N, Dementieva I, Sicheri F, Therrien M, Hancock J F, Ikura M, Koide S, O'Bryan J P. Inhibition of RAS function through targeting an allosteric regulatory site. Nat Chem Biol. 2017; 13 (1): 62-8. doi: 10.1038/nchembio.2231. PubMed PMID: 27820802; PMCID: 5193369.
2. Fellouse F A, Esaki K, Birtalan S, Raptis D, Cancasci V J, Koide A, Jhurani P, Vasser M, Wiesmann C, Kossiakoff A A, Koide S, Sidhu SS. High-throughput generation of synthetic antibodies from highly functional minimalist phage-displayed libraries. J Mol Biol. 2007; 373 (4): 924-40. Epub 2007 Sep. 11. doi: 10.1016/j.jmb.2007.08.005. PubMed PMID: 17825836.
3. Nishikori S, Hattori T, Fuchs S M, Yasui N, Wojcik J, Koide A, Strahl B D, Koide S. Broad ranges of affinity and specificity of anti-histone antibodies revealed by a quantitative Peptide immunoprecipitation assay. J Mol Biol. 2012; 424 (5): 391-9. Epub 2012 Oct. 9. doi: 10.1016/j.jmb.2012.09.022. PubMed PMID: 23041298; PMCID: 3502729.
4. Patricelli M P, Janes M R, Li L S, Hansen R, Peters U, Kessler L V, Chen Y, Kucharski J M, Feng J, Ely T, Chen J H, Firdaus S J, Babbar A, Ren P, Liu Y. Selective Inhibition of Oncogenic KRAS Output with Small Molecules Targeting the Inactive State. Cancer Discov. 2016; 6 (3): 316-29. Epub 2016 Jan. 8. doi: 10.1158/2159-8290.Cd-15-1105. PubMed PMID: 26739882.
5. doi.org/10.1084/jem.20201414

Example 2

This Example provides a description of binding partners that bind with specificity to AMG510 that is covalently linked to peptides.

To produce the results described in this Example, some methods as described in Example 1 were adapted. For this Example, AMG510 (purchased from Selleckchem) was conjugated to a peptide corresponding to KRAS(G12C) residues 4-18:

(SEQ ID NO: 22)
H2N-YKLVVVGACGVGKSA(dPEG4)(K-long chain Biotin)-amide and a poly-Ser peptide containing a central Cys:

(SEQ ID NO: 23)
H2N-SSSSCSSSSW(K-long chain Biotin)-amide.

Figure 6:
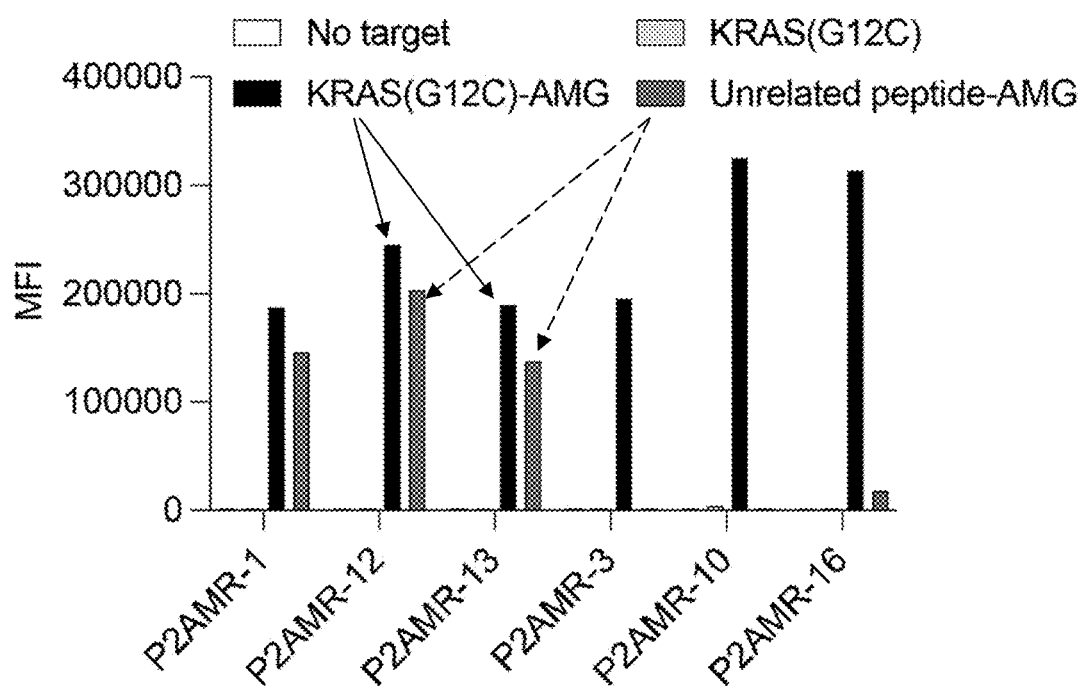
FIG. 6. Binding of antibody clones to AMG510 conjugated to the KRAS(G12C) peptide and the poly-Ser peptide. For each antibody clone, the bars are from left to right are No target, KRAS(G12C), KRAS(G12C)-AMG, and Unrelated peptide-AMG. Signals for the two negative controls, no target and the KRAS(G12C) peptide without a conjugated drug, were too low to be visible in the graph. The antibody clones were displayed on the yeast cell surface, and binding of the targets conjugated to fluorescently labeled streptavidin was detected using flow cytometry.

A human single-chain Fv yeast-display library was sorted using these peptides as targets by using established methods [1-3]. After rounds of library sorting, individual clones were screened. We developed three antibodies that bound to AMG510 conjugated to both KRAS(G12C) and poly-Ser peptide (FIG. 6). Consequently, these antibodies recognize predominantly the AMG510 moiety but not the peptide moiety of the conjugates. Additionally, we developed other clones that are selective to AMG510 conjugated to the KRAS(G12C) peptide.

Figure 7:
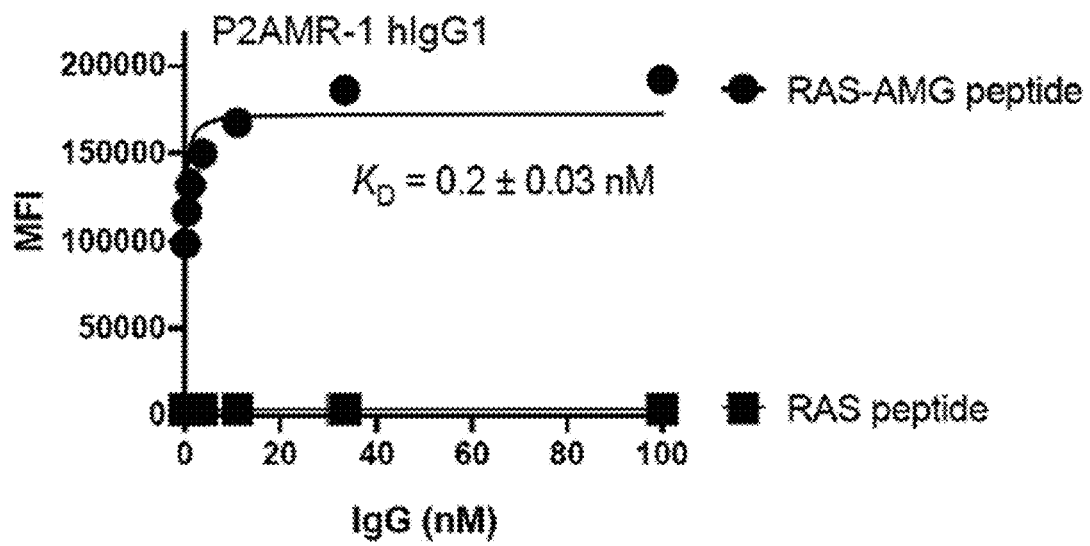
FIG. 7. Binding of the P2AMR-1 clone in the human IgG1 format to AMG510 conjugated to the KRAS(G12C) peptide (circles) and the same peptide without drug conjugation (squares). The peptide was immobilized to streptavidin-coated beads, and the antibody bound to the beads were detected with a fluorescently labeled secondary antibody. The apparent $K_D$ value is shown. Data shown here are from triplicate measurements. Error bars are within the size of the symbols.
Figure 8:
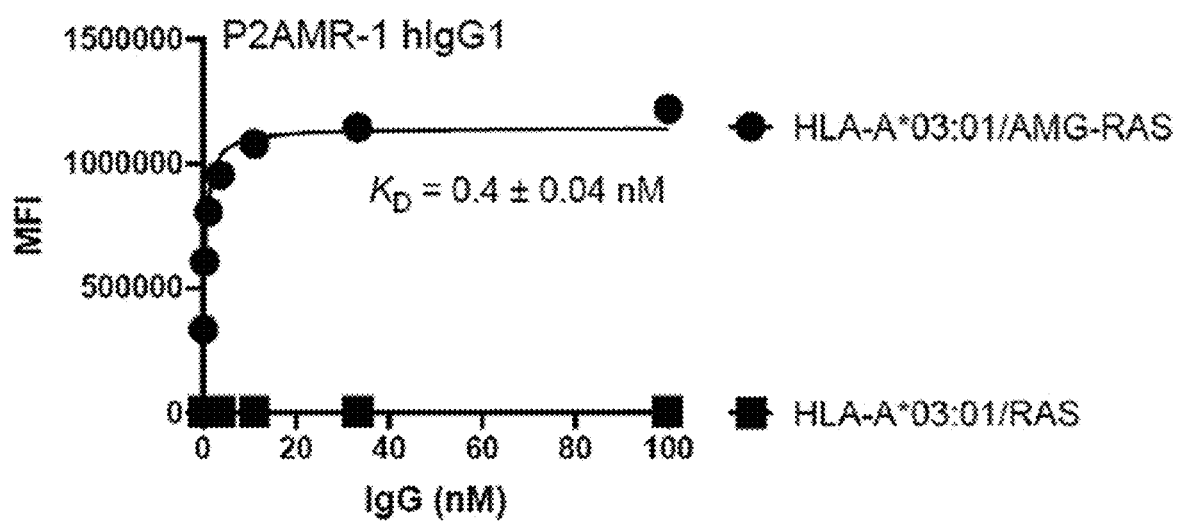
FIG. 8. Recognition of AMG510 presented on class I MHC molecule. The AMG510-RAS (G12C) conjugate (circles) and unconjugated peptide (squares) were loaded onto HLA-A*03:01 and immobilized on streptavidin-coated beads. Antibody binding was detected using the same method as in FIG. 2. The apparent $K_D$ value is shown. Data shown here are from triplicate measurements. Error bars are within the size of the symbols.

One such clone, P2AMR-1 was then produced in the format of human IgG1 and further characterized. It bound to AMG510 conjugated to the KRAS(G12C) peptide with high apparent affinity in a bead binding assay (FIG. 7)[(4)]. The antibody clone also bound tightly to AMG510 conjugated a shorter KRAS(G12C) peptide, VVGACGVGK (SEQ ID NO: 1), in the context of HLA-A*03:01 (BioLegend Flex-T) (FIG. 8).

Figure 16:
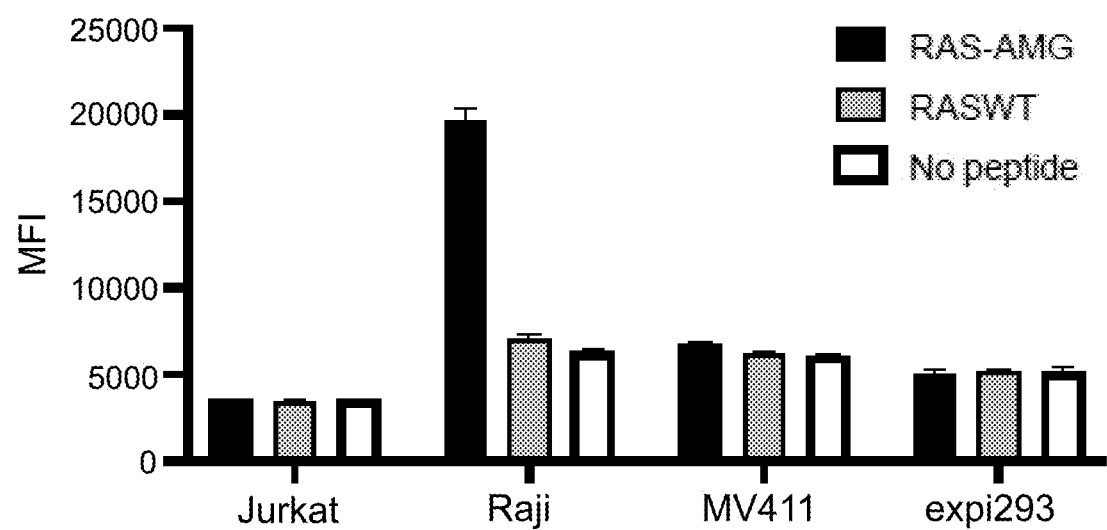
FIG. 16. Graph showing binding of P2AMR-1 IgG to cells preincubated with the KRAS(G12C) peptide-AMG510 conjugate, KRAS(wild type) peptide, or no peptide.

P2AMR-1 detected AMG510 conjugated to KRAS (G12C) peptide that had been added to Raji cells, which are known to express HLA-A*03:01. By contrast, P2AMR-1 did not detect KRAS(wild type) peptide loaded in the same manner (FIG. 16). In addition, P2AMR-1 did not bind to AMG510 conjugated to the KRAS(G12C) peptide added to cells that are not known to express HLA-A*03:01, e.g., MV4-11 and Expi293 cells (FIG. 16).

These results demonstrate that that the presently provided antibodies, which represent binding partners of this disclosure, recognize the AMG510 moiety in a manner agnostic of the conjugation partner, and they suggest that our antibodies and their derivatives can be used to identify cells that present AMG510-KRAS (G12C) peptide conjugate on MHC molecules on the cell surface.

More generally, these results suggest methods for targeting any cells that harbor intracellular targets that form covalent adducts with small molecule ligands.

This example demonstrates the following non-limiting binding partners, restricted to AMG510 covalent modifications of the described substrates. CDR residues (Kabat scheme) are shown in bold.

P2AMR-1
V_L:

(SEQ ID NO: 24)
QSVLIQPRSVSGSPGQSVTISCTGTSSDVGGYNYVSWYQQHPGKAPKLM

IYDVSKRPSGVPDRFSGSKSGNTASLTVSGLQAEDEADYYCGSYADTDT

IVFGTGTKLTVL
(Bolded CDR sequences are disclosed as SEQ ID NOS
187, 188, and 189, respectively, in order of
appearance)

V_H:

(SEQ ID NO: 25)
QVQLVQSEPEVKKPGSSVKLSCKASGGTFSTDAITWVRQAPGQGLEYMG

GIIPLLDSVDYAQRFQGRVTVSADKSTGTAYMEVRSLGSEDTAKYYCAK

WSSVDTGLDYWGQGTLVTVSS
(Bolded CDR sequences are disclosed as SEQ ID NOS
190, 191, and 192, respectively, in order of
appearance)

P2AMR-12 (this clone has only the heavy chain)
V_H:

(SEQ ID NO: 26)
QVQLQESGPGLVKPSETLSLTCTVSGDSIINDPHYWGWIRQSPGKGLEW

IGSTSHSGHTYFNPSLKSRVSMSIDVAKNQFSLNVRSVTAADTAVYYCA

RMRYYYSGTYPVYYFDYWGQGTLVTVSS
(Bolded CDR sequences are disclosed as SEQ ID NOS
193, 194, and 195, respectively, in order of
appearance)

-continued

P2AMR-13

V$_L$:
(SEQ ID NO: 27)
SYVLTQPPSASGTPGQRVTISCSGSSSNIGSNFVSWYQQLPGTAPKLLI

SSNNQRPSGVPDRFSGSKSDTSASLAISGLQSEDEADYYCAAWDDSLNG

PVFGGGTQLTVL
(Bolded CDR sequences are disclosed as SEQ ID NOS 196, 197, and 198, respectively, in order of appearance)

V$_H$:
(SEQ ID NO: 28)
QVQLVQSEAEVKKPGSSVKVSCKASGGTFSRYGVSWVRQAPGQGLEWMG

GIIPMFGTANYAQKFQGRVTITADESTSTAYMELRSLRSEDTAVYYCAR

GDNSAYSDAFNIWGQGTMVTVSS
(Bolded CDR sequences are disclosed as SEQ ID NOS 199, 200, and 201, respectively, in order of appearance)

This reference listing pertains to Example 2.

1. Chao G, Lau W L, Hackel B J, Sazinsky S L, Lippow S M, Wittrup K D. Isolating and engineering human antibodies using yeast surface display. Nat Protoc. 2006; 1 (2): 755-68. Epub 2007 Apr. 5. doi: 10.1038/nprot.2006.94. PubMed PMID: 17406305.
2. Feldhaus M J, Siegel R W, Opresko L K, Coleman J R, Feldhaus J M, Yeung Y A, Cochran J R, Heinzelman P, Colby D, Swers J, Graff C, Wiley H S, Wittrup K D. Flow-cytometric isolation of human antibodies from a nonimmune Saccharomyces cerevisiae surface display library. Nat Biotechnol. 2003; 21 (2): 163-70. Epub 2003 Jan. 22. doi: 10.1038/nbt785nbt785 [pii]. PubMed PMID: 12536217.
3. Hattori T, Taft J M, Swist K M, Luo H, Witt H, Slattery M, Koide A, Ruthenburg A J, Krajewski K, Strahl B D, White K P, Farnham P J, Zhao Y, Koide S. Recombinant antibodies to histone post-translational modifications. Nat Methods. 2013; 10 (10): 992-5. doi: 10.1038/nmeth.2605. PubMed PMID: 23955773; PMCID: 3828030.
4. Nishikori S, Hattori T, Fuchs S M, Yasui N, Wojcik J, Koide A, Strahl B D, Koide S. Broad ranges of affinity and specificity of anti-histone antibodies revealed by a quantitative Peptide immunoprecipitation assay. J Mol Biol. 2012; 424 (5): 391-9. Epub 2012 Oct. 9. doi: 10.1016/j.jmb.2012.09.022. PubMed PMID: 23041298; PMCID: 3502729.

Example 3

This Example describes antibodies that bind to peptide-drug conjugates, but only in the context of specific MHC display of the described peptide-drug conjugates. The antibodies were produced as follows.

Antigen Preparation

KRAS(G12C) peptides ((H2N-VVGACGVGK-OH (SEQ ID NO: 1) and H2N-VVVGACGVGK-OH (SEQ ID NO: 2)) were reacted with AMG510 (Selleckchem) and loaded onto Flex-T HLA-A*03:01 and Flex-T HLA-A*11:01 (produced by Biolegend), or onto HLA-A*03:01 and HLA-A*11:01 produced in house. KRAS(WT) peptide ((H2N-VVGAGGVGK-OH (SEQ ID NO: 29)) was loaded onto the HLA molecules in the same manner. EGFR peptide (H2N-QLMPFGCLL-OH (SEQ ID NO: 30)) was reacted with Osimertinib (Selleckchem) and loaded onto Flex-T HLA-A*02:01 or HLA-A*02:01 produced in house. As a control, the same peptide was reacted with beta-mercaptoethanol and loaded onto the HLA molecule. BTK peptide (H2N-YMANGCLLNY-OH (SEQ ID NO: 31)) was reacted with Ibrutinib (Selleckchem) and loaded onto Flex-T HLA-A*01:01 or HLA-A*01:01 produced in house. As a control, the same peptide was reacted with beta-mercaptoethanol and loaded onto the HLA molecule. The peptide-loaded HLA mixtures prepared with Flex-T HLA proteins were used without further purification. The peptide-loaded HLA mixtures prepared with HLA samples prepared in house were further purified using size-exclusion chromatography with a Superdex S200 column.

Antibody Phage-Display Library Sorting

Sorting of an antibody phage-display library was performed as described previously[1]. Briefly, a phage-display library was first sorted with all four antigens at 100 nM in the first round, followed by sorting with a single antigen at 100, 50, and 20 nM in the second, third, and fourth rounds, respectively. To enrich for clones with the desired specificity, counterselection was performed using KRAS(WT) peptide-loaded MHC molecules or beta-mercaptoethanol-treated peptide-loaded MHC molecules in the second, third, and fourth rounds.

Binding of individual phage clones were tested using the multiplex bead binding assay[2].

Antibody Yeast-Display Library Sorting and Clone Characterization

Display of antibody clones in the form of single-chain Fv (scFv) on the yeast surface, library sorting using fluorescence-activated cell sorting, and characterization of individual clones were performed essentially as described previously (Hattori et al. PMID 23955773; Cao et al. PMID 17406305).

Deep Mutational Scanning

Deep mutational scanning was performed following general procedures published previously (PMID 32841599). A yeast-display library, in the scFv format, contanined variants in which a single position was diversified with the NNK codon. A yeast display libray was subjected to FACS using an antigen of interest to enrich a pool of clones that bound the antigen and a pool of clones that did not bind the antigen. The DNA sequences of the enriched pools were determined, and amino acid substitutions were deduced.

Antibody Production

The genes encoding selected antibody clones were transferred from the phage-display vector to IgG expression vectors (pFUSEss-CHIg-hG1 and pFUSE2ss-CLIg-hK, InvivoGen), and IgG proteins were produced using the ExpiCHO cell line (Thermo Fisher) and purified using a Protein Capture Devices with Protein A (GORE).

Figure 9:
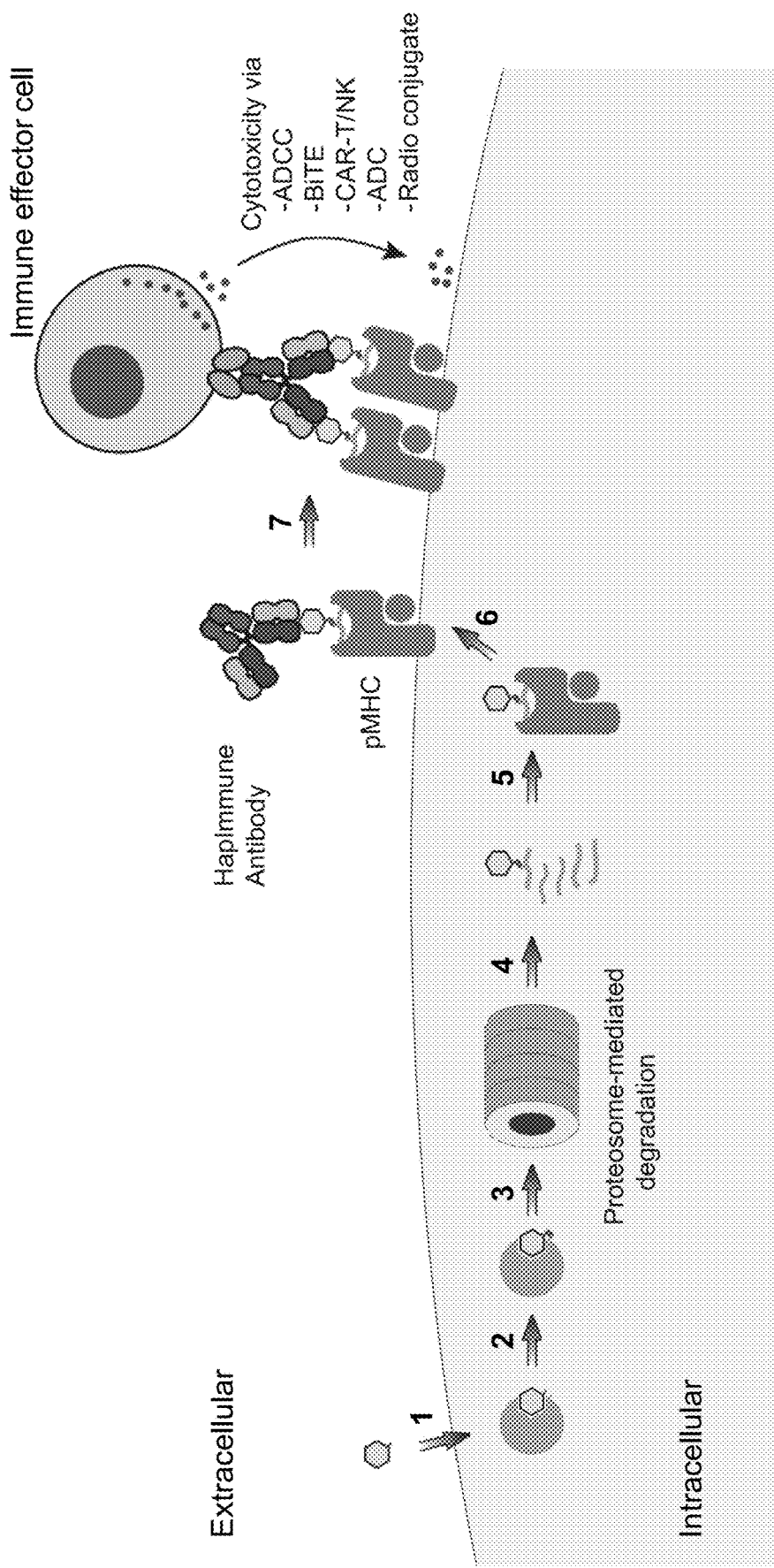
FIG. 9. Cartoon representation of the disclosed concept referred to as HapImmune.

Data presented in this Example relates to FIGS. 9-15, 17, which provide the following information:

FIG. 9 provides a cartoon representation of a concept of the disclosure referred to as HapImmune. The numbers 1-7 denote relevant steps. 1. A covalent inhibitor is administered, and it enters the cell harboring the target protein. 2. The inhibitor binds the target and forms a covalent bond with the target. 3 and 4. As a part of natural protein turnover (or induced protein degradation in the case of a PROTAC), the target-drug conjugate is degraded by the proteosome system. As a result, peptides with the conjugated drug are produced. 5. A peptide conjugate is incorporated into a compatible MHC molecule. 6. The MHC/peptide-drug conjugate complex translocates to the surface of the cell. A HapImmune antibody recognizes the complex. 7. The surface bound antibody recruits an immune effector cell, such as an NK cell, which in turn initiates cell killing activities. Multiple modalities are envisioned for effecting cell killing activities, including ADCC, ADCP, CDC, BITE, CAR-T, CAR-NK, ADC, and radioisotope conjugate, but they are not explicitly depicted here.

Figure 10:
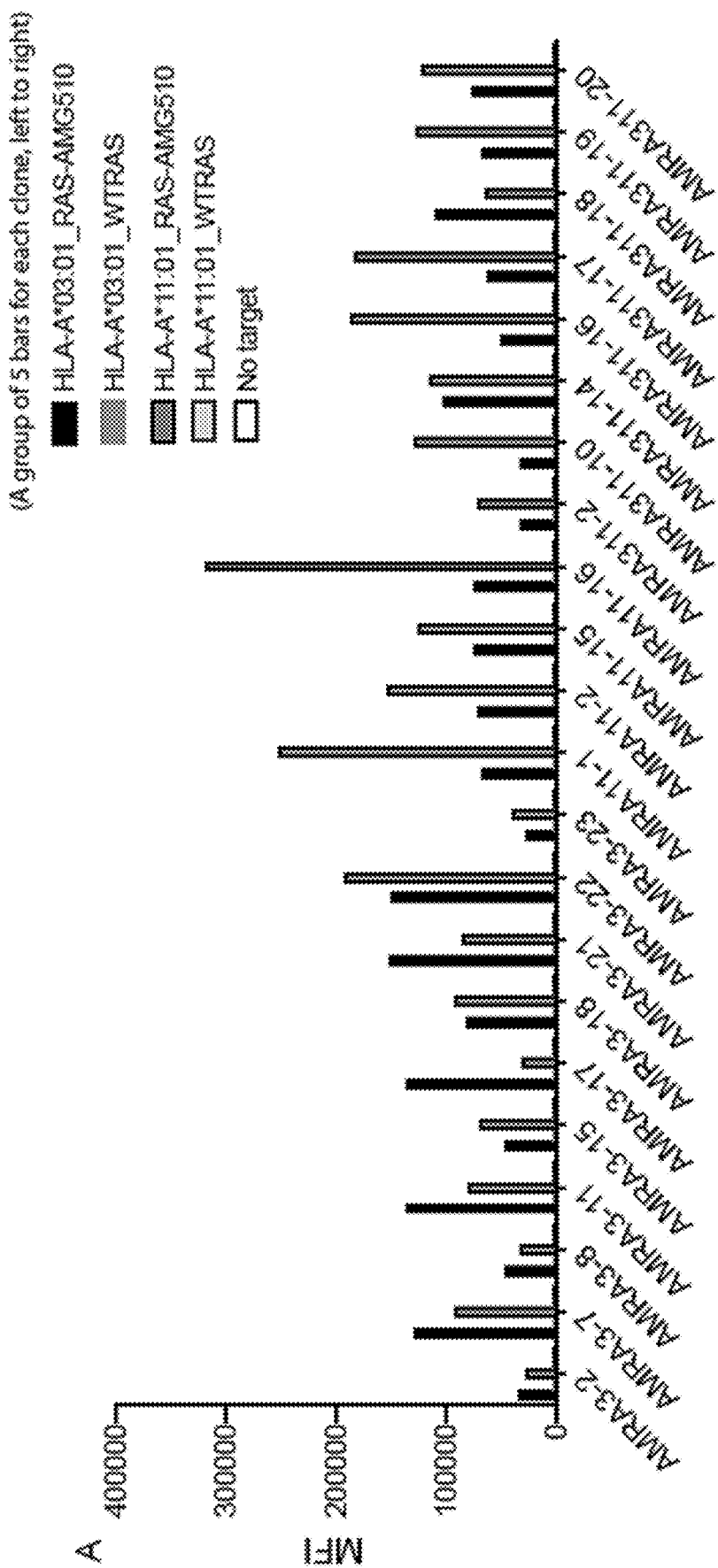
FIG. 10. Data representing development of antibodies that bind MHC/peptide-drug conjugate complexes. (A) Multiplex bead-binding assay (MBBA) of phages displaying different antibody clones. (B) MBBA assay of phages displaying different antibody clones to: HLA-A*01:01 in complex with the BTK peptide conjugated with Ibrutinib. (C) MBBA assay of phages displaying different antibody clones to: HLA-A*02:01 in complex with the EGFR peptide conjugated with Osimertinib.
Figure 10:
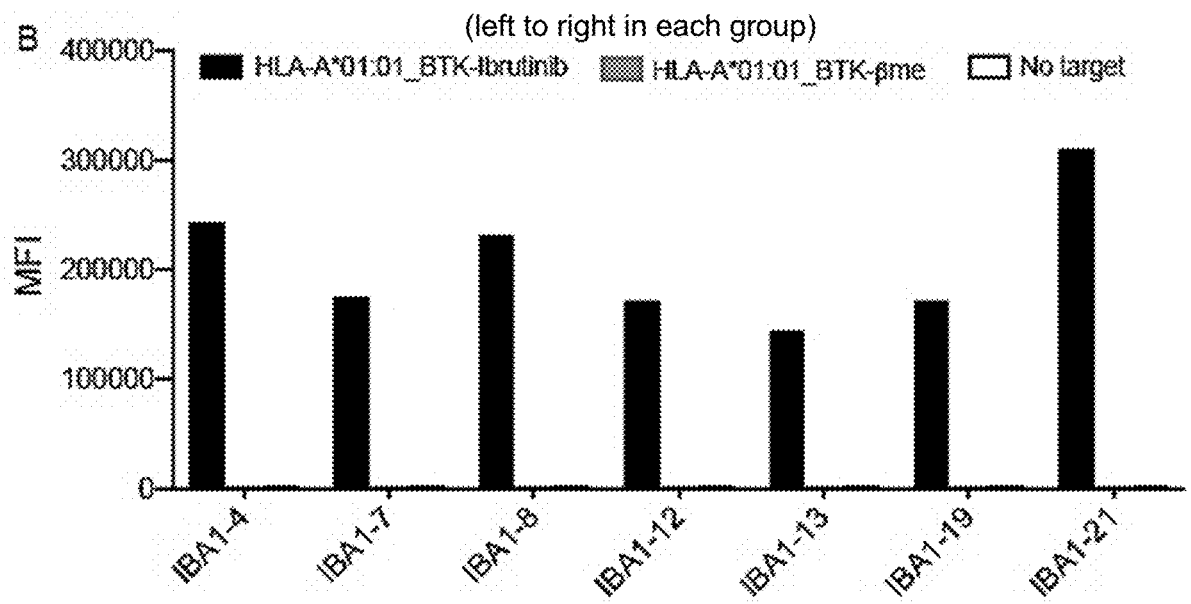
Figure 10:
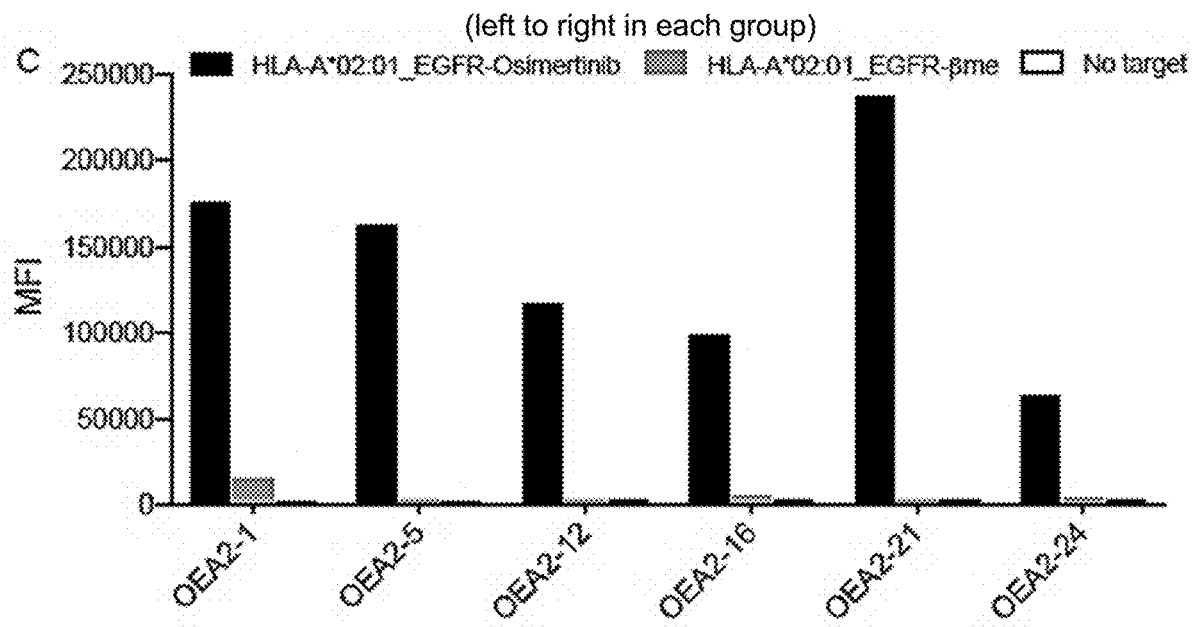

FIG. 10 shows data from development of antibodies that bind MHC/peptide-drug conjugate complexes. (A) Multiplex bead-binding assay (MBBA)[1] of phages displaying different antibody clones. For each phage clone, binding to a total of five antigens presented on beads was tested: HLA-A*03:01 in complex with the KRAS(G12C) peptide conjugated with AMG510 (denoted as HLA-A*03:01_RAS-AMG510 in the figure); HLA-A*03:01 in complex with the KRAS(wild type) peptide (denoted as HLA-A*03:01_WTRAS); HLA-A*11:01 in complex with the KRAS (G12C) peptide conjugated with AMG510 (denoted as HLA-A*11:01_RAS-AMG510); HLA-A*11:01 in complex with the KRAS(wild type) peptide (denoted as HLA-A*11:01_WTRAS); beads presenting no antigen (denoted as No target). (B) MBBA assay of phages displaying different antibody clones to: HLA-A*01:01 in complex with the BTK peptide conjugated with Ibrutinib (denoted as HLA-A*01:01_BTK-Ibrutinib in the figure); HLA-A*01:01 in complex with the BTK peptide conjugated with beta-mercaptoethanol (denoted as HLA-A*01:01_BTK-ßme); beads presenting no antigen (denoted as No target). (C) MBBA assay of phages displaying different antibody clones to: HLA-A*02:01 in complex with the EGFR peptide conjugated with Osimertinib (denoted as HLA-A*02:01_EGFR-Osimertinib in the figure); HLA-A*02:01 in complex with the EGFR peptide conjugated with beta-mercaptoethanol (denoted as HLA-A*02:01_EGFR-ßme); beads presenting no antigen (denoted as No target).

Figure 11:
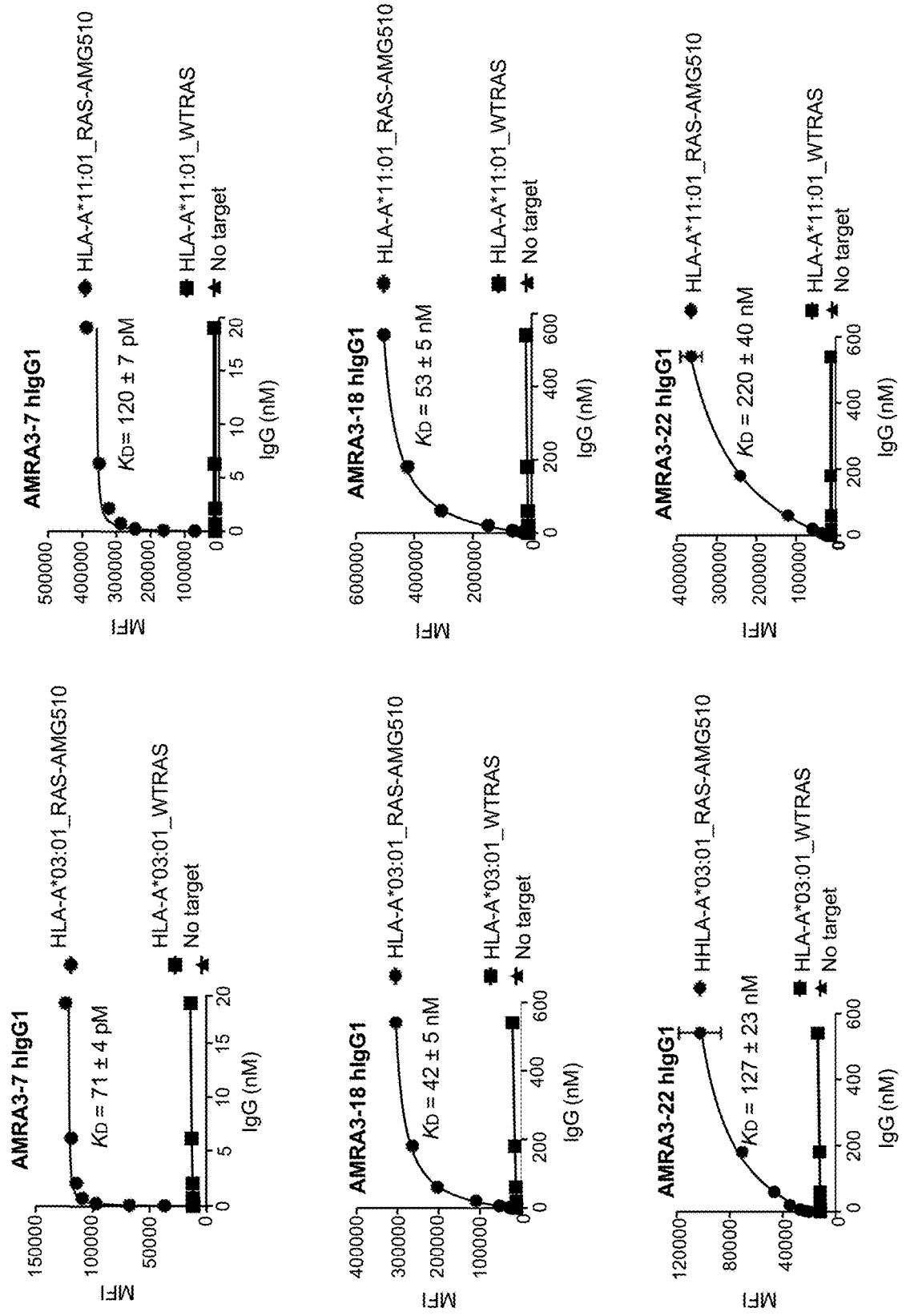
FIG. 11. Binding titration graphs using the multiplex bead-binding assay (MBBA) of purified antibodies targeted to the KRAS(G12C)-AMG510 conjugate. Clone names are shown over each graph. Antigen nomenclature is described in FIG. 10.
Figure 11:
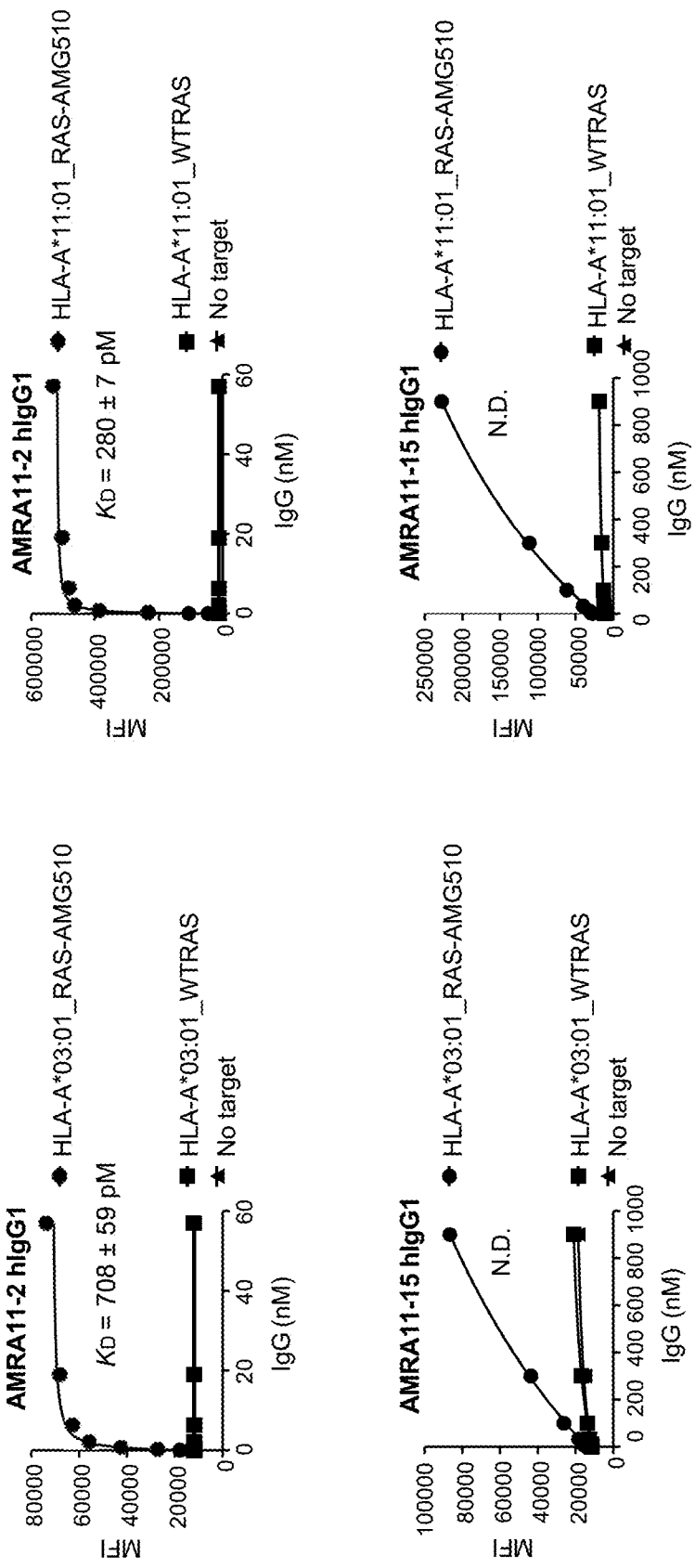
Figure 11:
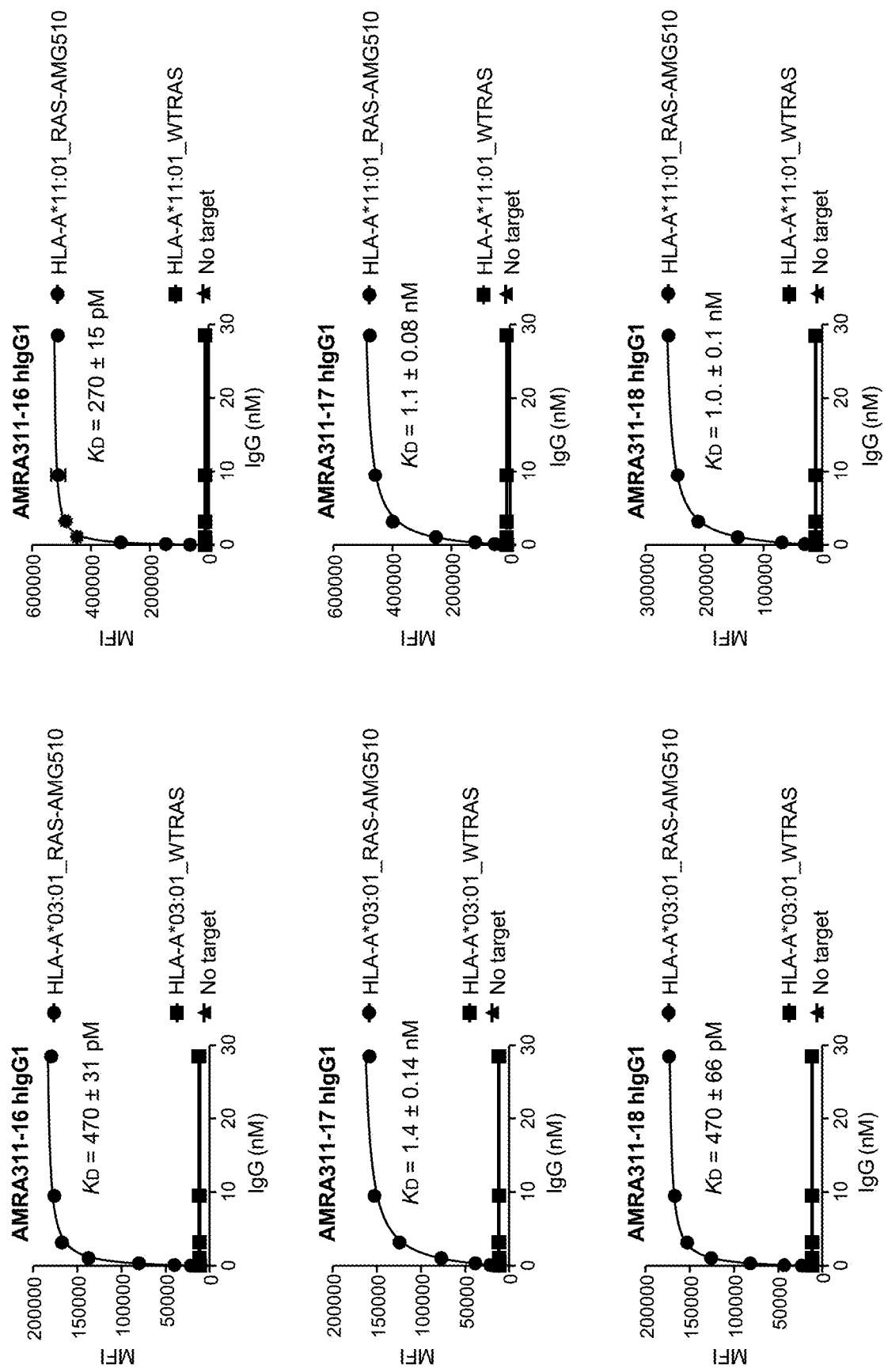

FIG. 11 shows results from binding titration using the multiplex bead-binding assay (MBBA) of purified antibodies targeted to the KRAS(G12C)-AMG510 conjugate. Clone names are shown over each graph. Antigen nomenclature is described in FIG. 10. The left column shows binding data with HLA-A*03:01 complexes, whereas the right column shows data with HLA-A*11:01 complexes. Apparent dissociation constant ($K_D$) values were determined using nonlinear least-squared fitting of a 1:1 binding function. The data for the wild-type RAS peptide complexes and for the no target were all close to the baseline and overlap, and thus their apparent $K_D$ values were not determined. Data shown here are from triplicate measurements. Error bars are within the size of the symbols.

Figure 12:
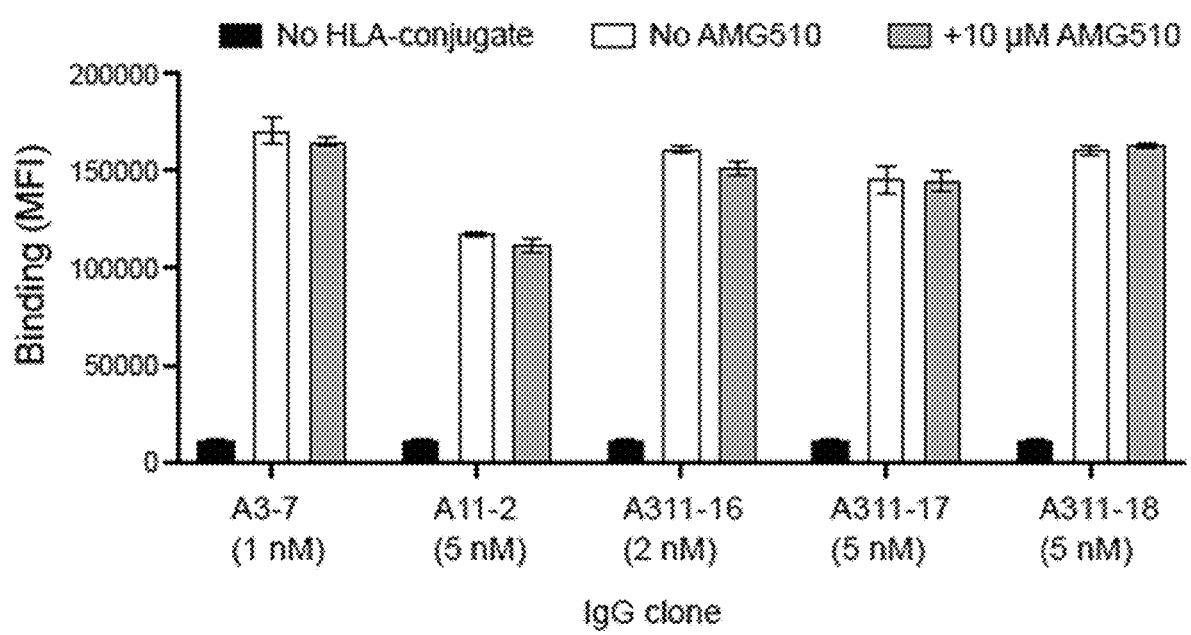
FIG. 12. Graph showing that binding of antibodies to the AMG510-peptide conjugate in complex with an HLA was not affected by the presence of the free drug, AMG510.

FIG. 12 demonstrates that binding of antibodies to the drug-peptide conjugate in complex with an MHC was not affected by the presence of the free drug. MBBA binding signals of select "AMR" series antibodies to HLA-A*03:01 in complex with the KRAS(G12C) peptide conjugated with AMG510 in the absence (the white bars) and presence (the gray bars) of 10 μM free AMG510 are shown. The antibody concentrations were adjusted to give sub-saturating signals and are shown in parentheses. Data shown here are from triplicate measurements.

Figure 13:
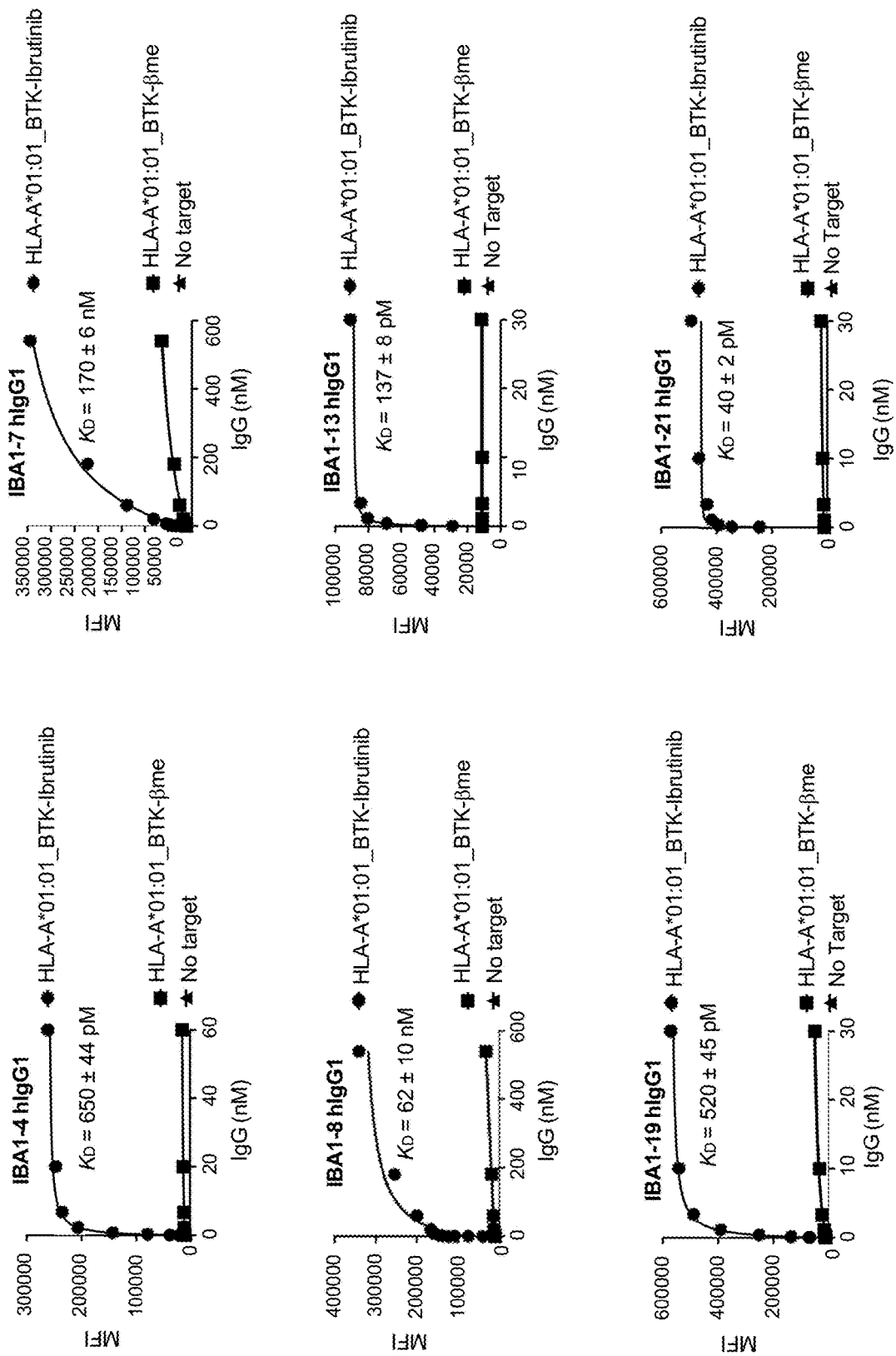
FIG. 13. Graphs of binding titrations using the multiplex bead-binding assay (MBBA) of purified antibodies targeted to the BTK-Ibrutinib conjugate. Clone names are shown over each graph. Antigen nomenclature is described in FIG. 10.

FIG. 13 shows results from binding titrations using the multiplex bead-binding assay (MBBA) of purified antibodies targeted to the BTK-Ibrutinib conjugate. Clone names are shown over each graph. Antigen nomenclature is described in FIG. 10. Apparent dissociation constant ($K_D$) values were determined using nonlinear least-squared fitting of a 1:1 binding function. The data for the beta-mercaptoethanol-conjugated peptide in complex with HLA-A*01:01 and for the no target were all close to the baseline and overlap, and thus their apparent $K_D$ values were not determined. Data shown here are from triplicate measurements. Error bars are within the size of the symbols.

Figure 14:
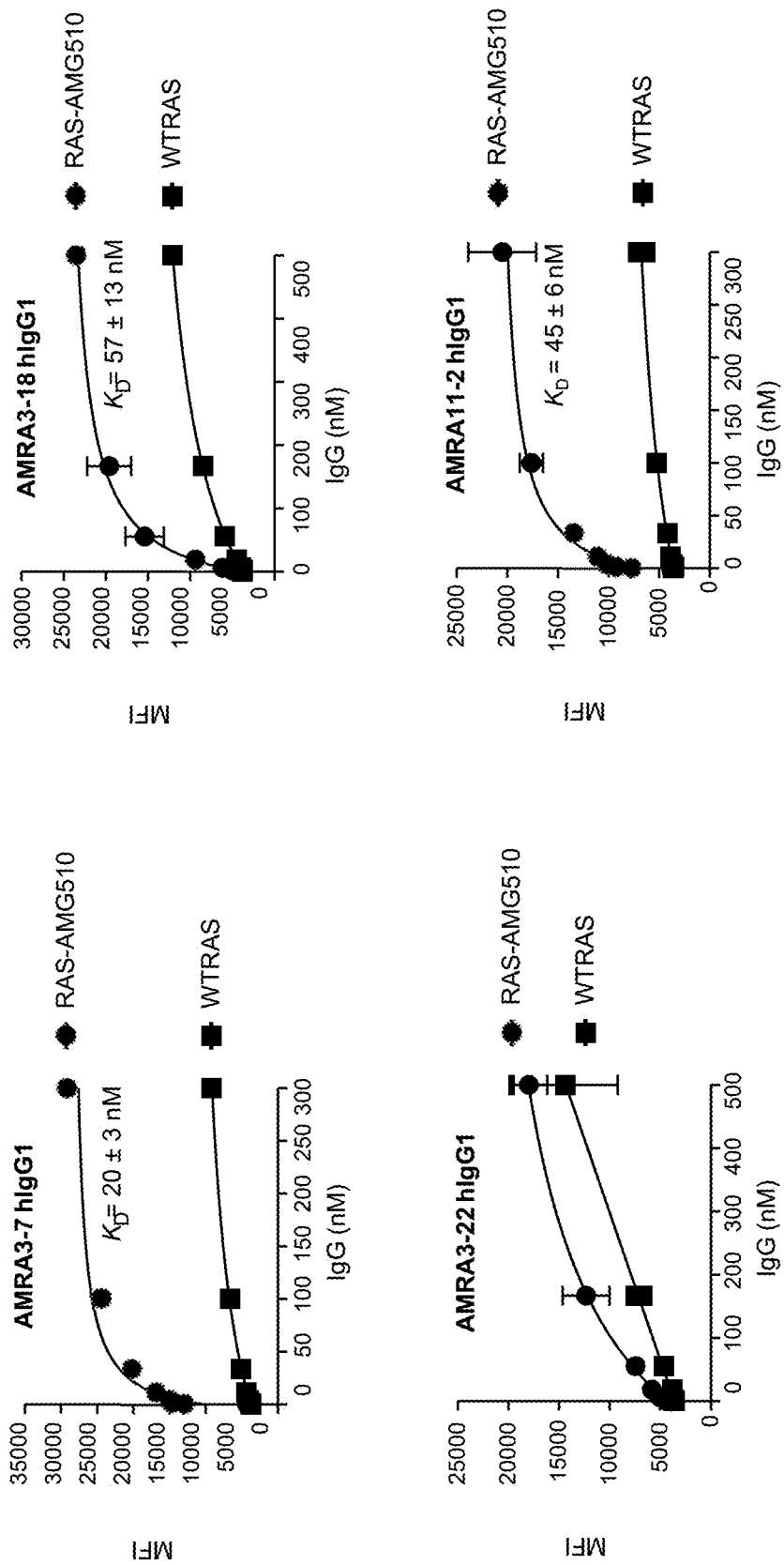
FIG. 14. Graphs of binding titrations of purified antibodies to the KRAS(G12C)-AMG510 conjugate presented by endogenous HLA molecules on the cell surface. Raji cells were first incubated with the KRAS (G12C)-AMG510 conjugate or the KRAS(wild type) peptide, and excess conjugate and peptide were washed away. The antibody levels detected using a fluorescently labeled secondary antibody are shown as a function of IgG concentration used for staining. Apparent dissociation constant ($K_D$)) values were determined using nonlinear least-squared fitting of a 1:1 binding function. Data shown here are from triplicate measurements.
Figure 14:
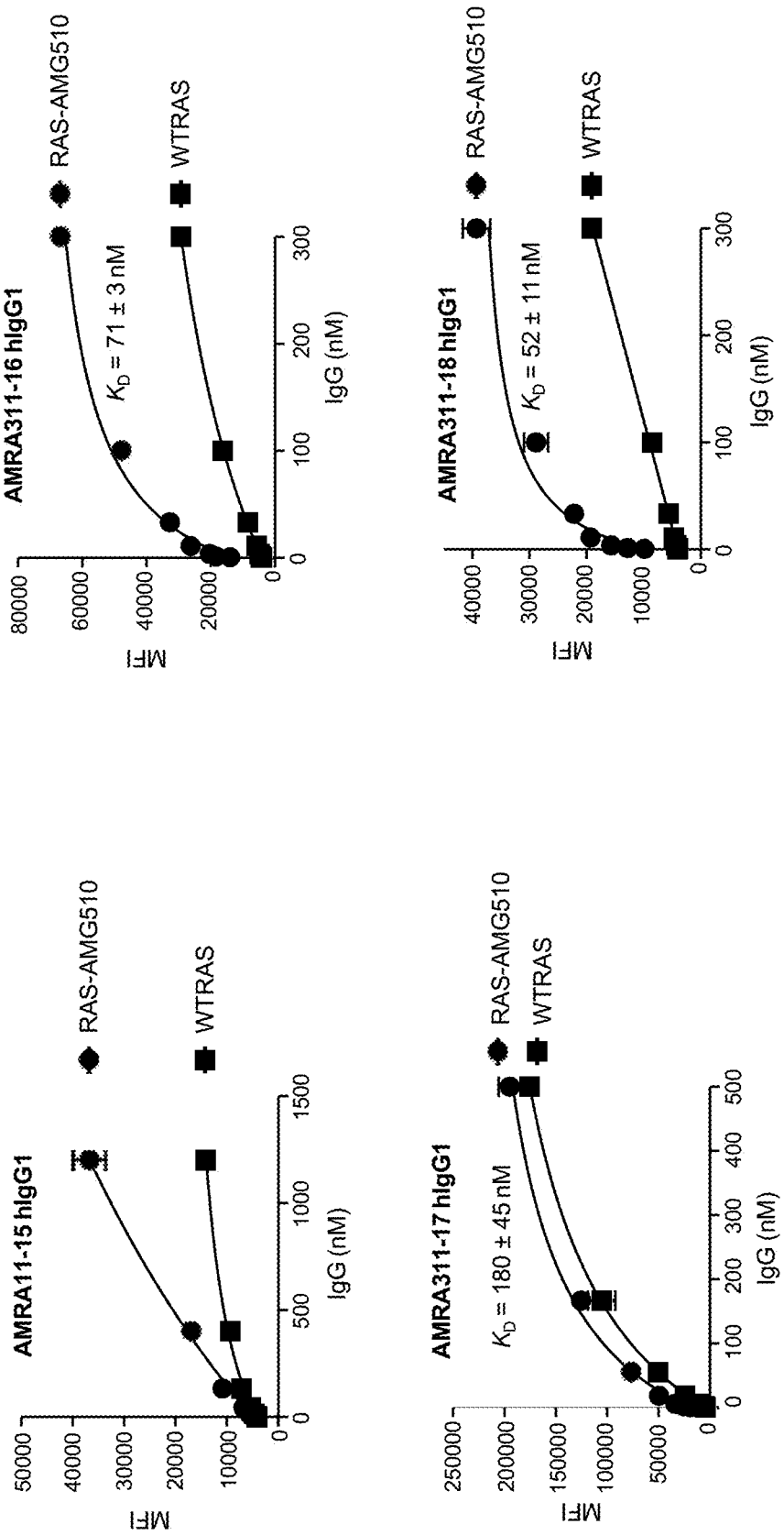

FIG. 14 shows results from binding titrations of purified antibodies to the KRAS(G12C)-AMG510 conjugate presented by endogenous MHC molecules on the cell surface. Raji cells were first incubated with the KRAS(G12C)-AMG510 conjugate or the KRAS(wild type) peptide, and excess conjugate and peptide were washed away. Surface-bound antibody levels detected using a fluorescently labeled secondary antibody are shown as a function of IgG concentration used for staining. Apparent dissociation constant ($K_D$) values were determined using nonlinear least-squared fitting of a 1:1 binding function. Data shown here are from triplicate measurements.

Figure 15:
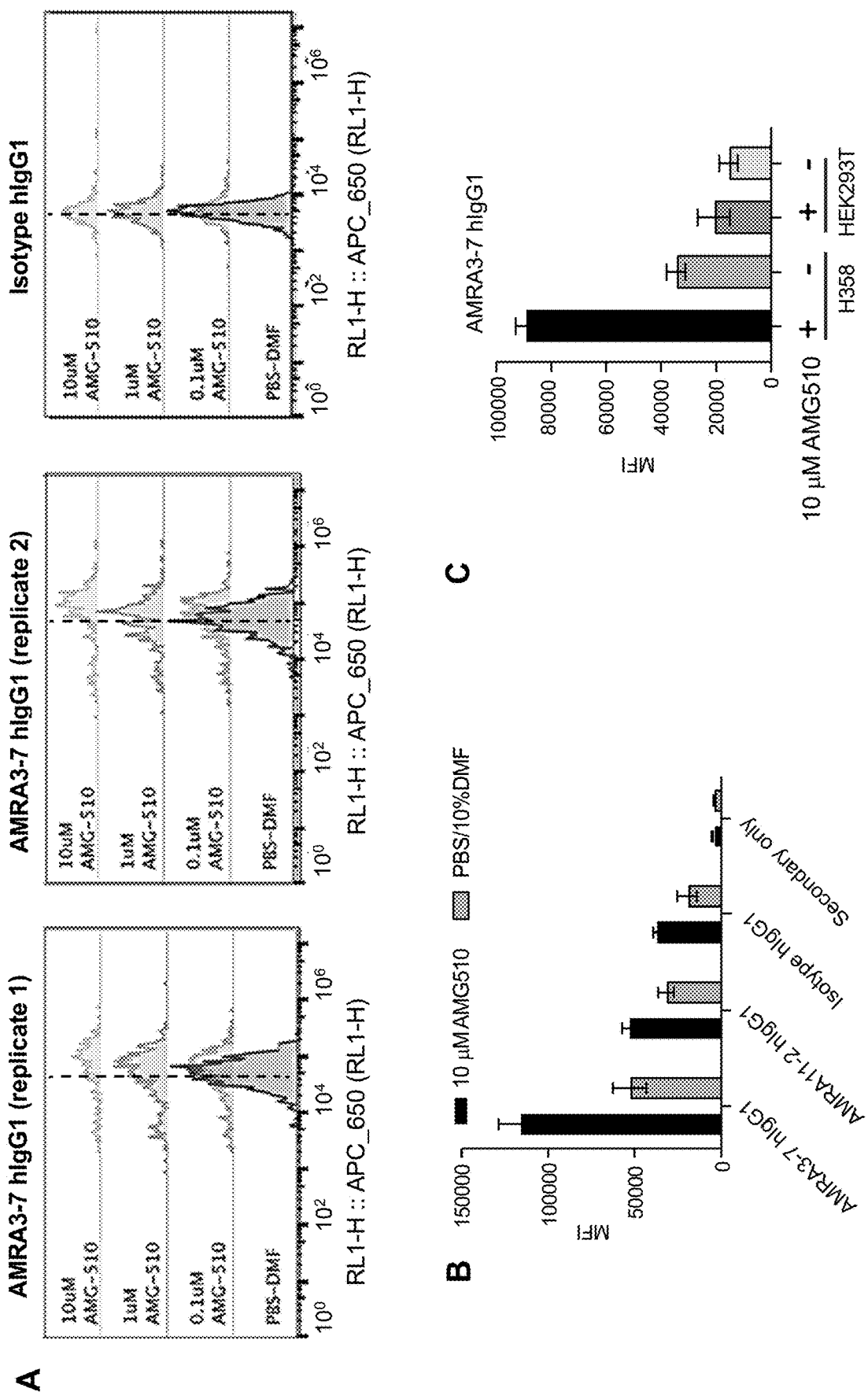
FIG. 15. Antibody binding to a KRAS(G12C)-expressing cell line pretreated with AMG510. (A) Flow cytometry histograms. (B) Quantification of the median fluorescence intensity of H358 cells treated with or without AMG510. (C) Quantification of the median fluorescence intensity of H358 cells and HEK293T cells (a negative control) treated with or without AMG510 and stained with the AMRA3-7 antibody.

FIG. 15 shows results from an antibody binding to a KRAS(G12C)-expressing cell line pretreated with AMG510. The non-small cell lung cancer cell line H358 was incubated with AMG510 for 2 days and then stained with antibodies targeting the KRAS G12C) peptide-AMG510 conjugate or an isotype control, followed by detection with a secondary antibody. (A) Flow cytometry histograms. (B) Quantification of the median fluorescence intensity of H358 cells treated with or without AMG510. The antibodies used are indicated along the horizontal axis. (C) Quantification of the median fluorescence intensity of H358 cells and HEK293T cells (a negative control) treated with or without AMG510 and stained with the AMRA3-7 antibody.

FIG. 16 is related to Example 2 and shows binding of P2AMR-1 IgG to cells preincubated with the KRAS(G12C) peptide-AMG510 conjugate, KRAS(wild type) peptide, or no peptide. The antibody was precomplexed with a dye-labeled secondary antibody in order to enhance the effective binding (avidity). The antibody bound to the Raji cells that express HLA-A*03:01 when the cells were incubated with the conjugate.

Figure 17:
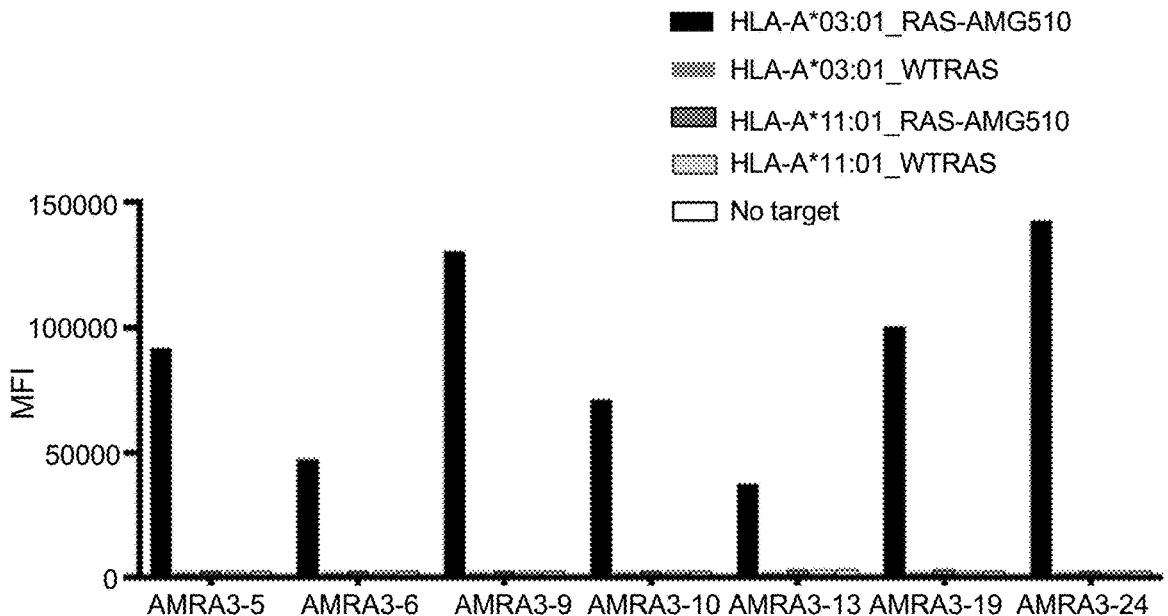
FIG. 17. Graphs showing binding of purified antibodies in the IgG format to the indicated drug-peptide/HLA complexes as measured using the multiplex bead binding assay (MBBA). (A) Antibody clones identified with AMG510 conjugated to KRAS(G12C) peptide in complex with HLA-A*03:01 as the antigen. (B) Antibody clones identified with AMG510 conjugated to KRAS(G12C) peptide in complex with HLA-*11:01 as the antigen.
Figure 17:
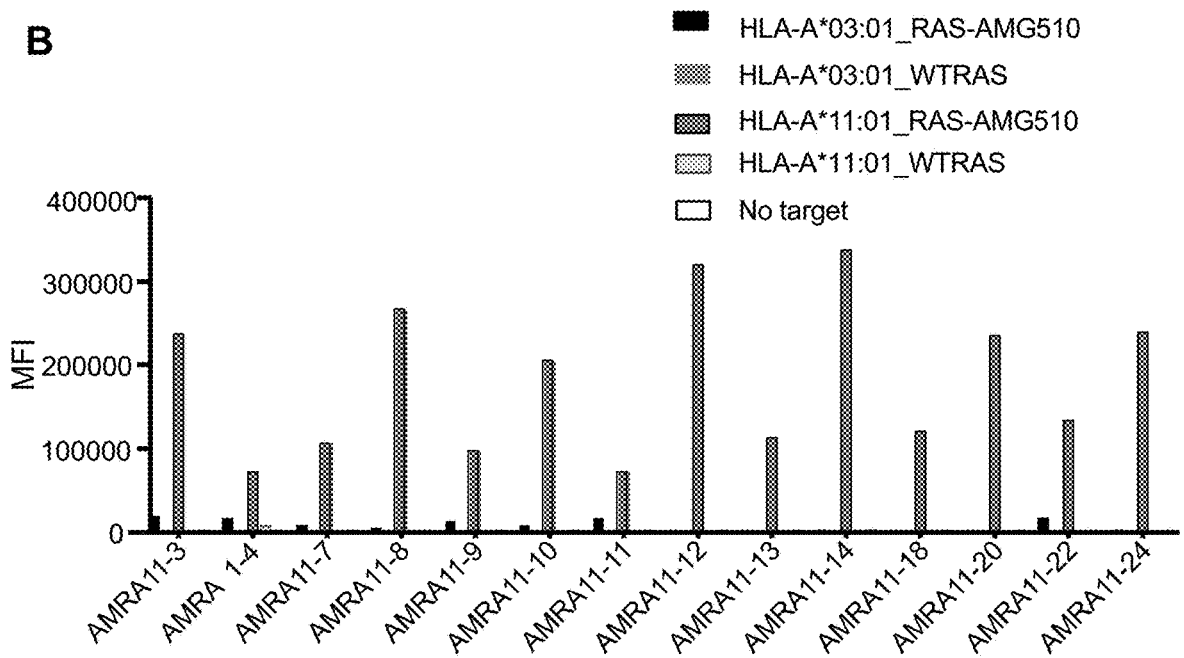

FIG. 17 shows results from binding of purified antibodies in the IgG format to the indicated drug-peptide/MHC complexes as measured using the multiplex bead binding assay (MBBA).

Figure 18:
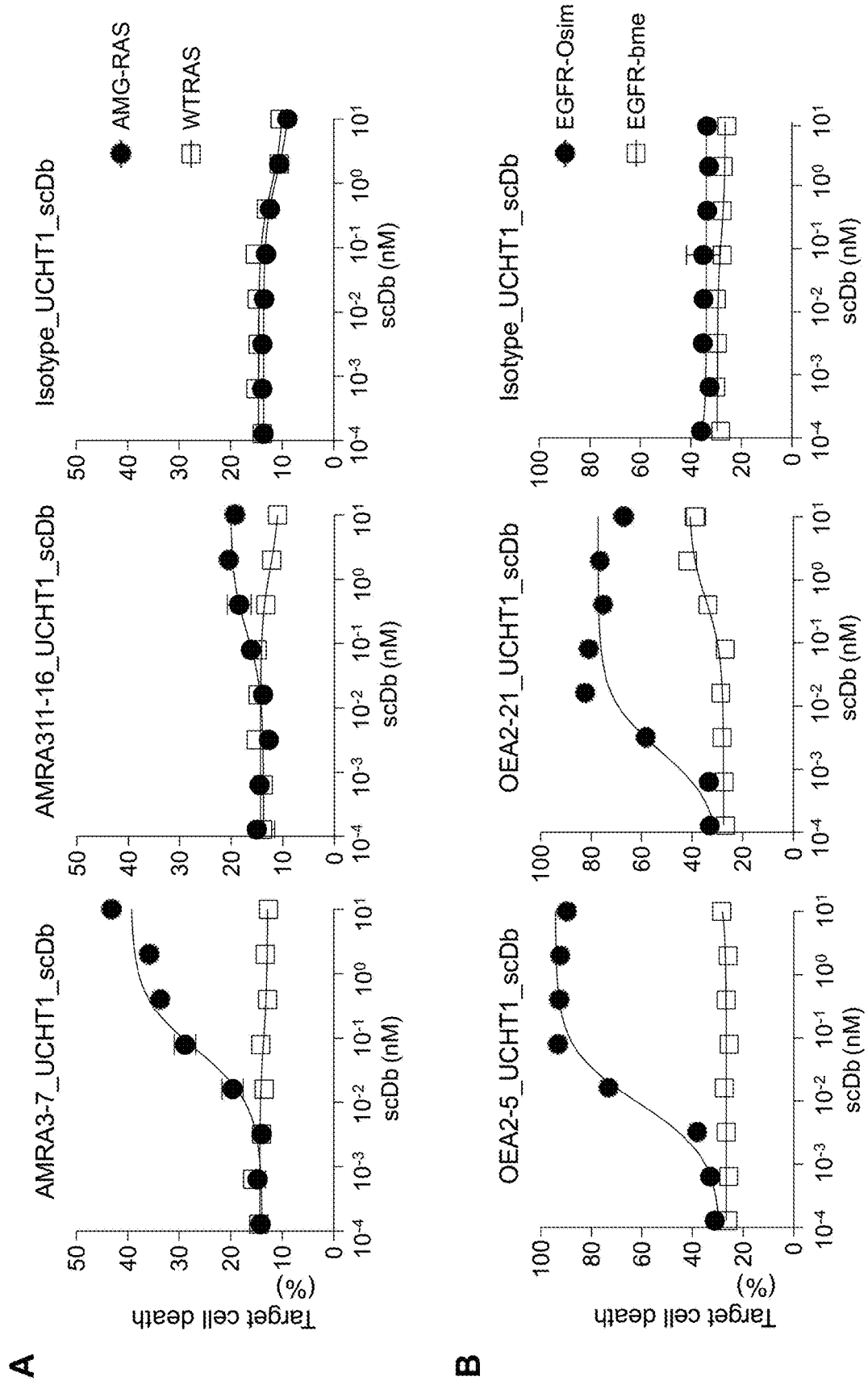
FIG. 18. Graphs showing the cytotoxic effect of single-chain Diabodies (scDbs) on cells pulsed with an exogenous peptide-drug conjugate. (A) Raji cells were first pulsed with AMG510 conjugated to a peptide corresponding to a fragment of KRAS(G12C) or a control peptide corresponding to KRAS(wild type). The pulsed cells were co-cultured with human T cells (Effector:Target=3:1) in the presence of single-chain Diabodies (scDbs) at the indicated concentrations. After incubation, dead cells were stained and detected by flow cytometry. Data shown here are from triplicate measurements. Error bars indicate the s.d. Where error bars are not visible, the errors are smaller than the symbols. (B) Equivalent experiments using T2 cells and Osimertinib conjugated with an EGFR peptide. As a negative control, peptide conjugated with beta-mercaptoethanol was used.
Figure 19:
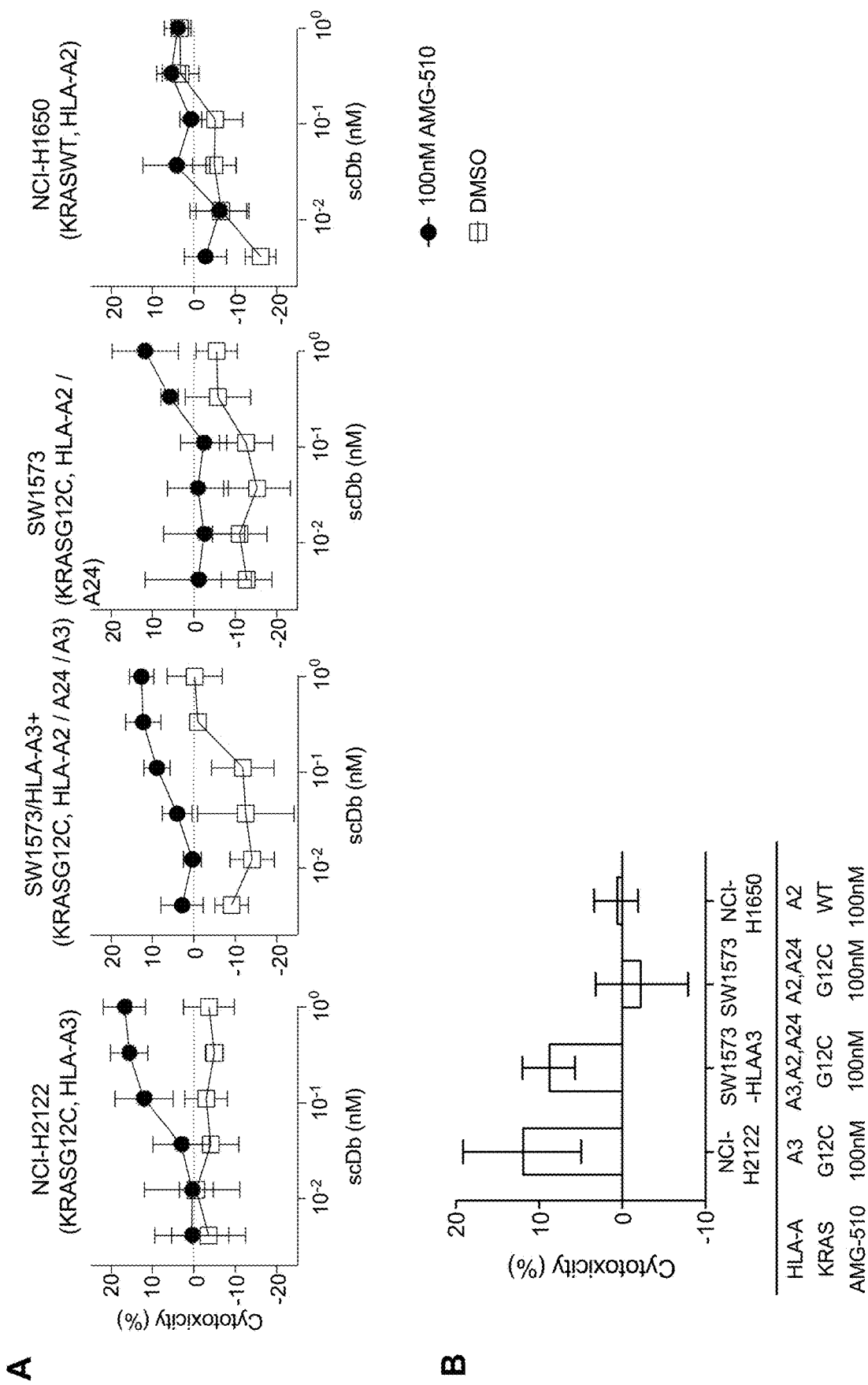
FIG. 19. Graphs showing specific cytotoxic effect of AMRA3-7_UCHT1 scDb on drug-treated lung cancer cell lines. (A) Lung cancer cell lines were treated with 100 nM AMG510 for 24 hr, then co-cultured with human T-cells (E:T=5:1) in the presence of AMRA3-7_UCHT1 scDb. After incubation, cell viability was measured. The scDb antibody showed a dose-dependent cytotoxic effect only on the AMG510-treated cells with the cognate KRAS mutation (G12C) and HLA (HLA-A3). (B) Cytotoxic effect of scDb at 0.1 nM concentration. Data shown here are from quadruplicate measurements.

FIGS. 18 and 19 are discussed in Example 4.

Figure 20:
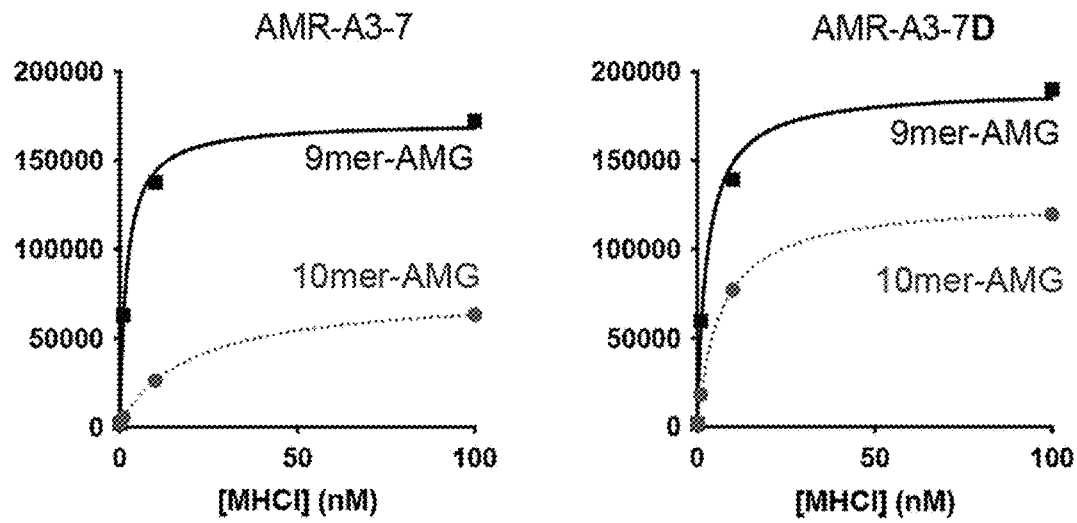
FIG. 20. Binding titration curves of AMR-A3-7 and AMR-A3-7D displayed on the yeast cell surface. Binding to HLA-A*03:01 presenting AMG510 conjugated to the Cys residue in the 9mer and 10mer RAS (G12C) peptides, VVGACGVGK (SEQ ID NO: 1) and VVVGACGVGK (SEQ ID NO: 2), respectively, is shown.

FIG. 20 shows results from binding titration curves of AMR-A3-7 and AMR-A3-7D displayed on the yeast surface. Binding to HLA-A*03:01 presenting AMG510 conjugated to the Cys residue in the 9mer and 10mer RAS (G12C) peptides, VVGACGVGK (SEQ ID NO: 1) and VVVGACGVGK (SEQ ID NO: 2), respectively, is shown.

Figure 23:
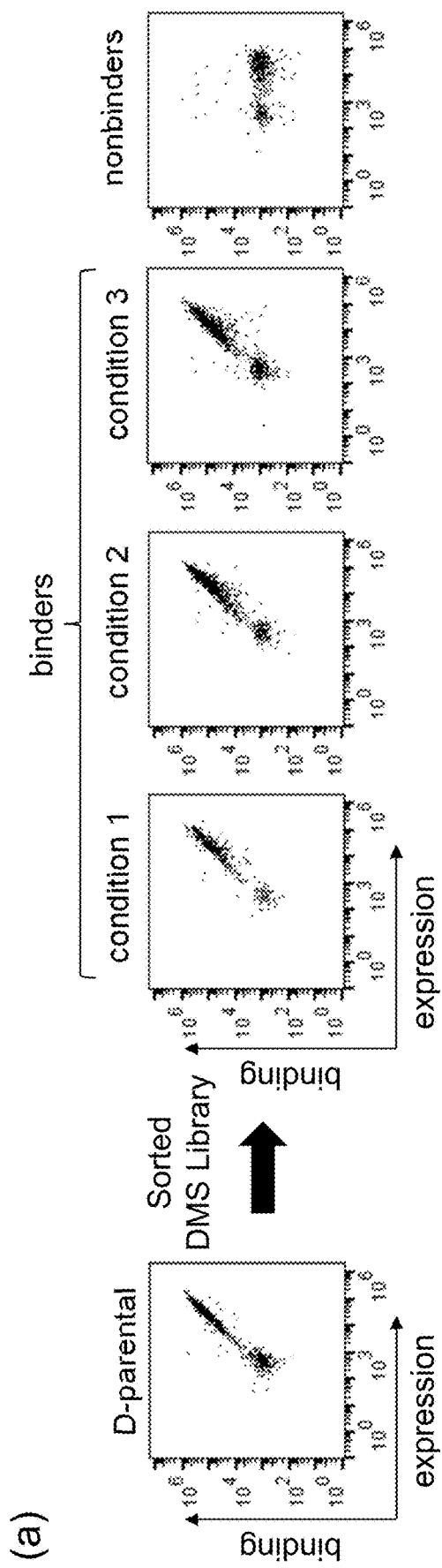
FIG. 23. Deep mutational scanning of AMR-A3-7D. (a) Representative flow cytometry profiles of yeast cells displaying AMRA3-7D and its deep mutational scanning library populations. (b) The prevalence of mutations at each position in the sorted subsets of the deep mutational scanning library is shown in a heat map format.
Figure 23:
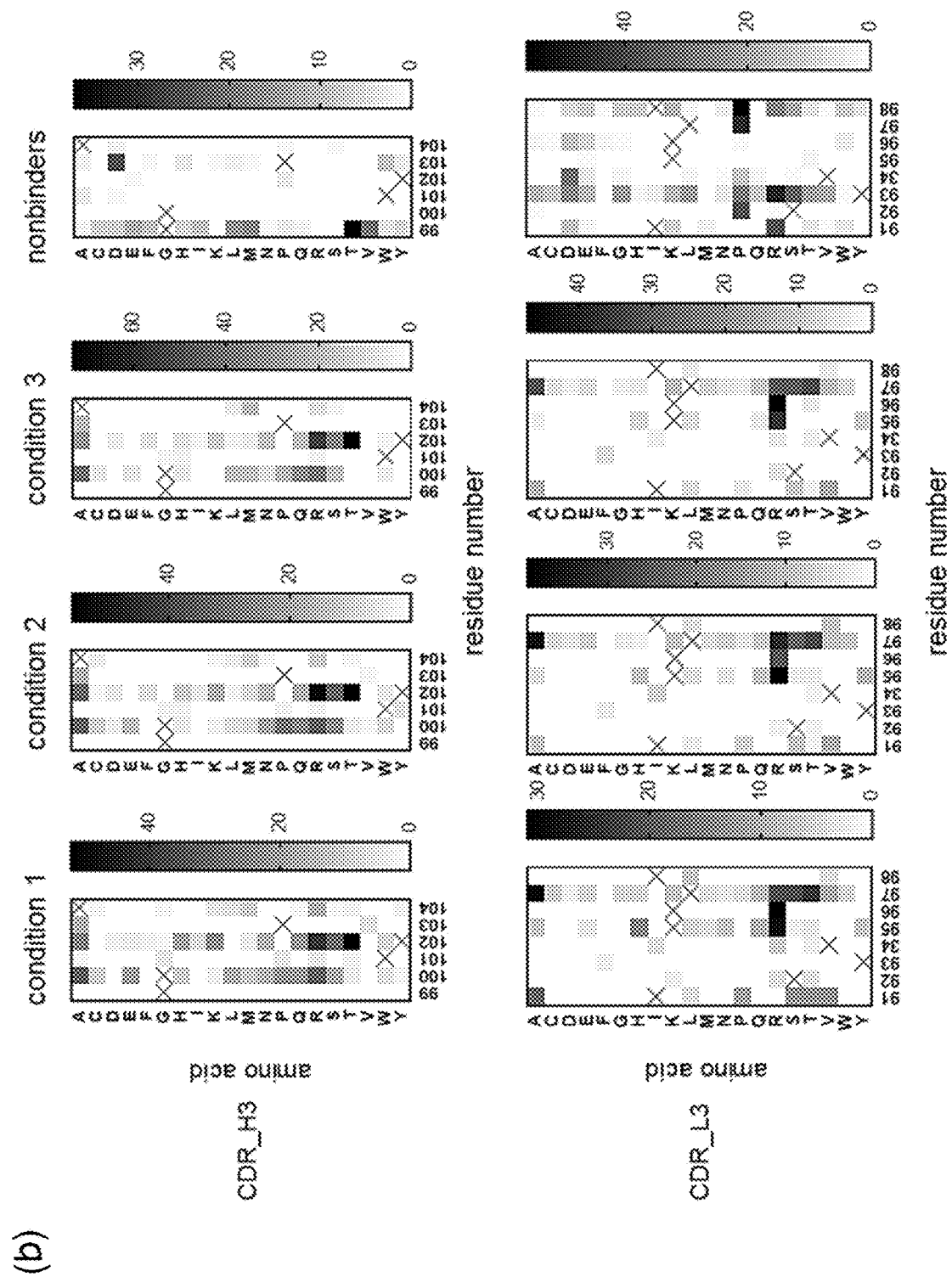
Figure 24:
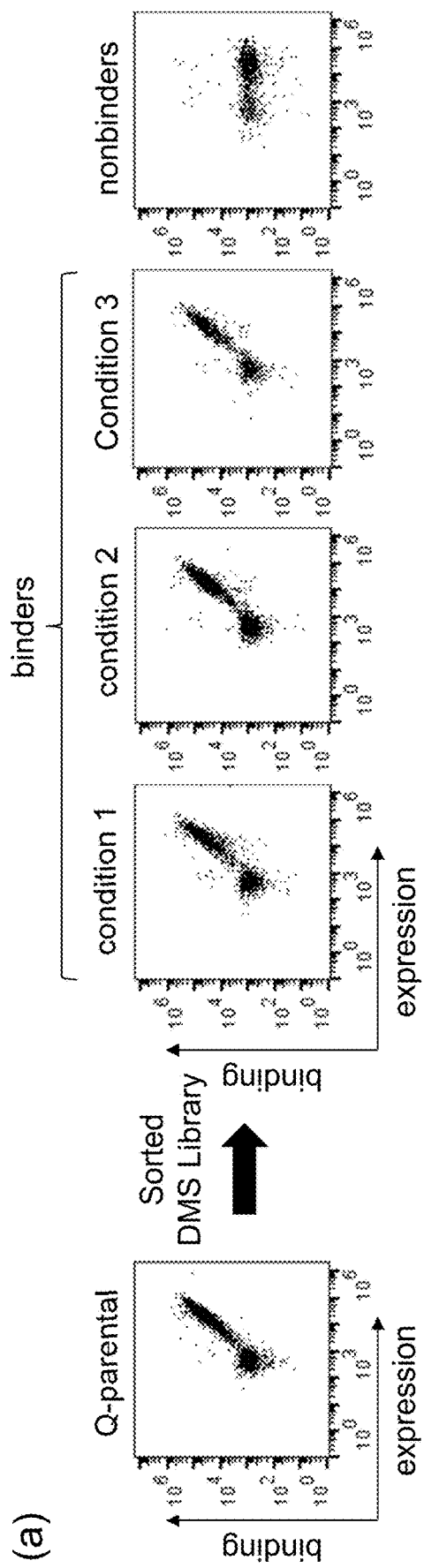
FIG. 24. Deep mutational scanning of OEA2-5. (a) Representative flow cytometry profiles of yeast cells displaying OEA2-5 in the single-chain Fv format and its deep mutational scanning library populations. (b) The prevalence of mutations at each position in the sorted subsets of the deep mutational scanning library is shown in a heat map format.
Figure 24:
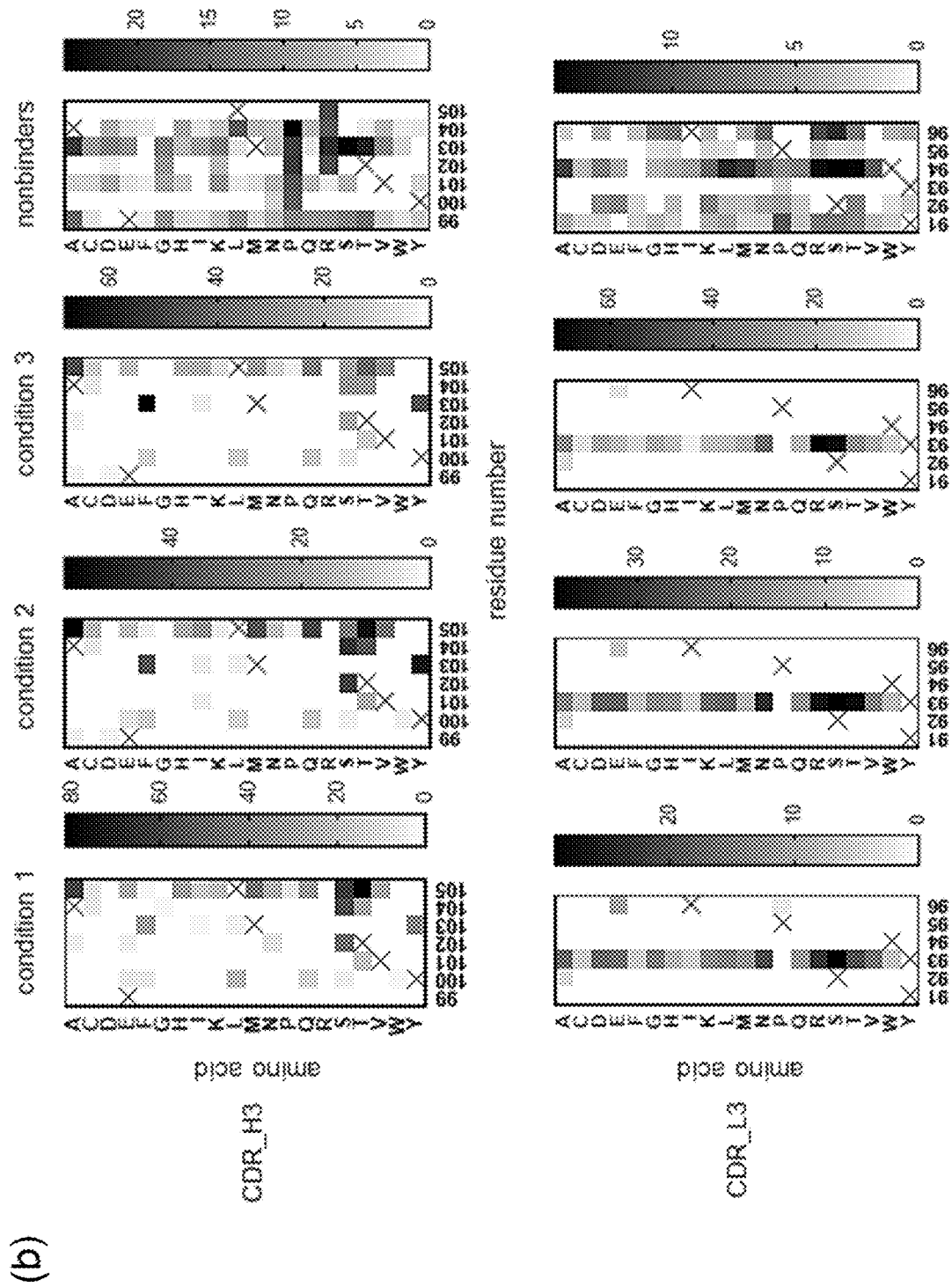

FIGS. 23 and 24 show results from deep mutational scanning of CDR-L3 and CDR-H3 of AMR-A3-7D and OEA2-5, respectively.

Specific and non-limiting examples of antibody sequences that bind in an MHC-drug conjugate-specific manner are as follows:

Exemplary Antibody Clones Binding to KRAS(G12C)-AMG510 conjugate presented on HLA-A*03:01 and HLA-A*11:01. CDR residues (Kabat scheme) in bold.

AMRA3-2

V$_L$:
(SEQ ID NO: 32)
DIQMTQSPSSLSASVGDRVTITCRASQSVSSAVAWYQQKPGKAPKLLIY
SASSLYSGVPSRFSGSRSGTDFTLTISSLQPEDFATYYCQQSGWSYPIT
FGQGTKVEIKRTV
(Bolded CDR sequences are disclosed as SEQ ID NOS 166, 167, and 202, respectively, in order of appearance)

V$_H$:
(SEQ ID NO: 33)
EVQLVESGGGLVQPGGSLRLSCAASGFTFYSSYIHWVRQAPGKGLEWVA
SISPYYGSTSYADSVKGRFTISADTSKNTAYLQMNSLRAEDTAVYYCAR
SSYYALDYWGQGTLVTVSS
(Bolded CDR sequences are disclosed as SEQ ID NOS 173, 203, and 204, respectively, in order of appearance)

AMRA3-7

V$_L$:
(SEQ ID NO: 34)
DIQMTQSPSSLSASVGDRVTITCRASQSVSSAVAWYQQKPGKAPKLLIY
SASSLYSGVPSRFSGSRSGTDFTLTISSLQPEDFATYYCQQISYVYSLI
TFGQGTKVEIKRTV
(Bolded CDR sequences are disclosed as SEQ ID NOS 166, 167, and 205, respectively, in order of appearance)

V$_H$:
(SEQ ID NO: 35)
EVQLVESGGGLVQPGGSLRLSCAASGFTFSSYSIHWVRQAPGKGLEWVA
SIYSSYGYTSYADSVKGRFTISADTSKNTAYLQMNSLRAEDTAVYYCAR
GGWYPAMDYWGQGTLVTVSS
(Bolded CDR sequences are disclosed as SEQ ID NOS 206, 207, and 171, respectively, in order of appearance)

AMRA3-7KK

V$_L$:
(SEQ ID NO: 36)
DIQMTQSPSSLSASVGDRVTITCRASQSVSSAVAWYQQKPGKAPKLLIY
SASSLYSGVPSRFSGSRSGTDFTLTISSLQPEDFATYYCQQISYVKKLI
TFGQGTKVEIKRTV
(Bolded CDR sequences are disclosed as SEQ ID NOS 166, 167, and 168, respectively, in order of appearance)

V$_H$:
(SEQ ID NO: 37)
EVQLVESGGGLVQPGGSLRLSCAASGFTFSSYSIHWVRQAPGKGLEWVA
SIYSSYGYTSYADSVKGRFTISADTSKNTAYLQMNSLRAEDTAVYYCAR
GGWYPAMDYWGQGTLVTVSS
(Bolded CDR sequences are disclosed as SEQ ID NOS 206, 207, and 171, respectively, in order of appearance)

AMRA3-7D

V$_L$:
(SEQ ID NO: 3)
DIQMTQSPSSLSASVGDRVTITCRASQSVSSAVAWYQQKPGKAPKLLIY
SASSLYSGVPSRFSGSRSGTDFTLTISSLQPEDFATYYCQQISYVKKLI
TFGQGTKVEIKRTV
(Bolded CDR sequences are disclosed as SEQ ID NOS 166, 167, and 168, respectively, in order of appearance)

V$_H$:
(SEQ ID NO: 4)
EVQLVESGGGLVQPGGSLRLSCAASGFTFSDYSIHWVRQAPGKGLEWVA
SISSSSGSTSYADSVKGRFTISADTSKNTAYLQMNSLRAEDTAVYYCAR
GGWYPAMDYWGQGTLVTVSS
(Bolded CDR sequences are disclosed as SEQ ID NOS 169, 170, and 171, respectively, in order of appearance)

AMRA3-8

V$_L$:
(SEQ ID NO: 38)
DIQMTQSPSSLSASVGDRVTITCRASQSVSSAVAWYQQKPGKAPKLLIY
SASSLYSGVPSRFSGSRSGTDFTLTISSLQPEDLATYYCQQYQYGYNLI
TFGQGTKVEIKRTV
(Bolded CDR sequences are disclosed as SEQ ID NOS 166, 167, and 208, respectively, in order of appearance)

V$_H$:
(SEQ ID NO: 39)
EVQLVESGGGLVQPGGSLRLSCAASGFTISYSSIHWVRQAPGKGLEWVA
SIYSYSGSTSYADSVKGRFTISADTSKNTAYLQMNSLRAEDTAVYYCAR
YSYGWVGPGWRAIDYWGQGTLVTVSS
(Bolded CDR sequences are disclosed as SEQ ID NOS 209, 210, and 211, respectively, in order of appearance)

AMRA3-11

V$_L$:
(SEQ ID NO: 40)
DIQMTQSPSSLSASVGDRVTITCRASQSVSSAVAWYQQKPGKAPKLLIY
SASSLYSGVPSRFSGSRSGTDFTLTISSLQPEDFATYYCQQSSSVYKLL
TFGQGTKVEIKRTV
(Bolded CDR sequences are disclosed as SEQ ID NOS 166, 167, and 212, respectively, in order of appearance)

V$_H$:
(SEQ ID NO: 41)
EVQLVESGGGLVQPGGSLRLSCAASGFTVYYSSIHWVRQAPGKGLEWVA
SISSSYSYTSYADSVKGRFTISADTSKNTAYLQMNSLRAEDTALYYCAR
GGPGWYRAMDYWGQGTLVTVSS
(Bolded CDR sequences are disclosed as SEQ ID NOS 209, 213, and 214, respectively, in order of appearance)

AMRA3-15

V$_L$:
(SEQ ID NO: 42)
DIQMTQSPSSLSASVGDRVTITCRASQSVSSAVAWYQQKPGKAPKLLIY
SASSLYSGVPSRFSGSRSGTDFTLTISSLQPEDFATYYCQQSSSSLITF
GQGTKVEIKRTV
(Bolded CDR sequences are disclosed as SEQ ID NOS 166, 167, and 180, respectively, in order of appearance)

V$_H$:
(SEQ ID NO: 43)
EVQLVESGGGLVQPGGSLRLSCAASGFTFSSSSIHWVRQAPGKGLEWVA
SISSSSGSTSYADSVKGRFTISADTSKNTAYLQMNSLRAEDTAVYYCAR
GYFYYGWWAMAFDYWGQGTLVTVSS
(Bolded CDR sequences are disclosed as SEQ ID NOS 215, 170, and 216, respectively, in order of appearance)

AMRA3-17
V<sub>L</sub>:
(SEQ ID NO: 44)
DIQMTQSPSSLSASVGDRVTITCRASQSVSSAVAWYQQKPGKAPKLLIY

SASSLYSGVPSRFSGSRSGTDFTLTISSLQPEDFATYYCQQSQWYEPLI

TFGQGTKVEIKRTV
(Bolded CDR sequences are disclosed as SEQ ID NOS
166, 167, and 217, respectively, in order of
appearance)

V<sub>H</sub>:
(SEQ ID NO: 45)
EVQLVESGGGLVQPGGSLRLSCAASGFTIYSSYIHWVRQAPGKGLEWVA

SISSSSGSTSYADSVKGRFTISADTSKNTAYLQMNSLRAEDTAVYYCAR

SYSYMSQWGWYQYSGMDYWGQGTLVTVSS
(Bolded CDR sequences are disclosed as SEQ ID NOS
173, 170, and 218, respectively, in order of
appearance)

AMRA3-18
V<sub>L</sub>:
(SEQ ID NO: 46)
DIQMTQSPSSLSASVGDRVTITCRASQSVSSAVAWYQQKPGKAPKLLIY

SASSLYSGVPSRFSGSRSGTDFTLTISSLQPEDFATYYCQQGSYTYRLI

TFGQGTKVEIKRTV
(Bolded CDR sequences are disclosed as SEQ ID NOS
166, 167, and 219, respectively, in order of
appearance)

V<sub>H</sub>:
(SEQ ID NO: 47)
EVQLVESGGGLVQPGGSLRLSCAASGFTVSYSSIHWVRQAPGKGLEWVA

SISSSSGYTSYADSVKGRFTISADTSKNTAYLQMNSLRAEDTAVYYCAR

YAWWAHGLDYWGQGTLVTVSS
(Bolded CDR sequences are disclosed as SEQ ID NOS
209, 220, and 221, respectively, in order of
appearance)

AMRA3-21
V<sub>L</sub>:
(SEQ ID NO: 48)
DIQMTQSPSSLSASVGDRVTITCRASQSVSSAVAWYQQKPGKAPKLLIY

SASSLYSGVPSRFSGSRSGTDFTLTISSLQPEDFATYYCQQASYWYNLF

TFGQGTKVEIKRTV
(Bolded CDR sequences are disclosed as SEQ ID NOS
166, 167, and 222, respectively, in order of
appearance)

V<sub>H</sub>:
(SEQ ID NO: 49)
EVQLVESGGGLVQPGGSLRLSCAASGFTISSYSIHWVRQAPGKGLEWVA

SIYSSYGYTSYADSVKGRFTISADTSKNTAYLQMNSLRAEDTAVYYCAR

QYSMHFPWGYGMDYWGQGTLVTVSS
(Bolded CDR sequences are disclosed as SEQ ID NOS
206, 207, and 223, respectively, in order of
appearance)

AMRA3-22
V<sub>L</sub>:
(SEQ ID NO: 50)
DIQMTQSPSSLSASVGDRVTITCRASQSVSSAVAWYQQKPGKAPKLLIY

SASSLYSGVPSRFSGSRSGTDFTLTISSLQPEDFATYYCQQSDMPPITF

GQGTKVEIKRTV
(Bolded CDR sequences are disclosed as SEQ ID NOS
166, 167, and 224, respectively, in order of
appearance)

V<sub>H</sub>:
(SEQ ID NO: 51)
EVQLVESGGGLVQPGGSLRLSCAASGFTFYSSSIHWVRQAPGKGLEWVA

YIYSSSGYTSYADSVKGRFTISADTSKNTAYLQMNSLRAEDTAVYYCAR

PVNYYYQGALDYWGQGTLVTVSS
(Bolded CDR sequences are disclosed as SEQ ID NOS
215, 225, and 226, respectively, in order of
appearance)

AMRA3-23
V<sub>L</sub>:
(SEQ ID NO: 52)
DIQMTQSPSSLSASVGDRVTITCRASQSVSSAVAWYQQKPGKAPKLLIY

SASSLYSGVPSRFSGSRSGTDFTLTISSLQPEDFATYYCQQYYVFPITF

GQGTKVEIKRTV
(Bolded CDR sequences are disclosed as SEQ ID NOS
166, 167, and 227, respectively, in order of
appearance)

V<sub>H</sub>:
(SEQ ID NO: 53)
EVQLVESGGGLVQPGGSLRLSCAASGFTVYSSSIHWVRQAPGKGLEWVA

SISPSSGYTYYADSVKGRFTISADTSKNTAYLQMNSLRAEDTAVYYCAR

YHYMFEYDKGESKWGYYGFDYWGQGTLVTVSS
(Bolded CDR sequences are disclosed as SEQ ID NOS
215, 228, and 229, respectively, in order of
appearance)

AMRA11-1
V<sub>L</sub>:
(SEQ ID NO: 54)
DIQMTQSPSSLSASVGDRVTITCRASQSVSSAVAWYQQKPGKAPKLLIY

SASSLYSGVPSRFSGSRSGTDFTLTISSLQPEDFATYYCQQSQYFPITF

GQGTKVEIKRTV
(Bolded CDR sequences are disclosed as SEQ ID NOS
166, 167, and 230, respectively, in order of
appearance)

V<sub>H</sub>:
(SEQ ID NO: 55)
EVQLVESGGGLVQPGGSLRLSCAASGFTISYSSIHWVRQAPGKGLEWVA

SIYSYYGYTSYADSVKGRFTISADTSKNTAYLQMNSLRAEDTAVYYCAR

NSWSWYSGVGMDYWGQGTLVTVSS
(Bolded CDR sequences are disclosed as SEQ ID NOS
209, 231, and 232, respectively, in order of
appearance)

AMRA11-2
V<sub>L</sub>:
(SEQ ID NO: 56)
DIQMTQSPSSLSASVGDRVTITCRASQSVSSAVAWYQQKPGKAPKLLIY

SASSLYSGVPSRFSGSRSGTDFTLTISSLQPEDFATYYCQQSSSSLITF

GQGTKVEIKRTV
(Bolded CDR sequences are disclosed as SEQ ID NOS
166, 167, and 180, respectively, in order of
appearance)

V<sub>H</sub>:
(SEQ ID NO: 57)
EVQLVESGGGLVQPGGSLRLSCAASGFTISSSSIHWVRQAPGKGLEWVA

SISSYSSSTYYADSVKGRFTISADTSKNTAYLQMNSLRAEDTAVYYCAR

YPYGWGWGGSGLDYWGQGTLVTVSS
(Bolded CDR sequences are disclosed as SEQ ID NOS
215, 233, and 234, respectively, in order of
appearance)

-continued

AMRA11-15
V_L:
(SEQ ID NO: 58)
DIQMTQSPSSLSASVGDRVTITCRASQSVSSAVAWYQQKPGKAPKLLIY

SASSLYSGVPSRFSGSRSGTDFTLTISSLQPEDFATYYCQQFDFQYLIT

FGQGTKVEIKRTV
(Bolded CDR sequences are disclosed as SEQ ID NOS
166, 167, and 235, respectively, in order of
appearance)

V_H:
(SEQ ID NO: 59)
EVQLVESGGGLVQPGGSLRLSCAASGFTVYYSSIHWVRQAPGKGLEWVA

SIYSYYGSTYYADSVKGRFTISADTSKNTAYLQMNSLRAEDTAVYYCAR

GEKWALDYWGQGTLVTVSS
(Bolded CDR sequences are disclosed as SEQ ID NOS
209, 236, and 237, respectively, in order of
appearance)

AMRA11-16
V_L:
(SEQ ID NO: 60)
DIQMTQSPSSLSASVGDRVTITCRASQSVSSAVAWYQQKPGKAPKLLIY

SASSLYSGVPSRFSGSRSGTDFTLTISSLQPEDFATYYCQQYMYYQPLI

TFGQGTKVEIKRTV
(Bolded CDR sequences are disclosed as SEQ ID NOS
166, 167, and 238, respectively, in order of
appearance)

V_H:
(SEQ ID NO: 61)
EVQLVESGGGLVQPGGSLRLSCAASGFTVYYSSIHWVRQAPGKGLEWVA

SISSSSGSTSYADSVKGRFTISADTSKNTAYLQMNSLRAEDTAVYYCAR

EPYNYNWYGMDYWGQGTLVTVSS
(Bolded CDR sequences are disclosed as SEQ ID NOS
209, 170, and 239, respectively, in order of
appearance)

AMRA311-2
V_L:
(SEQ ID NO: 62)
DIQMTQSPSSLSASVGDRVTITCRASQSVSSAVAWYQQKPGKAPKLLIY

SASSLYSGVPSRFSGSRSGTDFTLTISSLQPEDFATYYCQQSLWWPITF

GQGTKVEIKRTV
(Bolded CDR sequences are disclosed as SEQ ID NOS
166, 167, and 240, respectively, in order of
appearance)

V_H:
(SEQ ID NO: 63)
EVQLVESGGGLVQPGGSLRLSCAASGFTVSSSSIHWVRQAPGKGLEWVA

SIYSYSGYTSYADSVKGRFTISADTSKNTAYLQMNSLRAEDTAVYYCAR

HGSYGSWWALDYWGQGTLVTVSS
(Bolded CDR sequences are disclosed as SEQ ID NOS
215, 241, and 242, respectively, in order of
appearance)

AMRA311-10
V_L:
(SEQ ID NO: 64)
DIQMTQSPSSLSASVGDRVTITCRASQSVSSAVAWYQQKPGKAPKLLIY

SASSLYSGVPSRFSGSRSGTDFTLTISSLQPEDFATYYCQQYFYFPITF

GQGTKVEIKRTV
(Bolded CDR sequences are disclosed as SEQ ID NOS
166, 167, and 243, respectively, in order of
appearance)

V_H:
(SEQ ID NO: 65)
EVQLVESGGGLVQPGGSLRLSCAASGFTFYSSSIHWVRQAPGKGLEWVA

SISSYYGSTSYADSVKGRFTISADTSKNTAYLQMNSLRAEDTAVYYCAR

ASYYSGYGSSYPYYMGLDYWGQGTLVTVSS
(Bolded CDR sequences are disclosed as SEQ ID NOS
215, 244, and 245, respectively, in order of
appearance)

AMRA311-14
V_L:
(SEQ ID NO: 66)
DIQMTQSPSSLSASVGDRVTITCRASQSVSSAVAWYQQKPGKAPKLLIY

SASSLYSGVPSRFSGSRSGTDFTLTISSLQPEDFATYYCQQGSYRNPLL

TFGQGTKVEIKRTV
(Bolded CDR sequences are disclosed as SEQ ID NOS
166, 167, and 246, respectively, in order of
appearance)

V_H:
(SEQ ID NO: 67)
EVQLVESGGGLVQPGGSLRLSCAASGFTFSSYSIHWVRQAPGKGLEWVA

SISSSSGYTSYADSVKGRFTISADTSKNTAYLQMNSLRAEDTAVYYCAR

MNWSHYAMDYWGQGTLVTVSS
(Bolded CDR sequences are disclosed as SEQ ID NOS
206, 220, and 247, respectively, in order of
appearance)

AMRA311-16
V_L:
(SEQ ID NO: 68)
DIQMTQSPSSLSASVGDRVTITCRASQSVSSAVAWYQQKPGKAPKLLIY

SASSLYSGVPSRFSGSRSGTDFTLTISSLQPEDFATYYCQQSSSSLITF

GQGTKVEIKRTV
(Bolded CDR sequences are disclosed as SEQ ID NOS
166, 167, and 180, respectively, in order of
appearance)

V_H:
(SEQ ID NO: 69)
EVQLVESGGGLVQPGGSLRLSCAASGFTISSSSIHWVRQAPGKGLEWVA

YISSYSGYTYYADSVKGRFTISADTSKNTAYLQMNSLRAEDTAVYYCAR

YWYGHYHSYFGLDYWGQGTLVTVSS
(Bolded CDR sequences are disclosed as SEQ ID NOS
215, 248, and 249, respectively, in order of
appearance)

AMRA311-17
V_L:
(SEQ ID NO: 70)
DIQMTQSPSSLSASVGDRVTITCRASQSVSSAVAWYQQKPGKAPKLLIY

SASSLYSGVPSRFSGSRSGTDFTLTISSLQPEDFATYYCQQSSSSLITF

GQGTKVEIKRTV
(Bolded CDR sequences are disclosed as SEQ ID NOS
166, 167, and 180, respectively, in order of
appearance)

V_H:
(SEQ ID NO: 71)
EVQLVESGGGLVQPGGSLRLSCAASGFTISSSSIHWVRQAPGKGLEWVA

SISSYSGSTYYADSVKGRFTISADTSKNTAYLQMNSLRAEDTAVYYCAR

YPYGSHVYTGLDYWGQGTLVTVSS
(Bolded CDR sequences are disclosed as SEQ ID NOS
215, 250, and 251, respectively, in order of
appearance)

-continued

AMRA311-18
$V_L$:
(SEQ ID NO: 72)
DIQMTQSPSSLSASVGDRVTITCRASQSVSSAVAWYQQKPGKAPKLLIY

SASSLYSGVPSRFSGSRSGTDFTLTISSLQPEDFATYYCQQWNWADYLV

TFGQGTKVEIKRTV
(Bolded CDR sequences are disclosed as SEQ ID NOS 166, 167, and 252, respectively, in order of appearance)

$V_H$:
(SEQ ID NO: 73)
EVQLVESGGGLVQPGGSLRLSCAASGFTISSSSIHWVRQAPGKGLEWVA

SIYSSSGSTSYADSVKGRFTISADTSKNTAYLQMNSLRAEDTAVYYCAR

VYSSRYWGWGVAFDYWGQGTLVTVSS
(Bolded CDR sequences are disclosed as SEQ ID NOS 215, 253, and 254, respectively, in order of appearance)

AMRA311-19
$V_L$:
(SEQ ID NO: 74)
DIQMTQSPSSLSASVGDRVTITCRASQSVSSAVAWYQQKPGKAPKLLIY

SASSLYSGVPSRFSGSRSGTDFTLTISSLQPEDFATYYCQQYYWYSLIT

FGQGTKVEIKRTV
(Bolded CDR sequences are disclosed as SEQ ID NOS 166, 167, and 255, respectively, in order of appearance)

$V_H$:
(SEQ ID NO: 75)
EVQLVESGGGLVQPGGSLRLSCAASGFTVYSSSIHWVRQAPGKGLEWVA

YIYSSSGYTSYADSVKGRFTISADTSKNTAYLQMNSLRAEDTAVYYCAR

RSFPQWYNGSYTPWPAMDYWGQGTLVTVSS
(Bolded CDR sequences are disclosed as SEQ ID NOS 215, 225, and 256, respectively, in order of appearance)

AMRA311-20
$V_L$:
(SEQ ID NO: 76)
DIQMTQSPSSLSASVGDRVTITCRASQSVSSAVAWYQQKPGKAPKLLIY

SASSLYSGVPSRFSGSRSGTDFTLTISSLQPEDFATYYCQQYMWWPVTF

GQGTKVEIKRTV
(Bolded CDR sequences are disclosed as SEQ ID NOS 166, 167, and 257, respectively, in order of appearance)

$V_H$:
(SEQ ID NO: 77)
EVQLVESGGGLVQPGGSLRLSCAASGFTVSSSSIHWVRQAPGKGLEWVA

SIYSYSSYTSYADSVKGRFTISADTSKNTAYLQMNSLRAEDTAVYYCAR

PFYWGERYALDYWGQGTLVTVSS
(Bolded CDR sequences are disclosed as SEQ ID NOS 215, 258, and 259, respectively, in order of appearance)

Antibody clones that bind preferentially to KRAS (G12C)-AMG510 conjugate presented on HLA-A*03:01 relative to the same conjugate presented on HLA-A*11:01.

CDR residues (Kabat scheme) in bold.

AMRA3-5
$V_L$:
(SEQ ID NO: 78)
DIQMTQSPSSLSASVGDRVTITCRASQSVSSAVAWYQQKPGKAPKLLIY

SASSLYSGVPSRFSGSRSGTDFTLTISSLQPEDFATYYCQQSYSTLVTF

GQGTKVEIKRTV
(Bolded CDR sequences are disclosed as SEQ ID NOS 166, 167, and 260, respectively, in order of appearance)

$V_H$:
(SEQ ID NO: 79)
EVQLVESGGGLVQPGGSLRLSCAASGFTFYSSSIHWVRQAPGKGLEWVA

SIYSSYGSTSYADSVKGRFTISADTSKNTAYLQMNSLRAEDTAVYYCAR

IYGWSYQGWAGMDYWGQGTLVTVSS
(Bolded CDR sequences are disclosed as SEQ ID NOS 215, 261, and 262, respectively, in order of appearance)

AMRA3-6
$V_L$:
(SEQ ID NO: 80)
DIQMTQSPSSLSASVGDRVTITCRASQSVSSAVAWYQQKPGKAPKLLIY

SASSLYSGVPSRFSGSRSGTDFTLTISSLQPEDFATYYCQQSSSSLITF

GQGTKVEIKRTV
(Bolded CDR sequences are disclosed as SEQ ID NOS 166, 167, and 180, respectively, in order of appearance)

$V_H$:
(SEQ ID NO: 81)
EVQLVESGGGLVQPGGSLRLSCAASGFTISYSSIHWVRQAPGKGLEWVA

SIYPYYGSTSYADSVKGRFTISADTSKNTAYLQMNSLRAEDTAVYYCAR

GGDYYWGWYWVAMDYWGQGTLVTVSS
(Bolded CDR sequences are disclosed as SEQ ID NOS 209, 263, and 264, respectively, in order of appearance)

AMRA3-9
$V_L$:
(SEQ ID NO: 82)
DIQMTQSPSSLSASVGDRVTITCRASQSVSSAVAWYQQKPGKAPKLLIY

SASSLYSGVPSRFSGSRSGTDFTLTIXSLQPEDFATYYCQKSSSSLITF

GQGTKVEIKRTV
(Bolded CDR sequences are disclosed as SEQ ID NOS 166, 167, and 265, respectively, in order of appearance)

$V_H$:
(SEQ ID NO: 83)
EVQLVESGGGLVQPGGSLRLSCAASGFTFSSSYIHWVRQAPGKGLEWVA

SISSSYGSTSYADSVKGRFTISADTSKNTAYLQMNSLRAEDTAVYYCAR

MYYYTYPGMDYWGQGTLVTVSS
(Bolded CDR sequences are disclosed as SEQ ID NOS 173, 266, and 267, respectively, in order of appearance)

AMRA3-10
$V_L$:
(SEQ ID NO: 84)
DIQMTQSPSSLSASVGDRVTITCRASQSVSSAVAWYQQKPGKAPKLLIY

SASSLYSGVPSRFSGSRSGTDFTLTISSLQPEDFATYYCQKGSSYLLTF

GQGTKVEIKRTV
(Bolded CDR sequences are disclosed as SEQ ID NOS 166, 167, and 268, respectively, in order of appearance)

V_H:
(SEQ ID NO: 85)
EVQLVESGGGLVQPGGSLRLSCAASGFTIYSYSIHWVRQAPGKGLEWVASISPSSGYTSYADSVKGRFTISADTSKNTAYLQMNSLRAEDTAVYYCARYHYGGWSHYMSGMDYWGQGTLVTVSS
(Bolded CDR sequences are disclosed as SEQ ID NOS 206, 269, and 270, respectively, in order of appearance)

AMRA3-13
V_L:
(SEQ ID NO: 86)
DIQMTQSPSSLSASVGDRVTITCRASQSVSSAVAWYQQKPGKAPKLLIYSASSLYSGVPSRFSGSRSGTDFTLTISSLQPEDFATYYCQQNYYYHKLI TFGQGTKVEIKRTV
(Bolded CDR sequences are disclosed as SEQ ID NOS 166, 167, and 271, respectively, in order of appearance)

V_H:
(SEQ ID NO: 87)
EVQLVESGGGLVQPGGSLRLSCAASGFTFSYSSIHWVRQAPGKGLEWVASISSSYGYTSYADSVKGRFTISADTSKNTAYLQMNSLRAEDTAVYYCARGRYGGMDYWGQGTLVTVSS
(Bolded CDR sequences are disclosed as SEQ ID NOS 209, 272, and 273, respectively, in order of appearance)

AMRA3-19
V_L:
(SEQ ID NO: 88)
DIQMTQSPSSLSASVGDRVTITCRASQSVSSAVAWYQQKPGKAPKLLIYSASSLYSGVPSRFSGSRSGTDFTLTISSLQPEDFATYYCQQLSYVYKLI TFGQGTKVEIKRTV
(Bolded CDR sequences are disclosed as SEQ ID NOS 166, 167, and 274, respectively, in order of appearance)

V_H:
(SEQ ID NO: 89)
EVQLVESGGGLVQPGGSLRLSCAASGFTFSSSIHWVRQAPGKGLEWVASISSSYGYTSYADSVKGRFTISADTSKNTAYLQMNSLRAEDTAVYYCARGWYKAMDYWGQGTLVTVSS
(Bolded CDR sequences are disclosed as SEQ ID NOS 215, 272, and 275, respectively, in order of appearance)

AMRA3-24
V_L:
(SEQ ID NO: 90)
DIQMTQSPSSLSASVGDRVTITCRASQSVSSAVAWYQQKPGKAPKLLIYSASSLYSGVPSRFSGSRSGTDFTLTISSLQPEDFATYYCQQSSSSLITF GQGTKVEIKRTV
(Bolded CDR sequences are disclosed as SEQ ID NOS 166, 167, and 180, respectively, in order of appearance)

V_H:
(SEQ ID NO: 91)
EVQLVESGGGLVQPGGSLRLSCAASGFTFSYSSIHWVRQAPGKGLEWVASISSSYGSTYYADSVKGRFTISADTSKNTAYLQMNSLRAEDTAVYYCARMYYYYYPGIDYWGQGTLVTVSS
(Bolded CDR sequences are disclosed as SEQ ID NOS 209, 276, and 277, respectively, in order of appearance)

Antibody clones that bind preferentially to KRAS (G12C)-AMG510 conjugate presented on HLA-A*11:01 relative to KRAS(G12C)-AMG510 conjugate presented on HLA-A*03:01.

AMRA11-3
V_L:
(SEQ ID NO: 92)
DIQMTQSPSSLSASVGDRVTITCRASQSVSSAVAWYQQKPGKAPKLLIYSASSLYSGVPSRFSGSRSGTDFTLTISSLQPEDLATYYCQQYYYFPITF GQGTKVEIKRTV
(Bolded CDR sequences are disclosed as SEQ ID NOS 166, 167, and 278, respectively, in order of appearance)

V_H:
(SEQ ID NO: 93)
EVQLVESGGGLVQPGGSLRLSCAASGFTFSSSSIHWVRQAPGKGLEWVASISPYYGYTSYADSVKGRFTISADTSKNTAYLQMNSLRAEDTAVYYCARSPYYWYQYFYGWGLDYWGQGTLVTVSS
(Bolded CDR sequences are disclosed as SEQ ID NOS 215, 279, and 280, respectively, in order of appearance)

AMRA11-4
V_L:
(SEQ ID NO: 94)
DIQMTQSPSSLSASVGDRVTITCRASQSVSSAVAWYQQKPGKAPKLLIYSASSLYSGVPSRFSGSRSGTDFTLTISSLQPEDFATYYCQQSSSSLITF GQGTKVEIKRTV
(Bolded CDR sequences are disclosed as SEQ ID NOS 166, 167, and 180, respectively, in order of appearance)

V_H:
(SEQ ID NO: 95)
EVQLVESGGGLVQPGGSLRLSCAASGFTFSYSSIHWVRQAPGKGLEWVASISSSSGSTSYADSVKGRFTISADTSKNTAYLQMNSLRAEDTAVYYCARSPYWWNYMSAMDYWGQGTLVTVSS
(Bolded CDR sequences are disclosed as SEQ ID NOS 209, 170, and 281, respectively, in order of appearance)

AMRA11-7
V_L:
(SEQ ID NO: 96)
DIQMTQSPSSLSASVGDRVTITCRASQSVSSAVAWYQQKPGKAPKLLIYSASSLYSGVPSRFSGSRSGTDFTLTISSLQPEDFATYYCQQGWWWPFTF GQGTKVEIKRTV
(Bolded CDR sequences are disclosed as SEQ ID NOS 166, 167, and 282, respectively, in order of appearance)

V_H:
(SEQ ID NO: 97)
EVQLVESGGGLVQPGGSLRLSCAASGFTVSSYSIHWVRQAPGKGLEWVASISPYYGYTSYADSVKGRFTISADTSKNTAYLQMNSLRAEDTAVYYCARWSWQYYSGHSSWGLDYWGQGTLVTVSS
(Bolded CDR sequences are disclosed as SEQ ID NOS 206, 279, and 283, respectively, in order of appearance)

-continued

AMRA11-8
V_L:
(SEQ ID NO: 98)
DIQMTQSPSSLSASVGDRVTITCRASQSVSSAVAWYQQKPGKAPKLLIY

SASSLYSGVPSRFSGSRSGTDFTLTISSLQPEDFATYYCQQSWYFPLTF

GQGTKVEIKRTV
(Bolded CDR sequences are disclosed as SEQ ID NOS 166, 167, and 284, respectively, in order of appearance)

V_H:
(SEQ ID NO: 99)
EVQLVESGGGLVQPGGSLRLSCAASGFTVSSSSIHWVRQAPGKGLEWVA

SIYSYYGYTSYADSVKGRFTISADTSKNTAYLQMNSLRAEDTAVYYCAR

WYNEYYHDYYWDAMDYWGQGTLVTVSS
(Bolded CDR sequences are disclosed as SEQ ID NOS 215, 231, and 285, respectively, in order of appearance)

AMRA11-9
V_L:
(SEQ ID NO: 100)
DIQMTQSPSSLSASVGDRVTITCRASQSVSSAVAWYQQKPGKAPKLLIY

SASSLYSGVPSRFSGSRSGTDFTLTISSLQPEDFATYYCQQSSSSLITF

GQGTKVEIKRTV
(Bolded CDR sequences are disclosed as SEQ ID NOS 166, 167, and 180, respectively, in order of appearance)

V_H:
(SEQ ID NO: 101)
EVQLVESGGGLVQPGGSLRLSCAASGFTLYYSSIHWVRQAPGKGLEWVA

SISSSSGSTSYADSVKGRFTISADTSKNTAYLQMNSLRAEDTAVYYCAR

WMYWWSFALDYWGQGTLVTVSS
(Bolded CDR sequences are disclosed as SEQ ID NOS 209, 170, and 286, respectively, in order of appearance)

AMRA11-10
V_L:
(SEQ ID NO: 102)
DIQMTQSPSSLSASVGDRVTITCRASQSVSSAVAWYQQKPGKAPKLLIY

SASSLYSGVPSRFSGSRSGTDFTLTISSLQPEDFATYYCQQSYLWPITF

GQGTKVEIKRTV
(Bolded CDR sequences are disclosed as SEQ ID NOS 166, 167, and 287, respectively, in order of appearance)

V_H:
(SEQ ID NO: 103)
EVQLVESGGGLVQPGGSLRLSCAASGFTVSSSSIHWVRQAPGKGLEWVA

SIYSYYGYTSYADSVKGRFTISADTSKNTAYLQMNSLRAEDTAVYYCAR

WQYHYNYWYGMDYWGQGTLVTVSS
(Bolded CDR sequences are disclosed as SEQ ID NOS 215, 231, and 288, respectively, in order of appearance)

AMRA11-11
V_L:
(SEQ ID NO: 104)
DIQMTQSPSSLSASVGDRVTITCRASQSVSSAVAWYQQKPGKAPKLLIY

SASSLYSGVPSRFSGSRSGTDFTLTISSLQPEDFATYYCQQYPMSLITF

GQGTKVEIKRTV
(Bolded CDR sequences are disclosed as SEQ ID NOS 166, 167, and 289, respectively, in order of appearance)

V_H:
(SEQ ID NO: 105)
EVQLVESGGGLVQPGGSLRLSCAASGFTVSYSSIHWVRQAPGKGLEWVA

SISPYSGYTSYADSVKGRFTISADTSKNTAYLQMNSLRAEDTAVYYCAR

GYDYYAGLDYWGQGTLVTVSS
(Bolded CDR sequences are disclosed as SEQ ID NOS 209, 290, and 291, respectively, in order of appearance)

AMRA11-12
V_L:
(SEQ ID NO: 106)
DIQMTQSPSSLSASVGDRVTITCRASQSVSSAVAWYQQKPGKAPKLLIY

SASSLYSGVPSRFSGSRSGTDFTLTISSLQPEDFATYYCQQYYYFPITF

GQGTKVEIKRTV
(Bolded CDR sequences are disclosed as SEQ ID NOS 166, 167, and 278, respectively, in order of appearance)

V_H:
(SEQ ID NO: 107)
EVQLVESGGGLVQPGGSLRLSCAASGFTFSYYSIHWVRQAPGKGLEWVA

SISPYYGYTSYADSVKGRFTISADTSKNTAYLQMNSLRAEDTAVYYCAR

WESEYSGTYEDYWAGMDYWGQGTLVTVSS
(Bolded CDR sequences are disclosed as SEQ ID NOS 292, 279, and 293, respectively, in order of appearance)

AMRA11-13
V_L:
(SEQ ID NO: 108)
DIQMTQSPSSLSASVGDRVTITCRASQSVSSAVAWYQQKPGKAPKLLIY

SASSLYSGVPSRFSGSRSGTDFTLTISSLQPEDFATYYCQQYMWWPITF

GQGTKVEIKRTV
(Bolded CDR sequences are disclosed as SEQ ID NOS 166, 167, and 294, respectively, in order of appearance)

V_H:
(SEQ ID NO: 109)
EVQLVESGGGLVQPGGSLRLSCAASGFTISYSSIHWVRQAPGKGLEWVA

SISSSYSYTSYADSVKGRFTISADTSKNTAYLQMNSLRAEDTAVYYCAR

TGYWQGYLALDYWGQGTLVTVSS
(Bolded CDR sequences are disclosed as SEQ ID NOS 209, 213, and 295, respectively, in order of appearance)

AMRA11-14
V_L:
(SEQ ID NO: 110)
DIQMTQSPSSLSASVGDRVTITCRASQSVSSAVAWYQQKPGKAPKLLIY

SASSLYSGVPSRFSGSRSGTDFTLTISSLQPEDFATYYCQQSSSSLITF

GQGTKVEIKRTV
(Bolded CDR sequences are disclosed as SEQ ID NOS 166, 167, and 180, respectively, in order of appearance)

V_H:
(SEQ ID NO: 111)
EVQLVESGGGLVQPGGSLRLSCAASGFTISYSSIHWVRQAPGKGLEWVA

SISSSSGSTSYADSVKGRFTISADTSKNTAYLQMNSLRAEDTAVYYCAR

TYYYYWNSTPAMDYWGQGTLVTVSS
(Bolded CDR sequences are disclosed as SEQ ID NOS 209, 170, and 296, respectively, in order of appearance)

-continued

AMRA11-18

$V_L$:
(SEQ ID NO: 112)
DIQMTQSPSSLSASVGDRVTITCRASQSVSSAVAWYQQKPGKAPKLLIY

SASSLYSGVPSRFSGSRSGTDFTLTISSLQPEDFATYYCQQSYGYPVTF

GQGTKVEIKRTV
(Bolded CDR sequences are disclosed as SEQ ID NOS 166, 167, and 297, respectively, in order of appearance)

$V_H$:
(SEQ ID NO: 113)
EVQLVESGGGLVQPGGSLRLSCAASGFTFSSSSIHWVRQAPGKGLEWVA

SISSSYGYTSYADSVKGRFTISADTSKNTAYLQMNSLRAEDTAVYYCAR

WYNSSWYYSNWWYKGFGMDYWGQGTLVTVSS
(Bolded CDR sequences are disclosed as SEQ ID NOS 215, 272, and 298, respectively, in order of appearance)

AMRA11-20

$V_L$:
(SEQ ID NO: 114)
DIQMTQSPSSLSASVGDRVTITCRASQSVSSAVAWYQQKPGKAPKLLIY

SASSLYSGVPSRFSGSRSGTDFTLTISSLQPEDFATYYCQQYYSSLFTF

GQGTKVEIKRTV
(Bolded CDR sequences are disclosed as SEQ ID NOS 166, 167, and 299, respectively, in order of appearance)

$V_H$:
(SEQ ID NO: 115)
EVQLVESGGGLVQPGGSLRLSCAASGFTFYSSSIHWVRQAPGKGLEWVA

SISSSYGYTSYADSVKGRFTISADTSKNTAYLQMNSLRAEDTAVYYCAR

TSYTYPVYTYYGFDYWGQGTLVTVSS
(Bolded CDR sequences are disclosed as SEQ ID NOS 215, 272, and 300, respectively, in order of appearance)

AMRA11-22

$V_L$:
(SEQ ID NO: 116)
DIQMTQSPSSLSASVGDRVTITCRASQSVSSAVAWYQQKPGKAPKLLIY

SASSLYSGVPSRFSGSRSGTDFTLTISSLQPEDFATYYCQQSWYYPLTF

GQGTKVEIKRTV
(Bolded CDR sequences are disclosed as SEQ ID NOS 166, 167, and 301, respectively, in order of appearance)

$V_H$:
(SEQ ID NO: 117)
EVQLVESGGGLVQPGGSLRLSCAASGFTLYSSSIHWVRQAPGKGLEWVA

SISSSYGYTSYADSVKGRFTISADTSKNTAYLQMNSLRAEDTAVYYCAR

YRYSSWNRGAIDYWGQGTLVTVSS
(Bolded CDR sequences are disclosed as SEQ ID NOS 215, 272, and 302, respectively, in order of appearance)

AMRA11-24

$V_L$:
(SEQ ID NO: 118)
DIQMTQSPSSLSASVGDRVTITCRASQSVSSAVAWYQQKPGKAPKLLIY

SASSLYSGVPSRFSGSRSGTDFTLTISSLQPEDFATYYCQQSYWWPLTF

GQGTKVEIKRTV
(Bolded CDR sequences are disclosed as SEQ ID NOS 166, 167, and 303, respectively, in order of appearance)

-continued $V_H$:
(SEQ ID NO: 119)
EVQLVESGGGLVQPGGSLRLSCAASGFTVSSSSIHWVRQAPGKGLEWVA

SIYSYYGYTSYADSVKGRFTISADTSKNTAYLQMNSLRAEDTAVYYCAR

WSKSPWYYQGIDYWGQGTLVTVSS
(Bolded CDR sequences are disclosed as SEQ ID NOS 215, 231, and 304, respectively, in order of appearance)

Exemplary Antibody Clones Binding to BTK-Ibrutinib conjugate presented on HLA-A*01:01. CDR residues (Kabat scheme) in bold.

IBA1-4

$V_L$:
(SEQ ID NO: 120)
DIQMTQSPSSLSASVGDRVTITCRASQSVSSAVAWYQQKPGKAPKLLIY

SASSLYSGVPSRFSGSRSGTDFTLTISSLQPEDFATYYCQQYHYWASLI

TFGQGTKVEIKRTV
(Bolded CDR sequences are disclosed as SEQ ID NOS 166, 167, and 305, respectively, in order of appearance)

$V_H$:
(SEQ ID NO: 121)
EVQLVESGGGLVQPGGSLRLSCAASGFTVSSSSIHWVRQAPGKGLEWVA

SIYSYSGSTYYADSVKGRFTISADTSKNTAYLQMNSLRAEDTAVYYCAR

QYSSSYYVWPGMDYWGQGTLVTVSS
(Bolded CDR sequences are disclosed as SEQ ID NOS 215, 306, and 307, respectively, in order of appearance)

IBA1-7

$V_L$:
(SEQ ID NO: 122)
DIQMTQSPSSLSASVGDRVTITCRASQSVSSAVAWYQQKPGKAPKLLIY

SASSLYSGVPSRFSGSRSGTDFTLTISSLQPEDFATYYCQQSYWWKSLV

TFGQGTKVEIKRTV
(Bolded CDR sequences are disclosed as SEQ ID NOS 166, 167, and 308, respectively, in order of appearance)

$V_H$:
(SEQ ID NO: 123)
EVQLVESGGGLVQPGGSLRLSCAASGFTLSSSSIHWVRQAPGKGLEWVA

SISSYYGSTSYADSVKGRFTISADTSKNTAYLQMNSLRAEDTAVYYCAR

MHYSWQEYYSYDWGMDYWGQGTLVTVSS
(Bolded CDR sequences are disclosed as SEQ ID NOS 215, 244, and 309, respectively, in order of appearance)

IBA1-8

$V_L$:
(SEQ ID NO: 124)
DIQMTQSPSSLSASVGDRVTITCRASQSVSSAVAWYQQKPGKAPKLLIY

SASSLYSGVPSRFSGSRSGTDFTLTISSLQPEDFATYYCQQPYYPLITF

GQGTKVEIKRTV
(Bolded CDR sequences are disclosed as SEQ ID NOS 166, 167, and 310, respectively, in order of appearance)

-continued

V$_H$:
(SEQ ID NO: 125)
EVQLVESGGGLVQPGGSLRLSCAASGFTISYSSIHWVRQAPGKGLEWVA

SIYPSYGSTSYADSVKGRFTISADTSKNTAYLQMNSLRAEDTAVYYCAR

WQGYYQPALDYWGQGTLVTVSS
(Bolded CDR sequences are disclosed as SEQ ID NOS 209, 311, and 312, respectively, in order of appearance)

IBA1-12
V$_L$:
(SEQ ID NO: 126)
DIQMTQSPSSLSASVGDRVTITCRASQSVSSAVAWYQQKPGKAPKLLIY

SASSLYSGVPSRFSGSRSGTDFTLTISSLQPEDFATYYCQQSSKYYYPI

TFGQGTKVEIKRTV
(Bolded CDR sequences are disclosed as SEQ ID NOS 166, 167, and 313, respectively, in order of appearance)

V$_H$:
(SEQ ID NO: 127)
EVQLVESGGGLVQPGGSLRLSCAASGFTISSSSIHWVRQAPGKGLEWVA

SISPYYGYTSYADSVKGRFTISADTSKNTAYLQMNSLRAEDTAVYYCAR

WGYGWYWYGLDYWGQGTLVTVSS
(Bolded CDR sequences are disclosed as SEQ ID NOS 215, 279, and 314, respectively, in order of appearance)

IBA1-13
V$_L$:
(SEQ ID NO: 128)
DIQMTQSPSSLSASVGDRVTITCRASQSVSSAVAWYQQKPGKAPKLLIY

SASSLYSGVPSRFSGSRSGTDFTLTISSLQPEDFATYYCQQGHDMNPVT

FGQGTKVEIKRTV
(Bolded CDR sequences are disclosed as SEQ ID NOS 166, 167, and 315, respectively, in order of appearance)

V$_H$:
(SEQ ID NO: 129)
EVQLVESGGGLVQPGGSLRLSCAASGFTLSSSSIHWVRQAPGKGLEWVA

SIYSSYGYTTYADSVKGRFTISADTSKNTAYLQMNSLRAEDTAVYYCAR

YYYYWYGGMDYWGQGTLVTVSS
(Bolded CDR sequences are disclosed as SEQ ID NOS 215, 316, and 317, respectively, in order of appearance)

IBA1-19
V$_L$:
(SEQ ID NO: 130)
DIQMTQSPSSLSASVGDRVTITCRASQSVSSAVAWYQQKPGKAPKLLIY

SASSLYSGVPSRFSGSRSGTDFTLTISSLQPEDFATYYCQQSWMSDSLI

TFGQGTKVEIKRTV
(Bolded CDR sequences are disclosed as SEQ ID NOS 166, 167, and 318, respectively, in order of appearance)

V$_H$:
(SEQ ID NO: 131)
EVQLVESGGGLVQPGGSLRLSCAASGFTFSYSSIHWVRQAPGKGLEWVA

SIYPSSGYTSYADSVKGRFTISADTSKNTAYLQMNSLRAEDTAVYYCAR

GWWYWMAWDYAMDYWGQGTLVTVSS
(Bolded CDR sequences are disclosed as SEQ ID NOS 209, 319, and 320, respectively, in order of appearance)

IBA1-21
V$_L$:
(SEQ ID NO: 132)
DIQMTQSPSSLSASVGDRVTITCRASQSVSSAVAWYQQKPGKAPKLLIY

SASSLYSGVPSRFSGSRSGTDFTLTISSLQPEDFATYYCQQMQYSGWLI

TFGQGTKVEIKRTV
(Bolded CDR sequences are disclosed as SEQ ID NOS 166, 167, and 321, respectively, in order of appearance)

V$_H$:
(SEQ ID NO: 133)
EVQLVESGGGLVQPGGSLRLSCAASGFTISSSSIHWVRQAPGKGLEWVA

SISSYYGYTSYADSVKGRFTISADTSKNTAYLQMNSLRAEDTAVYYCAR

YYSYSSGYGYYDYFDWGAMDYWGQGTLVTVSS
(Bolded CDR sequences are disclosed as SEQ ID NOS 215, 322, and 323, respectively, in order of appearance)

Exemplary Antibody Clones binding to EGFR-Osimertinib conjugate presented on HLA-A*02:01. CDR residues (Kabat scheme) in bold.

OEA2-1
V$_L$:
(SEQ ID NO: 134)
DIQMTQSPSSLSASVGDRVTITCRASQSVSSAVAWYQQKPGKAPKLLIY

SASSLYSGVPSRFSGSRSGTDFTLTISSLQPEDFATYYCQQSSSSLITF

GQGTKVEIKRTV
(Bolded CDR sequences are disclosed as SEQ ID NOS 166, 167, and 180, respectively, in order of appearance)

V$_H$:
(SEQ ID NO: 135)
EVQLVESGGGLVQPGGSLRLSCAASGFTFSSSSIHWVRQAPGKGLEWVA

SISSSSGSTSYADSVKGRFTISADTSKNTAYLQMNSLRAEDTAVYYCAR

YYGYVWGGYWGWWYSKALDYWGQGTLVTVSS
(Bolded CDR sequences are disclosed as SEQ ID NOS 215, 170, and 324, respectively, in order of appearance)

OEA2-5
V$_L$:
(SEQ ID NO: 5)
DIQMTQSPSSLSASVGDRVTITCRASQSVSSAVAWYQQKPGKAPKLLIY

SASSLYSGVPSRFSGSRSGTDFTLTISSLQPEDFATYYCQQYSYWPITF

GQGTKVEIKRTV
(Bolded CDR sequences are disclosed as SEQ ID NOS 166, 167, and 172, respectively, in order of appearance)

V$_H$:
(SEQ ID NO: 6)
EVQLVESGGGLVQPGGSLRLSCAASGFTISSSYIHWVRQAPGKGLEWVA

YISPSYGSTSYADSVKGRFTISADTSKNTAYLQMNSLRAEDTAVYYCAR

EYVTMALDYWGQGTLVTVSS

-continued
(Bolded CDR sequences are disclosed as SEQ ID NOS
173, 174, and 175, respectively, in order of
appearance)

OEA2-12
$V_L$:
(SEQ ID NO: 136)
DIQMTQSPSSLSASVGDRVTITCRASQSVSSAVAWYQQKPGKAPKLLIY

SASSLYSGVPSRFSGSRSGTDFTLTISSLQPEDFATYYCQQYDWNYYLV

TFGQGTKVEIKRTV
(Bolded CDR sequences are disclosed as SEQ ID NOS
166, 167, and 325, respectively, in order of
appearance)

$V_H$:
(SEQ ID NO: 137)
EVQLVESGGGLVQPGGSLRLSCAASGFTIYSSSIHWVRQAPGKGLEWVA

SISSYYGYTSYADSVKGRFTISADTSKNTAYLQMNSLRAEDTAVYYCAR

YQYYGSLYYSQQWAMDYWGQGTLVTVSS
(Bolded CDR sequences are disclosed as SEQ ID NOS
215, 322, and 326, respectively, in order of
appearance)

OEA2-16
$V_L$:
(SEQ ID NO: 138)
DIQMTQSPSSLSASVGDRVTITCRASQSVSSAVAWYQQKPGKAPKLLIY

SASSLYSGVPSRFSGSRSGTDFTLTISSLQPEDFATYYCQQSSSSLITF

GQGTKVEIKRTV
(Bolded CDR sequences are disclosed as SEQ ID NOS
166, 167, and 180, respectively, in order of
appearance)

$V_H$:
(SEQ ID NO: 139)
EVQLVESGGGLVQPGGSLRLSCAASGFTFSSSSIHWVRQAPGKGLEWVA

SISSSSGSTSYADSVKGRFTISADTSKNTAYLQMNSLRAEDTAVYYCAR

SPSSPYFMSWGWYWQYGIDYWGQGTLVTVSS
(Bolded CDR sequences are disclosed as SEQ ID NOS
215, 170, and 327, respectively, in order of
appearance)

OEA2-21
$V_L$:
(SEQ ID NO: 140)
DIQMTQSPSSLSASVGDRVTITCRASQSVSSAVAWYQQKPGKAPKLLIY

SASSLYSGVPSRFSGSRSGTDFTLTISSLQPEDFATYYCQQSSWGGLVT

FGQGTKVEIKRTV
(Bolded CDR sequences are disclosed as SEQ ID NOS
166, 167, and 328, respectively, in order of
appearance)

$V_H$:
(SEQ ID NO: 141)
EVQLVESGGGLVQPGGSLRLSCAASGFTFSSSYIHWVRQAPGKGLEWVA

SISPSYGYTSYADSVKGRFTISADTSKNTAYLQMNSLRAEDTAVYYCAR

DMYEWWHWAIDYWGQGTLVTVSS
(Bolded CDR sequences are disclosed as SEQ ID NOS
173, 329, and 330, respectively, in order of
appearance)

OEA2-24
$V_L$:
(SEQ ID NO: 142)
DIQMTQSPSSLSASVGDRVTITCRASQSVSSAVAWYQQKPGKAPKLLIY

SASSLYSGVPSRFSGSRSGTDFTLTISSLQPEDFATYYCQQSSSSLITF

GQGTKVEIKRTV
(Bolded CDR sequences are disclosed as SEQ ID NOS
166, 167, and 180, respectively, in order of
appearance)

$V_H$:
(SEQ ID NO: 143)
EVQLVESGGGLVQPGGSLRLSCAASGFTFSSSSIHWVRQAPGKGLEWVA

SISSSSGSTSYADSVKGRFTISADTSKNTAYLQMNSLRAEDTAVYYCAR

YGHYLYYWGWGWYWSAALDYWGQGTLVTVSS
(Bolded CDR sequences are disclosed as SEQ ID NOS
215, 170, and 331, respectively, in order of
appearance)

References Related to Example 3

1. Miller K R, Koide A, Leung B, Fitzsimmons J, Yoder B, Yuan H, Jay M, Sidhu S S, Koide S, Collins E J. T cell receptor-like recognition of tumor in vivo by synthetic antibody fragment. PloS one. 2012; 7 (8): e43746. Epub 2012 Aug. 24. doi: 10.1371/journal.pone.0043746. PubMed PMID: 22916301; PMCID: 3423377.
2. Hattori T, Koide A, Panchenko T, Romero L A, Teng K W, Corrado A D, Koide S. Multiplex bead binding assays using off-the-shelf components and common flow cytometers. J Immunol Methods. 2020:112952. Epub 2020 Dec. 29. doi: 10.1016/j.jim.2020.112952. PubMed PMID: 33358997.

Example 4

This Example demonstrates single-chain Diabody (scDb) formats of Hapimmune antibodies and their effectiveness in cell killing. Data from non-limiting embodiments are presented in FIGS. 18 and 19. The results are summarized as in the brief descriptions of FIGS. 18 and 19.

To obtain the results for FIG. 18, Raji cells and T2 cells (ATCC) were cultured in RPMI supplemented with 10% fetal bovine serum (FBS) and penicillin/streptomycin. The cytotoxic effect of scDbs was measured by following the protocol published previously (ref: PMID 26813960). Briefly, Raji cells or T2 cells were stained with carboxyfluorescein succinimidyl ester (CSFE, ThermoFisher, 65-0850-84), then incubated with the final 10 μM KRAS(G12C)-AMG510 conjugate or 1 μM EGFR-Osimertinib in the presence of 10 μg/mL human beta-2 microglobulin for 4 hr. The cells were harvested using centrifugation and washed in media to remove the unbound conjugate and peptide. Peptide-drug-pulsed cells were then co-cultured with human T-cells (E:T=3:1) in the presence of single-chain Diabodies (scDbs) for 19-21 hr. After incubation, cells were harvested and washed with PBS, then stained with Fixable Viability Dye eFluor660 (ThermoFisher, 65-0864-14). After washing cells, the cells were analyzed on iQue screener (Sartorius).

To obtain the results for FIG. 19, lung cancer cell lines were cultured in RPMI supplemented with 10% fetal bovine serum (FBS) and penicillin/streptomycin. For cytotoxicity assays, 1×10⁴ cells/well were seeded in 96-well flat bottom plates and incubated at 37° C., 5% $CO_2$ for 24 hours. Media were replaced with fresh media supplemented with 100 nM AMG510 or DMSO, then the cells were incubated for 24 hours at 37° C. After incubation, cells were co-cultured with human T cells (E:T=5:1) and AMRA3-7_UCHT1 scDb in the presence of 100 IU/mL IL-2 for 24 hr at 37° C. Cell viability was assessed by using PrestoBlue™ Cell Viability Reagent (ThermoFisher, A13261). Cytotoxicity was calculated by taking the fluorescent signal of a given well, subtracting the fluorescent signal from the wells that contain only T-cells, and normalizing to the fluorescent signal from the wells without scDb.

Exemplary Single-Chain Diabody Clones Targeting Both HLA-A*03:01 RAS-AMG510 and HLA-A*11:01 RAS-AMG510

The italicized sequences represent AviTag and HisTag, respectively.

```
AMRA3-7_UCHT1_scDb
(SEQ ID NO: 144, sequence without tag disclosed as
SEQ ID NO: 161)
DIVRSDIQMTQSPSSLSASVGDRVTITCRASQSVSSAVAWYQQKPGKAPK

LLIYSASSLYSGVPSRFSGSRSGTDFTLTISSLQPEDFATYYCQQISYVY

SLITFGQGTKVEIKGGGGSEVQLQQSGPELVKPGASMKISCKASGYSFTG

YTMNWVKQSHGKNLEWMGLINPYKGVSTYNQKFKDKATLTVDKSSSTAYM

ELLSLTSEDSAVYYCARSGYYGDSDWYFDVWGQGTTLTVSSGGGGSGGGG

SGGGGSDIQMTQTTSSLSASLGDRVTISCRASQDIRNYLNWYQQKPDGTV

KLLIYYTSRLHSGVPSKFSGSGSGTDYSLTISNLEQEDIATYFCQQGNTL

PWTFAGGTKLEIKGGGGSEVQLVESGGGLVQPGGSLRLSCAASGFTFSSY

SIHWVRQAPGKGLEWVASIYSSYGYTSYADSVKGRFTISADTSKNTAYLQ

MNSLRAEDTAVYYCARGGWYPAMDYWGQGTLVTVSSLEGGGGLNDIFEAQ

KIEWHESRHHHHHH

AMRA311-16_UCHT1_scDb
(SEQ ID NO: 145, sequence without tag disclosed as
SEQ ID NO: 162)
DIVRSDIQMTQSPSSLSASVGDRVTITCRASQSVSSAVAWYQQKPGKAPK

LLIYSASSLYSGVPSRFSGSRSGTDFTLTISSLQPEDFATYYCQQSSSSL

ITFGQGTKVEIKGGGGSEVQLQQSGPELVKPGASMKISCKASGYSFTGYT

MNWVKQSHGKNLEWMGLINPYKGVSTYNQKFKDKATLTVDKSSSTAYMEL

LSLTSEDSAVYYCARSGYYGDSDWYFDVWGQGTTLTVSSGGGGSGGGGSG

GGGSDIQMTQTTSSLSASLGDRVTISCRASQDIRNYLNWYQQKPDGTVKL

LIYYTSRLHSGVPSKFSGSGSGTDYSLTISNLEQEDIATYFCQQGNTLPW

TFAGGTKLEIKGGGGSEVQLVESGGGLVQPGGSLRLSCAASGFTISSSSI

HWVRQAPGKGLEWVAYISSYSGYTYYADSVKGRFTISADTSKNTAYLQMN

SLRAEDTAVYYCARYWYGHYHSYFGLDYWGQGTLVTVSSLEGGGGLNDIF

EAQKIEWHESRHHHHHH

Exemplary single-chain Diabody Clones Targeting
HLA-A*02:01_EGFR-Osimertinib
The italicized sequences represent AviTag and
HisTag, respectively.
OEA2-5_UCHT1_scDb
(SEQ ID NO: 146, sequence without tag disclosed as
SEQ ID NO: 163)
DIVRSDIQMTQSPSSLSASVGDRVTITCRASQSVSSAVAWYQQKPGKAPK

LLIYSASSLYSGVPSRFSGSRSGTDFTLTISSLQPEDFATYYCQQYSYWP

ITFGQGTKVEIKGGGGSEVQLQQSGPELVKPGASMKISCKASGYSFTGYT

MNWVKQSHGKNLEWMGLINPYKGVSTYNQKFKDKATLTVDKSSSTAYMEL

LSLTSEDSAVYYCARSGYYGDSDWYFDVWGQGTTLTVSSGGGGSGGGGSG

GGGSDIQMTQTTSSLSASLGDRVTISCRASQDIRNYLNWYQQKPDGTVKL

LIYYTSRLHSGVPSKFSGSGSGTDYSLTISNLEQEDIATYFCQQGNTLPW

TFAGGTKLEIKGGGGSEVQLVESGGGLVQPGGSLRLSCAASGFTISSSYI

HWVRQAPGKGLEWVAYISPSYGSTSYADSVKGRFTISADTSKNTAYLQMN

SLRAEDTAVYYCAREYVTMALDYWGQGTLVTVSSLEGGGGLNDIFEAQKI

EWHESRHHHHHH

OEA2-21_UCHT1_scDb
(SEQ ID NO: 147, sequence without tag disclosed as
SEQ ID NO: 164)
DIVRSDIQMTQSPSSLSASVGDRVTITCRASQSVSSAVAWYQQKPGKAPK

LLIYSASSLYSGVPSRFSGSRSGTDFTLTISSLQPEDFATYYCQQSSWGG

LVTFGQGTKVEIKGGGGSEVQLQQSGPELVKPGASMKISCKASGYSFTGY

TMNWVKQSHGKNLEWMGLINPYKGVSTYNQKFKDKATLTVDKSSSTAYME

LLSLTSEDSAVYYCARSGYYGDSDWYFDVWGQGTTLTVSSGGGGSGGGGS

GGGGSDIQMTQTTSSLSASLGDRVTISCRASQDIRNYLNWYQQKPDGTVK

LLIYYTSRLHSGVPSKFSGSGSGTDYSLTISNLEQEDIATYFCQQGNTLP

WTFAGGTKLEIKGGGGSEVQLVESGGGLVQPGGSLRLSCAASGFTFSSSY

IHWVRQAPGKGLEWVASISPSYGYTSYADSVKGRFTISADTSKNTAYLQM

NSLRAEDTAVYYCARDMYEWWHWAIDYWGQGTLVTVSSLEGGGGLNDIFE

AQKIEWHESRHHHHHH
```

Example 5

This Example demonstrates scDb and 2+1 CrossMab antibodies constructed with the AMRA3-7 clone and their effectiveness in cell killing. Data from non-limiting embodiments are presented in FIGS. 21-22.

Figure 21:
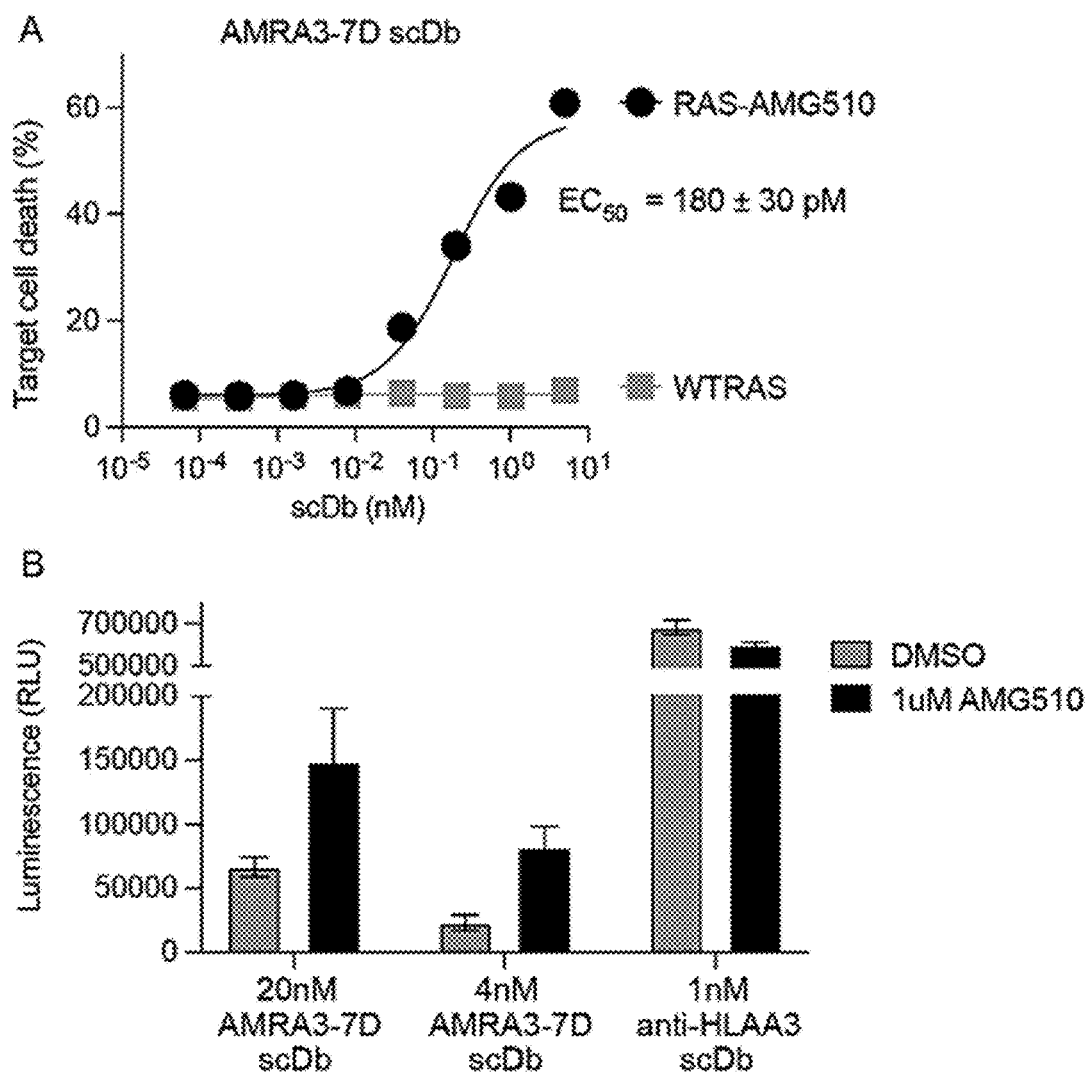
FIG. 21. Graphs showing cell killing effects of AMRA3-7D scDb. (A) Dose-dependent cell killing effect of AMRA3-7D scDb tested with Raji cells that were first pulsed with AMG510 conjugated to a peptide corresponding to a fragment of KRAS(G12C) or a control peptide corresponding to KRAS(wild type). (B) Cell killing effect of AMRA3-7D scDb tested against H2122 non-small cell lung cancer cell line treated with AMG510 or DMSO only (negative control).
Figure 22:
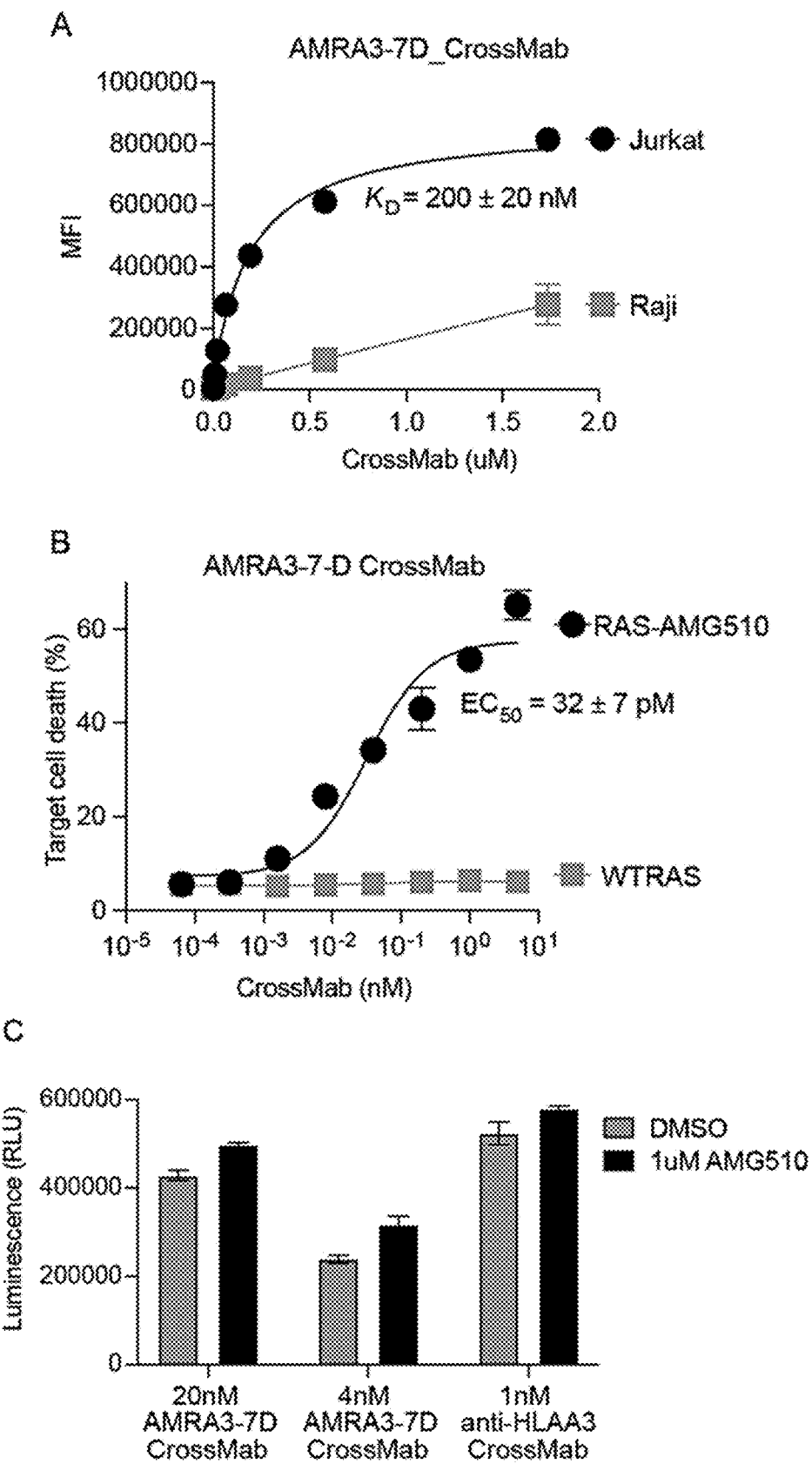
FIG. 22. Cell binding and killing effects of AMRA3-7D CrossMab. (A) Binding of AMRA3-7D to Jurkat cells, which express CD3 and to Raji cells, which do not express CD3. (B) Dose-dependent cell killing effect of AMRA3-7D CrossMab tested with Raji cells that were first pulsed with AMG510 conjugated to a peptide corresponding to a fragment of KRAS(G12C) or a control peptide, corresponding to KRAS(wild type). (C) Cell killing effect of AMRA3-7D CrossMab tested with H2122 non-small cell lung cancer cell line treated with AMG510 or DMSO only (negative control).

To obtain the results for FIG. 21 (A) and FIG. 22 (B), Raji cells (ATCC) were cultured in RPMI supplemented with 10% fetal bovine serum (FBS) and penicillin/streptomycin. The cytotoxic effects of scDb and CrossMab were measured by following the protocol published previously (ref: PMID 26813960). Briefly, Raji cells were stained with carboxyfluorescein succinimidyl ester (CSFE, ThermoFisher, 65-0850-84), then incubated with 10 μM KRAS(G12C)-AMG510 conjugate or 10 μM KRAS(WT) peptide (final concentrations) in the presence of 10 μg/mL human beta-2 microglobulin for 4 hr. The cells were harvested by centrifugation and washed in media to remove the unbound conjugate and peptide. Peptide-drug-pulsed cells were then co-cultured with human T-cells (E:T=3:1) in the presence of scDb or CrossMab for 19 hr. After incubation, cells were harvested and washed with PBS, then stained with Fixable Viability Dye eFluor660 (ThermoFisher, 65-0864-14). After washing again, cells were analyzed on iQue screener (Satorius).

To obtain the results for FIGS. 21 (B) and 22 (C), H2122 cells (ATCC) were cultured in RPMI supplemented with 10% fetal bovine serum (FBS) and penicillin/streptomycin. For cytotoxicity assays, $5 \times 10^3$ cells/well were seeded in 96-well flat bottom plates in the presence of 1 mM AMG510 or DMSO and 5 μg/mL human beta-2 microglobulin, and then were incubated at 37° C., 5% $CO_2$ for 48 hours. After incubation, cells were co-cultured with human T cells (E:T=10:1) and AMRA3-7D scDb or CrossMab in the presence of 10 ng/ml IL7 and IL15 for 24 hr at 37° C. Dead cells were measured by using CytoTox-Glo cytotoxic assay (Promega, G9290). The luminescent signal of a given well was calculated by subtracting the signal from wells that contain H2122 and T-cells without scDb or CrossMab constructs.

To obtain the results for FIG. 22 (A), Jurkat and Raji cells (ATCC) were cultured in RPMI supplemented with 10% fetal bovine serum (FBS) and penicillin/streptomycin. Cells were washed twice with PBS, then incubated with AMRA3-7D CrossMab at 4° C. for 30 min. After washing three times with PBS containing 1% BSA (PBS/BSA), cells were stained with Alexa647 Goat Anti-Human IgG Fc (Jackson ImmunoResearch, 109-605-098). After incubation, cells were washed three times with PBS/BSA and analyzed on iQue screener (Sartorius).

```
AMRA3-7D_UCHT1_scDb
(SEQ ID NO: 148, sequence without tag disclosed as
SEQ ID NO: 165)
DIVRSDIQMTQSPSSLSASVGDRVTITCRASQSVSSAVAWYQQKPGKAPK

LLIYSASSLYSGVPSRFSGSRSGTDFTLTISSLQPEDFATYYC**QQISYVK

KLIT**FGQGTKVEIKGGGGSEVQLQQSGPELVKPGASMKISCKASGYSFTG

YTMNWVKQSHGKNLEWMGLINPYKGVSTYNQKFKDKATLTVDKSSSTAYM

ELLSLTSEDSAVYYCARSGYYGDSDWYFDVWGQGTTLTVSSGGGGSGGGG

SGGGGSDIQMTQTTSSLSASLGDRVTISCRASQDIRNYLNWYQQKPDGTV

KLLIYYTSRLHSGVPSKFSGSGSGTDYSLTISNLEQEDIATYFCQQGNTL

PWTFAGGTKLEIKGGGGSEVQLVESGGGLVQPGGSLRLSCAASGFTFS**DY

SIHWVRQAPGKGLEWVASISSSSGSTSYADSVKGRFTISADTSKNTAYLQ

MNSLRAEDTAVYYCARGGWYPAMDYWGQGTLVTVSSLEGGGGLNDIFEAQ

KIEWHESRHHHHHH
(Bolded CDR sequences are disclosed as SEQ ID NOS
166, 167, 168, 169, 170, and 171, respectively,
in order of appearance)

AMRA3-7D_CrossMab
>Chain A. QMY30735.1
                                        (SEQ ID NO: 149)
EVQLLESGGGLVQPGGSLRLSCAASGFTFSTYAMNWVRQAPGKGLEWVSR

IRSKYNNYATYYADSVKGRFTISRDDSKNTLYLQMNSLRAEDTAVYYCVR

HGNFGNSYVSWFAYWGQGTLVTVSSASVAAPSVFIFPPSDEQLKSGTASV

VCLLNNFYPREAKVQWKVDNALQSGNSQESVTEQDSKDSTYSLSSTLTLS

KADYEKHKVYACEVTHQGLSSPVTKSFNRGEC

>Chain B.
                                        (SEQ ID NO: 150)
EVQLVESGGGLVQPGGSLRLSCAASGFTFSDYSIHWVRQAPGKGLEWVAS

ISSSSGSTSYADSVKGRFTISADTSKNTAYLQMNSLRAEDTAVYYCARGG

WYPAMDYWGQGTLVTVSSASTKGPSVFPLAPSSKSTSGGTAALGCLVEDY

FPEPVTVSWNSGALTSGVHTFPAVLQSSGLYSLSSVVTVPSSSLGTQTYI

CNVNHKPSNTKVDEKVEPKSCDGGGGSGGGGSQAVVTQEPSLTVSPGGTV

TLTCGSSTGAVTTSNYANWVQEKPGQAFRGLIGGTNKRAPGTPARFSGSL

LGGKAALTLSGAQPEDEAEYYCALWYSNLWVFGGGTKLTVLSSASTKGPS

VFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTH

TCPPCPAPEAAGGPSVFLFPPKPKDTLMISRTPEVTCVVVDVSHEDPEVK

FNWYVDGVEVHNAKTKPREEQYNSTYRVVSVLTVLHQDWLNGKEYKCKVS

NKALGAPIEKTISKAKGQPREPQVYTLPPCRDELTKNQVSLWCLVKGFYP

SDIAVEWESNGQPENNYKTTPPVLDSDGSFFLYSKLTVDKSRWQQGNVFS

CSVMHEALHNHYTQKSLSLSP

>Chain C.
                                        (SEQ ID NO: 151)
EVQLVESGGGLVQPGGSLRLSCAASGFTFSDYSIHWVRQAPGKGLEWVAS

ISSSSGSTSYADSVKGRFTISADTSKNTAYLQMNSLRAEDTAVYYCARGG

WYPAMDYWGQGTLVTVSSASTKGPSVFPLAPSSKSTSGGTAALGCLVEDY

FPEPVTVSWNSGALTSGVHTFPAVLQSSGLYSLSSVVTVPSSSLGTQTYI

CNVNHKPSNTKVDEKVEPKSCDKTHTCPPCPAPEAAGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALGAPIEKTISKAKGQPREPQVC

TLPPSRDELTKNQVSLSCAVKGFYPSDIAVEWESNGQPENNYKTTPPVLD

SDGSFFLVSKLTVDKSRWQQGNVFSCSVMHEALHNHYTQKSLSLSP

>Chain D.
                                        (SEQ ID NO: 152)
DIQMTQSPSSLSASVGDRVTITCRASQSVSSAVAWYQQKPGKAPKLLIYS

ASSLYSGVPSRFSGSRSGTDFTLTISSLQPEDFATYYCQQISYVKKLITF

GQGTKVEIKRTVAAPSVFIFPPSDRKLKSGTASVVCLLNNFYPREAKVQW

KVDNALQSGNSQESVTEQDSKDSTYSLSSTLTLSKADYEKHKVYACEVTH

QGLSSPVTKSFNRGEC
```

FIG. 21 shows the cytotoxic effect of AMRA3-7D in the single-chain Diabody (scDb) format. (A) Raji cells were first pulsed with AMG510 conjugated to a peptide corresponding to a fragment of KRAS(G12C) or a control peptide corresponding to KRAS(wild type). Pulsed cells were co-cultured with human T cells (Effector:Target=3:1) in the presence of scDb at the indicated concentrations. After incubation for 17 hours, dead cells were stained and detected by flow cytometry. (B) H2122 cells were first incubated with AMG510 or DMSO. The cells were then co-cultured with human T cells (Effector:Target=10:1) in the presence of scDb at the indicated concentrations. After incubation, dead cells were measured by detecting a distinct intracellular protease activity released from membrane-compromised cells. Data shown here are from triplicate measurements. Error bars indicate the s.d. Where error bars are not visible, the errors are smaller than the symbols. Anti-HLA-A3 is a positive control.

FIG. 22 shows the CD3 binding properties and cytotoxic effects of AMRA3-7D in the CrossMab format. (A) Binding titration curve of AMRA3-7 CrossMab to Jurkat (CD3 positive) and Raji (CD3 negative) cells. The apparent $K_D$ value is shown. Note that cells were not pulsed with any peptides. (B, C) Cytotoxic effects of AMRA3-7D CrossMab on Raji cells pulsed with an exogenous peptide-drug conjugate (B) and on H2122 cells treated with the drug (C). Methods are the same as in FIG. 22. Data shown here are from triplicate measurements. Error bars indicate the s.d. Where error bars are not visible, the errors are smaller than the symbols. Anti-HLA-A3 serves as a positive control.

Example 6

This example demonstrates deep mutational analysis of the AMR-A3-7D and OEA2-5 antibodies. Data from non-limiting embodiments is presented in FIGS. 23 and 24.

To identify mutations in CDRs of AMR-A3-7D and OEA2-5 that retain antigen binding, we performed deep mutational scanning on residues CDR-L3 and CDR-H3. In the yeast display format, each of the CDR-L3 and CDR-H3 residues were mutated to all genetically encoded amino acids using the NNK codon (N=A, T, G and C; K=G and T), one residue at a time. The resulting pool of mutants was combined, and the library was subjected to FACS using the relevant antigen, i.e., AMG510-KRAS(G12C) peptide in complex with HLA-A*03:01 for AMR-A3-7D and Osimertinib-EGFR in complex with HLA-A*02:01. We used different antigen concentrations in order to adjust the stringency of library sorting. Vectors recovered from binding-capable and binding-incapable pools were analyzed by deep sequencing on an Illumina MiSeq instrument. Mutations found in different pools were deduced from the DNA sequencing analysis.

From this analysis, the disclosure provides the following permissible mutations at each CDR position as shown in the tables below. As references, the VL and VH sequences of the parent clones are shown, with the analyzed CDR residues in bold an italics. In embodiments, the disclosure includes each mutation alone, and all combination of mutations. Thus, as evident from the Tables, the disclosure included the described CDRs with 1, 2, 3, 4, 5, 6, 7, or 8 mutations as indicated in the Tables. The disclosure includes additional amino acid chances, such as in CDR1, CDR2, and in the framework sequences.

AMRA3-7D
$V_L$:

(SEQ ID NO: 3)
DIQMTQSPSS LSASVGDRVT ITCRASQSVS SAVAWYQQKP

GKAPKLLIYS ASSLYSGVPS RFSGSRSGTD FTLTISSLQP

EDFATYYCQQ *ISYVKKLITF* GQGTKVEIKR TV
(Bolded CDR sequences are disclosed as SEQ ID NOS 166, 167, and 168, respectively, in order of appearance)

$V_H$:

(SEQ ID NO: 4)
EVQLVESGGG LVQPGGSLRL SCAASGFTFS DYSIHWVRQA

PGKGLEWVAS ISSSSGSTSY ADSVKGRFTI SADTSKNTAY

LQMNSLRAED TAVYYCAR*GG* *WYPAMDY*WGQ GTLVTVSS
(Bolded CDR sequences are disclosed as SEQ ID NOS 169, 170, and 171, respectively, in order of appearance)

TABLE A

Parental and consensus sequences disclosed as SEQ ID NOS 153-154, respectively

| Position (VL) | Parental amino acid residue | Permissible mutation | Consensus amino acid residue |
|---|---|---|---|
| 91 | I | A, L, P, S, T, V | A, I, L, P, S, T, V |
| 92 | S | K, R, T | K, R, S, T |
| 93 | Y | F | F, Y |
| 94 | V | I, R, T | I, R, T, V |
| 95 | K | A, E, H, L, M, N, Q, R, S, T, Y | A, E, H, K, L, M, N, Q, R, S, T, Y |

TABLE A-continued

Parental and consensus sequences disclosed as SEQ ID NOS 153-154, respectively

| Position (VL) | Parental amino acid residue | Permissible mutation | Consensus amino acid residue |
|---|---|---|---|
| 96 | K | R | K, R |
| 97 | L | A, C, D, E, G, H, K, M, N, P, Q, R, S, T, V, W | A, C, D, E, G, H, K, L, M, N, P, Q, R, S, T, V, W |
| 98 | I | L, V | I, L, V |

TABLE B

Parental and consensus sequences disclosed as SEQ ID NOS 155-156, respectively

| Position (VH) | Parental amino acid residue | Permissible mutation | Consensus amino acid residue |
|---|---|---|---|
| 99 | G | | G |
| 100 | G | A, C, E, H, K, L, M, N, P, Q, R, S, T, W, Y | A, C, E, G, H, K, L, M, N, P, Q, R, S, T, W, Y |
| 101 | W | G, P, R, T | G, P, R, T, W |
| 102 | Y | A, D, E, F, G, H, I, K, M, N, Q, R, S, T, W | A, D, E, F, G, H, I, K, M, N, Q, R, S, T, W, Y |
| 103 | P | A, V | A, P, V |
| 104 | A | C, G, K, L, M, Q, R, S, T, Y | A, C, G, K, L, M, Q, R, S, T, Y |

Deep Mutational Scanning of OEA2-5

$V_L$:

(SEQ ID NO: 5)
DIQMTQSPSS LSASVGDRVT ITCRASQSVS SAVAWYQQKP

GKAPKLLIYS ASSLYSGVPS RFSGSRSGTD FTLTISSLQP

EDFATYYCQQ *YSYWPIT*FGQ GTKVEIKRTV
(Bolded CDR sequences are disclosed as SEQ ID NOS 166, 167, and 172, respectively, in order of appearance)

$V_H$:

(SEQ ID NO: 6)
EVQLVESGGG LVQPGGSLRL SCAASGFTIS SSYIHWVRQA

PGKGLEWVAY ISPSYGSTSY ADSVKGRFTI SADTSKNTAY

LQMNSLRAED TAVYYCAR*EY* *VTMALDY*WGQ GTLVTVSS
(Bolded CDR sequences are disclosed as SEQ ID NOS 173, 174, and 175, respectively, in order of appearance)

TABLE C

Parental and consensus sequences disclosed as SEQ ID NOS 157-158, respectively

| Position (VH) | Parental amino acid residue | Permissible mutation | Consensus amino acid residue |
|---|---|---|---|
| 91 | Y | | Y |
| 92 | S | A | A, S |
| 93 | Y | A, C, D, E, F, G, H, I, K, L, M, N, Q, R, S, T, V, W | A, C, D, E, F, G, H, I, K, L, M, N, Q, R, S, T, V, W, Y |
| 94 | W | | W |

TABLE C-continued

Parental and consensus sequences disclosed
as SEQ ID NOS 157-158, respectively

| Position (VH) | Parental amino acid residue | Permissible mutation | Consensus amino acid residue |
|---|---|---|---|
| 95 | P |  | P |
| 96 | I | E, P | E, I, P |

TABLE D

Parental and consensus sequences disclosed
as SEQ ID NOS 159-160, respectively

| Position (VH) | Parental amino acid residue | Permissible mutation | Consensus amino acid residue |
|---|---|---|---|
| 99 | E | D | D, E |
| 100 | Y | E, F, L, Q, S, W | E, F, L, Q, S, W, Y |
| 101 | V | T, I | I, T, V |
| 102 | T | A, E, N, S | A, E, N, S, T |
| 103 | M | F, Y | F, M, Y |
| 104 | A | C, G, S, T | A, C, G, S, T |
| 105 | L | A, C, E, F, H, I, K, M, N, P, Q, S, T, V | A, C, E, F, H, I, K, L, M, N, P, Q, S, T, V |

As will be evident from the foregoing tables, in one embodiment, the binding partner comprises a light chain that comprises a complementary determining region 3 (CDR3) that comprises the sequence SEQ ID NO: 154 and a heavy chain that comprises a CDR3 that comprises the sequence of SEQ ID NO:156. In another embodiment, the binding partner the binding partner comprises a light chain that comprises a CDR3 that comprises the sequence of SEQ ID NO:158 and a heavy chain that comprises a CDR3 that comprises the sequence of SEQ ID NO:160.

FIG. 23 describes deep mutational scanning analysis of the CDR-L3 and H3 residues of AMR-A3-7D. (a) Representative flow cytometry profiles of yeast cells displaying AMRA3-7D or its deep mutational scanning library populations. Binding to 5 nM HLA-A*03:01 presenting AMG510 conjugated to the Cys residue in the peptides, VVGACGVGK (SEQ ID NO: 1), was measured. The profile of the parental antibody, AMRA3-7D, is shown on the left, and those for sorted subsets of the deep mutational scanning library are shown on the right. The library was sorted with 1, 3, and 10 nM target, referred to as conditions 1, 2 and 3, respectively, and the nonbinder pool was sorted with 50 nM target. (b) The prevalence of mutations in the sorted subsets of the deep mutational scanning library is presented in a heat map format. The number of deep sequencing reads were normalized to the total reads for each sorted pool and multiplied by 1000. Crosses indicate the wild-type amino acid.

FIG. 24 describes results from deep mutational scanning analysis of CDR-L3 and H3 residues of OEA2-5. (a) Representative flow cytometry profiles of yeast cells displaying OEA2-5 in single-chain Fv format and its deep mutational scanning library populations. Binding to 1.5 nM streptavidin tetramer saturated with biotinylated HLA-A*02:01 presenting Osimertinib conjugated to the Cys residue in the peptides, QLMPFGCLL (SEQ ID NO: 30), was measured. The profile of the parental antibody, OEA2-5, is shown on the left, and those for sorted subsets of the deep mutational scanning library are shown on the right. The library was sorted with 12.5, 2.5, and 0.5 nM target, referred to as conditions 1, 2 and 3, respectively, and the nonbinder pool was sorted with 12.5 nM target. (b) The prevalence of mutations in the sorted subsets of the deep mutational scanning library is presented in a heat map format. The number of deep sequencing reads were normalized to the total reads for each sorted pool and multiplied by 1000. Crosses indicate the wild-type amino acid.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

SEQUENCE LISTING

```
Sequence total quantity: 420
SEQ ID NO: 1         moltype = AA  length = 9
FEATURE              Location/Qualifiers
REGION               1..9
                     note = Description of Artificial Sequence: Synthetic peptide
source               1..9
                     mol_type = protein
                     organism = synthetic construct
SEQUENCE: 1
VVGACGVGK                                                                    9

SEQ ID NO: 2         moltype = AA  length = 10
FEATURE              Location/Qualifiers
REGION               1..10
                     note = Description of Artificial Sequence: Synthetic peptide
source               1..10
                     mol_type = protein
                     organism = synthetic construct
SEQUENCE: 2
VVVGACGVGK                                                                  10

SEQ ID NO: 3         moltype = AA  length = 112
FEATURE              Location/Qualifiers
REGION               1..112
                     note = Description of Artificial Sequence: Synthetic
                     polypeptide
source               1..112
```

```
                            mol_type = protein
                            organism = synthetic construct
SEQUENCE: 3
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ ISYVKKLITF GQGTKVEIKR TV           112

SEQ ID NO: 4                moltype = AA  length = 118
FEATURE                     Location/Qualifiers
REGION                      1..118
                            note = Description of Artificial Sequence: Synthetic
                             polypeptide
source                      1..118
                            mol_type = protein
                            organism = synthetic construct
SEQUENCE: 4
EVQLVESGGG LVQPGGSLRL SCAASGFTFS DYSIHWVRQA PGKGLEWVAS ISSSSGSTSY    60
ADSVKGRFTI SADTSKNTAY LQMNSLRAED TAVYYCARGG WYPAMDYWGQ GTLVTVSS    118

SEQ ID NO: 5                moltype = AA  length = 110
FEATURE                     Location/Qualifiers
REGION                      1..110
                            note = Description of Artificial Sequence: Synthetic
                             polypeptide
source                      1..110
                            mol_type = protein
                            organism = synthetic construct
SEQUENCE: 5
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ YSYWPITFGQ GTKVEIKRTV              110

SEQ ID NO: 6                moltype = AA  length = 118
FEATURE                     Location/Qualifiers
REGION                      1..118
                            note = Description of Artificial Sequence: Synthetic
                             polypeptide
source                      1..118
                            mol_type = protein
                            organism = synthetic construct
SEQUENCE: 6
EVQLVESGGG LVQPGGSLRL SCAASGFTIS SSYIHWVRQA PGKGLEWVAY ISPSYGSTSY    60
ADSVKGRFTI SADTSKNTAY LQMNSLRAED TAVYYCAREY VTMALDYWGQ GTLVTVSS    118

SEQ ID NO: 7                moltype = AA  length = 18
FEATURE                     Location/Qualifiers
source                      1..18
                            mol_type = protein
                            organism = Thosea asigna virus
SEQUENCE: 7
EGRGSLLTCG DVEENPGP                                                  18

SEQ ID NO: 8                moltype = AA  length = 17
FEATURE                     Location/Qualifiers
source                      1..17
                            mol_type = protein
                            organism = Teschovirus A
SEQUENCE: 8
ATNFSLKQAG DVENPGP                                                   17

SEQ ID NO: 9                moltype = AA  length = 19
FEATURE                     Location/Qualifiers
source                      1..19
                            mol_type = protein
                            organism = Equine rhinitis A virus
SEQUENCE: 9
QCTNYALKLA GDVESNPGP                                                 19

SEQ ID NO: 10               moltype = AA  length = 21
FEATURE                     Location/Qualifiers
source                      1..21
                            mol_type = protein
                            organism = Foot-and-mouth disease virus
SEQUENCE: 10
VKQTLNFDLK LAGDVESNPG P                                              21

SEQ ID NO: 11               moltype = AA  length = 8
FEATURE                     Location/Qualifiers
REGION                      1..8
                            note = Description of Artificial Sequence: Synthetic peptide
source                      1..8
```

```
                        mol_type = protein
                        organism = synthetic construct
SEQUENCE: 11
GGGGSAAA                                                                8

SEQ ID NO: 12           moltype = AA   length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 12
GGGGSGGGGS GGGGSGGGGS                                                  20

SEQ ID NO: 13           moltype = AA   length = 6
FEATURE                 Location/Qualifiers
REGION                  1..6
                        note = Description of Artificial Sequence: Synthetic 6xHis
                          tag
source                  1..6
                        mol_type = protein
                        organism = synthetic construct
SEQUENCE: 13
HHHHHH                                                                  6

SEQ ID NO: 14           moltype = AA   length = 107
FEATURE                 Location/Qualifiers
REGION                  1..107
                        note = Description of Artificial Sequence: Synthetic
                          polypeptide
source                  1..107
                        mol_type = protein
                        organism = synthetic construct
SEQUENCE: 14
DIQMTQSPSS LSASVGDRVT ITCRASQSVS SAVAWYQQKP GKAPKLLIYS ASSLYSGVPS       60
RFSGSRSGTD FTLTISSLQP EDFATYYCQQ DWYFPITFGQ GTKVEIK                    107

SEQ ID NO: 15           moltype = AA   length = 128
FEATURE                 Location/Qualifiers
REGION                  1..128
                        note = Description of Artificial Sequence: Synthetic
                          polypeptide
source                  1..128
                        mol_type = protein
                        organism = synthetic construct
SEQUENCE: 15
EVQLVESGGG LVQPGGSLRL SCAASGFTFS SYYIHWVRQA PGKGLEWVAS ISPSSGSTYY       60
ADSVKGRFTI SADTSKNTAY LQMNSLRAED TAVYYCARYG GRSYWQKDS YFYQHGLDYW      120
GQGTLVSS                                                              128

SEQ ID NO: 16           moltype = AA   length = 107
FEATURE                 Location/Qualifiers
REGION                  1..107
                        note = Description of Artificial Sequence: Synthetic
                          polypeptide
source                  1..107
                        mol_type = protein
                        organism = synthetic construct
SEQUENCE: 16
DIQMTQSPSS LSASVGDRVT ITCRASQSVS SAVAWYQQKP GKAPKLLIYS ASSLYSGVPS       60
RFSGSRSGTD FTLTISSLQP EDFATYYCQQ SSSSLITFGQ GTKVEIK                    107

SEQ ID NO: 17           moltype = AA   length = 125
FEATURE                 Location/Qualifiers
REGION                  1..125
                        note = Description of Artificial Sequence: Synthetic
                          polypeptide
source                  1..125
                        mol_type = protein
                        organism = synthetic construct
SEQUENCE: 17
EVQLVESGGG LVQPGGSLRL SCAASGFTFS SSSIHWVRQA PGKGLEWVAS ISSYSGYTSY       60
ADSVKGRFTI SADTSKNTAY LQMNSLRAED TAVYYCARSY SYSEFRYYYS GQGMDYWGQG     120
TLVSS                                                                 125

SEQ ID NO: 18           moltype = AA   length = 107
FEATURE                 Location/Qualifiers
REGION                  1..107
```

```
                       note = Description of Artificial Sequence: Synthetic
                        polypeptide
source                 1..107
                       mol_type = protein
                       organism = synthetic construct
SEQUENCE: 18
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SSSSLITFGQ GTKVEIK                 107

SEQ ID NO: 19          moltype = AA   length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 19
EVQLVESGGG LVQPGGSLRL SCAASGFTFS SSSIHWVRQA PGKGLEWVAS ISSSSGSTSY    60
ADSVKGRFTI SADTSKNTAY LQMNSLRAED TAVYYCARSN YGWRWHLVGM DYWGQGTLVT   120
VSS                                                                 123

SEQ ID NO: 20          moltype = AA   length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 20
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SSSSLITFGQ GTKVEIK                 107

SEQ ID NO: 21          moltype = AA   length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 21
EVQLVESGGG LVQPGGSLRL SCAASGFTFS SSSIHWVRQA PGKGLEWVAS ISSSSGSTSY    60
ADSVKGRFTI SADTSKNTAY LQMNSLRAED TAVYYCARSP YVYYWYMVGF DYWGQGTLVT   120
VSS                                                                 123

SEQ ID NO: 22          moltype = AA   length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 22
YKLVVVGACG VGKSA                                                    15

SEQ ID NO: 23          moltype = AA   length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 23
SSSSCSSSSW                                                          10

SEQ ID NO: 24          moltype = AA   length = 110
FEATURE                Location/Qualifiers
REGION                 1..110
                       note = Description of Artificial Sequence: Synthetic
                        polypeptide
source                 1..110
                       mol_type = protein
                       organism = synthetic construct
SEQUENCE: 24
QSVLIQPRSV SGSPGQSVTI SCTGTSSDVG GYNYVSWYQQ HPGKAPKLMI YDVSKRPSGV    60
PDRFSGSKSG NTASLTVSGL QAEDEADYYC GSYADTDTIV FGTGTKLTVL              110
```

```
SEQ ID NO: 25            moltype = AA   length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 25
QVQLVQSEPE VKKPGSSVKL SCKASGGTFS TDAITWVRQA PGQGLEYMGG IIPLLDSVDY    60
AQRFQGRVTV SADKSTGTAY MEVRSLGSED TAKYYCAKWS SVDTGLDYWG QGTLVTVSS    119

SEQ ID NO: 26            moltype = AA   length = 126
FEATURE                  Location/Qualifiers
REGION                   1..126
                         note = Description of Artificial Sequence: Synthetic
                          polypeptide
source                   1..126
                         mol_type = protein
                         organism = synthetic construct
SEQUENCE: 26
QVQLQESGPG LVKPSETLSL TCTVSGDSII NDPHYWGWIR QSPGKGLEWI GSTSHSGHTY    60
FNPSLKSRVS MSIDVAKNQF SLNVRSVTAA DTAVYYCARM RYYYSGTYPV YYFDYWGQGT   120
LVTVSS                                                              126

SEQ ID NO: 27            moltype = AA   length = 110
FEATURE                  Location/Qualifiers
REGION                   1..110
                         note = Description of Artificial Sequence: Synthetic
                          polypeptide
source                   1..110
                         mol_type = protein
                         organism = synthetic construct
SEQUENCE: 27
SYVLTQPPSA SGTPGQRVTI SCSGSSSNIG SNFVSWYQQL PGTAPKLLIS SNNQRPSGVP    60
DRFSGSKSDT SASLAISGLQ SEDEADYYCA AWDDSLNGPV FGGGTQLTVL              110

SEQ ID NO: 28            moltype = AA   length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 28
QVQLVQSEAE VKKPGSSVKV SCKASGGTFS RYGVSWVRQA PGQGLEWMGG IIPMFGTANY    60
AQKFQGRVTI TADESTSTAY MELRSLRSED TAVYYCARGD NSAYSDAFNI WGQGTMVTVS   120
S                                                                   121

SEQ ID NO: 29            moltype = AA   length = 9
FEATURE                  Location/Qualifiers
source                   1..9
                         mol_type = protein
                         organism = Homo sapiens
SEQUENCE: 29
VVGAGGVGK                                                             9

SEQ ID NO: 30            moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 30
QLMPFGCLL                                                             9

SEQ ID NO: 31            moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 31
YMANGCLLNY                                                           10

SEQ ID NO: 32            moltype = AA   length = 111
```

```
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 32
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SGWSYPITFG QGTKVEIKRT V            111

SEQ ID NO: 33           moltype = AA   length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 33
EVQLVESGGG LVQPGGSLRL SCAASGFTFY SSYIHWVRQA PGKGLEWVAS ISPYYGSTSY    60
ADSVKGRFTI SADTSKNTAY LQMNSLRAED TAVYYCARSS YYALDYWGQG TLVTVSS      117

SEQ ID NO: 34           moltype = AA   length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 34
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ ISYVYSLITF GQGTKVEIKR TV           112

SEQ ID NO: 35           moltype = AA   length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 35
EVQLVESGGG LVQPGGSLRL SCAASGFTFS SYSIHWVRQA PGKGLEWVAS IYSSYGYTSY    60
ADSVKGRFTI SADTSKNTAY LQMNSLRAED TAVYYCARGG WYPAMDYWGQ GTLVTVSS     118

SEQ ID NO: 36           moltype = AA   length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 36
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ ISYVKKLITF GQGTKVEIKR TV           112

SEQ ID NO: 37           moltype = AA   length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 37
EVQLVESGGG LVQPGGSLRL SCAASGFTFS SYSIHWVRQA PGKGLEWVAS IYSSYGYTSY    60
ADSVKGRFTI SADTSKNTAY LQMNSLRAED TAVYYCARGG WYPAMDYWGQ GTLVTVSS     118

SEQ ID NO: 38           moltype = AA   length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
```

```
SEQUENCE: 38
DIQMTQSPSS LSASVGDRVT ITCRASQSVS SAVAWYQQKP GKAPKLLIYS ASSLYSGVPS    60
RFSGSRSGTD FTLTISSLQP EDLATYYCQQ YQYGYNLITF GQGTKVEIKR TV           112

SEQ ID NO: 39           moltype = AA  length = 124
FEATURE                 Location/Qualifiers
REGION                  1..124
                        note = Description of Artificial Sequence: Synthetic
                        polypeptide
source                  1..124
                        mol_type = protein
                        organism = synthetic construct
SEQUENCE: 39
EVQLVESGGG LVQPGGSLRL SCAASGFTIS YSSIHWVRQA PGKGLEWVAS IYSYSGSTSY    60
ADSVKGRFTI SADTSKNTAY LQMNSLRAED TAVYYCARYS YGWVGPGWRA IDYWGQGTLV   120
TVSS                                                                124

SEQ ID NO: 40           moltype = AA  length = 112
FEATURE                 Location/Qualifiers
REGION                  1..112
                        note = Description of Artificial Sequence: Synthetic
                        polypeptide
source                  1..112
                        mol_type = protein
                        organism = synthetic construct
SEQUENCE: 40
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SSSVYKLLTF GQGTKVEIKR TV           112

SEQ ID NO: 41           moltype = AA  length = 120
FEATURE                 Location/Qualifiers
REGION                  1..120
                        note = Description of Artificial Sequence: Synthetic
                        polypeptide
source                  1..120
                        mol_type = protein
                        organism = synthetic construct
SEQUENCE: 41
EVQLVESGGG LVQPGGSLRL SCAASGFTVY YSSIHWVRQA PGKGLEWVAS ISSSYSYTSY    60
ADSVKGRFTI SADTSKNTAY LQMNSLRAED TALYYCARGG PGWYRAMDYW GQGTLVTVSS   120

SEQ ID NO: 42           moltype = AA  length = 110
FEATURE                 Location/Qualifiers
REGION                  1..110
                        note = Description of Artificial Sequence: Synthetic
                        polypeptide
source                  1..110
                        mol_type = protein
                        organism = synthetic construct
SEQUENCE: 42
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SSSSLITFGQ GTKVEIKRTV              110

SEQ ID NO: 43           moltype = AA  length = 123
FEATURE                 Location/Qualifiers
REGION                  1..123
                        note = Description of Artificial Sequence: Synthetic
                        polypeptide
source                  1..123
                        mol_type = protein
                        organism = synthetic construct
SEQUENCE: 43
EVQLVESGGG LVQPGGSLRL SCAASGFTFS SSSIHWVRQA PGKGLEWVAS ISSSSGSTSY    60
ADSVKGRFTI SADTSKNTAY LQMNSLRAED TAVYYCARGY FYYGWWAMAF DYWGQGTLVT   120
VSS                                                                 123

SEQ ID NO: 44           moltype = AA  length = 112
FEATURE                 Location/Qualifiers
REGION                  1..112
                        note = Description of Artificial Sequence: Synthetic
                        polypeptide
source                  1..112
                        mol_type = protein
                        organism = synthetic construct
SEQUENCE: 44
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SQWYEPLITF GQGTKVEIKR TV           112

SEQ ID NO: 45           moltype = AA  length = 127
```

```
FEATURE              Location/Qualifiers
REGION               1..127
                     note = Description of Artificial Sequence: Synthetic
                      polypeptide
source               1..127
                     mol_type = protein
                     organism = synthetic construct
SEQUENCE: 45
EVQLVESGGG LVQPGGSLRL SCAASGFTIY SSYIHWVRQA PGKGLEWVAS ISSSSGSTSY    60
ADSVKGRFTI SADTSKNTAY LQMNSLRAED TAVYYCARSY SYMSQWGWYQ YSGMDYWGQG   120
TLVTVSS                                                             127

SEQ ID NO: 46        moltype = AA  length = 112
FEATURE              Location/Qualifiers
REGION               1..112
                     note = Description of Artificial Sequence: Synthetic
                      polypeptide
source               1..112
                     mol_type = protein
                     organism = synthetic construct
SEQUENCE: 46
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ GSYTYRLITF GQGTKVEIKR TV           112

SEQ ID NO: 47        moltype = AA  length = 119
FEATURE              Location/Qualifiers
REGION               1..119
                     note = Description of Artificial Sequence: Synthetic
                      polypeptide
source               1..119
                     mol_type = protein
                     organism = synthetic construct
SEQUENCE: 47
EVQLVESGGG LVQPGGSLRL SCAASGFTVS YSSIHWVRQA PGKGLEWVAS ISSSSGYTSY    60
ADSVKGRFTI SADTSKNTAY LQMNSLRAED TAVYYCARYA WWAHGLDYWG QGTLVTVSS    119

SEQ ID NO: 48        moltype = AA  length = 112
FEATURE              Location/Qualifiers
REGION               1..112
                     note = Description of Artificial Sequence: Synthetic
                      polypeptide
source               1..112
                     mol_type = protein
                     organism = synthetic construct
SEQUENCE: 48
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ ASYWYNLFTF GQGTKVEIKR TV           112

SEQ ID NO: 49        moltype = AA  length = 123
FEATURE              Location/Qualifiers
REGION               1..123
                     note = Description of Artificial Sequence: Synthetic
                      polypeptide
source               1..123
                     mol_type = protein
                     organism = synthetic construct
SEQUENCE: 49
EVQLVESGGG LVQPGGSLRL SCAASGFTIS SYSIHWVRQA PGKGLEWVAS IYSSYGYTSY    60
ADSVKGRFTI SADTSKNTAY LQMNSLRAED TAVYYCARQY SMHFPWGYGM DYWGQGTLVT   120
VSS                                                                 123

SEQ ID NO: 50        moltype = AA  length = 110
FEATURE              Location/Qualifiers
REGION               1..110
                     note = Description of Artificial Sequence: Synthetic
                      polypeptide
source               1..110
                     mol_type = protein
                     organism = synthetic construct
SEQUENCE: 50
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SDMPPITFGQ GTKVEIKRTV              110

SEQ ID NO: 51        moltype = AA  length = 121
FEATURE              Location/Qualifiers
REGION               1..121
                     note = Description of Artificial Sequence: Synthetic
                      polypeptide
source               1..121
```

```
                         mol_type = protein
                         organism = synthetic construct
SEQUENCE: 51
EVQLVESGGG LVQPGGSLRL SCAASGFTFY SSSIHWVRQA PGKGLEWVAY IYSSSGYTSY   60
ADSVKGRFTI SADTSKNTAY LQMNSLRAED TAVYYCARPV NYYYQGALDY WGQGTLVTVS  120
S                                                                 121

SEQ ID NO: 52            moltype = AA  length = 110
FEATURE                  Location/Qualifiers
REGION                   1..110
                         note = Description of Artificial Sequence: Synthetic
                          polypeptide
source                   1..110
                         mol_type = protein
                         organism = synthetic construct
SEQUENCE: 52
DIQMTQSPSS LSASVGDRVT ITCRASQSVS SAVAWYQQKP GKAPKLLIYS ASSLYSGVPS   60
RFSGSRSGTD FTLTISSLQP EDFATYYCQQ YYVFPITFGQ GTKVEIKRTV            110

SEQ ID NO: 53            moltype = AA  length = 130
FEATURE                  Location/Qualifiers
REGION                   1..130
                         note = Description of Artificial Sequence: Synthetic
                          polypeptide
source                   1..130
                         mol_type = protein
                         organism = synthetic construct
SEQUENCE: 53
EVQLVESGGG LVQPGGSLRL SCAASGFTVY SSSIHWVRQA PGKGLEWVAS ISPSSGYTYY   60
ADSVKGRFTI SADTSKNTAY LQMNSLRAED TAVYYCARYH YMFEYDKGES KWGYYGFDYW  120
GQGTLVTVSS                                                        130

SEQ ID NO: 54            moltype = AA  length = 110
FEATURE                  Location/Qualifiers
REGION                   1..110
                         note = Description of Artificial Sequence: Synthetic
                          polypeptide
source                   1..110
                         mol_type = protein
                         organism = synthetic construct
SEQUENCE: 54
DIQMTQSPSS LSASVGDRVT ITCRASQSVS SAVAWYQQKP GKAPKLLIYS ASSLYSGVPS   60
RFSGSRSGTD FTLTISSLQP EDFATYYCQQ SQYFPITFGQ GTKVEIKRTV            110

SEQ ID NO: 55            moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 55
EVQLVESGGG LVQPGGSLRL SCAASGFTIS YSSIHWVRQA PGKGLEWVAS IYSYYGYTSY   60
ADSVKGRFTI SADTSKNTAY LQMNSLRAED TAVYYCARNS WSWYSGVGMD YWGQGTLVTV  120
SS                                                                122

SEQ ID NO: 56            moltype = AA  length = 110
FEATURE                  Location/Qualifiers
REGION                   1..110
                         note = Description of Artificial Sequence: Synthetic
                          polypeptide
source                   1..110
                         mol_type = protein
                         organism = synthetic construct
SEQUENCE: 56
DIQMTQSPSS LSASVGDRVT ITCRASQSVS SAVAWYQQKP GKAPKLLIYS ASSLYSGVPS   60
RFSGSRSGTD FTLTISSLQP EDFATYYCQQ SSSSLITFGQ GTKVEIKRTV            110

SEQ ID NO: 57            moltype = AA  length = 123
FEATURE                  Location/Qualifiers
REGION                   1..123
                         note = Description of Artificial Sequence: Synthetic
                          polypeptide
source                   1..123
                         mol_type = protein
                         organism = synthetic construct
SEQUENCE: 57
EVQLVESGGG LVQPGGSLRL SCAASGFTIS SSSIHWVRQA PGKGLEWVAS ISSYSSSTYY   60
```

```
ADSVKGRFTI SADTSKNTAY LQMNSLRAED TAVYYCARYP YGWGWGGSGL DYWGQGTLVT    120
VSS                                                                 123

SEQ ID NO: 58           moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 58
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ FDFQYLITFG QGTKVEIKRT V             111

SEQ ID NO: 59           moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 59
EVQLVESGGG LVQPGGSLRL SCAASGFTVY YSSIHWVRQA PGKGLEWVAS IYSYYGSTYY    60
ADSVKGRFTI SADTSKNTAY LQMNSLRAED TAVYYCARGE KWALDYWGQG TLVTVSS       117

SEQ ID NO: 60           moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 60
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ YMYYQPLITF GQGTKVEIKR TV            112

SEQ ID NO: 61           moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 61
EVQLVESGGG LVQPGGSLRL SCAASGFTVY YSSIHWVRQA PGKGLEWVAS ISSSSGSTSY    60
ADSVKGRFTI SADTSKNTAY LQMNSLRAED TAVYYCAREP YNYNWYGMDY WGQGTLVTVS    120
S                                                                   121

SEQ ID NO: 62           moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 62
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SLWWPITFGQ GTKVEIKRTV               110

SEQ ID NO: 63           moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 63
EVQLVESGGG LVQPGGSLRL SCAASGFTVS SSSIHWVRQA PGKGLEWVAS IYSYSGYTSY    60
ADSVKGRFTI SADTSKNTAY LQMNSLRAED TAVYYCARHG SYGSWWALDY WGQGTLVTVS    120
S                                                                   121

SEQ ID NO: 64           moltype = AA  length = 110
FEATURE                 Location/Qualifiers
```

```
REGION          1..110
                note = Description of Artificial Sequence: Synthetic
                 polypeptide
source          1..110
                mol_type = protein
                organism = synthetic construct
SEQUENCE: 64
DIQMTQSPSS LSASVGDRVT ITCRASQSVS SAVAWYQQKP GKAPKLLIYS ASSLYSGVPS     60
RFSGSRSGTD FTLTISSLQP EDFATYYCQQ YFYFPITFGQ GTKVEIKRTV               110

SEQ ID NO: 65           moltype = AA  length = 128
FEATURE                 Location/Qualifiers
REGION                  1..128
                        note = Description of Artificial Sequence: Synthetic
                         polypeptide
source                  1..128
                        mol_type = protein
                        organism = synthetic construct
SEQUENCE: 65
EVQLVESGGG LVQPGGSLRL SCAASGFTFY SSSIHWVRQA PGKGLEWVAS ISSYYGSTSY     60
ADSVKGRFTI SADTSKNTAY LQMNSLRAED TAVYYCARAS YYSGYGSSYP YYMGLDYWGQ    120
GTLVTVSS                                                             128

SEQ ID NO: 66           moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 66
DIQMTQSPSS LSASVGDRVT ITCRASQSVS SAVAWYQQKP GKAPKLLIYS ASSLYSGVPS     60
RFSGSRSGTD FTLTISSLQP EDFATYYCQQ GSYRNPLLTF GQGTKVEIKR TV            112

SEQ ID NO: 67           moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 67
EVQLVESGGG LVQPGGSLRL SCAASGFTFS SYSIHWVRQA PGKGLEWVAS ISSSSGYTSY     60
ADSVKGRFTI SADTSKNTAY LQMNSLRAED TAVYYCARMN WSHYAMDYWG QGTLVTVSS     119

SEQ ID NO: 68           moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 68
DIQMTQSPSS LSASVGDRVT ITCRASQSVS SAVAWYQQKP GKAPKLLIYS ASSLYSGVPS     60
RFSGSRSGTD FTLTISSLQP EDFATYYCQQ SSSSLITFGQ GTKVEIKRTV               110

SEQ ID NO: 69           moltype = AA  length = 123
FEATURE                 Location/Qualifiers
REGION                  1..123
                        note = Description of Artificial Sequence: Synthetic
                         polypeptide
source                  1..123
                        mol_type = protein
                        organism = synthetic construct
SEQUENCE: 69
EVQLVESGGG LVQPGGSLRL SCAASGFTIS SSSIHWVRQA PGKGLEWVAY ISSYSGYTYY     60
ADSVKGRFTI SADTSKNTAY LQMNSLRAED TAVYYCARYW YGHYHSYFGL DYWGQGTLVT    120
VSS                                                                  123

SEQ ID NO: 70           moltype = AA  length = 110
FEATURE                 Location/Qualifiers
REGION                  1..110
                        note = Description of Artificial Sequence: Synthetic
                         polypeptide
source                  1..110
                        mol_type = protein
```

```
                        organism = synthetic construct
SEQUENCE: 70
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SSSSLITFGQ GTKVEIKRTV              110

SEQ ID NO: 71           moltype = AA   length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 71
EVQLVESGGG LVQPGGSLRL SCAASGFTIS SSSIHWVRQA PGKGLEWVAS ISSYSGSTYY    60
ADSVKGRFTI SADTSKNTAY LQMNSLRAED TAVYYCARYP YGSHVYTGLD YWGQGTLVTV   120
SS                                                                  122

SEQ ID NO: 72           moltype = AA   length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 72
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ WNWADYLVTF GQGTKVEIKR TV           112

SEQ ID NO: 73           moltype = AA   length = 124
FEATURE                 Location/Qualifiers
REGION                  1..124
                        note = Description of Artificial Sequence: Synthetic
                         polypeptide
source                  1..124
                        mol_type = protein
                        organism = synthetic construct
SEQUENCE: 73
EVQLVESGGG LVQPGGSLRL SCAASGFTIS SSSIHWVRQA PGKGLEWVAS IYSSSGSTSY    60
ADSVKGRFTI SADTSKNTAY LQMNSLRAED TAVYYCARVY SSRYWGWGVA FDYWGQGTLV   120
TVSS                                                                124

SEQ ID NO: 74           moltype = AA   length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 74
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ YYWYSLITFG QGTKVEIKRT V            111

SEQ ID NO: 75           moltype = AA   length = 128
FEATURE                 Location/Qualifiers
REGION                  1..128
                        note = Description of Artificial Sequence: Synthetic
                         polypeptide
source                  1..128
                        mol_type = protein
                        organism = synthetic construct
SEQUENCE: 75
EVQLVESGGG LVQPGGSLRL SCAASGFTVY SSSIHWVRQA PGKGLEWVAY IYSSSGYTSY    60
ADSVKGRFTI SADTSKNTAY LQMNSLRAED TAVYYCARRS FPQWYNGSYT PWPAMDYWGQ   120
GTLVTVSS                                                            128

SEQ ID NO: 76           moltype = AA   length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 76
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ YMWWPVTFGQ GTKVEIKRTV              110
```

```
SEQ ID NO: 77              moltype = AA   length = 121
FEATURE                    Location/Qualifiers
REGION                     1..121
                           note = Description of Artificial Sequence: Synthetic
                            polypeptide
source                     1..121
                           mol_type = protein
                           organism = synthetic construct
SEQUENCE: 77
EVQLVESGGG LVQPGGSLRL SCAASGFTVS SSSIHWVRQA PGKGLEWVAS IYSYSSYTSY    60
ADSVKGRFTI SADTSKNTAY LQMNSLRAED TAVYYCARPF YWGERYALDY WGQGTLVTVS   120
S                                                                   121

SEQ ID NO: 78              moltype = AA   length = 110
FEATURE                    Location/Qualifiers
REGION                     1..110
                           note = Description of Artificial Sequence: Synthetic
                            polypeptide
source                     1..110
                           mol_type = protein
                           organism = synthetic construct
SEQUENCE: 78
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SYSTLVTFGQ GTKVEIKRTV              110

SEQ ID NO: 79              moltype = AA   length = 123
FEATURE                    Location/Qualifiers
REGION                     1..123
                           note = Description of Artificial Sequence: Synthetic
                            polypeptide
source                     1..123
                           mol_type = protein
                           organism = synthetic construct
SEQUENCE: 79
EVQLVESGGG LVQPGGSLRL SCAASGFTFY SSSIHWVRQA PGKGLEWVAS IYSSYGSTSY    60
ADSVKGRFTI SADTSKNTAY LQMNSLRAED TAVYYCARIY GWSYQGWAGM DYWGQGTLVT   120
VSS                                                                 123

SEQ ID NO: 80              moltype = AA   length = 110
FEATURE                    Location/Qualifiers
REGION                     1..110
                           note = Description of Artificial Sequence: Synthetic
                            polypeptide
source                     1..110
                           mol_type = protein
                           organism = synthetic construct
SEQUENCE: 80
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SSSSLITFGQ GTKVEIKRTV              110

SEQ ID NO: 81              moltype = AA   length = 124
FEATURE                    Location/Qualifiers
REGION                     1..124
                           note = Description of Artificial Sequence: Synthetic
                            polypeptide
source                     1..124
                           mol_type = protein
                           organism = synthetic construct
SEQUENCE: 81
EVQLVESGGG LVQPGGSLRL SCAASGFTIS YSSIHWVRQA PGKGLEWVAS IYPYYGSTSY    60
ADSVKGRFTI SADTSKNTAY LQMNSLRAED TAVYYCARGG DYYWGWYWVA MDYWGQGTLV   120
TVSS                                                                124

SEQ ID NO: 82              moltype = AA   length = 110
FEATURE                    Location/Qualifiers
REGION                     1..110
                           note = Description of Artificial Sequence: Synthetic
                            polypeptide
VARIANT                    76
                           note = MOD_RES - Any amino acid
source                     1..110
                           mol_type = protein
                           organism = synthetic construct
SEQUENCE: 82
DIQMTQSPSS LSASVGDRVT ITCRASQSVS SAVAWYQQKP GKAPKLLIYS ASSLYSGVPS    60
RFSGSRSGTD FTLTIXSLQP EDFATYYCQK SSSSLITFGQ GTKVEIKRTV              110

SEQ ID NO: 83              moltype = AA   length = 120
```

```
FEATURE              Location/Qualifiers
REGION               1..120
                     note = Description of Artificial Sequence: Synthetic
                      polypeptide
source               1..120
                     mol_type = protein
                     organism = synthetic construct
SEQUENCE: 83
EVQLVESGGG LVQPGGSLRL SCAASGFTFS SSYIHWVRQA PGKGLEWVAS ISSSYGSTSY   60
ADSVKGRFTI SADTSKNTAY LQMNSLRAED TAVYYCARMY YYTYPGMDYW GQGTLVTVSS  120

SEQ ID NO: 84        moltype = AA  length = 110
FEATURE              Location/Qualifiers
REGION               1..110
                     note = Description of Artificial Sequence: Synthetic
                      polypeptide
source               1..110
                     mol_type = protein
                     organism = synthetic construct
SEQUENCE: 84
DIQMTQSPSS LSASVGDRVT ITCRASQSVS SAVAWYQQKP GKAPKLLIYS ASSLYSGVPS   60
RFSGSRSGTD FTLTISSLQP EDFATYYCQK GSSYLLTFGQ GTKVEIKRTV             110

SEQ ID NO: 85        moltype = AA  length = 124
FEATURE              Location/Qualifiers
REGION               1..124
                     note = Description of Artificial Sequence: Synthetic
                      polypeptide
source               1..124
                     mol_type = protein
                     organism = synthetic construct
SEQUENCE: 85
EVQLVESGGG LVQPGGSLRL SCAASGFTIY SYSIHWVRQA PGKGLEWVAS ISPSSGYTSY   60
ADSVKGRFTI SADTSKNTAY LQMNSLRAED TAVYYCARYH YGGWSHYMSG MDYWGQGTLV  120
TVSS                                                              124

SEQ ID NO: 86        moltype = AA  length = 112
FEATURE              Location/Qualifiers
REGION               1..112
                     note = Description of Artificial Sequence: Synthetic
                      polypeptide
source               1..112
                     mol_type = protein
                     organism = synthetic construct
SEQUENCE: 86
DIQMTQSPSS LSASVGDRVT ITCRASQSVS SAVAWYQQKP GKAPKLLIYS ASSLYSGVPS   60
RFSGSRSGTD FTLTISSLQP EDFATYYCQQ NYYYHKLITF GQGTKVEIKR TV          112

SEQ ID NO: 87        moltype = AA  length = 117
FEATURE              Location/Qualifiers
REGION               1..117
                     note = Description of Artificial Sequence: Synthetic
                      polypeptide
source               1..117
                     mol_type = protein
                     organism = synthetic construct
SEQUENCE: 87
EVQLVESGGG LVQPGGSLRL SCAASGFTFS YSSIHWVRQA PGKGLEWVAS ISSSYGYTSY   60
ADSVKGRFTI SADTSKNTAY LQMNSLRAED TAVYYCARGR YGGMDYWGQG TLVTVSS     117

SEQ ID NO: 88        moltype = AA  length = 112
FEATURE              Location/Qualifiers
REGION               1..112
                     note = Description of Artificial Sequence: Synthetic
                      polypeptide
source               1..112
                     mol_type = protein
                     organism = synthetic construct
SEQUENCE: 88
DIQMTQSPSS LSASVGDRVT ITCRASQSVS SAVAWYQQKP GKAPKLLIYS ASSLYSGVPS   60
RFSGSRSGTD FTLTISSLQP EDFATYYCQQ LSYVYKLITF GQGTKVEIKR TV          112

SEQ ID NO: 89        moltype = AA  length = 117
FEATURE              Location/Qualifiers
REGION               1..117
                     note = Description of Artificial Sequence: Synthetic
                      polypeptide
source               1..117
                     mol_type = protein
```

```
                             -continued
                        organism = synthetic construct
SEQUENCE: 89
EVQLVESGGG LVQPGGSLRL SCAASGFTFY SSSIHWVRQA PGKGLEWVAS ISSSYGYTSY    60
ADSVKGRFTI SADTSKNTAY LQMNSLRAED TAVYYCARGW YKAMDYWGQG TLVTVSS     117

SEQ ID NO: 90           moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 90
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SSSSLITFGQ GTKVEIKRTV              110

SEQ ID NO: 91           moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 91
EVQLVESGGG LVQPGGSLRL SCAASGFTFS YSSIHWVRQA PGKGLEWVAS ISSSYGSTYY    60
ADSVKGRFTI SADTSKNTAY LQMNSLRAED TAVYYCARMY YYYPGIDYW GQGTLVTVSS   120

SEQ ID NO: 92           moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 92
DIQMTQSPSS LSASVGDRVT ITCRASQSVS SAVAWYQQKP GKAPKLLIYS ASSLYSGVPS    60
RFSGSRSGTD FTLTISSLQP EDLATYYCQQ YYYFPITFGQ GTKVEIKRTV              110

SEQ ID NO: 93           moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 93
EVQLVESGGG LVQPGGSLRL SCAASGFTFS SSSIHWVRQA PGKGLEWVAS ISPYYGYTSY    60
ADSVKGRFTI SADTSKNTAY LQMNSLRAED TAVYYCARSP YYWYQYFYGW GLDYWGQGTL   120
VTVSS                                                               125

SEQ ID NO: 94           moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 94
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SSSSLITFGQ GTKVEIKRTV              110

SEQ ID NO: 95           moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 95
EVQLVESGGG LVQPGGSLRL SCAASGFTFS YSSIHWVRQA PGKGLEWVAS ISSSGSTSY    60
ADSVKGRFTI SADTSKNTAY LQMNSLRAED TAVYYCARSP YWWNYMSAMD YWGQGTLVTV  120
SS                                                                 122
```

```
SEQ ID NO: 96            moltype = AA   length = 110
FEATURE                  Location/Qualifiers
REGION                   1..110
                         note = Description of Artificial Sequence: Synthetic
                         polypeptide
source                   1..110
                         mol_type = protein
                         organism = synthetic construct
SEQUENCE: 96
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ GWWWPFTFGQ GTKVEIKRTV              110

SEQ ID NO: 97            moltype = AA   length = 125
FEATURE                  Location/Qualifiers
REGION                   1..125
                         note = Description of Artificial Sequence: Synthetic
                         polypeptide
source                   1..125
                         mol_type = protein
                         organism = synthetic construct
SEQUENCE: 97
EVQLVESGGG LVQPGGSLRL SCAASGFTVS SYSIHWVRQA PGKGLEWVAS ISPYYGYTSY    60
ADSVKGRFTI SADTSKNTAY LQMNSLRAED TAVYYCARWS WQYYSGHSSW GLDYWGQGTL   120
VTVSS                                                               125

SEQ ID NO: 98            moltype = AA   length = 110
FEATURE                  Location/Qualifiers
REGION                   1..110
                         note = Description of Artificial Sequence: Synthetic
                         polypeptide
source                   1..110
                         mol_type = protein
                         organism = synthetic construct
SEQUENCE: 98
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SWYFPLTFGQ GTKVEIKRTV              110

SEQ ID NO: 99            moltype = AA   length = 125
FEATURE                  Location/Qualifiers
REGION                   1..125
                         note = Description of Artificial Sequence: Synthetic
                         polypeptide
source                   1..125
                         mol_type = protein
                         organism = synthetic construct
SEQUENCE: 99
EVQLVESGGG LVQPGGSLRL SCAASGFTVS SSSIHWVRQA PGKGLEWVAS IYSYYGYTSY    60
ADSVKGRFTI SADTSKNTAY LQMNSLRAED TAVYYCARWY NEYYHDYYWD AMDYWGQGTL   120
VTVSS                                                               125

SEQ ID NO: 100           moltype = AA   length = 110
FEATURE                  Location/Qualifiers
REGION                   1..110
                         note = Description of Artificial Sequence: Synthetic
                         polypeptide
source                   1..110
                         mol_type = protein
                         organism = synthetic construct
SEQUENCE: 100
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SSSSLITFGQ GTKVEIKRTV              110

SEQ ID NO: 101           moltype = AA   length = 120
FEATURE                  Location/Qualifiers
REGION                   1..120
                         note = Description of Artificial Sequence: Synthetic
                         polypeptide
source                   1..120
                         mol_type = protein
                         organism = synthetic construct
SEQUENCE: 101
EVQLVESGGG LVQPGGSLRL SCAASGFTLY YSSIHWVRQA PGKGLEWVAS ISSSSGSTSY    60
ADSVKGRFTI SADTSKNTAY LQMNSLRAED TAVYYCARWM YWWSFALDYW GQGTLVTVSS  120

SEQ ID NO: 102           moltype = AA   length = 110
FEATURE                  Location/Qualifiers
REGION                   1..110
                         note = Description of Artificial Sequence: Synthetic
                         polypeptide
```

```
source                  1..110
                        mol_type = protein
                        organism = synthetic construct
SEQUENCE: 102
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SYLWPITFGQ GTKVEIKRTV              110

SEQ ID NO: 103          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 103
EVQLVESGGG LVQPGGSLRL SCAASGFTVS SSSIHWVRQA PGKGLEWVAS IYSYYGYTSY    60
ADSVKGRFTI SADTSKNTAY LQMNSLRAED TAVYYCARWQ YHYNYWYGMD YWGQGTLVTV   120
SS                                                                  122

SEQ ID NO: 104          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 104
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ YPMSLITFGQ GTKVEIKRTV              110

SEQ ID NO: 105          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 105
EVQLVESGGG LVQPGGSLRL SCAASGFTVS YSSIHWVRQA PGKGLEWVAS ISPYSGYTSY    60
ADSVKGRFTI SADTSKNTAY LQMNSLRAED TAVYYCARGY DYYAGLDYWG QGTLVTVSS    119

SEQ ID NO: 106          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 106
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ YYYFPITFGQ GTKVEIKRTV              110

SEQ ID NO: 107          moltype = AA  length = 127
FEATURE                 Location/Qualifiers
REGION                  1..127
                        note = Description of Artificial Sequence: Synthetic
                         polypeptide
source                  1..127
                        mol_type = protein
                        organism = synthetic construct
SEQUENCE: 107
EVQLVESGGG LVQPGGSLRL SCAASGFTFS YYSIHWVRQA PGKGLEWVAS ISPYYGYTSY    60
ADSVKGRFTI SADTSKNTAY LQMNSLRAED TAVYYCARWE SEYSGTYEDY WAGMDYWGQG   120
TLVTVSS                                                             127

SEQ ID NO: 108          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 108
DIQMTQSPSS LSASVGDRVT ITCRASQSVS SAVAWYQQKP GKAPKLLIYS ASSLYSGVPS    60
```

```
RFSGSRSGTD FTLTISSLQP EDFATYYCQQ YMWWPITFGQ GTKVEIKRTV          110

SEQ ID NO: 109          moltype = AA   length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 109
EVQLVESGGG LVQPGGSLRL SCAASGFTIS YSSIHWVRQA PGKGLEWVAS ISSSYSYTSY  60
ADSVKGRFTI SADTSKNTAY LQMNSLRAED TAVYYCARTG YWQGYLALDY WGQGTLVTVS 120
S                                                                121

SEQ ID NO: 110          moltype = AA   length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 110
DIQMTQSPSS LSASVGDRVT ITCRASQSVS SAVAWYQQKP GKAPKLLIYS ASSLYSGVPS  60
RFSGSRSGTD FTLTISSLQP EDFATYYCQQ SSSSLITFGQ GTKVEIKRTV           110

SEQ ID NO: 111          moltype = AA   length = 123
FEATURE                 Location/Qualifiers
REGION                  1..123
                        note = Description of Artificial Sequence: Synthetic
                         polypeptide
source                  1..123
                        mol_type = protein
                        organism = synthetic construct
SEQUENCE: 111
EVQLVESGGG LVQPGGSLRL SCAASGFTIS YSSIHWVRQA PGKGLEWVAS ISSSSGSTSY  60
ADSVKGRFTI SADTSKNTAY LQMNSLRAED TAVYYCARTY YYYWNSTPAM DYWGQGTLVT 120
VSS                                                              123

SEQ ID NO: 112          moltype = AA   length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 112
DIQMTQSPSS LSASVGDRVT ITCRASQSVS SAVAWYQQKP GKAPKLLIYS ASSLYSGVPS  60
RFSGSRSGTD FTLTISSLQP EDFATYYCQQ SYGYPVTFGQ GTKVEIKRTV           110

SEQ ID NO: 113          moltype = AA   length = 129
FEATURE                 Location/Qualifiers
REGION                  1..129
                        note = Description of Artificial Sequence: Synthetic
                         polypeptide
source                  1..129
                        mol_type = protein
                        organism = synthetic construct
SEQUENCE: 113
EVQLVESGGG LVQPGGSLRL SCAASGFTFS SSSIHWVRQA PGKGLEWVAS ISSSYGYTSY  60
ADSVKGRFTI SADTSKNTAY LQMNSLRAED TAVYYCARWY NSSWYYSNWW YKGFGMDYWG 120
QGTLVTVSS                                                        129

SEQ ID NO: 114          moltype = AA   length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 114
DIQMTQSPSS LSASVGDRVT ITCRASQSVS SAVAWYQQKP GKAPKLLIYS ASSLYSGVPS  60
RFSGSRSGTD FTLTISSLQP EDFATYYCQQ YYSSLFTFGQ GTKVEIKRTV           110

SEQ ID NO: 115          moltype = AA   length = 124
FEATURE                 Location/Qualifiers
```

```
REGION                  1..124
                        note = Description of Artificial Sequence: Synthetic
                         polypeptide
source                  1..124
                        mol_type = protein
                        organism = synthetic construct
SEQUENCE: 115
EVQLVESGGG LVQPGGSLRL SCAASGFTFY SSSIHWVRQA PGKGLEWVAS ISSSYGYTSY    60
ADSVKGRFTI SADTSKNTAY LQMNSLRAED TAVYYCARTS YTYPVYTYYG FDYWGQGTLV   120
TVSS                                                                124

SEQ ID NO: 116          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 116
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SWYYPLTFGQ GTKVEIKRTV              110

SEQ ID NO: 117          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 117
EVQLVESGGG LVQPGGSLRL SCAASGFTLY SSSIHWVRQA PGKGLEWVAS ISSSYGYTSY    60
ADSVKGRFTI SADTSKNTAY LQMNSLRAED TAVYYCARYR YSSWNRGAID YWGQGTLVTV   120
SS                                                                  122

SEQ ID NO: 118          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 118
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SYWWPLTFGQ GTKVEIKRTV              110

SEQ ID NO: 119          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 119
EVQLVESGGG LVQPGGSLRL SCAASGFTVS SSSIHWVRQA PGKGLEWVAS IYSYYGYTSY    60
ADSVKGRFTI SADTSKNTAY LQMNSLRAED TAVYYCARWS KSPWYYQGID YWGQGTLVTV   120
SS                                                                  122

SEQ ID NO: 120          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 120
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ YHYWASLITF GQGTKVEIKR TV           112

SEQ ID NO: 121          moltype = AA  length = 123
FEATURE                 Location/Qualifiers
REGION                  1..123
                        note = Description of Artificial Sequence: Synthetic
                         polypeptide
source                  1..123
```

```
                        mol_type = protein
                        organism = synthetic construct
SEQUENCE: 121
EVQLVESGGG LVQPGGSLRL SCAASGFTVS SSSIHWVRQA PGKGLEWVAS IYSYSGSTYY    60
ADSVKGRFTI SADTSKNTAY LQMNSLRAED TAVYYCARQY SSSYYVWPGM DYWGQGTLVT   120
VSS                                                                 123

SEQ ID NO: 122          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 122
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SYWWKSLVTF GQGTKVEIKR TV           112

SEQ ID NO: 123          moltype = AA  length = 126
FEATURE                 Location/Qualifiers
REGION                  1..126
                        note = Description of Artificial Sequence: Synthetic
                         polypeptide
source                  1..126
                        mol_type = protein
                        organism = synthetic construct
SEQUENCE: 123
EVQLVESGGG LVQPGGSLRL SCAASGFTLS SSSIHWVRQA PGKGLEWVAS ISSYYGSTSY    60
ADSVKGRFTI SADTSKNTAY LQMNSLRAED TAVYYCARMH YSWQEYYSYD WGMDYWGQGT   120
LVTVSS                                                              126

SEQ ID NO: 124          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 124
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ PYYPLITFGQ GTKVEIKRTV              110

SEQ ID NO: 125          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 125
EVQLVESGGG LVQPGGSLRL SCAASGFTIS YSSIHWVRQA PGKGLEWVAS IYPSYGSTSY    60
ADSVKGRFTI SADTSKNTAY LQMNSLRAED TAVYYCARWQ GYYQPALDYW GQGTLVTVSS   120

SEQ ID NO: 126          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 126
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SSKYYYPITF GQGTKVEIKR TV           112

SEQ ID NO: 127          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 127
EVQLVESGGG LVQPGGSLRL SCAASGFTIS SSSIHWVRQA PGKGLEWVAS ISPYYGYTSY    60
ADSVKGRFTI SADTSKNTAY LQMNSLRAED TAVYYCARWG YGWYWYGLDY WGQGTLVTVS   120
```

```
S                                                                     121

SEQ ID NO: 128          moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 128
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ GHDMNPVTFG QGTKVEIKRT V            111

SEQ ID NO: 129          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 129
EVQLVESGGG LVQPGGSLRL SCAASGFTLS SSSIHWVRQA PGKGLEWVAS IYSSYGYTYY    60
ADSVKGRFTI SADTSKNTAY LQMNSLRAED TAVYYCARYY YYWYGGMDYW GQGTLVTVSS   120

SEQ ID NO: 130          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 130
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SWMSDSLITF GQGTKVEIKR TV           112

SEQ ID NO: 131          moltype = AA  length = 123
FEATURE                 Location/Qualifiers
REGION                  1..123
                        note = Description of Artificial Sequence: Synthetic
                         polypeptide
source                  1..123
                        mol_type = protein
                        organism = synthetic construct
SEQUENCE: 131
EVQLVESGGG LVQPGGSLRL SCAASGFTFS YSSIHWVRQA PGKGLEWVAS IYPSSGYTSY    60
ADSVKGRFTI SADTSKNTAY LQMNSLRAED TAVYYCARGW WYWMAWDYAM DYWGQGTLVT   120
VSS                                                                 123

SEQ ID NO: 132          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 132
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ MQYSGWLITF GQGTKVEIKR TV           112

SEQ ID NO: 133          moltype = AA  length = 130
FEATURE                 Location/Qualifiers
REGION                  1..130
                        note = Description of Artificial Sequence: Synthetic
                         polypeptide
source                  1..130
                        mol_type = protein
                        organism = synthetic construct
SEQUENCE: 133
EVQLVESGGG LVQPGGSLRL SCAASGFTIS SSSIHWVRQA PGKGLEWVAS ISSYYGYTSY    60
ADSVKGRFTI SADTSKNTAY LQMNSLRAED TAVYYCARYY SYSSGYGYYD YFDWGAMDYW   120
GQGTLVTVSS                                                          130

SEQ ID NO: 134          moltype = AA  length = 110
FEATURE                 Location/Qualifiers
REGION                  1..110
```

```
                        note = Description of Artificial Sequence: Synthetic
                           polypeptide
source                  1..110
                        mol_type = protein
                        organism = synthetic construct
SEQUENCE: 134
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SSSSLITFGQ GTKVEIKRTV              110

SEQ ID NO: 135          moltype = AA   length = 129
FEATURE                 Location/Qualifiers
REGION                  1..129
                        note = Description of Artificial Sequence: Synthetic
                           polypeptide
source                  1..129
                        mol_type = protein
                        organism = synthetic construct
SEQUENCE: 135
EVQLVESGGG LVQPGGSLRL SCAASGFTFS SSSIHWVRQA PGKGLEWVAS ISSSSGSTSY    60
ADSVKGRFTI SADTSKNTAY LQMNSLRAED TAVYYCARYY GYVWGGYWGW WYSKALDYWG   120
QGTLVTVSS                                                          129

SEQ ID NO: 136          moltype = AA   length = 112
FEATURE                 Location/Qualifiers
REGION                  1..112
                        note = Description of Artificial Sequence: Synthetic
                           polypeptide
source                  1..112
                        mol_type = protein
                        organism = synthetic construct
SEQUENCE: 136
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ YDWNYYLVTF GQGTKVEIKR TV           112

SEQ ID NO: 137          moltype = AA   length = 126
FEATURE                 Location/Qualifiers
REGION                  1..126
                        note = Description of Artificial Sequence: Synthetic
                           polypeptide
source                  1..126
                        mol_type = protein
                        organism = synthetic construct
SEQUENCE: 137
EVQLVESGGG LVQPGGSLRL SCAASGFTIY SSSIHWVRQA PGKGLEWVAS ISSYYGYTSY    60
ADSVKGRFTI SADTSKNTAY LQMNSLRAED TAVYYCARYQ YYGSLYYSQQ WAMDYWGQGT   120
LVTVSS                                                             126

SEQ ID NO: 138          moltype = AA   length = 110
FEATURE                 Location/Qualifiers
REGION                  1..110
                        note = Description of Artificial Sequence: Synthetic
                           polypeptide
source                  1..110
                        mol_type = protein
                        organism = synthetic construct
SEQUENCE: 138
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SSSSLITFGQ GTKVEIKRTV              110

SEQ ID NO: 139          moltype = AA   length = 129
FEATURE                 Location/Qualifiers
REGION                  1..129
                        note = Description of Artificial Sequence: Synthetic
                           polypeptide
source                  1..129
                        mol_type = protein
                        organism = synthetic construct
SEQUENCE: 139
EVQLVESGGG LVQPGGSLRL SCAASGFTFS SSSIHWVRQA PGKGLEWVAS ISSSSGSTSY    60
ADSVKGRFTI SADTSKNTAY LQMNSLRAED TAVYYCARSP SSPYFMSWGW YWQYGIDYWG   120
QGTLVTVSS                                                          129

SEQ ID NO: 140          moltype = AA   length = 111
FEATURE                 Location/Qualifiers
REGION                  1..111
                        note = Description of Artificial Sequence: Synthetic
                           polypeptide
source                  1..111
                        mol_type = protein
```

```
                    organism = synthetic construct
SEQUENCE: 140
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SSWGGLVTFG QGTKVEIKRT V            111

SEQ ID NO: 141          moltype = AA   length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 141
EVQLVESGGG LVQPGGSLRL SCAASGFTFS SSYIHWVRQA PGKGLEWVAS ISPSYGYTSY    60
ADSVKGRFTI SADTSKNTAY LQMNSLRAED TAVYYCARDM YEWWHWAIDY WGQGTLVTVS   120
S                                                                  121

SEQ ID NO: 142          moltype = AA   length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 142
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ SSSSLITFGQ GTKVEIKRTV             110

SEQ ID NO: 143          moltype = AA   length = 129
FEATURE                 Location/Qualifiers
REGION                  1..129
                        note = Description of Artificial Sequence: Synthetic
                         polypeptide
source                  1..129
                        mol_type = protein
                        organism = synthetic construct
SEQUENCE: 143
EVQLVESGGG LVQPGGSLRL SCAASGFTFS SSSIHWVRQA PGKGLEWVAS ISSSSGSTSY    60
ADSVKGRFTI SADTSKNTAY LQMNSLRAED TAVYYCARYG HYLYYWGWGW YWSAALDYWG   120
QGTLVTVSS                                                          129

SEQ ID NO: 144          moltype = AA   length = 514
FEATURE                 Location/Qualifiers
REGION                  1..514
                        note = Description of Artificial Sequence: Synthetic
                         polypeptide
source                  1..514
                        mol_type = protein
                        organism = synthetic construct
SEQUENCE: 144
DIVRSDIQMT QSPSSLSASV GDRVTITCRA SQSVSSAVAW YQQKPGKAPK LLIYSASSLY    60
SGVPSRFSGS RSGTDFTLTI SSLQPEDFAT YYCQQISYVY SLITFGQGTK VEIKGGGGSE   120
VQLQQSGPEL VKPGASMKIS CKASGYSFTG YTMNWVKQSH GKNLEWMGLI NPYKGVSTYN   180
QKFKDKATLT VDKSSSTAYM ELLSLTSEDS AVYYCARSGY YGDSDWYFDV WGQGTTLTVS   240
SGGGGSGGGG SGGGGSDIQM TQTTSSLSAS LGDRVTISCR ASQDIRNYLN WYQQKPDGTV   300
KLLIYYTSRL HSGVPSKFSG SGSGTDYSLT ISNLEQEDIA TYFCQQGNTL PWTFAGGTKL   360
EIKGGGGSEV QLVESGGGLV QPGGSLRLSC AASGFTFSSS SIHWVRQAPG KGLEWVASIY   420
SSYGYTSYAD SVKGRFTISA DTSKNTAYLQ MNSLRAEDTA VYYCARGGWY PAMDYWGQGT   480
LVTVSSLEGG GGLNDIFEAQ KIEWHESRHH HHHH                              514

SEQ ID NO: 145          moltype = AA   length = 517
FEATURE                 Location/Qualifiers
REGION                  1..517
                        note = Description of Artificial Sequence: Synthetic
                         polypeptide
source                  1..517
                        mol_type = protein
                        organism = synthetic construct
SEQUENCE: 145
DIVRSDIQMT QSPSSLSASV GDRVTITCRA SQSVSSAVAW YQQKPGKAPK LLIYSASSLY    60
SGVPSRFSGS RSGTDFTLTI SSLQPEDFAT YYCQQSSSSL ITFGQGTKVE IKGGGGSEVQ   120
LQQSGPELVK PGASMKISCK ASGYSFTGYT MNWVKQSHGK NLEWMGLINP YKGVSTYNQK   180
FKDKATLTVD KSSSTAYMEL LSLTSEDSAV YYCARSGYYG DSDWYFDVWG QGTTLTVSSG   240
GGGSGGGGSG GGGSDIQMTQ TTSSLSASLG DRVTISCRAS QDIRNYLNWY QQKPDGTVKL   300
LIYYTSRLHS GVPSKFSGSG SGTDYSLTIS NLEQEDIATY FCQQGNTLPW TFAGGTKLEI   360
KGGGGSEVQL VESGGGLVQP GGSLRLSCAA SGFTISSSSI HWVRQAPGKG LEWVAYISSY   420
SGTYYYADSV KGRFTISADT SKNTAYLQMN SLRAEDTAVY YCARYWYGHY HSYFGLDYWG   480
```

```
QGTLVTVSSL EGGGGLNDIF EAQKIEWHES RHHHHHH                              517

SEQ ID NO: 146           moltype = AA   length = 512
FEATURE                  Location/Qualifiers
REGION                   1..512
                         note = Description of Artificial Sequence: Synthetic
                         polypeptide
source                   1..512
                         mol_type = protein
                         organism = synthetic construct
SEQUENCE: 146
DIVRSDIQMT QSPSSLSASV GDRVTITCRA SQSVSSAVAW YQQKPGKAPK LLIYSASSLY     60
SGVPSRFSGS RSGTDFTLTI SSLQPEDFAT YYCQQYSYWP ITFGQGTKVE IKGGGGSEVQ    120
LQQSGPELVK PGASMKISCK ASGYSFTGYT MNWVKQSHGK NLEWMGLINP YKGVSTYNQK    180
FKDKATLTVD KSSSTAYMEL LSLTSEDSAV YYCARSGYYG DSDWYFDVWG QGTTLTVSSG    240
GGGSGGGGSG GGGSDIQMTQ TTSSLSASLG DRVTISCRAS QDIRNYLNWY QQKPDGTVKL    300
LIYYTSRLHS GVPSKFSGSG SGTDYSLTIS NLEQEDIATY FCQQGNTLPW TFAGGTKLEI    360
KGGGGSEVQL VESGGGLVQP GGSLRLSCAA SGFTISSSYI HWVRQAPGKG LEWVAYISPS    420
YGSTSYADSV KGRFTISADT SKNTAYLQMN SLRAEDTAVY YCAREYVTMA LDYWGQGTLV    480
TVSSLEGGGG LNDIFEAQKI EWHESRHHHH HH                                  512

SEQ ID NO: 147           moltype = AA   length = 516
FEATURE                  Location/Qualifiers
REGION                   1..516
                         note = Description of Artificial Sequence: Synthetic
                         polypeptide
source                   1..516
                         mol_type = protein
                         organism = synthetic construct
SEQUENCE: 147
DIVRSDIQMT QSPSSLSASV GDRVTITCRA SQSVSSAVAW YQQKPGKAPK LLIYSASSLY     60
SGVPSRFSGS RSGTDFTLTI SSLQPEDFAT YYCQQSSWGG LVTFGQGTKV EIKGGGGSEV    120
QLQQSGPELV KPGASMKISC KASGYSFTGY TMNWVKQSHG KNLEWMGLIN PYKGVSTYNQ    180
KFKDKATLTV DKSSSTAYME LLSLTSEDSA VYYCARSGYG GDSDWYFDVW GQGTTLTVSS    240
GGGGSGGGGS GGGGSDIQMT QTTSSLSASL GDRVTISCRA SQDIRNYLNW YQQKPDGTVK    300
LLIYYTSRLH SGVPSKFSGS GSGTDYSLTI SNLEQEDIAT YFCQQGNTLP WTFAGGTKLE    360
IKGGGGSEVQ LVESGGGLVQ PGGSLRLSCA ASGFTFSSSY IHWVRQAPGK GLEWVASISP    420
SYGYTSYADS VKGRFTISAD TSKNTAYLQM NSLRAEDTAV YYCARDMYEW WHWAIDYWGQ    480
GTLVTVSSLE GGGGLNDIFE AQKIEWHESR HHHHHH                              516

SEQ ID NO: 148           moltype = AA   length = 514
FEATURE                  Location/Qualifiers
REGION                   1..514
                         note = Description of Artificial Sequence: Synthetic
                         polypeptide
source                   1..514
                         mol_type = protein
                         organism = synthetic construct
SEQUENCE: 148
DIVRSDIQMT QSPSSLSASV GDRVTITCRA SQSVSSAVAW YQQKPGKAPK LLIYSASSLY     60
SGVPSRFSGS RSGTDFTLTI SSLQPEDFAT YYCQQIYVK KLITFGQGTK VEIKGGGGSE    120
VQLQQSGPEL VKPGASMKIS CKASGYSFTG YTMNWVKQSH GKNLEWMGLI NPYKGVSTYN    180
QKFKDKATLT VDKSSSTAYM ELLSLTSEDS AVYYCARSGY YGDSDWYFDV WGQGTTLTVS    240
SGGGGSGGGG SGGGGSDIQM TQTTSSLSAS LGDRVTISCR ASQDIRNYLN WYQQKPDGTV    300
KLLIYYTSRL HSGVPSKFSG SGSGTDYSLT ISNLEQEDIA TYFCQQGNTL PWTFAGGTKL    360
EIKGGGGSEV QLVESGGGLV QPGGSLRLSC AASGFTFSDY SIHWVRQAPG KGLEWVASIS    420
SSSGSTSYAD SVKGRFTISA DTSKNTAYLQ MNSLRAEDTA VYYCARGGWY PAMDYWGQGT    480
LVTVSSLEGG GGLNDIFEAQ KIEWHESRHH HHHH                                514

SEQ ID NO: 149           moltype = AA   length = 232
FEATURE                  Location/Qualifiers
REGION                   1..232
                         note = Description of Artificial Sequence: Synthetic
                         polypeptide
source                   1..232
                         mol_type = protein
                         organism = synthetic construct
SEQUENCE: 149
EVQLLESGGG LVQPGGSLRL SCAASGFTFS TYAMNWVRQA PGKGLEWVSR IRSKYNNYAT     60
YYADSVKGRF TISRDDSKNT LYLQMNSLRA EDTAVYYCVR HGNFGNSYVS WFAYWGQGTL    120
VTVSSASVAA PSVFIFPPSD EQLKSGTASV VCLLNNFYPR EAKVQWKVDN ALQSGNSQES    180
VTEQDSKDST YSLSSTLTLS KADYEKHKVY ACEVTHQGLS SPVTKSFNRG EC             232

SEQ ID NO: 150           moltype = AA   length = 671
FEATURE                  Location/Qualifiers
REGION                   1..671
                         note = Description of Artificial Sequence: Synthetic
                         polypeptide
source                   1..671
```

```
                        mol_type = protein
                        organism = synthetic construct
SEQUENCE: 150
EVQLVESGGG LVQPGGSLRL SCAASGFTFS DYSIHWVRQA PGKGLEWVAS ISSSSGSTSY    60
ADSVKGRFTI SADTSKNTAY LQMNSLRAED TAVYYCARGG WYPAMDYWGQ GTLVTVSSAS   120
TKGPSVFPLA PSSKSTSGGT AALGCLVEDY FPEPVTVSWN SGALTSGVHT FPAVLQSSGL   180
YSLSSVVTVP SSSLGTQTYI CNVNHKPSNT KVDEKVEPKS CDGGGSGGG  GSQAVVTQEP   240
SLTVSPGGTV TLTCGSSTGA VTTSNYANWV QEKPGQAFRG LIGGTNKRAP GTPARFSGSL   300
LGGKAALTLS GAQPEDEAEY YCALWYSNLW VFGGGTKLTV LSSASTKGPS VPPLAPSSKS   360
TSGGTAALGC LVKDYFPEPV TVSWNSGALT SGVHTFPAVL QSSGLYSLSS VVTVPSSSLG   420
TQTYICNVNH KPSNTKVDKK VEPKSCDKTH TCPPCPAPEA AGGPSVFLFP PKPKDTLMIS   480
RTPEVTCVVV DVSHEDPEVK FNWYVDGVEV HNAKTKPREE QYNSTYRVVS VLTVLHQDWL   540
NGKEYKCKVS NKALGAPIEK TISKAKGQPR EPQVYTLPPC RDELTKNQVS LWCLVKGFYP   600
SDIAVEWESN GQPENNYKTT PPVLDSDGSF FLYSKLTVDK SRWQQGNVFS CSVMHEALHN   660
HYTQKSLSLS P                                                       671

SEQ ID NO: 151          moltype = AA  length = 446
FEATURE                 Location/Qualifiers
REGION                  1..446
                        note = Description of Artificial Sequence: Synthetic
                         polypeptide
source                  1..446
                        mol_type = protein
                        organism = synthetic construct
SEQUENCE: 151
EVQLVESGGG LVQPGGSLRL SCAASGFTFS DYSIHWVRQA PGKGLEWVAS ISSSSGSTSY    60
ADSVKGRFTI SADTSKNTAY LQMNSLRAED TAVYYCARGG WYPAMDYWGQ GTLVTVSSAS   120
TKGPSVFPLA PSSKSTSGGT AALGCLVEDY FPEPVTVSWN SGALTSGVHT FPAVLQSSGL   180
YSLSSVVTVP SSSLGTQTYI CNVNHKPSNT KVDEKVEPKS CDKTHTCPPC PAPEAAGGPS   240
VPLFPPKPKD TLMISRTPEV TCVVVDVSHE DPEVKFNWYV DGVEVHNAKT KPREEQYNST   300
YRVVSVLTVL HQDWLNGKEY KCKVSNKALG APIEKTISKA KGQPREPQVC TLPPSRDELT   360
KNQVSLSCAV KGFYPSDIAV EWESNGQPEN NYKTTPPVLD SDGSFFLVSK LTVDKSRWQQ   420
GNVFSCSVMH EALHNHYTQK SLSLSP                                       446

SEQ ID NO: 152          moltype = AA  length = 216
FEATURE                 Location/Qualifiers
REGION                  1..216
                        note = Description of Artificial Sequence: Synthetic
                         polypeptide
source                  1..216
                        mol_type = protein
                        organism = synthetic construct
SEQUENCE: 152
DIQMTQSPSS LSASVGDRVT ITCRASQSVS SAVAWYQQKP GKAPKLLIYS ASSLYSGVPS    60
RFSGSRSGTD FTLTISSLQP EDFATYYCQQ ISYVKKLITF GQGTKVEIKR TVAAPSVFIF   120
PPSDRKLKSG TASVVCLLNN FYPREAKVQW KVDNALQSGN SQESVTEQDS KDSTYSLSST   180
LTLSKADYEK HKVYACEVTH QGLSSPVTKS FNRGEC                             216

SEQ ID NO: 153          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 153
ISYVKKLI                                                             8

SEQ ID NO: 154          moltype =     length =
SEQUENCE: 154
000

SEQ ID NO: 155          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 155
GGWYPA                                                               6

SEQ ID NO: 156          moltype =     length =
SEQUENCE: 156
000

SEQ ID NO: 157          moltype = AA  length = 6
FEATURE                 Location/Qualifiers
REGION                  1..6
```

```
                         note = Description of Artificial Sequence: Synthetic peptide
source                   1..6
                         mol_type = protein
                         organism = synthetic construct
SEQUENCE: 157
YSYWPI                                                                             6

SEQ ID NO: 158           moltype =    length =
SEQUENCE: 158
000

SEQ ID NO: 159           moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 159
EYVTMAL                                                                            7

SEQ ID NO: 160           moltype =    length =
SEQUENCE: 160
000

SEQ ID NO: 161           moltype = AA   length = 488
FEATURE                  Location/Qualifiers
REGION                   1..488
                         note = Description of Artificial Sequence: Synthetic
                         polypeptide
source                   1..488
                         mol_type = protein
                         organism = synthetic construct
SEQUENCE: 161
DIVRSDIQMT QSPSSLSASV GDRVTITCRA SQSVSSAVAW YQQKPGKAPK LLIYSASSLY    60
SGVPSRFSGS RSGTDFTLTI SSLQPEDFAT YYCQQISYVY SLITFGQGTK VEIKGGGGSE   120
VQLQQSGPEL VKPGASMKIS CKASGYSFTG YTMNWVKQSH GKNLEWMGLI NPYKGVSTYN   180
QKFKDKATLT VDKSSSTAYM ELLSLTSEDS AVYYCARSGY YGDSDWYFDV WGQGTTLTVS   240
SGGGGSGGGG SGGGGSDIQM TQTTSSLSAS LGDRVTISCR ASQDIRNYLN WYQQKPDGTV   300
KLLLIYYTSRL HSGVPSKFSG SGSGTDYSLT ISNLEQEDIA TYFCQQGNTL PWTFAGGTKL   360
EIKGGGGSEV QLVESGGGLV QPGGSLRLSC AASGFTFSSY SIHWVRQAPG KGLEWVASIY   420
SSYGYTSYAD SVKGRFTISA DTSKNTAYLQ MNSLRAEDTA VYYCARGGWY PAMDYWGQGT   480
LVTVSSLE                                                           488

SEQ ID NO: 162           moltype = AA   length = 491
FEATURE                  Location/Qualifiers
REGION                   1..491
                         note = Description of Artificial Sequence: Synthetic
                         polypeptide
source                   1..491
                         mol_type = protein
                         organism = synthetic construct
SEQUENCE: 162
DIVRSDIQMT QSPSSLSASV GDRVTITCRA SQSVSSAVAW YQQKPGKAPK LLIYSASSLY    60
SGVPSRFSGS RSGTDFTLTI SSLQPEDFAT YYCQQSSSSL ITFGQGTKVE IKGGGGSEVQ   120
LQQSGPELVK PGASMKISCK ASGYSFTGYT MNWVKQSHGK NLEWMGLINP YKGVSTYNQK   180
FKDKATLTVD KSSSTAYMEL LSLTSEDSAV YYCARSGYYG DSDWYFDVWG QGTTLTVSSG   240
GGGSGGGGSG GGGSDIQMTQ TTSSLSASLG DRVTISCRAS QDIRNYLNWY QQKPDGTVKL   300
LIYYTSRLHS GVPSKFSGSG SGTDYSLTIS NLEQEDIATY FCQQGNTLPW TFAGGTKLEI   360
KGGGGSEVQL VESGGGLVQP GGSLRLSCAA SGFTISSSSI HWVRQAPGKG LEWVAYISSY   420
SGYTYYADSV KGRFTISADT SKNTAYLQMN SLRAEDTAVY YCARYWYGHY HSYFGLDYWG   480
QGTLVTVSSL E                                                       491

SEQ ID NO: 163           moltype = AA   length = 486
FEATURE                  Location/Qualifiers
REGION                   1..486
                         note = Description of Artificial Sequence: Synthetic
                         polypeptide
source                   1..486
                         mol_type = protein
                         organism = synthetic construct
SEQUENCE: 163
DIVRSDIQMT QSPSSLSASV GDRVTITCRA SQSVSSAVAW YQQKPGKAPK LLIYSASSLY    60
SGVPSRFSGS RSGTDFTLTI SSLQPEDFAT YYCQQYSYWP ITFGQGTKVE IKGGGGSEVQ   120
LQQSGPELVK PGASMKISCK ASGYSFTGYT MNWVKQSHGK NLEWMGLINP YKGVSTYNQK   180
FKDKATLTVD KSSSTAYMEL LSLTSEDSAV YYCARSGYYG DSDWYFDVWG QGTTLTVSSG   240
GGGSGGGGSG GGGSDIQMTQ TTSSLSASLG DRVTISCRAS QDIRNYLNWY QQKPDGTVKL   300
LIYYTSRLHS GVPSKFSGSG SGTDYSLTIS NLEQEDIATY FCQQGNTLPW TFAGGTKLEI   360
KGGGGSEVQL VESGGGLVQP GGSLRLSCAA SGFTISSSYI HWVRQAPGKG LEWVAYISPS   420
```

```
YGSTSYADSV KGRFTISADT SKNTAYLQMN SLRAEDTAVY YCAREYVTMA LDYWGQGTLV    480
TVSSLE                                                              486

SEQ ID NO: 164          moltype = AA  length = 490
FEATURE                 Location/Qualifiers
REGION                  1..490
                        note = Description of Artificial Sequence: Synthetic
                         polypeptide
source                  1..490
                        mol_type = protein
                        organism = synthetic construct
SEQUENCE: 164
DIVRSDIQMT QSPSSLSASV GDRVTITCRA SQSVSSAVAW YQQKPGKAPK LLIYSASSLY     60
SGVPSRFSGS RSGTDFTLTI SSLQPEDFAT YYCQQSSWGG LVTFGQGTKV EIKGGGGSEV    120
QLQQSGPELV KPGASMKISC KASGYSFTGY TMNWVKQSHG KNLEWMGLIN PYKGVSTYNQ    180
KFKDKATLTV DKSSSTAYME LLSLTSEDSA VYYCARSGYY GDSDWYFDVW GQGTTLTVSS    240
GGGGSGGGGS GGGGSDIQMT QTTSSLSASL GDRVTISCRA SQDIRNYLNW YQQKPDGTVK    300
LLIYYTSRLH SGVPSKFSGS GSGTDYSLTI SNLEQEDIAT YFCQQGNTLP WTFAGGTKLE    360
IKGGGGSEVQ LVESGGGLVQ PGGSLRLSCA ASGFTFSSSY IHWVRQAPGK GLEWVASISP    420
SYGYTSYADS VKGRFTISAD TSKNTAYLQM NSLRAEDTAV YYCARDMYEW WHWAIDYWGQ    480
GTLVTVSSLE                                                          490

SEQ ID NO: 165          moltype = AA  length = 488
FEATURE                 Location/Qualifiers
REGION                  1..488
                        note = Description of Artificial Sequence: Synthetic
                         polypeptide
source                  1..488
                        mol_type = protein
                        organism = synthetic construct
SEQUENCE: 165
DIVRSDIQMT QSPSSLSASV GDRVTITCRA SQSVSSAVAW YQQKPGKAPK LLIYSASSLY     60
SGVPSRFSGS RSGTDFTLTI SSLQPEDFAT YYCQQISYVK KLITFGQGTK VEIKGGGGSE    120
VQLQQSGPEL VKPGASMKIS CKASGYSFTG YTMNWVKQSH GKNLEWMGLI NPYKGVSTYN    180
QKFKDKATLT VDKSSSTAYM ELLSLTSEDS AVYYCARSGY YGDSDWYFDV WGQGTTLTVS    240
SGGGGSGGGG SGGGGSDIQM TQTTSSLSAS LGDRVTISCR ASQDIRNYLN WYQQKPDGTV    300
KLLIYYTSRL HSGVPSKFSG SGSGTDYSLT ISNLEQEDIA TYFCQQGNTL PWTFAGGTKL    360
EIKGGGGSEV QLVESGGGLV QPGGSLRLSC AASGFTFSDY SIHWVRQAPG KGLEWVASIS    420
SSSGSTSYAD SVKGRFTISA DTSKNTAYLQ MNSLRAEDTA VYYCARGGWY PAMDYWGQGT    480
LVTVSSLE                                                            488

SEQ ID NO: 166          moltype = AA  length = 11
FEATURE                 Location/Qualifiers
source                  1..11
                        mol_type = protein
                        organism = synthetic construct
SEQUENCE: 166
RASQSVSSAV A                                                         11

SEQ ID NO: 167          moltype = AA  length = 7
FEATURE                 Location/Qualifiers
source                  1..7
                        mol_type = protein
                        organism = synthetic construct
SEQUENCE: 167
SASSLYS                                                               7

SEQ ID NO: 168          moltype = AA  length = 11
FEATURE                 Location/Qualifiers
source                  1..11
                        mol_type = protein
                        organism = synthetic construct
SEQUENCE: 168
QQISYVKKLI T                                                         11

SEQ ID NO: 169          moltype = AA  length = 5
FEATURE                 Location/Qualifiers
source                  1..5
                        mol_type = protein
                        organism = synthetic construct
SEQUENCE: 169
DYSIH                                                                 5

SEQ ID NO: 170          moltype = AA  length = 17
FEATURE                 Location/Qualifiers
source                  1..17
                        mol_type = protein
                        organism = synthetic construct
SEQUENCE: 170
```

SISSSSGSTS YADSVKG                                                                                    17

SEQ ID NO: 171          moltype = AA  length = 9
FEATURE                 Location/Qualifiers
source                  1..9
                        mol_type = protein
                        organism = synthetic construct
SEQUENCE: 171
GGWYPAMDY                                                                                              9

SEQ ID NO: 172          moltype = AA  length = 9
FEATURE                 Location/Qualifiers
source                  1..9
                        mol_type = protein
                        organism = synthetic construct
SEQUENCE: 172
QQYSYWPIT                                                                                              9

SEQ ID NO: 173          moltype = AA  length = 5
FEATURE                 Location/Qualifiers
source                  1..5
                        mol_type = protein
                        organism = synthetic construct
SEQUENCE: 173
SSYIH                                                                                                  5

SEQ ID NO: 174          moltype = AA  length = 17
FEATURE                 Location/Qualifiers
source                  1..17
                        mol_type = protein
                        organism = synthetic construct
SEQUENCE: 174
YISPSYGSTS YADSVKG                                                                                    17

SEQ ID NO: 175          moltype = AA  length = 9
FEATURE                 Location/Qualifiers
source                  1..9
                        mol_type = protein
                        organism = synthetic construct
SEQUENCE: 175
EYVTMALDY                                                                                              9

SEQ ID NO: 176          moltype = AA  length = 9
FEATURE                 Location/Qualifiers
source                  1..9
                        mol_type = protein
                        organism = synthetic construct
SEQUENCE: 176
QQDWYFPIT                                                                                              9

SEQ ID NO: 177          moltype = AA  length = 9
FEATURE                 Location/Qualifiers
source                  1..9
                        mol_type = protein
                        organism = synthetic construct
SEQUENCE: 177
FTFSSYYIH                                                                                              9

SEQ ID NO: 178          moltype = AA  length = 17
FEATURE                 Location/Qualifiers
source                  1..17
                        mol_type = protein
                        organism = synthetic construct
SEQUENCE: 178
SISPSSGSTY YADSVKG                                                                                    17

SEQ ID NO: 179          moltype = AA  length = 21
FEATURE                 Location/Qualifiers
source                  1..21
                        mol_type = protein
                        organism = synthetic construct
SEQUENCE: 179
YGGRSYWQKQ DSYFYQHGLD Y                                                                               21

SEQ ID NO: 180          moltype = AA  length = 9
FEATURE                 Location/Qualifiers
source                  1..9
                        mol_type = protein
                        organism = synthetic construct

```
SEQUENCE: 180
QQSSSSLIT                                                                    9

SEQ ID NO: 181          moltype = AA   length = 9
FEATURE                 Location/Qualifiers
source                  1..9
                        mol_type = protein
                        organism = synthetic construct
SEQUENCE: 181
FTFSSSSIH                                                                    9

SEQ ID NO: 182          moltype = AA   length = 17
FEATURE                 Location/Qualifiers
source                  1..17
                        mol_type = protein
                        organism = synthetic construct
SEQUENCE: 182
SISSYSGYTS YADSVKG                                                          17

SEQ ID NO: 183          moltype = AA   length = 18
FEATURE                 Location/Qualifiers
source                  1..18
                        mol_type = protein
                        organism = synthetic construct
SEQUENCE: 183
SYSYSEFRYY YSGQGMDY                                                         18

SEQ ID NO: 184          moltype = AA   length = 14
FEATURE                 Location/Qualifiers
source                  1..14
                        mol_type = protein
                        organism = synthetic construct
SEQUENCE: 184
SNYGWRWHLV GMDY                                                             14

SEQ ID NO: 185          moltype = AA   length = 8
FEATURE                 Location/Qualifiers
source                  1..8
                        mol_type = protein
                        organism = synthetic construct
SEQUENCE: 185
TFSSSSIH                                                                     8

SEQ ID NO: 186          moltype = AA   length = 14
FEATURE                 Location/Qualifiers
source                  1..14
                        mol_type = protein
                        organism = synthetic construct
SEQUENCE: 186
SPYVYYWYMV GFDY                                                             14

SEQ ID NO: 187          moltype = AA   length = 14
FEATURE                 Location/Qualifiers
source                  1..14
                        mol_type = protein
                        organism = synthetic construct
SEQUENCE: 187
TGTSSDVGGY NYVS                                                             14

SEQ ID NO: 188          moltype = AA   length = 7
FEATURE                 Location/Qualifiers
source                  1..7
                        mol_type = protein
                        organism = synthetic construct
SEQUENCE: 188
DVSKRPS                                                                      7

SEQ ID NO: 189          moltype = AA   length = 10
FEATURE                 Location/Qualifiers
source                  1..10
                        mol_type = protein
                        organism = synthetic construct
SEQUENCE: 189
GSYADTDTIV                                                                  10

SEQ ID NO: 190          moltype = AA   length = 5
FEATURE                 Location/Qualifiers
source                  1..5
                        mol_type = protein
```

```
                                          -continued

SEQUENCE: 190
TDAIT                                                                          5

SEQ ID NO: 191           moltype = AA   length = 17
FEATURE                  Location/Qualifiers
source                   1..17
                         mol_type = protein
                         organism = synthetic construct
SEQUENCE: 191
GIIPLLDSVD YAQRFQG                                                            17

SEQ ID NO: 192           moltype = AA   length = 10
FEATURE                  Location/Qualifiers
source                   1..10
                         mol_type = protein
                         organism = synthetic construct
SEQUENCE: 192
WSSVDTGLDY                                                                    10

SEQ ID NO: 193           moltype = AA   length = 7
FEATURE                  Location/Qualifiers
source                   1..7
                         mol_type = protein
                         organism = synthetic construct
SEQUENCE: 193
NDPHYWG                                                                        7

SEQ ID NO: 194           moltype = AA   length = 16
FEATURE                  Location/Qualifiers
source                   1..16
                         mol_type = protein
                         organism = synthetic construct
SEQUENCE: 194
STSHSGHTYF NPSLKS                                                             16

SEQ ID NO: 195           moltype = AA   length = 16
FEATURE                  Location/Qualifiers
source                   1..16
                         mol_type = protein
                         organism = synthetic construct
SEQUENCE: 195
MRYYYSGTYP VYYFDY                                                             16

SEQ ID NO: 196           moltype = AA   length = 13
FEATURE                  Location/Qualifiers
source                   1..13
                         mol_type = protein
                         organism = synthetic construct
SEQUENCE: 196
SGSSSNIGSN FVS                                                                13

SEQ ID NO: 197           moltype = AA   length = 7
FEATURE                  Location/Qualifiers
source                   1..7
                         mol_type = protein
                         organism = synthetic construct
SEQUENCE: 197
SNNQRPS                                                                        7

SEQ ID NO: 198           moltype = AA   length = 11
FEATURE                  Location/Qualifiers
source                   1..11
                         mol_type = protein
                         organism = synthetic construct
SEQUENCE: 198
AAWDDSLNGP V                                                                  11

SEQ ID NO: 199           moltype = AA   length = 5
FEATURE                  Location/Qualifiers
source                   1..5
                         mol_type = protein
                         organism = synthetic construct
SEQUENCE: 199
RYGVS                                                                          5

SEQ ID NO: 200           moltype = AA   length = 17
FEATURE                  Location/Qualifiers
source                   1..17
```

```
                        mol_type = protein
                        organism = synthetic construct
SEQUENCE: 200
GIIPMFGTAN YAQKFQG                                                    17

SEQ ID NO: 201          moltype = AA   length = 12
FEATURE                 Location/Qualifiers
source                  1..12
                        mol_type = protein
                        organism = synthetic construct
SEQUENCE: 201
GDNSAYSDAF NI                                                         12

SEQ ID NO: 202          moltype = AA   length = 10
FEATURE                 Location/Qualifiers
source                  1..10
                        mol_type = protein
                        organism = synthetic construct
SEQUENCE: 202
QQSGWSYPIT                                                            10

SEQ ID NO: 203          moltype = AA   length = 17
FEATURE                 Location/Qualifiers
source                  1..17
                        mol_type = protein
                        organism = synthetic construct
SEQUENCE: 203
SISPYYGSTS YADSVKG                                                    17

SEQ ID NO: 204          moltype = AA   length = 8
FEATURE                 Location/Qualifiers
source                  1..8
                        mol_type = protein
                        organism = synthetic construct
SEQUENCE: 204
SSYYALDY                                                              8

SEQ ID NO: 205          moltype = AA   length = 11
FEATURE                 Location/Qualifiers
source                  1..11
                        mol_type = protein
                        organism = synthetic construct
SEQUENCE: 205
QQISYVYSLI T                                                          11

SEQ ID NO: 206          moltype = AA   length = 5
FEATURE                 Location/Qualifiers
source                  1..5
                        mol_type = protein
                        organism = synthetic construct
SEQUENCE: 206
SYSIH                                                                 5

SEQ ID NO: 207          moltype = AA   length = 17
FEATURE                 Location/Qualifiers
source                  1..17
                        mol_type = protein
                        organism = synthetic construct
SEQUENCE: 207
SIYSSYGYTS YADSVKG                                                    17

SEQ ID NO: 208          moltype = AA   length = 11
FEATURE                 Location/Qualifiers
source                  1..11
                        mol_type = protein
                        organism = synthetic construct
SEQUENCE: 208
QQYQYGYNLI T                                                          11

SEQ ID NO: 209          moltype = AA   length = 5
FEATURE                 Location/Qualifiers
source                  1..5
                        mol_type = protein
                        organism = synthetic construct
SEQUENCE: 209
YSSIH                                                                 5

SEQ ID NO: 210          moltype = AA   length = 17
FEATURE                 Location/Qualifiers
```

```
source                      1..17
                            mol_type = protein
                            organism = synthetic construct
SEQUENCE: 210
SIYSYSGSTS YADSVKG                                                              17

SEQ ID NO: 211              moltype = AA  length = 15
FEATURE                     Location/Qualifiers
source                      1..15
                            mol_type = protein
                            organism = synthetic construct
SEQUENCE: 211
YSYGWVGPGW RAIDY                                                                15

SEQ ID NO: 212              moltype = AA  length = 11
FEATURE                     Location/Qualifiers
source                      1..11
                            mol_type = protein
                            organism = synthetic construct
SEQUENCE: 212
QQSSSVYKLL T                                                                    11

SEQ ID NO: 213              moltype = AA  length = 17
FEATURE                     Location/Qualifiers
source                      1..17
                            mol_type = protein
                            organism = synthetic construct
SEQUENCE: 213
SISSSYSYTS YADSVKG                                                              17

SEQ ID NO: 214              moltype = AA  length = 11
FEATURE                     Location/Qualifiers
source                      1..11
                            mol_type = protein
                            organism = synthetic construct
SEQUENCE: 214
GGPGWYRAMD Y                                                                    11

SEQ ID NO: 215              moltype = AA  length = 5
FEATURE                     Location/Qualifiers
source                      1..5
                            mol_type = protein
                            organism = synthetic construct
SEQUENCE: 215
SSSIH                                                                            5

SEQ ID NO: 216              moltype = AA  length = 14
FEATURE                     Location/Qualifiers
source                      1..14
                            mol_type = protein
                            organism = synthetic construct
SEQUENCE: 216
GYFYYGWWAM AFDY                                                                 14

SEQ ID NO: 217              moltype = AA  length = 11
FEATURE                     Location/Qualifiers
source                      1..11
                            mol_type = protein
                            organism = synthetic construct
SEQUENCE: 217
QQSQWYEPLI T                                                                    11

SEQ ID NO: 218              moltype = AA  length = 18
FEATURE                     Location/Qualifiers
source                      1..18
                            mol_type = protein
                            organism = synthetic construct
SEQUENCE: 218
SYSYMSQWGW YQYSGMDY                                                             18

SEQ ID NO: 219              moltype = AA  length = 11
FEATURE                     Location/Qualifiers
source                      1..11
                            mol_type = protein
                            organism = synthetic construct
SEQUENCE: 219
QQGSYTYRLI T                                                                    11

SEQ ID NO: 220              moltype = AA  length = 17
```

```
FEATURE                 Location/Qualifiers
source                  1..17
                        mol_type = protein
                        organism = synthetic construct
SEQUENCE: 220
SISSSSGYTS YADSVKG                                                      17

SEQ ID NO: 221          moltype = AA   length = 10
FEATURE                 Location/Qualifiers
source                  1..10
                        mol_type = protein
                        organism = synthetic construct
SEQUENCE: 221
YAWWAHGLDY                                                              10

SEQ ID NO: 222          moltype = AA   length = 11
FEATURE                 Location/Qualifiers
source                  1..11
                        mol_type = protein
                        organism = synthetic construct
SEQUENCE: 222
QQASYWYNLF T                                                            11

SEQ ID NO: 223          moltype = AA   length = 14
FEATURE                 Location/Qualifiers
source                  1..14
                        mol_type = protein
                        organism = synthetic construct
SEQUENCE: 223
QYSMHFPWGY GMDY                                                         14

SEQ ID NO: 224          moltype = AA   length = 9
FEATURE                 Location/Qualifiers
source                  1..9
                        mol_type = protein
                        organism = synthetic construct
SEQUENCE: 224
QQSDMPPIT                                                               9

SEQ ID NO: 225          moltype = AA   length = 17
FEATURE                 Location/Qualifiers
source                  1..17
                        mol_type = protein
                        organism = synthetic construct
SEQUENCE: 225
YIYSSSGYTS YADSVKG                                                      17

SEQ ID NO: 226          moltype = AA   length = 12
FEATURE                 Location/Qualifiers
source                  1..12
                        mol_type = protein
                        organism = synthetic construct
SEQUENCE: 226
PVNYYYQGAL DY                                                           12

SEQ ID NO: 227          moltype = AA   length = 9
FEATURE                 Location/Qualifiers
source                  1..9
                        mol_type = protein
                        organism = synthetic construct
SEQUENCE: 227
QQYVFPIT                                                                9

SEQ ID NO: 228          moltype = AA   length = 17
FEATURE                 Location/Qualifiers
source                  1..17
                        mol_type = protein
                        organism = synthetic construct
SEQUENCE: 228
SISPSSGYTY YADSVKG                                                      17

SEQ ID NO: 229          moltype = AA   length = 21
FEATURE                 Location/Qualifiers
source                  1..21
                        mol_type = protein
                        organism = synthetic construct
SEQUENCE: 229
YHYMFEYDKG ESKWGYYGFD Y                                                 21
```

-continued

SEQ ID NO: 230  moltype = AA  length = 9
FEATURE         Location/Qualifiers
source          1..9
                mol_type = protein
                organism = synthetic construct
SEQUENCE: 230
QQSQYFPIT                                                               9

SEQ ID NO: 231  moltype = AA  length = 17
FEATURE         Location/Qualifiers
source          1..17
                mol_type = protein
                organism = synthetic construct
SEQUENCE: 231
SIYSYYGYTS YADSVKG                                                      17

SEQ ID NO: 232  moltype = AA  length = 13
FEATURE         Location/Qualifiers
source          1..13
                mol_type = protein
                organism = synthetic construct
SEQUENCE: 232
NSWSWYSGVG MDY                                                          13

SEQ ID NO: 233  moltype = AA  length = 17
FEATURE         Location/Qualifiers
source          1..17
                mol_type = protein
                organism = synthetic construct
SEQUENCE: 233
SISSYSSSTY YADSVKG                                                      17

SEQ ID NO: 234  moltype = AA  length = 14
FEATURE         Location/Qualifiers
source          1..14
                mol_type = protein
                organism = synthetic construct
SEQUENCE: 234
YPYGWGWGGS GLDY                                                         14

SEQ ID NO: 235  moltype = AA  length = 10
FEATURE         Location/Qualifiers
source          1..10
                mol_type = protein
                organism = synthetic construct
SEQUENCE: 235
QQFDFQYLIT                                                              10

SEQ ID NO: 236  moltype = AA  length = 17
FEATURE         Location/Qualifiers
source          1..17
                mol_type = protein
                organism = synthetic construct
SEQUENCE: 236
SIYSYYGSTY YADSVKG                                                      17

SEQ ID NO: 237  moltype = AA  length = 8
FEATURE         Location/Qualifiers
source          1..8
                mol_type = protein
                organism = synthetic construct
SEQUENCE: 237
GEKWALDY                                                                8

SEQ ID NO: 238  moltype = AA  length = 11
FEATURE         Location/Qualifiers
source          1..11
                mol_type = protein
                organism = synthetic construct
SEQUENCE: 238
QQYMYYQPLI T                                                            11

SEQ ID NO: 239  moltype = AA  length = 12
FEATURE         Location/Qualifiers
source          1..12
                mol_type = protein
                organism = synthetic construct
SEQUENCE: 239
EPYNYNWYGM DY                                                           12

```
SEQ ID NO: 240              moltype = AA  length = 9
FEATURE                     Location/Qualifiers
source                      1..9
                            mol_type = protein
                            organism = synthetic construct
SEQUENCE: 240
QQSLWWPIT                                                                   9

SEQ ID NO: 241              moltype = AA  length = 17
FEATURE                     Location/Qualifiers
source                      1..17
                            mol_type = protein
                            organism = synthetic construct
SEQUENCE: 241
SIYSYSGYTS YADSVKG                                                         17

SEQ ID NO: 242              moltype = AA  length = 12
FEATURE                     Location/Qualifiers
source                      1..12
                            mol_type = protein
                            organism = synthetic construct
SEQUENCE: 242
HGSYGSWWAL DY                                                              12

SEQ ID NO: 243              moltype = AA  length = 9
FEATURE                     Location/Qualifiers
source                      1..9
                            mol_type = protein
                            organism = synthetic construct
SEQUENCE: 243
QQYFYFPIT                                                                   9

SEQ ID NO: 244              moltype = AA  length = 17
FEATURE                     Location/Qualifiers
source                      1..17
                            mol_type = protein
                            organism = synthetic construct
SEQUENCE: 244
SISSYYGSTS YADSVKG                                                         17

SEQ ID NO: 245              moltype = AA  length = 19
FEATURE                     Location/Qualifiers
source                      1..19
                            mol_type = protein
                            organism = synthetic construct
SEQUENCE: 245
ASYYSGYGSS YPYYMGLDY                                                       19

SEQ ID NO: 246              moltype = AA  length = 11
FEATURE                     Location/Qualifiers
source                      1..11
                            mol_type = protein
                            organism = synthetic construct
SEQUENCE: 246
QQGSYRNPLL T                                                               11

SEQ ID NO: 247              moltype = AA  length = 10
FEATURE                     Location/Qualifiers
source                      1..10
                            mol_type = protein
                            organism = synthetic construct
SEQUENCE: 247
MNWSHYAMDY                                                                 10

SEQ ID NO: 248              moltype = AA  length = 17
FEATURE                     Location/Qualifiers
source                      1..17
                            mol_type = protein
                            organism = synthetic construct
SEQUENCE: 248
YISSYSGYTY YADSVKG                                                         17

SEQ ID NO: 249              moltype = AA  length = 14
FEATURE                     Location/Qualifiers
source                      1..14
                            mol_type = protein
                            organism = synthetic construct
SEQUENCE: 249
```

```
YWYGHYHSYF GLDY                                                                  14

SEQ ID NO: 250          moltype = AA   length = 17
FEATURE                 Location/Qualifiers
source                  1..17
                        mol_type = protein
                        organism = synthetic construct SEQUENCE: 250
SISSYSGSTY YADSVKG                                                               17

SEQ ID NO: 251          moltype = AA   length = 13
FEATURE                 Location/Qualifiers
source                  1..13
                        mol_type = protein
                        organism = synthetic construct SEQUENCE: 251
YPYGSHVYTG LDY                                                                   13

SEQ ID NO: 252          moltype = AA   length = 11
FEATURE                 Location/Qualifiers
source                  1..11
                        mol_type = protein
                        organism = synthetic construct SEQUENCE: 252
QQWNWADYLV T                                                                     11

SEQ ID NO: 253          moltype = AA   length = 17
FEATURE                 Location/Qualifiers
source                  1..17
                        mol_type = protein
                        organism = synthetic construct SEQUENCE: 253
SIYSSSGSTS YADSVKG                                                               17

SEQ ID NO: 254          moltype = AA   length = 15
FEATURE                 Location/Qualifiers
source                  1..15
                        mol_type = protein
                        organism = synthetic construct SEQUENCE: 254
VYSSRYWGWG VAFDY                                                                 15

SEQ ID NO: 255          moltype = AA   length = 10
FEATURE                 Location/Qualifiers
source                  1..10
                        mol_type = protein
                        organism = synthetic construct SEQUENCE: 255
QQYYWYSLIT                                                                       10

SEQ ID NO: 256          moltype = AA   length = 19
FEATURE                 Location/Qualifiers
source                  1..19
                        mol_type = protein
                        organism = synthetic construct SEQUENCE: 256
RSFPQWYNGS YTPWPAMDY                                                             19

SEQ ID NO: 257          moltype = AA   length = 9
FEATURE                 Location/Qualifiers
source                  1..9
                        mol_type = protein
                        organism = synthetic construct SEQUENCE: 257
QQYMWWPVT                                                                         9

SEQ ID NO: 258          moltype = AA   length = 17
FEATURE                 Location/Qualifiers
source                  1..17
                        mol_type = protein
                        organism = synthetic construct SEQUENCE: 258
SIYSYSSYTS YADSVKG                                                               17

SEQ ID NO: 259          moltype = AA   length = 12
FEATURE                 Location/Qualifiers
source                  1..12
                        mol_type = protein
                        organism = synthetic construct
```

```
SEQUENCE: 259
PFYWGERYAL DY                                                                  12

SEQ ID NO: 260         moltype = AA  length = 9
FEATURE                Location/Qualifiers
source                 1..9
                       mol_type = protein
                       organism = synthetic construct
SEQUENCE: 260
QQSYSTLVT                                                                       9

SEQ ID NO: 261         moltype = AA  length = 17
FEATURE                Location/Qualifiers
source                 1..17
                       mol_type = protein
                       organism = synthetic construct
SEQUENCE: 261
SIYSSYGSTS YADSVKG                                                             17

SEQ ID NO: 262         moltype = AA  length = 14
FEATURE                Location/Qualifiers
source                 1..14
                       mol_type = protein
                       organism = synthetic construct
SEQUENCE: 262
IYGWSYQGWA GMDY                                                                14

SEQ ID NO: 263         moltype = AA  length = 17
FEATURE                Location/Qualifiers
source                 1..17
                       mol_type = protein
                       organism = synthetic construct
SEQUENCE: 263
SIYPYYGSTS YADSVKG                                                             17

SEQ ID NO: 264         moltype = AA  length = 15
FEATURE                Location/Qualifiers
source                 1..15
                       mol_type = protein
                       organism = synthetic construct
SEQUENCE: 264
GGDYYWGWYW VAMDY                                                               15

SEQ ID NO: 265         moltype = AA  length = 9
FEATURE                Location/Qualifiers
source                 1..9
                       mol_type = protein
                       organism = synthetic construct
SEQUENCE: 265
QKSSSSLIT                                                                       9

SEQ ID NO: 266         moltype = AA  length = 17
FEATURE                Location/Qualifiers
source                 1..17
                       mol_type = protein
                       organism = synthetic construct
SEQUENCE: 266
SISSSYGSTS YADSVKG                                                             17

SEQ ID NO: 267         moltype = AA  length = 11
FEATURE                Location/Qualifiers
source                 1..11
                       mol_type = protein
                       organism = synthetic construct
SEQUENCE: 267
MYYYTYPGMD Y                                                                   11

SEQ ID NO: 268         moltype = AA  length = 9
FEATURE                Location/Qualifiers
source                 1..9
                       mol_type = protein
                       organism = synthetic construct
SEQUENCE: 268
QKGSSYLLT                                                                       9

SEQ ID NO: 269         moltype = AA  length = 17
FEATURE                Location/Qualifiers
source                 1..17
                       mol_type = protein
```

```
                                organism = synthetic construct
SEQUENCE: 269
SISPSSGYTS YADSVKG                                                               17

SEQ ID NO: 270                  moltype = AA   length = 15
FEATURE                         Location/Qualifiers
source                          1..15
                                mol_type = protein
                                organism = synthetic construct
SEQUENCE: 270
YHYGGWSHYM SGMDY                                                                 15

SEQ ID NO: 271                  moltype = AA   length = 11
FEATURE                         Location/Qualifiers
source                          1..11
                                mol_type = protein
                                organism = synthetic construct
SEQUENCE: 271
QQNYYYHKLI T                                                                     11

SEQ ID NO: 272                  moltype = AA   length = 17
FEATURE                         Location/Qualifiers
source                          1..17
                                mol_type = protein
                                organism = synthetic construct
SEQUENCE: 272
SISSSYGYTS YADSVKG                                                               17

SEQ ID NO: 273                  moltype = AA   length = 8
FEATURE                         Location/Qualifiers
source                          1..8
                                mol_type = protein
                                organism = synthetic construct
SEQUENCE: 273
GRYGGMDY                                                                          8

SEQ ID NO: 274                  moltype = AA   length = 11
FEATURE                         Location/Qualifiers
source                          1..11
                                mol_type = protein
                                organism = synthetic construct
SEQUENCE: 274
QQLSYVYKLI T                                                                     11

SEQ ID NO: 275                  moltype = AA   length = 8
FEATURE                         Location/Qualifiers
source                          1..8
                                mol_type = protein
                                organism = synthetic construct
SEQUENCE: 275
GWYKAMDY                                                                          8

SEQ ID NO: 276                  moltype = AA   length = 17
FEATURE                         Location/Qualifiers
source                          1..17
                                mol_type = protein
                                organism = synthetic construct
SEQUENCE: 276
SISSSYGSTY YADSVKG                                                               17

SEQ ID NO: 277                  moltype = AA   length = 11
FEATURE                         Location/Qualifiers
source                          1..11
                                mol_type = protein
                                organism = synthetic construct
SEQUENCE: 277
MYYYYYPGID Y                                                                     11

SEQ ID NO: 278                  moltype = AA   length = 9
FEATURE                         Location/Qualifiers
source                          1..9
                                mol_type = protein
                                organism = synthetic construct
SEQUENCE: 278
QQYYYFPIT                                                                         9

SEQ ID NO: 279                  moltype = AA   length = 17
FEATURE                         Location/Qualifiers
source                          1..17
```

```
                            mol_type = protein
                            organism = synthetic construct
SEQUENCE: 279
SISPYYGYTS YADSVKG                                                      17

SEQ ID NO: 280              moltype = AA  length = 16
FEATURE                     Location/Qualifiers
source                      1..16
                            mol_type = protein
                            organism = synthetic construct
SEQUENCE: 280
SPYWYQYFY GWGLDY                                                        16

SEQ ID NO: 281              moltype = AA  length = 13
FEATURE                     Location/Qualifiers
source                      1..13
                            mol_type = protein
                            organism = synthetic construct
SEQUENCE: 281
SPYWWNYMSA MDY                                                          13

SEQ ID NO: 282              moltype = AA  length = 9
FEATURE                     Location/Qualifiers
source                      1..9
                            mol_type = protein
                            organism = synthetic construct
SEQUENCE: 282
QQGWWWPFT                                                               9

SEQ ID NO: 283              moltype = AA  length = 16
FEATURE                     Location/Qualifiers
source                      1..16
                            mol_type = protein
                            organism = synthetic construct
SEQUENCE: 283
WSWQYYSGHS SWGLDY                                                       16

SEQ ID NO: 284              moltype = AA  length = 9
FEATURE                     Location/Qualifiers
source                      1..9
                            mol_type = protein
                            organism = synthetic construct
SEQUENCE: 284
QQSWYFPLT                                                               9

SEQ ID NO: 285              moltype = AA  length = 16
FEATURE                     Location/Qualifiers
source                      1..16
                            mol_type = protein
                            organism = synthetic construct
SEQUENCE: 285
WYNEYYHDYY WDAMDY                                                       16

SEQ ID NO: 286              moltype = AA  length = 11
FEATURE                     Location/Qualifiers
source                      1..11
                            mol_type = protein
                            organism = synthetic construct
SEQUENCE: 286
WMYWWSFALD Y                                                            11

SEQ ID NO: 287              moltype = AA  length = 9
FEATURE                     Location/Qualifiers
source                      1..9
                            mol_type = protein
                            organism = synthetic construct
SEQUENCE: 287
QQSYLWPIT                                                               9

SEQ ID NO: 288              moltype = AA  length = 13
FEATURE                     Location/Qualifiers
source                      1..13
                            mol_type = protein
                            organism = synthetic construct
SEQUENCE: 288
WQYHYNYWYG MDY                                                          13

SEQ ID NO: 289              moltype = AA  length = 9
FEATURE                     Location/Qualifiers
```

```
source                        1..9
                              mol_type = protein
                              organism = synthetic construct
SEQUENCE: 289
QQYPMSLIT                                                              9

SEQ ID NO: 290                moltype = AA   length = 17
FEATURE                       Location/Qualifiers
source                        1..17
                              mol_type = protein
                              organism = synthetic construct
SEQUENCE: 290
SISPYSGYTS YADSVKG                                                    17

SEQ ID NO: 291                moltype = AA   length = 10
FEATURE                       Location/Qualifiers
source                        1..10
                              mol_type = protein
                              organism = synthetic construct
SEQUENCE: 291
GYDYYAGLDY                                                            10

SEQ ID NO: 292                moltype = AA   length = 5
FEATURE                       Location/Qualifiers
source                        1..5
                              mol_type = protein
                              organism = synthetic construct
SEQUENCE: 292
YYSIH                                                                  5

SEQ ID NO: 293                moltype = AA   length = 12
FEATURE                       Location/Qualifiers
source                        1..12
                              mol_type = protein
                              organism = synthetic construct
SEQUENCE: 293
WESEYSGTYE DY                                                         12

SEQ ID NO: 294                moltype = AA   length = 9
FEATURE                       Location/Qualifiers
source                        1..9
                              mol_type = protein
                              organism = synthetic construct
SEQUENCE: 294
QQYMWWPIT                                                              9

SEQ ID NO: 295                moltype = AA   length = 12
FEATURE                       Location/Qualifiers
source                        1..12
                              mol_type = protein
                              organism = synthetic construct
SEQUENCE: 295
TGYWQGYLAL DY                                                         12

SEQ ID NO: 296                moltype = AA   length = 14
FEATURE                       Location/Qualifiers
source                        1..14
                              mol_type = protein
                              organism = synthetic construct
SEQUENCE: 296
TYYYYWNSTP AMDY                                                       14

SEQ ID NO: 297                moltype = AA   length = 9
FEATURE                       Location/Qualifiers
source                        1..9
                              mol_type = protein
                              organism = synthetic construct
SEQUENCE: 297
QQSYGYPVT                                                              9

SEQ ID NO: 298                moltype = AA   length = 20
FEATURE                       Location/Qualifiers
source                        1..20
                              mol_type = protein
                              organism = synthetic construct
SEQUENCE: 298
WYNSSWYYSN WWYKGFGMDY                                                 20

SEQ ID NO: 299                moltype = AA   length = 9
```

```
FEATURE                 Location/Qualifiers
source                  1..9
                        mol_type = protein
                        organism = synthetic construct
SEQUENCE: 299
QQYYSSLFT                                                                        9

SEQ ID NO: 300          moltype = AA   length = 15
FEATURE                 Location/Qualifiers
source                  1..15
                        mol_type = protein
                        organism = synthetic construct
SEQUENCE: 300
TSYTYPVYTY YGFDY                                                                15

SEQ ID NO: 301          moltype = AA   length = 9
FEATURE                 Location/Qualifiers
source                  1..9
                        mol_type = protein
                        organism = synthetic construct
SEQUENCE: 301
QQSWYYPLT                                                                        9

SEQ ID NO: 302          moltype = AA   length = 13
FEATURE                 Location/Qualifiers
source                  1..13
                        mol_type = protein
                        organism = synthetic construct
SEQUENCE: 302
YRYSSWNRGA IDY                                                                  13

SEQ ID NO: 303          moltype = AA   length = 9
FEATURE                 Location/Qualifiers
source                  1..9
                        mol_type = protein
                        organism = synthetic construct
SEQUENCE: 303
QQSYWWPLT                                                                        9

SEQ ID NO: 304          moltype = AA   length = 13
FEATURE                 Location/Qualifiers
source                  1..13
                        mol_type = protein
                        organism = synthetic construct
SEQUENCE: 304
WSKSPWYYQG IDY                                                                  13

SEQ ID NO: 305          moltype = AA   length = 11
FEATURE                 Location/Qualifiers
source                  1..11
                        mol_type = protein
                        organism = synthetic construct
SEQUENCE: 305
QQYHYWASLI T                                                                    11

SEQ ID NO: 306          moltype = AA   length = 17
FEATURE                 Location/Qualifiers
source                  1..17
                        mol_type = protein
                        organism = synthetic construct
SEQUENCE: 306
SIYSYSGSTY YADSVKG                                                              17

SEQ ID NO: 307          moltype = AA   length = 14
FEATURE                 Location/Qualifiers
source                  1..14
                        mol_type = protein
                        organism = synthetic construct
SEQUENCE: 307
QYSSSYYVWP GMDY                                                                 14

SEQ ID NO: 308          moltype = AA   length = 11
FEATURE                 Location/Qualifiers
source                  1..11
                        mol_type = protein
                        organism = synthetic construct
SEQUENCE: 308
QQSYWWKSLV T                                                                    11
```

```
SEQ ID NO: 309          moltype = AA   length = 17
FEATURE                 Location/Qualifiers
source                  1..17
                        mol_type = protein
                        organism = synthetic construct
SEQUENCE: 309
MHYSWQEYYS YDWGMDY                                                        17

SEQ ID NO: 310          moltype = AA   length = 9
FEATURE                 Location/Qualifiers
source                  1..9
                        mol_type = protein
                        organism = synthetic construct
SEQUENCE: 310
QQPYYPLIT                                                                  9

SEQ ID NO: 311          moltype = AA   length = 17
FEATURE                 Location/Qualifiers
source                  1..17
                        mol_type = protein
                        organism = synthetic construct
SEQUENCE: 311
SIYPSYGSTS YADSVKG                                                        17

SEQ ID NO: 312          moltype = AA   length = 11
FEATURE                 Location/Qualifiers
source                  1..11
                        mol_type = protein
                        organism = synthetic construct
SEQUENCE: 312
WQGYYQPALD Y                                                              11

SEQ ID NO: 313          moltype = AA   length = 11
FEATURE                 Location/Qualifiers
source                  1..11
                        mol_type = protein
                        organism = synthetic construct
SEQUENCE: 313
QQSSKYYYPI T                                                              11

SEQ ID NO: 314          moltype = AA   length = 12
FEATURE                 Location/Qualifiers
source                  1..12
                        mol_type = protein
                        organism = synthetic construct
SEQUENCE: 314
WGYGWYWYGL DY                                                             12

SEQ ID NO: 315          moltype = AA   length = 10
FEATURE                 Location/Qualifiers
source                  1..10
                        mol_type = protein
                        organism = synthetic construct
SEQUENCE: 315
QQGHDMNPVT                                                                10

SEQ ID NO: 316          moltype = AA   length = 17
FEATURE                 Location/Qualifiers
source                  1..17
                        mol_type = protein
                        organism = synthetic construct
SEQUENCE: 316
SIYSSYGYTY YADSVKG                                                        17

SEQ ID NO: 317          moltype = AA   length = 11
FEATURE                 Location/Qualifiers
source                  1..11
                        mol_type = protein
                        organism = synthetic construct
SEQUENCE: 317
YYYYWYGGMD Y                                                              11

SEQ ID NO: 318          moltype = AA   length = 11
FEATURE                 Location/Qualifiers
source                  1..11
                        mol_type = protein
                        organism = synthetic construct
SEQUENCE: 318
QQSWMSDSLI T                                                              11
```

```
SEQ ID NO: 319          moltype = AA   length = 17
FEATURE                 Location/Qualifiers
source                  1..17
                        mol_type = protein
                        organism = synthetic construct
SEQUENCE: 319
SIYPSSGYTS YADSVKG                                                      17

SEQ ID NO: 320          moltype = AA   length = 14
FEATURE                 Location/Qualifiers
source                  1..14
                        mol_type = protein
                        organism = synthetic construct
SEQUENCE: 320
GWWYWMAWDY AMDY                                                         14

SEQ ID NO: 321          moltype = AA   length = 11
FEATURE                 Location/Qualifiers
source                  1..11
                        mol_type = protein
                        organism = synthetic construct
SEQUENCE: 321
QQMQYSGWLI T                                                            11

SEQ ID NO: 322          moltype = AA   length = 17
FEATURE                 Location/Qualifiers
source                  1..17
                        mol_type = protein
                        organism = synthetic construct
SEQUENCE: 322
SISSYYGYTS YADSVKG                                                      17

SEQ ID NO: 323          moltype = AA   length = 21
FEATURE                 Location/Qualifiers
source                  1..21
                        mol_type = protein
                        organism = synthetic construct
SEQUENCE: 323
YYSYSSGYGY YDYFDWGAMD Y                                                 21

SEQ ID NO: 324          moltype = AA   length = 20
FEATURE                 Location/Qualifiers
source                  1..20
                        mol_type = protein
                        organism = synthetic construct
SEQUENCE: 324
YYGYVWGGYW GWWYSKALDY                                                   20

SEQ ID NO: 325          moltype = AA   length = 11
FEATURE                 Location/Qualifiers
source                  1..11
                        mol_type = protein
                        organism = synthetic construct
SEQUENCE: 325
QQYDWNYYLV T                                                            11

SEQ ID NO: 326          moltype = AA   length = 17
FEATURE                 Location/Qualifiers
source                  1..17
                        mol_type = protein
                        organism = synthetic construct
SEQUENCE: 326
YQYYGSLYYS QQWAMDY                                                      17

SEQ ID NO: 327          moltype = AA   length = 20
FEATURE                 Location/Qualifiers
source                  1..20
                        mol_type = protein
                        organism = synthetic construct
SEQUENCE: 327
SPSSPYFMSW GWYWQYGIDY                                                   20

SEQ ID NO: 328          moltype = AA   length = 10
FEATURE                 Location/Qualifiers
source                  1..10
                        mol_type = protein
                        organism = synthetic construct
SEQUENCE: 328
```

```
QQSSWGGLVT                                                                    10

SEQ ID NO: 329          moltype = AA  length = 17
FEATURE                 Location/Qualifiers
source                  1..17
                        mol_type = protein
                        organism = synthetic construct
SEQUENCE: 329
SISPSYGYTS YADSVKG                                                            17

SEQ ID NO: 330          moltype = AA  length = 12
FEATURE                 Location/Qualifiers
source                  1..12
                        mol_type = protein
                        organism = synthetic construct
SEQUENCE: 330
DMYEWWHWAI DY                                                                 12

SEQ ID NO: 331          moltype = AA  length = 20
FEATURE                 Location/Qualifiers
source                  1..20
                        mol_type = protein
                        organism = synthetic construct
SEQUENCE: 331
YGHYLYYWGW GWYWSAALDY                                                         20

SEQ ID NO: 332          moltype = AA  length = 11
FEATURE                 Location/Qualifiers
source                  1..11
                        mol_type = protein
                        organism = synthetic construct
SEQUENCE: 332
QQASYVKKLI T                                                                  11

SEQ ID NO: 333          moltype = AA  length = 11
FEATURE                 Location/Qualifiers
source                  1..11
                        mol_type = protein
                        organism = synthetic construct
SEQUENCE: 333
QQLSYVKKLI T                                                                  11

SEQ ID NO: 334          moltype = AA  length = 11
FEATURE                 Location/Qualifiers
source                  1..11
                        mol_type = protein
                        organism = synthetic construct
SEQUENCE: 334
QQPSYVKKLI T                                                                  11

SEQ ID NO: 335          moltype = AA  length = 11
FEATURE                 Location/Qualifiers
source                  1..11
                        mol_type = protein
                        organism = synthetic construct
SEQUENCE: 335
QQSSYVKKLI T                                                                  11

SEQ ID NO: 336          moltype = AA  length = 11
FEATURE                 Location/Qualifiers
source                  1..11
                        mol_type = protein
                        organism = synthetic construct
SEQUENCE: 336
QQTSYVKKLI T                                                                  11

SEQ ID NO: 337          moltype = AA  length = 11
FEATURE                 Location/Qualifiers
source                  1..11
                        mol_type = protein
                        organism = synthetic construct
SEQUENCE: 337
QQVSYVKKLI T                                                                  11

SEQ ID NO: 338          moltype = AA  length = 11
FEATURE                 Location/Qualifiers
source                  1..11
                        mol_type = protein
                        organism = synthetic construct
```

-continued

```
SEQUENCE: 338
QQIKYVKKLI T                                                                   11

SEQ ID NO: 339         moltype = AA  length = 11
FEATURE                Location/Qualifiers
source                 1..11
                       mol_type = protein
                       organism = synthetic construct
SEQUENCE: 339
QQIRYVKKLI T                                                                   11

SEQ ID NO: 340         moltype = AA  length = 11
FEATURE                Location/Qualifiers
source                 1..11
                       mol_type = protein
                       organism = synthetic construct
SEQUENCE: 340
QQITYVKKLI T                                                                   11

SEQ ID NO: 341         moltype = AA  length = 11
FEATURE                Location/Qualifiers
source                 1..11
                       mol_type = protein
                       organism = synthetic construct
SEQUENCE: 341
QQISFVKKLI T                                                                   11

SEQ ID NO: 342         moltype = AA  length = 11
FEATURE                Location/Qualifiers
source                 1..11
                       mol_type = protein
                       organism = synthetic construct
SEQUENCE: 342
QQISYIKKLI T                                                                   11

SEQ ID NO: 343         moltype = AA  length = 11
FEATURE                Location/Qualifiers
source                 1..11
                       mol_type = protein
                       organism = synthetic construct
SEQUENCE: 343
QQISYRKKLI T                                                                   11

SEQ ID NO: 344         moltype = AA  length = 11
FEATURE                Location/Qualifiers
source                 1..11
                       mol_type = protein
                       organism = synthetic construct
SEQUENCE: 344
QQISYTKKLI T                                                                   11

SEQ ID NO: 345         moltype = AA  length = 11
FEATURE                Location/Qualifiers
source                 1..11
                       mol_type = protein
                       organism = synthetic construct
SEQUENCE: 345
QQISYVAKLI T                                                                   11

SEQ ID NO: 346         moltype = AA  length = 11
FEATURE                Location/Qualifiers
source                 1..11
                       mol_type = protein
                       organism = synthetic construct
SEQUENCE: 346
QQISYVEKLI T                                                                   11

SEQ ID NO: 347         moltype = AA  length = 11
FEATURE                Location/Qualifiers
source                 1..11
                       mol_type = protein
                       organism = synthetic construct
SEQUENCE: 347
QQISYVHKLI T                                                                   11

SEQ ID NO: 348         moltype = AA  length = 11
FEATURE                Location/Qualifiers
source                 1..11
                       mol_type = protein
```

```
                         organism = synthetic construct
SEQUENCE: 348
QQISYVLKLI T                                                            11

SEQ ID NO: 349           moltype = AA   length = 11
FEATURE                  Location/Qualifiers
source                   1..11
                         mol_type = protein
                         organism = synthetic construct
SEQUENCE: 349
QQISYVMKLI T                                                            11

SEQ ID NO: 350           moltype = AA   length = 11
FEATURE                  Location/Qualifiers
source                   1..11
                         mol_type = protein
                         organism = synthetic construct
SEQUENCE: 350
QQISYVNKLI T                                                            11

SEQ ID NO: 351           moltype = AA   length = 11
FEATURE                  Location/Qualifiers
source                   1..11
                         mol_type = protein
                         organism = synthetic construct
SEQUENCE: 351
QQISYVQKLI T                                                            11

SEQ ID NO: 352           moltype = AA   length = 11
FEATURE                  Location/Qualifiers
source                   1..11
                         mol_type = protein
                         organism = synthetic construct
SEQUENCE: 352
QQISYVRKLI T                                                            11

SEQ ID NO: 353           moltype = AA   length = 11
FEATURE                  Location/Qualifiers
source                   1..11
                         mol_type = protein
                         organism = synthetic construct
SEQUENCE: 353
QQISYVSKLI T                                                            11

SEQ ID NO: 354           moltype = AA   length = 11
FEATURE                  Location/Qualifiers
source                   1..11
                         mol_type = protein
                         organism = synthetic construct
SEQUENCE: 354
QQISYVTKLI T                                                            11

SEQ ID NO: 355           moltype = AA   length = 11
FEATURE                  Location/Qualifiers
source                   1..11
                         mol_type = protein
                         organism = synthetic construct
SEQUENCE: 355
QQISYVYKLI T                                                            11

SEQ ID NO: 356           moltype = AA   length = 11
FEATURE                  Location/Qualifiers
source                   1..11
                         mol_type = protein
                         organism = synthetic construct
SEQUENCE: 356
QQISYVKRLI T                                                            11

SEQ ID NO: 357           moltype = AA   length = 11
FEATURE                  Location/Qualifiers
source                   1..11
                         mol_type = protein
                         organism = synthetic construct
SEQUENCE: 357
QQISYVKKAI T                                                            11

SEQ ID NO: 358           moltype = AA   length = 11
FEATURE                  Location/Qualifiers
source                   1..11
```

|   |   |   |
|---|---|---|
| SEQUENCE: 358 | | |
| QQISYVKKCI T | | 11 |
| SEQ ID NO: 359 | moltype = AA   length = 11 | |
| FEATURE | Location/Qualifiers | |
| source | 1..11 | |
| | mol_type = protein | |
| | organism = synthetic construct | |
| SEQUENCE: 359 | | |
| QQISYVKKDI T | | 11 |
| SEQ ID NO: 360 | moltype = AA   length = 11 | |
| FEATURE | Location/Qualifiers | |
| source | 1..11 | |
| | mol_type = protein | |
| | organism = synthetic construct | |
| SEQUENCE: 360 | | |
| QQISYVKKEI T | | 11 |
| SEQ ID NO: 361 | moltype = AA   length = 11 | |
| FEATURE | Location/Qualifiers | |
| source | 1..11 | |
| | mol_type = protein | |
| | organism = synthetic construct | |
| SEQUENCE: 361 | | |
| QQISYVKKGI T | | 11 |
| SEQ ID NO: 362 | moltype = AA   length = 11 | |
| FEATURE | Location/Qualifiers | |
| source | 1..11 | |
| | mol_type = protein | |
| | organism = synthetic construct | |
| SEQUENCE: 362 | | |
| QQISYVKKHI T | | 11 |
| SEQ ID NO: 363 | moltype = AA   length = 11 | |
| FEATURE | Location/Qualifiers | |
| source | 1..11 | |
| | mol_type = protein | |
| | organism = synthetic construct | |
| SEQUENCE: 363 | | |
| QQISYVKKKI T | | 11 |
| SEQ ID NO: 364 | moltype = AA   length = 11 | |
| FEATURE | Location/Qualifiers | |
| source | 1..11 | |
| | mol_type = protein | |
| | organism = synthetic construct | |
| SEQUENCE: 364 | | |
| QQISYVKKMI T | | 11 |
| SEQ ID NO: 365 | moltype = AA   length = 11 | |
| FEATURE | Location/Qualifiers | |
| source | 1..11 | |
| | mol_type = protein | |
| | organism = synthetic construct | |
| SEQUENCE: 365 | | |
| QQISYVKKNI T | | 11 |
| SEQ ID NO: 366 | moltype = AA   length = 11 | |
| FEATURE | Location/Qualifiers | |
| source | 1..11 | |
| | mol_type = protein | |
| | organism = synthetic construct | |
| SEQUENCE: 366 | | |
| QQISYVKKPI T | | 11 |
| SEQ ID NO: 367 | moltype = AA   length = 11 | |
| FEATURE | Location/Qualifiers | |
| source | 1..11 | |
| | mol_type = protein | |
| | organism = synthetic construct | |
| SEQUENCE: 367 | | |
| QQISYVKKQI T | | 11 |
| SEQ ID NO: 368 | moltype = AA   length = 11 | |
| FEATURE | Location/Qualifiers | |

|  |  |  |
|---|---|---|
| source | 1..11<br>mol_type = protein<br>organism = synthetic construct | |
| SEQUENCE: 368<br>QQISYVKKRI T | | 11 |
| SEQ ID NO: 369<br>FEATURE<br>source | moltype = AA   length = 11<br>Location/Qualifiers<br>1..11<br>mol_type = protein<br>organism = synthetic construct | |
| SEQUENCE: 369<br>QQISYVKKSI T | | 11 |
| SEQ ID NO: 370<br>FEATURE<br>source | moltype = AA   length = 11<br>Location/Qualifiers<br>1..11<br>mol_type = protein<br>organism = synthetic construct | |
| SEQUENCE: 370<br>QQISYVKKTI T | | 11 |
| SEQ ID NO: 371<br>FEATURE<br>source | moltype = AA   length = 11<br>Location/Qualifiers<br>1..11<br>mol_type = protein<br>organism = synthetic construct | |
| SEQUENCE: 371<br>QQISYVKKVI T | | 11 |
| SEQ ID NO: 372<br>FEATURE<br>source | moltype = AA   length = 11<br>Location/Qualifiers<br>1..11<br>mol_type = protein<br>organism = synthetic construct | |
| SEQUENCE: 372<br>QQISYVKKWI T | | 11 |
| SEQ ID NO: 373<br>FEATURE<br>source | moltype = AA   length = 11<br>Location/Qualifiers<br>1..11<br>mol_type = protein<br>organism = synthetic construct | |
| SEQUENCE: 373<br>QQISYVKKLL T | | 11 |
| SEQ ID NO: 374<br>FEATURE<br>source | moltype = AA   length = 11<br>Location/Qualifiers<br>1..11<br>mol_type = protein<br>organism = synthetic construct | |
| SEQUENCE: 374<br>QQISYVKKLV T | | 11 |
| SEQ ID NO: 375<br>FEATURE<br>source | moltype = AA   length = 9<br>Location/Qualifiers<br>1..9<br>mol_type = protein<br>organism = synthetic construct | |
| SEQUENCE: 375<br>GAWYPAMDY | | 9 |
| SEQ ID NO: 376<br>FEATURE<br>source | moltype = AA   length = 9<br>Location/Qualifiers<br>1..9<br>mol_type = protein<br>organism = synthetic construct | |
| SEQUENCE: 376<br>GCWYPAMDY | | 9 |
| SEQ ID NO: 377<br>FEATURE<br>source | moltype = AA   length = 9<br>Location/Qualifiers<br>1..9<br>mol_type = protein<br>organism = synthetic construct | |
| SEQUENCE: 377<br>GEWYPAMDY | | 9 |
| SEQ ID NO: 378 | moltype = AA   length = 9 | |

```
FEATURE                 Location/Qualifiers
source                  1..9
                        mol_type = protein
                        organism = synthetic construct
SEQUENCE: 378
GHWYPAMDY                                                                    9

SEQ ID NO: 379          moltype = AA  length = 9
FEATURE                 Location/Qualifiers
source                  1..9
                        mol_type = protein
                        organism = synthetic construct
SEQUENCE: 379
GKWYPAMDY                                                                    9

SEQ ID NO: 380          moltype = AA  length = 9
FEATURE                 Location/Qualifiers
source                  1..9
                        mol_type = protein
                        organism = synthetic construct
SEQUENCE: 380
GLWYPAMDY                                                                    9

SEQ ID NO: 381          moltype = AA  length = 9
FEATURE                 Location/Qualifiers
source                  1..9
                        mol_type = protein
                        organism = synthetic construct
SEQUENCE: 381
GMWYPAMDY                                                                    9

SEQ ID NO: 382          moltype = AA  length = 9
FEATURE                 Location/Qualifiers
source                  1..9
                        mol_type = protein
                        organism = synthetic construct
SEQUENCE: 382
GNWYPAMDY                                                                    9

SEQ ID NO: 383          moltype = AA  length = 9
FEATURE                 Location/Qualifiers
source                  1..9
                        mol_type = protein
                        organism = synthetic construct
SEQUENCE: 383
GPWYPAMDY                                                                    9

SEQ ID NO: 384          moltype = AA  length = 9
FEATURE                 Location/Qualifiers
source                  1..9
                        mol_type = protein
                        organism = synthetic construct
SEQUENCE: 384
GQWYPAMDY                                                                    9

SEQ ID NO: 385          moltype = AA  length = 9
FEATURE                 Location/Qualifiers
source                  1..9
                        mol_type = protein
                        organism = synthetic construct
SEQUENCE: 385
GRWYPAMDY                                                                    9

SEQ ID NO: 386          moltype = AA  length = 9
FEATURE                 Location/Qualifiers
source                  1..9
                        mol_type = protein
                        organism = synthetic construct
SEQUENCE: 386
GSWYPAMDY                                                                    9

SEQ ID NO: 387          moltype = AA  length = 9
FEATURE                 Location/Qualifiers
source                  1..9
                        mol_type = protein
                        organism = synthetic construct
SEQUENCE: 387
GTWYPAMDY                                                                    9
```

```
SEQ ID NO: 388            moltype = AA   length = 9
FEATURE                   Location/Qualifiers
source                    1..9
                          mol_type = protein
                          organism = synthetic construct
SEQUENCE: 388
GWWYPAMDY                                                                 9

SEQ ID NO: 389            moltype = AA   length = 9
FEATURE                   Location/Qualifiers
source                    1..9
                          mol_type = protein
                          organism = synthetic construct
SEQUENCE: 389
GYWYPAMDY                                                                 9

SEQ ID NO: 390            moltype = AA   length = 9
FEATURE                   Location/Qualifiers
source                    1..9
                          mol_type = protein
                          organism = synthetic construct
SEQUENCE: 390
GGGYPAMDY                                                                 9

SEQ ID NO: 391            moltype = AA   length = 9
FEATURE                   Location/Qualifiers
source                    1..9
                          mol_type = protein
                          organism = synthetic construct
SEQUENCE: 391
GGPYPAMDY                                                                 9

SEQ ID NO: 392            moltype = AA   length = 9
FEATURE                   Location/Qualifiers
source                    1..9
                          mol_type = protein
                          organism = synthetic construct
SEQUENCE: 392
GGRYPAMDY                                                                 9

SEQ ID NO: 393            moltype = AA   length = 9
FEATURE                   Location/Qualifiers
source                    1..9
                          mol_type = protein
                          organism = synthetic construct
SEQUENCE: 393
GGTYPAMDY                                                                 9

SEQ ID NO: 394            moltype = AA   length = 9
FEATURE                   Location/Qualifiers
source                    1..9
                          mol_type = protein
                          organism = synthetic construct
SEQUENCE: 394
GGWAPAMDY                                                                 9

SEQ ID NO: 395            moltype = AA   length = 9
FEATURE                   Location/Qualifiers
source                    1..9
                          mol_type = protein
                          organism = synthetic construct
SEQUENCE: 395
GGWDPAMDY                                                                 9

SEQ ID NO: 396            moltype = AA   length = 9
FEATURE                   Location/Qualifiers
source                    1..9
                          mol_type = protein
                          organism = synthetic construct
SEQUENCE: 396
GGWEPAMDY                                                                 9

SEQ ID NO: 397            moltype = AA   length = 9
FEATURE                   Location/Qualifiers
source                    1..9
                          mol_type = protein
                          organism = synthetic construct
SEQUENCE: 397
GGWFPAMDY                                                                 9
```

```
SEQ ID NO: 398            moltype = AA   length = 9
FEATURE                   Location/Qualifiers
source                    1..9
                          mol_type = protein
                          organism = synthetic construct
SEQUENCE: 398
GGWGPAMDY                                                                9

SEQ ID NO: 399            moltype = AA   length = 9
FEATURE                   Location/Qualifiers
source                    1..9
                          mol_type = protein
                          organism = synthetic construct
SEQUENCE: 399
GGWHPAMDY                                                                9

SEQ ID NO: 400            moltype = AA   length = 9
FEATURE                   Location/Qualifiers
source                    1..9
                          mol_type = protein
                          organism = synthetic construct
SEQUENCE: 400
GGWIPAMDY                                                                9

SEQ ID NO: 401            moltype = AA   length = 9
FEATURE                   Location/Qualifiers
source                    1..9
                          mol_type = protein
                          organism = synthetic construct
SEQUENCE: 401
GGWKPAMDY                                                                9

SEQ ID NO: 402            moltype = AA   length = 9
FEATURE                   Location/Qualifiers
source                    1..9
                          mol_type = protein
                          organism = synthetic construct
SEQUENCE: 402
GGWMPAMDY                                                                9

SEQ ID NO: 403            moltype = AA   length = 9
FEATURE                   Location/Qualifiers
source                    1..9
                          mol_type = protein
                          organism = synthetic construct
SEQUENCE: 403
GGWNPAMDY                                                                9

SEQ ID NO: 404            moltype = AA   length = 9
FEATURE                   Location/Qualifiers
source                    1..9
                          mol_type = protein
                          organism = synthetic construct
SEQUENCE: 404
GGWQPAMDY                                                                9

SEQ ID NO: 405            moltype = AA   length = 9
FEATURE                   Location/Qualifiers
source                    1..9
                          mol_type = protein
                          organism = synthetic construct
SEQUENCE: 405
GGWRPAMDY                                                                9

SEQ ID NO: 406            moltype = AA   length = 9
FEATURE                   Location/Qualifiers
source                    1..9
                          mol_type = protein
                          organism = synthetic construct
SEQUENCE: 406
GGWSPAMDY                                                                9

SEQ ID NO: 407            moltype = AA   length = 9
FEATURE                   Location/Qualifiers
source                    1..9
                          mol_type = protein
                          organism = synthetic construct
SEQUENCE: 407
```

| | | |
|---|---|---|
| GGWTPAMDY | | 9 |
| SEQ ID NO: 408<br>FEATURE<br>source | moltype = AA  length = 9<br>Location/Qualifiers<br>1..9<br>mol_type = protein<br>organism = synthetic construct | |
| SEQUENCE: 408<br>GGWWPAMDY | | 9 |
| SEQ ID NO: 409<br>FEATURE<br>source | moltype = AA  length = 9<br>Location/Qualifiers<br>1..9<br>mol_type = protein<br>organism = synthetic construct | |
| SEQUENCE: 409<br>GGWYAAMDY | | 9 |
| SEQ ID NO: 410<br>FEATURE<br>source | moltype = AA  length = 9<br>Location/Qualifiers<br>1..9<br>mol_type = protein<br>organism = synthetic construct | |
| SEQUENCE: 410<br>GGWYVAMDY | | 9 |
| SEQ ID NO: 411<br>FEATURE<br>source | moltype = AA  length = 9<br>Location/Qualifiers<br>1..9<br>mol_type = protein<br>organism = synthetic construct | |
| SEQUENCE: 411<br>GGWYPCMDY | | 9 |
| SEQ ID NO: 412<br>FEATURE<br>source | moltype = AA  length = 9<br>Location/Qualifiers<br>1..9<br>mol_type = protein<br>organism = synthetic construct | |
| SEQUENCE: 412<br>GGWYPGMDY | | 9 |
| SEQ ID NO: 413<br>FEATURE<br>source | moltype = AA  length = 9<br>Location/Qualifiers<br>1..9<br>mol_type = protein<br>organism = synthetic construct | |
| SEQUENCE: 413<br>GGWYPKMDY | | 9 |
| SEQ ID NO: 414<br>FEATURE<br>source | moltype = AA  length = 9<br>Location/Qualifiers<br>1..9<br>mol_type = protein<br>organism = synthetic construct | |
| SEQUENCE: 414<br>GGWYPLMDY | | 9 |
| SEQ ID NO: 415<br>FEATURE<br>source | moltype = AA  length = 9<br>Location/Qualifiers<br>1..9<br>mol_type = protein<br>organism = synthetic construct | |
| SEQUENCE: 415<br>GGWYPMMDY | | 9 |
| SEQ ID NO: 416<br>FEATURE<br>source | moltype = AA  length = 9<br>Location/Qualifiers<br>1..9<br>mol_type = protein<br>organism = synthetic construct | |
| SEQUENCE: 416<br>GGWYPQMDY | | 9 |
| SEQ ID NO: 417<br>FEATURE<br>source | moltype = AA  length = 9<br>Location/Qualifiers<br>1..9<br>mol_type = protein<br>organism = synthetic construct | |

```
SEQUENCE: 417
GGWYPRMDY                                                                       9

SEQ ID NO: 418         moltype = AA  length = 9
FEATURE                Location/Qualifiers
source                 1..9
                       mol_type = protein
                       organism = synthetic construct
SEQUENCE: 418
GGWYPSMDY                                                                       9

SEQ ID NO: 419         moltype = AA  length = 9
FEATURE                Location/Qualifiers
source                 1..9
                       mol_type = protein
                       organism = synthetic construct
SEQUENCE: 419
GGWYPTMDY                                                                       9

SEQ ID NO: 420         moltype = AA  length = 9
FEATURE                Location/Qualifiers
source                 1..9
                       mol_type = protein
                       organism = synthetic construct
SEQUENCE: 420
GGWYPYMDY                                                                       9
```

What is claimed is:

1. A method comprising: administering to a human subject a pharmaceutical composition comprising an antibody or antigen binding fragment thereof, wherein the human subject has been pretreated with AMG510 and has a cancer that expresses a G12C mutant KRAS protein that comprises the amino acid sequence of SEQ ID NO: 1, wherein the antibody or antigen binding fragment thereof binds to a peptide conjugate in complex with a major histocompatibility complex (MHC) that is HLA-A*03:01, wherein the peptide conjugate comprises a peptide from the G12C mutant KRAS protein that comprises the amino acid sequence of SEQ ID NO: 1 covalently linked to the AMG510, and wherein the antibody or antigen binding fragment thereof comprises
   (i) a heavy chain variable region (VH) comprising
      a heavy chain complementarity determining region 1 (HC CDR1) having the amino acid sequence set forth in SEQ ID NO: 169,
      a HC CDR2 having the amino acid sequence set forth in SEQ ID NO: 170, and
      a HC CDR3 having an amino acid sequence selected from the group consisting of the amino acid sequences set forth in SEQ ID NOs: 375-420; and
   (ii) a light chain variable region (VL) comprising
      a light chain (LC) CDR1 having the amino acid sequence set forth in SEQ ID NO: 166,
      a LC CDR2 having the amino acid sequence set forth in SEQ ID NO: 167, and
      a LC CDR3 having an amino acid sequence selected from the group consisting of the amino acid sequences set forth in SEQ ID NOs: 332-374.

2. The method of claim 1, wherein the cancer is renal cell carcinoma, breast cancer, prostate cancer, pancreatic cancer, lung cancer, liver cancer, ovarian cancer, cervical cancer, colon cancer, esophageal cancer, glioma, glioblastoma or another brain cancer, stomach cancer, bladder cancer, testicular cancer, head and neck cancer, melanoma or another skin cancer, a sarcoma, or a blood cancer.

3. The method of claim 1, wherein the AMG510 is covalently linked to a Cys residue of SEQ ID NO: 1.

4. The method of claim 1, wherein a dissociation constant (Kd) of the antibody or antigen binding fragment thereof to the peptide conjugate in complex with the MHC is lower than a Kd of the antibody or antigen binding fragment thereof to the peptide conjugate not in complex with the MHC.

5. The method of claim 1, wherein the cancer is a lung cancer, a colon cancer, or a pancreatic cancer.

6. The method of claim 1, wherein the antibody or antigen binding fragment thereof is an intact antibody, an antigen-binding (Fab) fragment, an Fab' fragment, an (Fab')2 fragment, an Fd, an Fv, a dAb, a single-chain Diabody (scDb), a single-chain variable fragment (scFv), or a CrossMab.

7. A method for treating a cancer that expresses a G12C mutant KRAS protein that comprises the amino acid sequence of SEQ ID NO: 1 in a human subject in need thereof, the method comprising administering to the human subject a therapeutically effective amount of a pharmaceutical composition comprising an antibody or antigen binding fragment thereof, wherein the human subject has been pretreated with AMG510, wherein the antibody or antigen binding fragment thereof binds to a peptide conjugate in complex with a major histocompatibility complex (MHC) that is HLA-A*03:01, wherein the peptide conjugate comprises a peptide from the G12C mutant KRAS protein that comprises the amino acid sequence of SEQ ID NO:1 covalently linked to the AMG510, and wherein the antibody or antigen binding fragment thereof comprises
   (i) a VH comprises
      a HC CDR1 having the amino acid sequence set forth in SEQ ID NO: 169,
      a HC CDR2 having the amino acid sequence set forth in SEQ ID NO: 170, and
      a HC CDR3 having the amino acid sequence set forth in SEQ ID NO: 171; and
   (ii) a VL comprises
      a LC CDR1 having the amino acid sequence set forth in SEQ ID NO: 166,
      a LC CDR2 having the amino acid sequence set forth in SEQ ID NO: 167, and a LC CDR3 having the amino acid sequence set forth in SEQ ID NO: 168.

8. The method of claim 7, wherein
(i) the VH comprises
   a HC CDR1 having the amino acid sequence set forth in SEQ ID NO: 169,
   a HC CDR2 having the amino acid sequence set forth in SEQ ID NO: 170, and
   a HC CDR3 having the amino acid sequence set forth in SEQ ID NO: 171; and
(ii) the VL comprises
   a LC CDR1 having the amino acid sequence set forth in SEQ ID NO: 166,
   a LC CDR2 having the amino acid sequence set forth in SEQ ID NO: 167, and
   a LC CDR3 having the amino acid sequence set forth in SEQ ID NO: 168; and
wherein the VH has the amino acid sequence as set forth in SEQ ID NO: 4, and the VL has the amino acid sequence as set forth in SEQ ID NO: 3.

* * * * *